(12) United States Patent
Jakobi et al.

(10) Patent No.: US 9,661,848 B2
(45) Date of Patent: May 30, 2017

(54) SUBSTITUTED 4-CYAN-3-(PYRIDYL)-4-PHENYLBUTANOATES, METHOD FOR THE PRODUCTION THEREOF AND USES AS HERBICIDES AND PLANT GROWTH REGULATORS

(71) Applicant: BAYER CROPSCIENCE AG, Monheim (DE)

(72) Inventors: Harald Jakobi, Frankfurt (DE); Marc Mosrin, Frankfurt am Main (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/654,057

(22) PCT Filed: Dec. 17, 2013

(86) PCT No.: PCT/EP2013/076924
§ 371 (c)(1),
(2) Date: Jun. 19, 2015

(87) PCT Pub. No.: WO2014/095879
PCT Pub. Date: Jun. 26, 2014

(65) Prior Publication Data
US 2015/0327546 A1 Nov. 19, 2015

(30) Foreign Application Priority Data
Dec. 21, 2012 (EP) ..................................... 12199221

(51) Int. Cl.
C07D 213/61 (2006.01)
A01N 43/40 (2006.01)

(52) U.S. Cl.
CPC ............ *A01N 43/40* (2013.01); *C07D 213/61* (2013.01)

(58) Field of Classification Search
CPC ............................. A01N 43/40; C07D 213/61
USPC ......................................................... 546/334
See application file for complete search history.

(56) References Cited

U.S. PATENT DOCUMENTS

| 8,975,412 B2 * | 3/2015 | Jakobi | .................... | A01N 43/40 546/330 |
| 9,049,863 B2 | 6/2015 | Jakobi et al. | | |
| 9,084,425 B2 * | 7/2015 | Mosrin | ................. | C07C 255/62 |
| 9,161,537 B2 * | 10/2015 | Jakobi | ................. | C07D 405/12 |
| 2014/0087945 A1 | 3/2014 | Jakobi et al. | | |

FOREIGN PATENT DOCUMENTS

| EP | 0005341 A2 | 11/1979 |
| EP | 266725 A1 | 5/1988 |
| EP | 0270830 A1 | 6/1988 |
| EP | 2474226 * | 7/2012 |
| JP | H04297454 A | 10/1992 |
| JP | 2004297455 A | 10/2004 |
| JP | 2005058979 A | 3/2005 |
| WO | 2010114978 A1 | 10/2010 |
| WO | 2011003775 A2 | 1/2011 |
| WO | 2011003776 A2 | 1/2011 |
| WO | 2011042378 A1 | 4/2011 |
| WO | 2011073143 A1 | 4/2011 |
| WO | 2011098417 A1 | 8/2011 |
| WO | 2012126764 A1 | 9/2012 |
| WO | 2012126765 A1 | 9/2012 |
| WO | WO 2016/055393 * | 4/2016 |

OTHER PUBLICATIONS

International Search Report from corresponding PCT/EP2013/076924, mailed Apr. 16, 2014.
Lacombe et al, "3,4-Diarylpiperidines as potent renin inhibitors", Biorganic & Medicinal Chemistry Letters 22 (2012), pp. 1953-1957.

* cited by examiner

*Primary Examiner* — Noble Jarrell
*Assistant Examiner* — Daniel Carcanague
(74) *Attorney, Agent, or Firm* — McBee Moore Woodward Vanik, IP LLC

(57) ABSTRACT

4-Cyano-3-(pyridyl)-4-phenylbutanoates, processes for their preparation and their use as herbicides and plant growth regulars
Compounds of the formula (I) or salts thereof

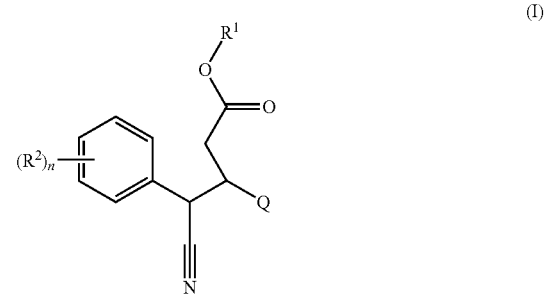

(I)

in which $R^1$, $(R^2)_n$ and Q are as defined in Claim 1 are suitable as herbicides for the control of harmful plants or as plant growth regulators.
The compounds can be prepared by the process claimed.

13 Claims, No Drawings

SUBSTITUTED 4-CYAN-3-(PYRIDYL)-4-PHENYLBUTANOATES, METHOD FOR THE PRODUCTION THEREOF AND USES AS HERBICIDES AND PLANT GROWTH REGULATORS

CROSS REFERENCE TO RELATED APPLICATIONS

This application is a §371 National Stage Application of PCT/EP2013/076924, filed 17 Dec. 2013, which claims priority to EP 12199221.8, filed 21 Dec. 2012.

BACKGROUND

Field of the Invention

The invention relates to the technical field of the herbicides and plant growth regulators, namely substituted 4-cyano-3-(pyridyl)-4-phenylbutanoates, which can be used for controlling unwanted vegetation, for the selective control of broad-leaved weeds and weed grasses in crops of useful plants and also for regulating and influencing plant growth of crop plants. Moreover the invention relates to processes for preparing substituted 4-cyano-3-(pyridyl)-4-phenylbutanoates and/or salts thereof.

Description of Related Art

Since, from the prior art listed and analysed below, 4-cyano-3-(heteroaryl)-4-phenylbutanoates—including individual herbicidal 4-cyano-3-(pyridyl)-4-phenylbutanoates—are already known, the invention relates in particular to substituted 4-cyano-3-(pyridyl)-4-phenylbutanoates, to processes for their preparation and to their use as herbicides and plant growth regulators.

Document EP 0 005 341 A2 discloses esters and amides of 4-cyano-3,4-diarylbutanoic acids and their herbicidal action. Also disclosed in generic form, in addition to 4-cyano-4-phenyl-3-phenylbutanoates and 4-cyano-4-heteroaryl-3-phenylbutanoates, are 4-cyano-3-heteroaryl-4-phenylbutanoates, where the definition of heteroaryl comprises, in addition to thienyl, also pyridyl. However, in the specific examples disclosed in EP 0 005 341 A2, the 4-cyano-3,4-diphenylbutanoic acids and their esters predominate, whereas the pyridine-substituted compounds are limited to two specific examples, namely 4-cyano-3-phenyl-4-(pyridin-3-yl)butanoic acid and its ethyl ester. In contrast, EP 0 005 341 A2 does not disclose any specific examples of 4-cyano-3-pyridyl-4-phenylbutanoates.

According to the teaching disclosed in EP-A-0 005 341 A2, the threo isomers of the compounds disclosed in EP 0 005 341 A2 are generally suitable for the non-selective control of harmful plants, whereas the erythro/threo isomer mixtures are preferred for the selective control of harmful plants in some crops of useful plants. Using 4-cyano-3,4-diphenylbutanoic acid unsubstituted in the phenyl radical as an example, EP 0 005 341 A2 furthermore shows that the two isomers which belong to the threo form have different activities.

Document EP 0 270 830 A1 discloses that threo isomers and erythro/threo isomer mixtures of 4-cyano-3,4-diarylbutanoic acid (esters) can be used as plant growth regulators, preventing the development of an infructescence in various harmful grasses. The aryl groups envisaged are unsubstituted or substituted phenyl radicals and also unsubstituted pyridine radicals or halogen-substituted pyridine radicals. The examples disclosed in document EP 0 270 830 A1, which mainly relate to (substituted) 4-cyano-3,4-diphenylbutanoic acid (esters), also include two specific 4-cyano-3-pyridyl-4-phenylbutanoic esters (cf. the first two compounds in Table Ig on page 33), namely ethyl 4-cyano-3-(pyridin-3-yl)-4-phenylbutanoate and methyl 4-cyano-3-(pyridin-4-yl)-4-(3-chlorophenyl)butanoate.

Document JP 04297454 A discloses 4-cyano-3-heteroaryl-4-phenylbutanoates and their use as herbicides. The heterocycles representing the letter "A" and the heterocycles located in the 3-position of the butanoate include, in addition to an unsubstituted quinoline, also a methyl-substituted pyridin-2-yl radical (6-methylpyridin-2-yl).

Document WO 2010/114978 A1 relates to the preparation of pharmaceutically active compounds (renin inhibitors). For the preparation of the renin inhibitors, the document discloses the use of 4-cyano-3-(3-pyridyl)-4-phenylbutanoates whose pyridine radical is substituted by a methoxy group.

The scientific publication published in Biorganic & Medicinal Chemistry Letters 22 (2012) 1953-1957 also relates to the preparation of pharmaceutically active compounds (renin inhibitors) and, in this context, discloses the use of ethyl 4-cyano-3-(heteroaryl)-4-phenylbutanoates (cf. compound 3 in Scheme 1 page 1955 in combination with Table 1, in which the aryl radicals referred to as Y are specified, on page 1954). According to Table 1, Y in the compound 37 mentioned refers to a pyridin-3-yl. Thus, during the synthesis of compound 37, in a first reaction step, by Michael addition (cf. Scheme 1), one of the intermediates formed was the compound ethyl 4-cyano-3-(pyridin-3-yl)-4-(2-chloro-4-bromophenyl)butanoate.

In their application, the crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavourable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

For the reasons mentioned, there is still a need for alternative, highly active herbicides for the selective application in plant crops or use on non-crop land. It is also desirable to provide alternative chemical active compounds which may be used in an advantageous manner as herbicides or plant growth regulators. Likewise desirable are compounds having herbicidal activity which are highly effective against economically important harmful plants even at relatively low application rates and can be used selectively in crop plants, preferably with good activity against harmful plants.

Against this background and against the background of the prior art analysed above, it was an object of the invention to provide alternative 4-cyano-3-(pyridyl)-4-phenylbutanoates not having the disadvantages of the compounds known from the prior art and suitable for use in crop plants or else on non-crop land and as plant growth regulators.

Particularly desirable are compounds having herbicidal activity which are highly effective against economically important harmful plants even at relatively low application rates and can be used selectively in crop plants, preferably with good activity against harmful plants.

SUMMARY

Surprisingly it has now been found that certain 4-cyano-3-(pyridyl)-4-phenylbutanoates, distinguished primarily by the selected substitution of the pyridine radical, have particular herbicidal activities and at the same time good selectivity and can be used with preference for controlling harmful plants in certain crops.

The object is thus achieved by 4-cyano-3-(pyridyl)-4-phenylbutanoates of the formula (I) or salts thereof

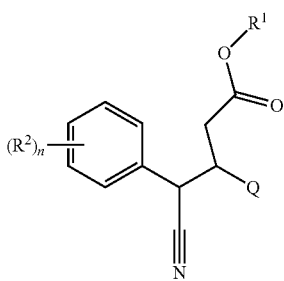

(I)

in which
$R^1$ represents hydrogen or a hydrolysable radical,
$(R^2)_n$ represents n substituents $R^2$,
  where $R^2$, if n=1, or each of the substituents $R^2$, if n is greater than 1, independently of the others represents halogen, cyano, nitro, hydroxy, $(C_1-C_8)$-alkyl, $(C_2-C_6)$-alkenyl, $(C_3-C_6)$-cycloalkenyl, $(C_3-C_6)$-cycloalkyl-$(C_1-C_8)$-alkyl, $(C_3-C_6)$-cycloalkenyl-$(C_1-C_8)$-alkyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_6)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^3$, $C(O)NR^4R^5$, $C(O)$-$Het^2$, $NR^6R^7$ or $Het^3$
or where in each case two groups $R^2$ located ortho at the ring together are a group of the formula
—$Z^1$-$A^{**}$-$Z^2$ in which
$A^{**}$ represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
$Z^1$ represents a direct bond, O or S and
$Z^2$ represents a direct bond, O or S,
where the group —$Z^1$-$A^{**}$-$Z^2$ together with the carbon atoms, attached to the group, of the phenyl ring form a fused-on 5- or 6-membered ring, $R^3$ represents hydrogen, $(C_1-C_6)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned below,
$R^4$, $R^5$, $R^6$ and $R^7$ independently of one another each represent hydrogen, $(C_1-C_6)$-alkyl, $(C_2-C_6)$-alkenyl or $(C_2-C_6)$-alkynyl, where each of the 3 last-mentioned radicals in each case independently of the others is unsubstituted or substituted by one or more radicals from the group consisting of halogen, nitro, cyano and phenyl which is optionally substituted, or
  $(C_3-C_6)$-cycloalkyl or phenyl, where each of the 2 last-mentioned radicals in each case independently of the other is unsubstituted or substituted by one or more radicals from the group consisting of halogen, nitro, cyano, $(C_1-C_4)$-alkyl, $(C_1-C_4)$-haloalkyl, phenyl and benzyl, where each of the 2 last-mentioned radicals is optionally substituted,
$Het^2$ and $Het^3$ independently of one another each represent a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo,
M represents an equivalent of a cation,
n represents 0, 1, 2, 3, 4 or 5, preferably 0, 1, 2 or 3, and
Q represents either pyridin-2-yl (Q1), pyridin-3-yl (Q2) or pyridin-4-yl (Q3)

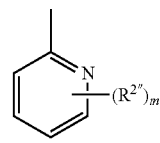

(Q1)

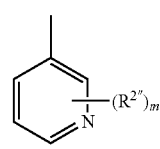

(Q2)

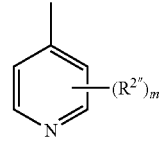

(Q3)

where
$(R^{2''})_m$ represents m substituents $R^{2''}$,
  where $R^{2''}$, if m=1, or each of the substituents $R^{2''}$, if m is greater than 1, independently of the others represents halogen, cyano, nitro, hydroxy, $(C_2-C_8)$-alkyl, $(C_2-C_6)$-alkenyl, $(C_3-C_6)$-cycloalkenyl, $(C_3-C_6)$-cycloalkyl-$(C_1-C_8)$-alkyl, $(C_3-C_6)$-cycloalkenyl-$(C_1-C_8)$-alkyl, $(C_2-C_6)$-alkynyl, $(C_2-C_8)$-alkoxy, $(C_1-C_8)$-alkylthio, $(C_1-C_8)$-alkylsulphinyl, $(C_1-C_8)$-alkylsulphonyl, $(C_1-C_6)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^{3''}$, $C(O)NR^{4''}R^{5''}$, $C(O)$-$Het^{2''}$, $NR^{6''}R^{7''}$ or $Het^{3''}$ $R^{3''}$ represents hydrogen, $(C_1-C_6)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned below, $R^{4''}$, $R^{5''}$, $R^{6''}$ and $R^{7''}$ independently of one another each represent hydrogen, $(C_1-C_6)$-alkyl, $(C_2-C_6)$-alkenyl or $(C_2-C_6)$-alkynyl, where each of the 3 last-mentioned radicals in each case independently of the others is unsubstituted or substituted by one or more radicals from the group consisting of halogen, nitro, cyano and phenyl which is optionally substituted, or $(C_3-C_6)$-cycloalkyl or phenyl, where each of the 2 last-mentioned radicals in each case independently of the other is unsubstituted or substituted by one or more radicals from the group consisting of halogen, nitro, cyano, $(C_1-C_4)$-alkyl, $(C_1-C_4)$-haloalkyl, phenyl and benzyl, where each of the 2 last-mentioned radicals is optionally substituted, $Het^{2''}$ and $Het^{3''}$ independently of one another each represent a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, M represents an equivalent of a cation, m represents 1, 2, 3 or 4.

DETAILED DESCRIPTION OF A PREFERRED EMBODIMENT

The essence of the invention relates to the substitution of the pyridine radicals representing Q. Hitherto, the potential of the targeted substitution of the respective pyridin-2-yl, pyridin-3-yl or pyridin-4-yl radical has not been recognized, in spite of earlier research in relation to 4-cyano-3-(pyridyl)-4-phenylbutanoates. Also, in the prior art which discloses the 4-cyano-3-(pyridyl)-4-phenylbutanoates having a substituted pyridine radical, there are no specific indications that firstly variation of the binding site of the pyridine located in the 3-position in the butanoate structure (i.e. pyridin-2-yl, pyridin-3-yl or pyridin-4-yl) and secondly the introduction of additional substituents at the pyridine radical in question may result in an enhanced herbicidal efficacy.

In the formula (I), the formula "$(R^2)_n$" means n radicals $R^2$ which are attached as substituents at the phenyl ring in question, where the radicals in the case of n greater than 1 may be identical or different and have the meaning mentioned in each case in more detail, and in the case of n=0 all radicals $R^2$=H, i.e. in the case n=0 an unsubstituted phenyl substituent is present.

Two groups $R^2$ located ortho at the ring are to be understood to mean two groups $R^2$ which are directly adjacent at the ring.

The compounds of the formula (I) according to the invention include all stereoisomers which can occur on the basis of the centres of asymmetry or double bonds in the molecule whose configuration is not designated specifically in the formula or which are not specified explicitly, and mixtures thereof, including the racemic compounds and the mixtures enriched partly with particular stereoisomers. The invention also includes all tautomers, such as keto and enol tautomers, and their mixtures and salts, if appropriate functional groups are present.

In positions 3 and 4 of the substituted butanoic acid skeleton, the compounds of the formula (I) contain two centres of chirality, and they therefore occur in at least four stereoisomers and mixtures thereof, i.e. 2 enantiomeric erythro isomers and 2 enantiomeric threo isomers. Depending on the substituents R', $(R^2)_n$ and $(R^{2''})_m$, one or more further centres of chirality may be present.

Accordingly, the invention also provides erythro/threo mixtures (diastereomer mixtures) of the compounds of the formula (I).

The invention also provides the racemic erythro isomers or the racemic threo isomers of the compounds of the formula (I).

The invention also provides the optically active (3R,4S) and (3S,4R) erythro isomers and mixtures thereof having an excess of one enantiomer.

The invention also provides the optically active (3R,4R) and (3S,4S) threo isomers and mixtures thereof having an excess of one enantiomer.

Owing to the two centres of chirality in positions 3 and 4, compounds of the same chemical constitution exist as 4 stereoisomeric configurations, namely two erythro enantiomers having the configurations (3S,4R) [=erythro-1] and (3R,4S) [=erythro-2], respectively, and two threo enantiomers having the configurations (3S,4S) [=threo-1] and (3R,4R) [=threo-2], respectively; see the scheme below:

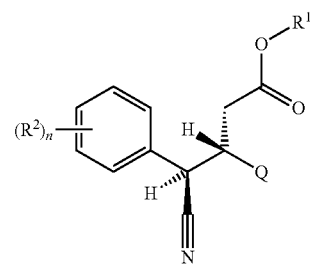

Erythro-1 (3S, 4R)

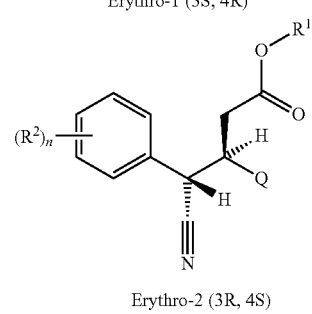

Erythro-2 (3R, 4S)

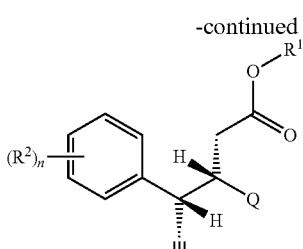

Threo-1 (3S, 4S)

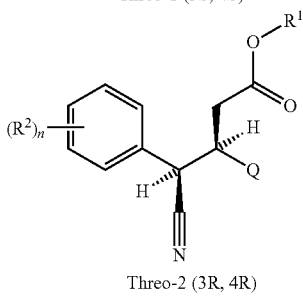

Threo-2 (3R, 4R)

The compounds (I) according to the invention represent diastereomer mixtures of the 4 stereoisomers, but also embrace the separated diastereomeric erythro or threo forms, in each case as a racemic mixture of the erythro enantiomers or threo enantiomers or as pure or stereochemically enriched enantiomers erythro-1, erythro-2, threo-1 or threo-2 mentioned above.

Preference is given to the diastereomer mixtures of the formula (I) (erythro/threo mixtures).

Preference is also given to the racemic erythro mixtures of the formula (I) of the aforementioned enantiomers erythro-1 and erythro-2 in a ratio of 50:50.

Preference is furthermore given to the racemic threo mixtures of the formula (I) of the aforementioned enantiomers threo-1 and threo-2 in a ratio of 50:50.

More preference is given to the (3R,4R) enantiomers threo-2 of the formula (Ia) or salts thereof

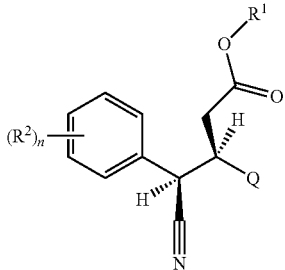

(Ia)

in which $R^1$, $(R^2)_n$ and Q are as defined in formula (I), where the stereochemical configuration at the carbon atom in position 3 of the butanoic acid derivative has a stereochemical purity of from 60 to 100% (R), preferably from 70 to 100% (R), more preferably from 80 to 100% (R), in particular from 90 to 100% (R), based on the present mixture of the threo enantiomers and the stereochemical configuration at the carbon atom in position 4 of the butanoic acid derivative has a stereochemical purity of from 60 to 100% (R), preferably from 70 to 100% (R), more preferably from 80 to 100% (R), in particular from 90 to 100% (R), based on the present mixture of the threo enantiomers.

In the case of $R^1$=H or in the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino or else the nitrogen atom in the pyridyl ring, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally usable salts, where the type of salt is otherwise generally immaterial. In general, suitable salts are the salts of those cations or the acid addition salts of those acids whose cations and anions, respectively, have no adverse effect on the herbicidal activity of the compounds (I).

Suitable cations are in particular ions of the alkali metals, preferably lithium, sodium or potassium, of the alkaline earth metals, preferably calcium or magnesium, and of the transition metals, preferably manganese, copper, zinc or iron. The cation used may also be ammonium or substituted ammonium, where one to four hydrogen atoms may be replaced here by $(C_1-C_4)$-alkyl, hydroxy-$(C_1-C_4)$-alkyl, $(C_1-C_4)$-alkoxy-$(C_1-C_4)$-alkyl, hydroxy-$(C_1-C_4)$-alkoxy-$(C_1-C_4)$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl) ammonium, trimethylbenzylammonium. Also suitable are phosphonium ions, sulphonium ions, preferably tri-$(C_1-C_4)$-alkylsulphonium, in particular trimethylsulphonium, or sulphoxonium ions, preferably tri-$(C_1-C_4)$-alkylsulphoxonium, in particular trimethylsulphoxonium. Anions of useful acid addition salts are primarily chloride, bromide, fluoride, hydrogensulphate, sulphate, dihydrogenphosphate, hydrogenphosphate, nitrate, bicarbonate, carbonate, hexafluorosilicate, hexafluorophosphate, benzoate and also the anions of $(C_1-C_4)$-alkanoic acids, preferably formate, acetate, propionate, butyrate or trifluoroacetate.

In formula (I) and in all subsequent formulae, chemical radicals are referred to by names which are collective terms for the enumeration of individual group members or specifically refer to individual chemical radicals. In general, terms are used which are familiar to the person skilled in the art and/or in particular have the meanings elucidated below.

A hydrolysable radical (see definition of $R^1$) is a radical which can be hydrolysed under the application conditions, for example a radical which can be hydrolysed even in the spray liquor or in particular under the physiological conditions in plants, where a compound of the formula (I) having the carboxylic ester group —CO—$OR^1$ ($R^1$ is not hydrogen) is hydrolysed to the compound of the formula (I) having the carboxylic acid group —CO—OH (i.e. the compound (I) where $R^1$=H). Expressly, the definition of the hydrolysable radicals also includes the radicals where $R^1$=hydrocarbon radical or heterocyclyl radical, the two last-mentioned radicals being unsubstituted or substituted, even if some of them are hydrolysable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc. This applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms. The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also include straight-chain or branched alkyl radicals having a greater number of carbon atoms, i.e. in the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in composite radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl.

Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl.

$(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine, bromine and iodine, in particular from the group consisting of fluorine, chlorine and bromine, very particularly from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals such as, for example, halocycloalkyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom.

Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

When the heterocyclyl radical or the heterocyclic ring is optionally substituted, it may be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-azaspiro[2.3]hexyl.

It is preferably a radical of a heteroaromatic ring having a heteroatom from the group consisting of N, O and S, for example the radical of a five- or six-membered ring, such as pyridyl, pyrrolyl, thienyl or furyl; it is furthermore preferably a radical of a corresponding heteroaromatic ring having 2, 3 or 4 heteroatoms, for example pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl;

more preference is also given here to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;

more preference is also given here to heteroaromatic radicals of five-membered heterocycles having two nitrogen atoms and one oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, more preference is also given here to heteroaromatic radicals of five-membered heterocycles having two nitrogen atoms and one sulphur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl;

more preference is also given here to heteroaromatic radicals of five-membered heterocycles having four nitrogen atoms, such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl, more preference is also given here to heteroaromatic radicals of six-membered heterocycles such as 1,2,4,5-tetrazin-3-yl;

more preference is also given here to heteroaromatic radicals of five-membered heterocycles having three nitrogen atoms and one oxygen or sulphur atom, such as 1,2,3,4-oxatriazol-5-yl; 1,2,3,5-oxatriazol-4-yl; 1,2,3,4-thiatriazol-5-yl; 1,2,3,5-thiatriazol-4-yl;

more preference is also given here to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the ring hetero atoms which are able to exist in different oxidation states, as in the case of N and S, for example.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phthalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulphinyl, alkylsulphonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon-containing radicals mentioned, corresponding unsaturated aliphatic and aromatic radicals, such as optionally substituted alkenyl, alkynyl, alkenyloxy, alkynyloxy, phenyl and phenoxy, etc. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of (followed by the group=list of the substituents)" is, wherever used, meant to be synonymous with "radicals selected from the group consisting of ( . . . )". The term "one or more radicals from the group consisting of (followed by the group=list of the substituents)" is, wherever used, meant to be synonymous with "one or more identical or different radicals selected from the group consisting of ( . . . )".

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

"Parent radical" refers to the respective base structure of a radical to which substituents of a substituent level are attached.

Preferred substituents for the substituent levels are, for example, amino, hydroxyl, halogen, nitro, cyano, mercapto, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphinyl, alkylsulphonyl, monoalkylaminosulphonyl, dialkylaminosulphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably phenyl or phenyl which is unsubstituted or substituted by one or more radicals from the group consisting of halogen, cyano, $(C_1-C_4)$-alkyl, $(C_1-C_4)$-haloalkyl, $(C_1-C_4)$-alkoxy-$(C_1-C_4)$alkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and nitro, in particular phenyl which is optionally substituted by one or more radicals from the group consisting of halogen, $(C_1-C_4)$-alkyl, $(C_1-C_4)$-haloalkyl and $(C_1-C_4)$-alkoxy.

In the case of radicals having carbon atoms, preference is given to those having 1 to 6 carbon atoms, preferably 1 to 4 carbon atoms, particularly 1 or 2 carbon atoms. Preference is generally given to substituents from the group of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulphonic acids, sulphinic acids, N-substituted sulphonamide acids, phosphonic acids or phosphinic acids.

Acyl is, for example, formyl, alkylcarbonyl such as [$(C_1-C_4)$-alkyl]carbonyl, phenylcarbonyl, alkyloxycarbonyl, phenyloxycarbonyl, benzyloxycarbonyl, alkylsulphonyl, alkylsulphinyl, N-alkyl-1-iminoalkyl and other radicals of organic acids. The radicals may each be substituted further in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [$(C_1-C_4)$-alkyl]carbonyl, phenylcarbonyl, alkylsulphonyl, alkylsulphinyl and other radicals of organic acids.

More preferably, acyl is an alkanoyl radical having 1 to 6 carbon atoms, in particular 1 to 4 carbon atoms. Here, $(C_1-C_4)$-alkanoyl is the radical of an alkanoic acid having 1 to 4 carbon atoms formed after removal of the OH group of the acid group, i.e. formyl, acetyl, n-propionyl, isopropionyl or n-, i-, sec- or tert-butanoyl.

The "yl position" of a radical denotes the carbon atom having the free bond.

Compounds of the formula (I) according to the invention and compounds of the formula (I) used according to the invention and/or salts thereof are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated separately in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

The compounds of the formula (I) also include all physical forms in which they may be present as a pure substance or, if appropriate, as a mixture with other substances, in particular also polymorphic crystal forms of the compounds of the formula (I) and salts thereof and solvent adducts (for example hydrates).

Primarily for reasons of higher herbicidal activity, better selectivity, better producibility, better formulatability and/or other relevant properties, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Compounds of the formula (I) according to the invention and their uses according to the invention with the preferred meanings listed below of the symbols or chemical radicals or chemical groups in question are of particular interest, irrespective of the respective other radicals according to the symbols R' and $(R^2)_n$ and the definition of n in formula (I) and the definition of the radicals (or chemical groups) according to the symbols $R^3$ to $R^7$, $Het^1$ to $Het^3$, M, R* and R**, $R^A$, $R^B$, $R^{aa}$, $R^{bb}$ and $R^{cc}$ in the corresponding sub-meanings of radicals in the formula (I).

Preference is given to the compounds of the formula (I) according to the invention, preferably of the formula (Ia), or salts thereof in which
$R^1$ represents hydrogen, alkyl, alkenyl or alkynyl, where each of the 3 last-mentioned radicals is unsubstituted or substituted and, including substituents, has up to 30 carbon atoms, preferably up to 24 carbon atoms, in particular up to 20 carbon atoms, or represents cycloalkyl, cycloalkenyl, cycloalkynyl or aryl, where each of the 4 last-mentioned radicals is unsubstituted or substituted and, including substituents, has up to 30 carbon atoms, preferably up to 24 carbon atoms, in particular up to 20 carbon atoms, or represents a heterocyclyl radical having 3 to 9 ring atoms which contains 1 to 4 heteroatoms from the group consisting of N, O and S, which is unsubstituted or substituted and which, including substituents, has 1 to 30 carbon atoms, preferably 1 to 24 carbon atoms, in particular 1 to 20 carbon atoms.

More preference is here also given to compounds (I), preferably of the formula (Ia), or salts thereof in which $R^1$ represents hydrogen.

More preference is here also given to compounds (I), preferably of the formula (Ia), or salts thereof in which
$R^1$ represents H, $(C_1-C_{18})$-alkyl, $(C_2-C_{18})$-alkenyl or $(C_2-C_{18})$-alkynyl, where each of the 3 last-mentioned radicals is unsubstituted or substituted and, including substituents, has up to 30 carbon atoms, preferably up to 24 carbon atoms, in particular up to 20 carbon atoms, or represents $(C_3-C_9)$-cycloalkyl, $(C_5-C_9)$-cycloalkenyl, $(C_5-C_9)$-cycloalkynyl or phenyl, where each of the 4 last-mentioned radicals is unsubstituted or substituted and, including substituents, has up to 30 carbon atoms, preferably up to 24 carbon atoms, in particular up to 20 carbon atoms.

More preference is here also given to compounds (I), preferably of the formula (Ia), or salts thereof in which
$R^1$ represents hydrogen, $(C_1-C_{18})$-alkyl, $(C_2-C_{18})$-alkenyl or $(C_2-C_{18})$-alkynyl, where each of the 3 last-mentioned radicals is unsubstituted or substituted by one or more radicals from the group consisting of the radicals [subgroups (a)-(d)]
  (a) halogen, cyano, thio, nitro, hydroxy, carboxy, $(C_1-C_8)$-alkoxy, $(C_2-C_8)$-alkenyloxy, $(C_2-C_8)$-alkynyloxy,$(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio, $(C_1-C_8)$-haloalkylthio, $(C_2-C_8)$-haloalkenylthio, $(C_2-C_8)$-haloalkynylthio, $(C_1-C_8)$-alkylsulphinyl, $(C_2-C_8)$-alkenylsulphinyl, $(C_2-C_8)$-alkynylsulphinyl, $(C_1-C_8)$-haloalkylsulphinyl, $(C_2-C_8)$-haloalkenylsulphinyl, $(C_2-C_8)$-haloalkynylsulphinyl, $(C_1-C_8)$-alkylsulphonyl, $(C_2-C_8)$-alkenylsulphonyl, $(C_2-C_8)$-alkynylsulphonyl, $(C_1-C_8)$-haloalkylsulphonyl, $(C_2-C_8)$-haloalkenylsulphonyl, $(C_2-C_8)$-haloalkynylsulphonyl, radicals of the formula —NR*R**, where R* and R** are defined as above or below, and $(C_3-C_8)$-cycloalkyl, $(C_5-C_8)$-cycloalkenyl, $(C_5-C_8)$-cycloalkynyl, $(C_3-C_8)$-cycloalkyl-$(C_1-C_6)$-alkoxy, $(C_3-C_8)$-cycloalkyl-$(C_1-C_6)$-alkyl-S(O)$_p$—, $(C_5-C_8)$-cycloalkenyl-$(C_1-C_6)$-alkoxy, $(C_5-C_8)$-cycloalkenyl-$(C_1-C_6)$-alkyl-S(O)$_p$—, $(C_5-C_8)$-cycloalkynyl-$(C_1-C_6)$-alkoxy, $(C_5-C_8)$-cycloalkynyl-$(C_1-C_6)$-alkyl-S(O)$_p$—, $(C_3-C_8)$-cycloalkoxy, $(C_3-C_8)$-cycloalkyl-S(O)$_p$—, $(C_5-C_8)$-cycloalkenyloxy, $(C_5-C_8)$-cycloalkenyl-S(O)$_p$—, $(C_5-C_8)$-cycloalkynyloxy, $(C_5-C_8)$-cycloalkynyl-S(O)$_p$—, $(C_3-C_8)$-cycloalkoxy-$(C_1-C_6)$-alkoxy, $(C_3-C_8)$-cycloalkoxy-$(C_1-C_6)$-alkyl-S(O)$_p$—, phenyl, phenyl-$(C_1-C_6)$-alkoxy, phenoxy, phenyl-S(O)$_p$—, phenyl-$(C_1-C_6)$-alkyl-S(O)$_p$—, phenoxy-$(C_1-C_6)$-alkoxy, phenoxy-$(C_1-C_6)$-alkyl-S(O)$_p$—, a radical Het$^1$, Het$^1$-S(O)$_p$—, Het$^1$-$(C_1-C_6)$-alkoxy, Het$^1$-O—, Het$^1$-O—$(C_1-C_6)$-alkoxy, where the heterocyclic radical Het$^1$ is defined as above or below,
    where each of the 29 last-mentioned radicals is unsubstituted in the acyclic moiety or substituted by one or more identical or different radicals $R^A$ and is unsubstituted in the cyclic moiety or substituted by one or more identical or different radicals $R^B$ and p is in each case independently of the others 0, 1 or 2, and
  preferably the radicals (a)
  halogen, cyano, nitro, hydroxy, carboxy, $(C_1-C_8)$-alkoxy, $(C_1-C_8)$-haloalkoxy, $(C_1-C_4)$-alkoxy-$(C_1-C_4)$-alkoxy, $(C_1-C_6)$-alkylthio, $(C_1-C_6)$-haloalkylthio, $(C_1-C_6)$-alkylsulphinyl,
  $(C_1-C_6)$-haloalkylsulphinyl,
  $(C_1-C_6)$-alkylsulphonyl, $(C_1-C_8)$-haloalkylsulphonyl,
  $(C_3-C_8)$-cycloalkyl,
  $(C_5-C_8)$-cycloalkenyl,
  $(C_5-C_8)$-cycloalkynyl,
  $(C_3-C_8)$-cycloalkyl-$(C_1-C_6)$-alkoxy,
  $(C_5-C_8)$-cycloalkenyl-$(C_1-C_6)$-alkoxy,
  $(C_5-C_8)$-cycloalkynyl-$(C_1-C_6)$-alkoxy,
  $(C_3-C_8)$-cycloalkoxy, $(C_3-C_8)$-cycloalkylthio,
  $(C_3-C_8)$-cycloalkylsulphinyl, $(C_3-C_8)$-cycloalkylsulphonyl,
  $(C_3-C_8)$-cycloalkoxy-$(C_1-C_6)$-alkoxy,
  phenyl, phenoxy, phenylthio, phenylsulphinyl, phenylsulphonyl,
  phenyl-$(C_1-C_6)$-alkoxy, phenyl-$(C_1-C_6)$-alkylthio,
  phenyl-$(C_1-C_6)$-alkylsulphinyl, phenyl-$(C_1-C_6)$-alkylsulphonyl,
  phenoxy-$(C_1-C_6)$-alkoxy, phenoxy-$(C_1-C_6)$-alkylthio,
  phenoxy-$(C_1-C_6)$-alkylsulphinyl and phenoxy-$(C_1-C_6)$-alkylsulphonyl,
    where each of the radicals mentioned with cyclic moieties is unsubstituted in the acyclic moiety or substituted by one or more identical or different radicals $R^A$ and is unsubstituted in the cyclic moiety or substituted by one or more identical or different radicals $R^B$,
  (b) radicals of the formulae —C(=O)—R$^C$, —C(=O)—O—R$^C$, —O—C(=O)—R$^C$, —O—C(=O)—O—R$^C$, —C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, —P(=O)(R$^C$)(R$^D$), —P(=O)(OR$^C$)(R$^D$), —P(=O)(OR$^C$)(OR$^D$) or —O—P(=O)(OR$^C$)(OR$^D$), preferably a radical of the formula —C(=O)—R$^C$, —C(=O)—O—R$^C$, —O—C(=O)—R$^C$ or —O—C(=O)—O—R$^C$, in particular a radical of the formula —C(=O)—O—R$^C$, —O—C(=O)—R$^C$ or —O—C(=O)—O—R$^C$,
  where R*, R**, R$^C$ and R$^D$ are as defined below,
  preferably the radicals (b1)
  [$(C_1-C_8)$-alkoxy]carbonyl, [$(C_1-C_8)$-alkoxy]thiocarbonyl, [$(C_2-C_8)$-alkenyloxy]carbonyl, [$(C_2-C_8)$-alkynyloxy]carbonyl, [$(C_1-C_8)$-alkylthio]carbonyl, [$(C_2-C_8)$-alkenylthio]carbonyl, [$(C_2-C_8)$-alkynylthio]carbonyl, $(C_1-C_8)$-alkanoyl, [$(C_2-C_8)$-alkenyl]carbonyl, [$(C_2-C_8)$-alkynyl]carbonyl, [$(C_1-C_8)$-alkyl]carbonylamino, [$(C_2-C_8)$-alkenyl]carbonylamino, [$(C_2-C_8)$-alkynyl]carbonylamino, [$(C_1-C_8)$-alkoxy]carbonylamino, [$(C_2-C_8)$-alkenyloxy]carbonylamino, [($C_2$-$C_8$)-alkynyloxy]carbonylamino, [($C_1$-$C_8$)-alkylamino]carbonylamino, [($C_1$-$C_6$)-alkyl]carbonyloxy, [($C_2$-$C_6$)-alkenyl]carbonyloxy, [($C_2$-$C_6$)-alkynyl]carbonyloxy, [($C_1$-$C_8$)-alkoxy]carbonyloxy, [($C_2$-$C_8$)-alkenyloxy]carbonyloxy and [($C_2$-$C_8$)-alkynyloxy]carbonyloxy, where each of the 23 last-mentioned radicals is unsubstituted or substituted by one or more radicals from the group consisting of halogen, $NO_2$, ($C_1$-$C_4$)-alkoxy and optionally halogen-, CN—, $NO_2$—, ($C_1$-$C_4$)-alkyl-, ($C_1$-$C_4$)-alkoxy- and ($C_1$-$C_4$)-alkylthio-substituted phenyl, and preferably the radicals (b2)
($C_3$-$C_8$)-cycloalkylcarbonyl,
($C_3$-$C_8$)-cycloalkyl-[($C_1$-$C_6$)-alkyl]carbonyl,
($C_3$-$C_8$)-cycloalkyl-[($C_1$-$C_6$)-alkoxy]carbonyl,
($C_3$-$C_8$)-cycloalkoxycarbonyl,
($C_3$-$C_8$)-cycloalkoxy-[($C_1$-$C_6$)-alkyl]carbonyl,
($C_3$-$C_8$)-cycloalkoxy-[($C_1$-$C_6$)-alkoxy]carbonyl,
($C_3$-$C_8$)-cycloalkylcarbonyloxy,
($C_3$-$C_8$)-cycloalkyl-[($C_1$-$C_6$)-alkyl]carbonyloxy,
($C_5$-$C_8$)-cycloalkenyl-[($C_1$-$C_6$)-alkyl]carbonyloxy,
($C_5$-$C_8$)-cycloalkynyl-[($C_1$-$C_6$)-alkyl]carbonyloxy,
($C_3$-$C_8$)-cycloalkyl-[($C_1$-$C_6$)-alkoxy]carbonyloxy,
($C_5$-$C_8$)-cycloalkenyl-[($C_1$-$C_6$)-alkoxy]carbonyloxy,
($C_5$-$C_8$)-cycloalkynyl-[($C_1$-$C_6$)-alkoxy]carbonyloxy,
($C_3$-$C_8$)-cycloalkoxycarbonyloxy,
($C_3$-$C_8$)-cycloalkoxy-[($C_1$-$C_6$)-alkyl]carbonyloxy,
($C_3$-$C_8$)-cycloalkoxy-[($C_1$-$C_6$)-alkoxy]carbonyloxy,
($C_3$-$C_8$)-cycloalkylcarbonylamino,
($C_3$-$C_8$)-cycloalkyl-[($C_1$-$C_6$)-alkyl]carbonylamino,
($C_5$-$C_8$)-cycloalkenyl-[($C_1$-$C_6$)-alkyl]carbonylamino,
($C_5$-$C_8$)-cycloalkynyl-[($C_1$-$C_6$)-alkyl]carbonylamino,
($C_3$-$C_8$)-cycloalkyl-[($C_1$-$C_6$)-alkoxy]carbonylamino,
($C_3$-$C_8$)-cycloalkoxycarbonylamino,
($C_3$-$C_8$)-cycloalkoxy-[($C_1$-$C_6$)-alkyl]carbonylamino and
($C_3$-$C_8$)-cycloalkoxy-[($C_1$-$C_6$)-alkoxy]carbonylamino,
phenylcarbonyl,
phenyl-[($C_1$-$C_6$)-alkyl]carbonyl,
phenyl-[($C_1$-$C_6$)-alkoxy]carbonyl,
phenoxycarbonyl,
phenoxy-[($C_1$-$C_6$)-alkyl]carbonyl,
phenoxy-[($C_1$-$C_6$)-alkoxy]carbonyl,
phenylcarbonyloxy,
phenyl-[($C_1$-$C_6$)-alkyl]carbonyloxy,
phenyl-[($C_1$-$C_6$)-alkoxy]carbonyloxy,
phenoxycarbonyloxy,
phenoxy-[($C_1$-$C_6$)-alkyl]carbonyloxy,
phenoxy-[($C_1$-$C_6$)-alkoxy]carbonyloxy,
phenylcarbonylamino,
phenyl-[($C_1$-$C_6$)-alkyl]carbonylamino,
phenyl-[($C_1$-$C_6$)-alkoxy]carbonylamino,
phenoxycarbonylamino,
phenoxy-[($C_1$-$C_6$)-alkyl]carbonylamino,
phenoxy-[($C_1$-$C_6$)-alkoxy]carbonylamino, where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and is unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and (c) radicals of the formulae —$SiR'_3$, —O—$SiR'_3$, $(R')_3$Si—($C_1$-$C_6$)-alkoxy, —CO—O—$NR'_2$, —O—N=$CR'_2$, —N=$CR'_2$, —O—$NR'_2$, —CH$(OR')_2$ and —O—$(CH_2)_q$—CH$(OR')_2$, in which each of the radicals R' independently of the others represents H, ($C_1$-$C_4$)-alkyl or phenyl which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or is substituted at two adjacent positions by a ($C_2$-$C_6$)-alkylene bridge, and q represents an integer from 0 to 6, and (d) radicals of the formula R"O—CHR'"CH(OR")—($C_1$-$C_6$)-alkoxy, in which each of the radicals R" independently of the others represents H or ($C_1$-$C_4$)-alkyl or together the radicals represent a ($C_1$-$C_6$)-alkylene group and R'" represents H or ($C_1$-$C_4$)-alkyl, or $R^1$ represents ($C_3$-$C_9$)-cycloalkyl, ($C_5$-$C_9$)-cycloalkenyl, ($C_5$-$C_9$)-cycloalkynyl or phenyl, where each of the 4 last-mentioned radicals is unsubstituted or substituted by one or more radicals from the group consisting of the radicals [subgroups (a')-(e')]

(a') halogen, cyano, thio, nitro, hydroxy, carboxy, ($C_1$-$C_8$)-alkyl, ($C_1$-$C_8$)-haloalkyl, ($C_1$-$C_4$)-alkoxy-($C_1$-$C_4$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio and radicals of the formulae —NR*R**, where the radicals R* and R** are defined below, (b') radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$), preferably a radical of the formula —C(=O)—$R^C$, —C(=O)—O—$R^C$, —O—C(=O)—$R^C$ or —O—C(=O)—O—$R^C$, in particular a radical of the formula —C(=O)—O—$R^C$, —O—C(=O)—$R^C$ or —O—C(=O)—O—$R^C$, where R*, R**, $R^C$ and $R^D$ are as defined below, and preferably the radicals (b1')

[($C_1$-$C_8$)-alkoxy]carbonyl, [($C_1$-$C_8$)-alkoxy]thiocarbonyl, [($C_2$-$C_8$)-alkenyloxy]carbonyl, [($C_2$-$C_8$)-alkynyloxy]carbonyl, [($C_1$-$C_8$)-alkylthio]carbonyl, [($C_2$-$C_8$)-alkenylthio]carbonyl, [($C_2$-$C_8$)-alkynylthio]carbonyl, ($C_1$-$C_8$)-alkanoyl, [($C_2$-$C_8$)-alkenyl]carbonyl, [($C_2$-$C_8$)-alkynyl]carbonyl, ($C_1$-$C_4$)-alkylimino, ($C_1$-$C_4$)-alkoxyimino, [($C_1$-$C_8$)-alkyl]carbonylamino, [($C_2$-$C_8$)-alkenyl]carbonylamino, [($C_2$-$C_8$)-alkynyl]carbonylamino, [($C_1$-$C_8$)-alkoxy]carbonylamino, [($C_2$-$C_8$)-alkenyloxy]carbonylamino, [($C_2$-$C_8$)-alkynyloxy]carbonylamino, [($C_1$-$C_8$)-alkylamino]carbonylamino, [($C_1$-$C_6$)-alkyl]carbonyloxy, [($C_2$-$C_6$)-alkenyl]carbonyloxy, [($C_2$-$C_6$)-alkynyl]carbonyloxy, [($C_1$-$C_8$)-alkoxy]carbonyloxy, [($C_2$-$C_8$)-alkenyloxy]carbonyloxy, [($C_2$-$C_8$)-alkynyloxy]carbonyloxy, ($C_1$-$C_8$)-alkylsulphinyl and ($C_1$-$C_8$)-alkylsulphonyl, where each of the 27 last-mentioned radicals is unsubstituted or substituted by one or more radicals from the group consisting of halogen, $NO_2$, $(C_1\text{-}C_4)$-alkoxy and optionally substituted phenyl, and preferably the radicals (b2')

$(C_3\text{-}C_8)$-cycloalkylcarbonyl,
$(C_3\text{-}C_8)$-cycloalkyl-[$(C_1\text{-}C_6)$-alkyl]carbonyl,
$(C_3\text{-}C_8)$-cycloalkyl-[$(C_1\text{-}C_6)$-alkoxy]carbonyl,
$(C_3\text{-}C_8)$-cycloalkoxycarbonyl,
$(C_3\text{-}C_8)$-cycloalkoxy-[$(C_1\text{-}C_6)$-alkyl]carbonyl,
$(C_3\text{-}C_8)$-cycloalkoxy-[$(C_1\text{-}C_6)$-alkoxy]carbonyl,
$(C_3\text{-}C_8)$-cycloalkylcarbonyloxy,
$(C_3\text{-}C_8)$-cycloalkyl-[$(C_1\text{-}C_6)$-alkyl]carbonyloxy,
$(C_5\text{-}C_8)$-cycloalkenyl-[$(C_1\text{-}C_6)$-alkyl]carbonyloxy,
$(C_5\text{-}C_8)$-cycloalkynyl-[$(C_1\text{-}C_6)$-alkyl]carbonyloxy,
$(C_3\text{-}C_8)$-cycloalkyl-[$(C_1\text{-}C_6)$-alkoxy]carbonyloxy,
$(C_5\text{-}C_8)$-cycloalkenyl-[$(C_1\text{-}C_6)$-alkoxy]carbonyloxy,
$(C_5\text{-}C_8)$-cycloalkynyl-[$(C_1\text{-}C_6)$-alkoxy]carbonyloxy,
$(C_3\text{-}C_8)$-cycloalkoxycarbonyloxy,
$(C_3\text{-}C_8)$-cycloalkoxy-[$(C_1\text{-}C_6)$-alkyl]carbonyloxy,
$(C_3\text{-}C_8)$-cycloalkoxy-[$(C_1\text{-}C_6)$-alkoxy]carbonyloxy,
$(C_3\text{-}C_8)$-cycloalkylcarbonylamino,
$(C_3\text{-}C_8)$-cycloalkyl-[$(C_1\text{-}C_6)$-alkyl]carbonylamino,
$(C_5\text{-}C_8)$-cycloalkenyl-[$(C_1\text{-}C_6)$-alkyl]carbonylamino,
$(C_5\text{-}C_8)$-cycloalkynyl-[$(C_1\text{-}C_6)$-alkyl]carbonylamino,
$(C_3\text{-}C_8)$-cycloalkyl-[$(C_1\text{-}C_6)$-alkoxy]carbonylamino,
$(C_3\text{-}C_8)$-cycloalkoxycarbonylamino,
$(C_3\text{-}C_8)$-cycloalkoxy-[$(C_1\text{-}C_6)$-alkyl]carbonylamino and
$(C_3\text{-}C_8)$-cycloalkoxy-[$(C_1\text{-}C_6)$-alkoxy]carbonylamino,
phenylcarbonyl,
phenyl-[$(C_1\text{-}C_6)$-alkyl]carbonyl,
phenyl-[$(C_1\text{-}C_6)$-alkoxy]carbonyl,
phenoxycarbonyl,
phenoxy-[$(C_1\text{-}C_6)$-alkyl]carbonyl,
phenoxy-[$(C_1\text{-}C_6)$-alkoxy]carbonyl,
phenylcarbonyloxy,
phenyl-[$(C_1\text{-}C_6)$-alkyl]carbonyloxy,
phenyl-[$(C_1\text{-}C_6)$-alkoxy]carbonyloxy,
phenoxycarbonyloxy,
phenoxy-[$(C_1\text{-}C_6)$-alkyl]carbonyloxy,
phenoxy-[$(C_1\text{-}C_6)$-alkoxy]carbonyloxy,
phenylcarbonylamino,
phenyl-[$(C_1\text{-}C_6)$-alkyl]carbonylamino,
phenyl-[$(C_1\text{-}C_6)$-alkoxy]carbonylamino,
phenoxycarbonylamino,
phenoxy-[$(C_1\text{-}C_6)$-alkyl]carbonylamino,
phenoxy-[$(C_1\text{-}C_6)$-alkoxy]carbonylamino,
where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and is unsubstituted at the ring or at the polycyclic system or substituted by one or more radicals from the group consisting of halogen, $(C_1\text{-}C_4)$-alkyl, $(C_1\text{-}C_4)$-alkoxy, $(C_1\text{-}C_4)$-haloalkyl, $(C_1\text{-}C_4)$-haloalkoxy and nitro, and (c') radicals of the formulae $-SiR'_3$, $-O-SiR'_3$, $(R')_3Si-(C_1\text{-}C_6)$-alkoxy, $-CO-O-NR'_2$, $-O-N=CR'_2$, $-N=CR'_2$, $-O-NR'_2$, $-CH(OR')_2$ and $-O-(CH_2)_q-CH(OR')_2$,
in which each of the radicals R' independently of the others represents H, $(C_1\text{-}C_4)$-alkyl or phenyl which is unsubstituted or substituted by one or more radicals from the group consisting of halogen, $(C_1\text{-}C_4)$-alkyl, $(C_1\text{-}C_4)$-alkoxy, $(C_1\text{-}C_4)$-haloalkyl, $(C_1\text{-}C_4)$-haloalkoxy and nitro or is substituted at two adjacent positions by a $(C_2\text{-}C_6)$-alkylene bridge, and q represents an integer from 0 to 6, and (d') radicals of the formula R''O—CHR'''CH(OR'')—$(C_1\text{-}C_6)$-alkoxy,
in which each of the radicals R'' independently of the others represents H or $(C_1\text{-}C_4)$-alkyl or together the radicals represent a $(C_1\text{-}C_6)$-alkylene group and R''' represents H or $(C_1\text{-}C_4)$-alkyl, and (e') a radical of the formula $Het^1$ which is unsubstituted or substituted by one or more identical or different radicals $R^B$, or $R^1$ represents a polycyclic radical based on $(C_3\text{-}C_9)$-cycloalkyl, $(C_5\text{-}C_9)$-cycloalkenyl, $(C_5\text{-}C_9)$-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals $R^B$, preferably unsubstituted or substituted by one or more radicals from the group consisting of halogen, cyano, nitro, hydroxy, carboxy, $(C_1\text{-}C_6)$-alkyl, $(C_1\text{-}C_6)$-haloalkyl, $(C_1\text{-}C_4)$-alkoxy-$(C_1\text{-}C_4)$-alkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_1\text{-}C_6)$-alkoxy, $(C_2\text{-}C_6)$-alkenyloxy, $(C_2\text{-}C_6)$-alkynyloxy, $(C_1\text{-}C_6)$-haloalkoxy, $(C_1\text{-}C_4)$-alkoxy-$(C_1\text{-}C_4)$-alkoxy, $(C_1\text{-}C_6)$-alkylthio, $(C_2\text{-}C_6)$-alkenylthio, $(C_2\text{-}C_6)$-alkynylthio, $(C_3\text{-}C_6)$-cycloalkyl, $(C_3\text{-}C_6)$-cycloalkoxy, [$(C_1\text{-}C_8)$-alkoxy]carbonyl, [$(C_1\text{-}C_6)$-haloalkoxy]carbonyl and oxo, or $R^1$ represents a heterocyclic radical $Het^1$ which is unsubstituted in the ring or in the polycyclic system or substituted by one or more identical or different radicals $R^B$, preferably unsubstituted or substituted by one or more radicals from the group consisting of halogen, cyano, thio, nitro, hydroxy, carboxy, $(C_1\text{-}C_6)$-alkyl, $(C_1\text{-}C_6)$-haloalkyl, $(C_1\text{-}C_4)$-alkoxy-$(C_1\text{-}C_4)$-alkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_1\text{-}C_6)$-alkoxy, $(C_2\text{-}C_6)$-alkenyloxy, $(C_2\text{-}C_6)$-alkynyloxy, $(C_1\text{-}C_6)$-haloalkoxy, $(C_1\text{-}C_4)$-alkoxy-$(C_1\text{-}C_4)$-alkoxy, $(C_1\text{-}C_6)$-alkylthio, $(C_2\text{-}C_6)$-alkenylthio, $(C_2\text{-}C_6)$-alkynylthio, $(C_3\text{-}C_6)$-cycloalkyl, $(C_3\text{-}C_6)$-cycloalkoxy, [$(C_1\text{-}C_8)$-alkoxy]carbonyl, [$(C_1\text{-}C_6)$-haloalkoxy]carbonyl and oxo,
where in the radicals mentioned above and in the radicals below $Het^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, R*, R** independently of one another (i.e. also of other groups NR*R**) each represent H, $(C_1\text{-}C_8)$-alkyl, $(C_2\text{-}C_8)$-alkenyl, $(C_2\text{-}C_8)$-alkynyl, $(C_1\text{-}C_4)$-alkoxy-$(C_1\text{-}C_4)$-alkyl, $(C_1\text{-}C_6)$-alkanoyl, [$(C_1\text{-}C_4)$-haloalkyl]carbonyl, [$(C_1\text{-}C_4)$-alkoxy]carbonyl, [$(C_1\text{-}C_4)$-haloalkoxy]carbonyl, $(C_3\text{-}C_6)$-cycloalkyl, $(C_3\text{-}C_6)$-cycloalkyl-$(C_1\text{-}C_4)$-alkyl, phenyl, phenyl-$(C_1\text{-}C_4)$-alkyl, where each of the 4 last-mentioned radicals is optionally substituted in the cycle by one or more identical or different radicals $R^{bb}$, or $R^*$ and $R^{**}$ together with the nitrogen atom represent preferably saturated a 3- to 8-membered heterocycle which, in addition to the nitrogen atom, may contain one or two further ring heteroatoms from the group consisting of N, O and S and which is unsubstituted or substituted by one or more radicals from the group consisting of $(C_1-C_4)$-alkyl, $(C_1-C_4)$-haloalkyl and oxo, $R^A$ represents halogen, cyano, hydroxy or $(C_1-C_6)$-alkoxy, $R^B$ represents halogen, cyano, hydroxy, oxo, nitro, $(C_1-C_6)$-alkyl, $(C_1-C_4)$-haloalkyl, cyano-$(C_1-C_4)$-alkyl, hydroxy-$(C_1-C_4)$-alkyl, nitro-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkyl, $(C_1-C_4)$-alkoxy-$(C_1-C_4)$-alkoxy, $(C_1-C_4)$-haloalkoxy-$(C_1-C_4)$-alkyl, $(C_1-C_4)$-haloalkoxy-$(C_1-C_4)$-alkoxy, $(C_1-C_6)$-alkylthio, $(C_2-C_6)$-alkenylthio, $(C_2-C_6)$-alkynylthio, $(C_1-C_6)$-alkylsulphinyl, $(C_1-C_6)$-haloalkylsulphinyl, $(C_1-C_6)$-alkylsulphonyl, $(C_1-C_6)$-haloalkylsulphonyl, a radical of the formula $R^{aa}$—C(=O) or $R^{aa}$—C(=O)—$(C_1-C_6)$-alkyl, the radicals $R^{aa}$ being defined further below, —NR*R**, R* and R** being defined further below, tri-[$(C_1-C_4)$alkyl]silyl, $(C_3-C_6)$-cycloalkyl, $(C_3-C_6)$-cycloalkoxy, $(C_3-C_6)$-cycloalkyl-$(C_1-C_4)$-alkyl, $(C_3-C_6)$-cycloalkyl-$(C_1-C_8)$-alkoxy, phenyl, phenyl-$(C_1-C_6)$-alkyl, phenoxy, phenoxy-$(C_1-C_6)$-alkyl, phenylamino, phenylamino-$(C_1-C_6)$-alkyl or a 5- or 6-membered monocyclic or 9- or 10-membered bicyclic heterocycle which contains 1, 2, 3 or 4 heteroatoms selected from the group consisting of O, N and S, where each of the 11 last-mentioned radicals is optionally substituted in the cyclic moiety by one or more identical or different radicals $R^{bb}$, $R^C$, $R^D$ are each independently of one another (also independently of radicals $R^C$, $R^D$ in other groups)
hydrogen, $(C_1-C_8)$-alkyl, $(C_2-C_8)$-alkenyl or $(C_2-C_8)$-alkynyl,
where each of the 3 last-mentioned radicals is unsubstituted or substituted by one or more radicals from the group consisting of halogen, cyano, nitro, hydroxy, $(C_1-C_6)$-alkoxy, $(C_2-C_6)$-alkenyloxy, $(C_2-C_6)$-alkynyloxy, $(C_1-C_8)$-haloalkoxy, $(C_1-C_4)$-alkoxy-$(C_1-C_4)$-alkoxy, $(C_1-C_8)$-alkylthio, $(C_1-C_8)$-haloalkylthio, $(C_1-C_8)$-alkylsulphinyl, $(C_1-C_8)$-haloalkylsulphinyl, $(C_1-C_8)$-alkylsulphonyl, $(C_1-C_8)$-haloalkylsulphonyl and tri-[$(C_1-C_4)$-alkyl]silyl, or
$(C_3-C_8)$-cycloalkyl, $(C_5-C_8)$-cycloalkenyl, $(C_5-C_8)$-cycloalkynyl, phenyl, $(C_3-C_8)$-cycloalkyl-$(C_1-C_6)$-alkyl, $(C_5-C_8)$-cycloalkenyl-$(C_1-C_6)$-alkyl, $(C_5-C_8)$-cycloalkynyl-$(C_1-C_6)$-alkyl, phenyl-$(C_1-C_6)$-alkyl, $(C_3-C_8)$-cycloalkyloxy-$(C_1-C_6)$-alkyl, $(C_3-C_8)$-cycloalkyl-S(O)$_p$—$(C_1-C_6)$-alkyl, $(C_5-C_8)$-cycloalkenyloxy-$(C_1-C_6)$-alkyl, $(C_5-C_8)$-cycloalkynyloxy-$(C_1-C_6)$-alkyl, phenoxy-$(C_1-C_6)$-alkyl, phenyl-S(O)$_p$—$(C_1-C_6)$-alkyl, $(C_3-C_8)$-cycloalkylamino-$(C_1-C_6)$-alkyl, $(C_5-C_8)$-cycloalkenylamino-$(C_1-C_6)$-alkyl, $(C_5-C_8)$-cycloalkynylamino-$(C_1-C_6)$-alkyl, phenylamino-$(C_1-C_6)$-alkyl, Het$^1$, Het$^1$-$(C_1-C_6)$-alkyl, Het$^1$-O—$(C_1-C_6)$-alkyl or Het$^1$-S(O)$_p$—$(C_1-C_6)$-alkyl, where Het$^1$ has the meaning mentioned,
where each of the 22 last-mentioned radicals is unsubstituted in the acyclic moiety or substituted by one or more identical or different radicals $R^A$ and is unsubstituted in the cyclic moiety or substituted by one or more identical or different radicals $R^B$ and p independently of the others in each case represents 0, 1 or 2, $R^{aa}$ independently of one another each represent hydrogen, OH, $(C_1-C_6)$-alkyl, $(C_1-C_4)$-haloalkyl, $(C_2-C_6)$-alkenyl, $(C_2-C_6)$-alkynyl, $(C_1-C_6)$-alkoxy, $(C_1-C_6)$-alkoxy-$(C_1-C_6)$-alkyl, $(C_1-C_6)$-alkoxy-$(C_1-C_6)$-alkyloxy, $(C_1-C_4)$-haloalkoxy, $(C_1-C_4)$-haloalkoxy-$(C_1-C_6)$-alkyl, $(C_1-C_4)$-haloalkoxy-$(C_1-C_6)$-alkoxy, $(C_3-C_6)$-alkenyloxy, $(C_3-C_6)$-alkenyloxy-$(C_1-C_6)$-alkyl, $(C_3-C_6)$-alkenyloxy-$(C_1-C_6)$-alkoxy, $(C_3-C_6)$-alkynyloxy, $(C_3-C_6)$-alkynyloxy-$(C_1-C_6)$-alkyl, $(C_3-C_6)$-alkynyloxy-$(C_1-C_6)$-alkoxy, —NR*R*, where R* and R** are as defined above, tri-[$(C_1-C_4)$alkyl]silyl, tri-[$(C_1-C_4)$alkyl]silyl-$(C_1-C_6)$-alkyl, tri-[$(C_1-C_4)$alkyl]silyl-$(C_1-C_6)$-alkoxy, $(C_3-C_6)$-cycloalkyl, $(C_3-C_6)$-cycloalkoxy, $(C_3-C_6)$-cycloalkyl-$(C_1-C_8)$-alkyl, $(C_3-C_6)$-cycloalkyl-$(C_1-C_8)$-alkoxy, $(C_5-C_6)$-cycloalkenyl, $(C_5-C_6)$-cycloalkenyl-$(C_1-C_6)$-alkyl, $(C_5-C_6)$-cycloalkenyloxy, $(C_5-C_6)$-cycloalkynyl, $(C_5-C_6)$-cycloalkynyl-$(C_1-C_6)$-alkyl, $(C_5-C_6)$-cycloalkynyl-$(C_1-C_6)$-alkoxy, phenyl, phenyl-$(C_1-C_6)$-alkyl, phenyl-$(C_1-C_6)$-alkoxy, phenoxy, phenoxy-$(C_1-C_6)$-alkyl, phenoxy-$(C_1-C_6)$-alkoxy, phenylthio, phenyl-S(O)$_p$—$(C_1-C_6)$-alkyl, phenyl-S(O)$_p$—$(C_1-C_6)$-alkoxy, where p independently of the others in each case represents 0, 1 or 2, phenylamino, phenylamino-$(C_1-C_6)$-alkyl, phenylamino-$(C_1-C_6)$-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the 20 last-mentioned radicals is optionally substituted in the cyclic moiety by one or more identical or different radicals $R^{cc}$, and $R^{bb}$ and $R^{cc}$ independently of one another each represent halogen, $(C_1-C_4)$-alkyl, $(C_1-C_4)$-haloalkyl, $(C_1-C_4)$-alkoxy or $(C_1-C_4)$-haloalkoxy.

More preference is here also given to compounds (I), preferably of the formula (Ia), or salts thereof in which $R^1$ represents hydrogen, $(C_1-C_{18})$-alkyl, $(C_2-C_{18})$-alkenyl or $(C_2-C_{18})$-alkynyl, preferably H, $(C_1-C_{12})$-alkyl, $(C_2-C_{12})$-alkenyl or $(C_2-C_{12})$-alkynyl, in particular H, $(C_1-C_8)$-alkyl, $(C_2-C_8)$-alkenyl or $(C_2-C_8)$-alkynyl, more preferably H or $(C_1-C_6)$-alkyl, $(C_2-C_6)$-alkenyl or $(C_2-C_6)$-alkynyl, more preferably $(C_1-C_4)$-alkyl,
where each of the 13 last-mentioned radicals containing carbon atoms is unsubstituted or substituted by one or more radicals from the group consisting of the radicals [subgroups (a)-(d)]
(a) halogen, cyano, thio, nitro, hydroxy, carboxy, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_1-C_6)$-alkylsulphinyl, $(C_2-C_6)$-alkenylsulphinyl, $(C_2-C_6)$-alkynylsulphinyl, $(C_1-C_6)$-haloalkylsulphinyl, $(C_2-C_6)$-haloalkenylsulphinyl, $(C_2-C_6)$-haloalkynylsulphinyl, $(C_1-C_6)$-alkylsulphonyl, $(C_2-C_6)$-alkenylsulphonyl, $(C_2-C_6)$-alkynylsulphonyl, $(C_1-C_6)$-haloalkylsulphonyl, $(C_2-C_6)$-haloalkenylsulphonyl, $(C_2-C_6)$-haloalkynylsulphonyl, radicals of the formula —NR*R**,
where R* and R** are defined below, and
$(C_3-C_6)$-cycloalkyl, $(C_5-C_6)$-cycloalkenyl, $(C_5-C_6)$-cycloalkynyl, $(C_3-C_6)$-cycloalkyl-$(C_1-C_4)$-alkoxy, $(C_5-C_6)$-cycloalkenyl-$(C_1-C_4)$-alkoxy, $(C_5-C_6)$- cycloalkynyl-$(C_1-C_4)$-alkoxy, $(C_3-C_6)$-cycloalkoxy, $(C_5-C_6)$-cycloalkenyloxy, $(C_5-C_6)$-cycloalkynyloxy, $(C_3-C_6)$-cycloalkoxy-$(C_1-C_4)$-alkoxy, phenyl, phenyl-$(C_1-C_6)$-alkoxy, phenoxy, phenoxy-$(C_1-C_4)$-alkoxy, phenyl-S(O)$_p$—, phenyl-$(C_1-C_6)$-alkyl-S(O)$_p$—, phenyloxy-$(C_1-C_6)$-alkyl-S(O)$_p$—, a radical Het$^1$, Het$^1$-$(C_1-C_6)$-alkoxy, Het$^1$-O—, Het$^1$-O—$(C_1-C_4)$-alkoxy, Het$^1$-$(C_1-C_6)$-alkoxy, Het$^1$-S(O)$_p$—, Het$^1$-O—$(C_1-C_4)$-alkyl-S(O)$_p$—, where the heterocyclic radical Het$^1$ is defined as above or below,
  where each of the 24 last-mentioned radicals is unsubstituted in the acyclic moiety or substituted by one or more identical or different radicals R$^A$ and is unsubstituted in the cyclic moiety or substituted by one or more identical or different radicals R$^B$ and p independently of the others in each case represents 0, 1 or 2,
and
preferably the radicals (a1)
halogen, cyano, nitro, hydroxy, carboxy, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $(C_1-C_6)$-haloalkylthio, $(C_1-C_6)$-alkylsulphinyl, $(C_1-C_6)$-haloalkylsulphinyl,
$(C_3-C_6)$-cycloalkyl, $(C_5-C_6)$-cycloalkenyl, $(C_5-C_6)$-cycloalkynyl, $(C_3-C_6)$-cycloalkyl-$(C_1-C_4)$-alkoxy, $(C_5-C_4)$-cycloalkenyl-$(C_1-C_4)$-alkoxy, $(C_5-C_4)$-cycloalkynyl-$(C_1-C_4)$-alkoxy, $(C_3-C_4)$-cycloalkoxy, $(C_3-C_4)$-cycloalkoxy-$(C_1-C_4)$-alkoxy, phenyl, phenyl-$(C_1-C_4)$-alkoxy, phenoxy and phenoxy-$(C_1-C_4)$-alkoxy, phenylthio, phenylsulphinyl, phenylsulphonyl,
  where each of the radicals (a1) is unsubstituted in the acyclic moiety or substituted by one or more identical or different radicals R$^A$ and is unsubstituted in the cyclic moiety or substituted by one or more identical or different radicals R$^B$,
(b) radicals of the formulae —C(=O)—R$^C$, —C(=O)—O—R$^C$, —O—C(=O)—R$^C$, —O—C(=O)—O—R$^C$, —C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, —P(=O)(R$^C$)(R$^D$), —P(=O)(OR$^C$)(R$^D$), —P(=O)(OR$^C$)(OR$^D$) or —O—P(=O)(OR$^C$)(OR$^D$), preferably a radical of the formula —C(=O)—R$^C$, —C(=O)—O—R$^C$, —O—C(=O)—R$^C$ or —O—C(=O)—O—R$^C$, in particular a radical of the formula —C(=O)—O—R$^C$, —O—C(=O)—R$^C$ or —O—C(=O)—O—R$^C$,
where R*, R**, R$^C$ and R$^D$ are as defined below,
preferably the radicals (b1)
[$(C_1-C_6)$-alkoxy]carbonyl, [$(C_1-C_6)$-alkoxy]thiocarbonyl, [$(C_2-C_6)$-alkenyloxy]carbonyl, [$(C_2-C_8)$-alkynyloxy]carbonyl, [$(C_1-C_6)$-alkylthio]carbonyl, [$(C_2-C_6)$-alkenylthio]carbonyl, [$(C_2-C_6)$-alkynylthio]carbonyl, $(C_1-C_6)$-alkanoyl, [$(C_2-C_6)$-alkenyl]carbonyl, [$(C_2-C_6)$-alkynyl]carbonyl, [$(C_1-C_6)$-alkyl]carbonylamino, [$(C_2-C_6)$-alkenyl]carbonylamino, [$(C_2-C_6)$-alkynyl]carbonylamino, [$(C_1-C_6)$-alkoxy]carbonylamino, [$(C_2-C_6)$-alkenyloxy]carbonylamino, [$(C_2-C_6)$-alkynyloxy]carbonylamino, [$(C_1-C_6)$-alkylamino]carbonylamino, [$(C_1-C_6)$-alkyl]carbonyloxy, [$(C_2-C_6)$-alkenyl]carbonyloxy, [$(C_2-C_6)$-alkynyl]carbonyloxy, [$(C_1-C_6)$-alkoxy]carbonyloxy, [$(C_2-C_6)$-alkenyloxy]carbonyloxy and [$(C_2-C_6)$-alkynyloxy]carbonyloxy,
  where each of the 23 last-mentioned radicals is unsubstituted or substituted by one or more radicals from the group consisting of halogen, NO$^2$, $(C_1-C_4)$-alkoxy and optionally halogen-, CN—, NO$_2$—, $(C_1-C_4)$-alkyl-, $(C_1-C_4)$-alkoxy- and $(C_1-C_4)$-alkylthio-substituted phenyl, and
preferably the radicals (b2)
$(C_3-C_6)$-cycloalkylcarbonyl,
$(C_3-C_6)$-cycloalkyl-[$(C_1-C_4)$-alkyl]carbonyl,
$(C_3-C_6)$-cycloalkyl-[$(C_1-C_4)$-alkoxy]carbonyl,
$(C_3-C_6)$-cycloalkoxycarbonyl,
$(C_3-C_6)$-cycloalkoxy-[$(C_1-C_4)$-alkyl]carbonyl,
$(C_3-C_6)$-cycloalkoxy-[$(C_1-C_4)$-alkoxy]carbonyl,
$(C_3-C_6)$-cycloalkylcarbonyloxy,
$(C_3-C_6)$-cycloalkyl-[$(C_1-C_4)$-alkyl]carbonyloxy,
$(C_5-C_6)$-cycloalkenyl-[$(C_1-C_4)$-alkyl]carbonyloxy,
$(C_5-C_6)$-cycloalkynyl-[$(C_1-C_4)$-alkyl]carbonyloxy,
$(C_3-C_6)$-cycloalkyl-[$(C_1-C_4)$-alkoxy]carbonyloxy,
$(C_5-C_6)$-cycloalkenyl-[$(C_1-C_4)$-alkoxy]carbonyloxy,
$(C_5-C_6)$-cycloalkynyl-[$(C_1-C_4)$-alkoxy]carbonyloxy,
$(C_3-C_6)$-cycloalkoxycarbonyloxy,
$(C_3-C_6)$-cycloalkoxy-[$(C_1-C_4)$-alkyl]carbonyloxy,
$(C_3-C_6)$-cycloalkoxy-[$(C_1-C_4)$-alkoxy]carbonyloxy,
$(C_3-C_6)$-cycloalkylcarbonylamino,
$(C_3-C_6)$-cycloalkyl-[$(C_1-C_4)$-alkyl]carbonylamino,
$(C_5-C_6)$-cycloalkenyl-[$(C_1-C_4)$-alkyl]carbonylamino,
$(C_5-C_6)$-cycloalkynyl-[$(C_1-C_4)$-alkyl]carbonylamino,
$(C_3-C_6)$-cycloalkyl-[$(C_1-C_4)$-alkoxy]carbonylamino,
$(C_3-C_6)$-cycloalkoxycarbonylamino,
$(C_3-C_6)$-cycloalkoxy-[$(C_1-C_4)$-alkyl]carbonylamino and
$(C_3-C_6)$-cycloalkoxy-[$(C_1-C_4)$-alkoxy]carbonylamino,
phenylcarbonyl,
phenyl-[$(C_1-C_4)$-alkyl]carbonyl,
phenyl-[$(C_1-C_4)$-alkoxy]carbonyl,
phenoxycarbonyl,
phenoxy-[$(C_1-C_4)$-alkyl]carbonyl,
phenoxy-[$(C_1-C_4)$-alkoxy]carbonyl,
phenylcarbonyloxy,
phenyl-[$(C_1-C_4)$-alkyl]carbonyloxy,
phenyl-[$(C_1-C_4)$-alkoxy]carbonyloxy,
phenoxycarbonyloxy,
phenoxy-[$(C_1-C_4)$-alkyl]carbonyloxy,
phenoxy-[$(C_1-C_4)$-alkoxy]carbonyloxy,
phenylcarbonylamino,
phenyl-[$(C_1-C_4)$-alkyl]carbonylamino,
phenyl-[$(C_1-C_4)$-alkoxy]carbonylamino,
phenoxycarbonylamino,
phenoxy-[$(C_1-C_4)$-alkyl]carbonylamino,
phenoxy-[$(C_1-C_4)$-alkoxy]carbonylamino,
  where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and is unsubstituted at the ring or at the polycyclic system or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and (c) radicals of the formulae —SiR'$_3$, —O—SiR'$_3$, (R')$_3$Si—(C$_1$-C$_4$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others represents H, $(C_1-C_4)$-alkyl or phenyl which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or is substituted at two adjacent positions by a $(C_2-C_6)$-alkylene bridge, and q represents an integer from 0 to 6, and (d) radicals of the formula R"O—CHR'"CH(OR")—(C$_1$-C$_6$)-alkoxy, in which each of the radicals R" independently of the others represents H or $(C_1-C_4)$-alkyl or together the radicals represent a $(C_1-C_6)$-alkylene group and R'" represents H or $(C_1-C_4)$-alkyl, or $R^1$ represents $(C_3-C_6)$-cycloalkyl, $(C_5-C_6)$-cycloalkenyl, $(C_5-C_6)$-cycloalkynyl or phenyl, where each of the 4 last-mentioned radicals is unsubstituted or substituted by one or more radicals from the group consisting of the radicals [subgroups (a')-(e')]

(a') halogen, cyano, thio, nitro, hydroxy, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio and radicals of the formulae —NR*R**, where the radicals R* and R** are defined below, (b') radicals of the formulae —C(=O)—R$^C$, —C(=O)—O—R$^C$, —O—C(=O)—R$^C$, —O—C(=O)—O—R$^C$, —C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, —P(=O)(R$^C$)(R$^D$), —P(=O)(OR$^C$)(R$^D$), —P(=O)(OR$^C$)(OR$^D$) or —O—P(=O)(OR$^C$)(OR$^D$), preferably a radical of the formula —C(=O)—R$^C$, —C(=O)—O—R$^C$, —O—C(=O)—R$^C$ or —O—C(=O)—O—R$^C$, in particular a radical of the formula —C(=O)—O—R$^C$, —O—C(=O)—R$^C$ or —O—C(=O)—O—R$^C$, where R*, R**, R$^C$ and R$^D$ are as defined below, and preferably the radicals (b1')

[(C$_1$-C$_6$)-alkoxy]carbonyl, [(C$_1$-C$_6$)-alkoxy]thiocarbonyl, [(C$_2$-C$_6$)-alkenyloxy]carbonyl, [(C$_2$-C$_6$)-alkynyloxy]carbonyl, [(C$_1$-C$_6$)-alkylthio]carbonyl, [(C$_2$-C$_6$)-alkenylthio]carbonyl, [(C$_2$-C$_6$)-alkynylthio]carbonyl, (C$_1$-C$_8$)-alkanoyl, [(C$_2$-C$_6$)-alkenyl]carbonyl, [(C$_2$-C$_6$)-alkynyl]carbonyl, (C$_1$-C$_4$)-alkylimino, (C$_1$-C$_4$)-alkoxyimino, [(C$_1$-C$_6$)-alkyl]carbonylamino, [(C$_2$-C$_6$)-alkenyl]carbonylamino, [(C$_2$-C$_6$)-alkynyl]carbonylamino, [(C$_1$-C$_6$)-alkoxy]carbonylamino, [(C$_2$-C$_6$)-alkenyloxy]carbonylamino, [(C$_2$-C$_6$)-alkynyloxy]carbonylamino, [(C$_1$-C$_6$)-alkylamino]carbonylamino, (C$_1$-C$_4$)-alkyl]carbonyloxy, [(C$_2$-C$_4$)-alkenyl]carbonyloxy, [(C$_2$-C$_4$)-alkynyl]carbonyloxy, [(C$_1$-C$_6$)-alkoxy]carbonyloxy, [(C$_2$-C$_6$)-alkenyloxy]carbonyloxy, [(C$_2$-C$_6$)-alkynyloxy]carbonyloxy, (C$_1$-C$_6$)-alkylsulphinyl and (C$_1$-C$_6$)-alkylsulphonyl, where each of the 27 last-mentioned radicals is unsubstituted or substituted by one or more radicals from the group consisting of halogen, NO$_2$, $(C_1-C_4)$-alkoxy and optionally substituted phenyl, and preferably the radicals (b2')

$(C_3-C_6)$-cycloalkylcarbonyl,
$(C_3-C_6)$-cycloalkyl-[(C$_1$-C$_4$)-alkyl]carbonyl,
$(C_3-C_6)$-cycloalkyl-[(C$_1$-C$_4$)-alkoxy]carbonyl,
$(C_3-C_6)$-cycloalkoxycarbonyl,
$(C_3-C_6)$-cycloalkoxy-[(C$_1$-C$_4$)-alkyl]carbonyl,
$(C_3-C_6)$-cycloalkoxy-[(C$_1$-C$_4$)-alkoxy]carbonyl,
$(C_3-C_6)$-cycloalkylcarbonyloxy,
$(C_3-C_6)$-cycloalkyl-[(C$_1$-C$_4$)-alkyl]carbonyloxy,
$(C_5-C_6)$-cycloalkenyl-[(C$_1$-C$_4$)-alkyl]carbonyloxy,
$(C_5-C_6)$-cycloalkynyl-[(C$_1$-C$_4$)-alkyl]carbonyloxy,
$(C_3-C_6)$-cycloalkyl-[(C$_1$-C$_4$)-alkoxy]carbonyloxy,
$(C_5-C_6)$-cycloalkenyl-[(C$_1$-C$_4$)-alkoxy]carbonyloxy,
$(C_5-C_6)$-cycloalkynyl-[(C$_1$-C$_4$)-alkoxy]carbonyloxy,
$(C_3-C_6)$-cycloalkoxycarbonyloxy,
$(C_3-C_6)$-cycloalkoxy-[(C$_1$-C$_4$)-alkyl]carbonyloxy,
$(C_3-C_6)$-cycloalkoxy-[(C$_1$-C$_4$)-alkoxy]carbonyloxy,
$(C_3-C_6)$-cycloalkylcarbonylamino,
$(C_3-C_6)$-cycloalkyl-[(C$_1$-C$_4$)-alkyl]carbonylamino,
$(C_5-C_6)$-cycloalkenyl-[(C$_1$-C$_4$)-alkyl]carbonylamino,
$(C_5-C_6)$-cycloalkynyl-[(C$_1$-C$_4$)-alkyl]carbonylamino,
$(C_3-C_6)$-cycloalkyl-[(C$_1$-C$_4$)-alkoxy]carbonylamino,
$(C_3-C_6)$-cycloalkoxycarbonylamino,
$(C_3-C_6)$-cycloalkoxy-[(C$_1$-C$_4$)-alkyl]carbonylamino and
$(C_3-C_6)$-cycloalkoxy-[(C$_1$-C$_4$)-alkoxy]carbonylamino,
phenylcarbonyl,
phenyl-[(C$_1$-C$_4$)-alkyl]carbonyl,
phenyl-[(C$_1$-C$_4$)-alkoxy]carbonyl,
phenoxycarbonyl,
phenoxy-[(C$_1$-C$_4$)-alkyl]carbonyl,
phenoxy-[(C$_1$-C$_4$)-alkoxy]carbonyl,
phenylcarbonyloxy,
phenyl-[(C$_1$-C$_4$)-alkyl]carbonyloxy,
phenyl-[(C$_1$-C$_4$)-alkoxy]carbonyloxy,
phenoxycarbonyloxy,
phenoxy-[(C$_1$-C$_4$)-alkyl]carbonyloxy,
phenoxy-[(C$_1$-C$_4$)-alkoxy]carbonyloxy,
phenylcarbonylamino,
phenyl-[(C$_1$-C$_4$)-alkyl]carbonylamino,
phenyl-[(C$_1$-C$_4$)-alkoxy]carbonylamino,
phenoxycarbonylamino,
phenoxy-[(C$_1$-C$_4$)-alkyl]carbonylamino,
phenoxy-[(C$_1$-C$_4$)-alkoxy]carbonylamino, where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and is unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and (c') radicals of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others represents H, ($C_1$-$C_4$)-alkyl or phenyl which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or is substituted at two adjacent positions by a ($C_2$-$C_6$)-alkylene bridge, and q represents an integer from 0 to 6, and (d') radicals of the formula R"O—CHR'"CH(OR")—($C_1$-$C_6$)-alkoxy, in which each of the radicals R'" independently of the others represents H or ($C_1$-$C_4$)-alkyl or together the radicals represent a ($C_1$-$C_6$)-alkylene group and R'" represents H or ($C_1$-$C_4$)-alkyl, and (e') a radical of the formula Het$^1$ which is unsubstituted or substituted by one or more identical or different radicals $R^B$, or represents a polycyclic radical based on ($C_3$-$C_6$)-cycloalkyl, ($C_5$-$C_6$)-cycloalkenyl, ($C_5$-$C_6$)-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals $R^B$, preferably unsubstituted or substituted by one or more radicals from the group consisting of halogen, cyano, nitro, hydroxy, carboxy, ($C_1$-$C_4$)-alkyl, ($C_1$-$C_4$)-haloalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_1$-$C_4$)-alkoxy, ($C_2$-$C_4$)-alkenyloxy, ($C_2$-$C_4$)-alkynyloxy, ($C_1$-$C_4$)-haloalkoxy, ($C_1$-$C_4$)-alkoxy-($C_1$-$C_4$)-alkoxy, ($C_1$-$C_4$)-alkylthio, ($C_2$-$C_4$)-alkenylthio, ($C_2$-$C_4$)-alkynylthio, ($C_3$-$C_6$)-cycloalkyl, ($C_3$-$C_6$)-cycloalkoxy, [($C_1$-$C_4$)-alkoxy]carbonyl, [($C_1$-$C_4$)-haloalkoxy]carbonyl and oxo, or $R^1$ represents a heterocyclic radical Het$^1$ which is unsubstituted in the ring or in the polycyclic system or substituted by one or more identical or different radicals $R^B$, preferably unsubstituted or substituted by one or more radicals from the group consisting of halogen, cyano, thio, nitro, hydroxy, carboxy, ($C_1$-$C_4$)-alkyl, ($C_1$-$C_6$)-haloalkyl, ($C_1$-$C_4$)-alkoxy-($C_1$-$C_4$)-alkyl, ($C_2$-$C_4$)-alkenyl, ($C_2$-$C_4$)-haloalkenyl, ($C_2$-$C_4$)-alkynyl, ($C_2$-$C_6$)-haloalkynyl, ($C_1$-$C_4$)-alkoxy, ($C_2$-$C_4$)-alkenyloxy, ($C_2$-$C_4$)-alkynyloxy, ($C_1$-$C_4$)-haloalkoxy, ($C_1$-$C_4$)-alkoxy-($C_1$-$C_4$)-alkoxy, ($C_1$-$C_4$)-alkylthio, ($C_2$-$C_4$)-alkenylthio, ($C_2$-$C_4$)-alkynylthio, ($C_3$-$C_6$)-cycloalkyl, ($C_3$-$C_6$)-cycloalkoxy, [($C_1$-$C_4$)-alkoxy]carbonyl, [($C_1$-$C_4$)-haloalkoxy]carbonyl and oxo, where Het$^1$, R*, R**, $R^A$, $R^B$, $R^C$, $R^D$, $R^{aa}$, $R^{bb}$ and $R^{cc}$ have the meanings already mentioned above, preferably Het$^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, R*, R** independently of one another (i.e. also of other groups NR*R**) each represent H, ($C_1$-$C_6$)-alkyl, ($C_2$-$C_6$)-alkenyl, ($C_2$-$C_6$)-alkynyl, ($C_1$-$C_4$)-alkoxy-($C_1$-$C_4$)-alkyl, ($C_1$-$C_6$)-alkanoyl, [($C_1$-$C_4$)-haloalkyl]carbonyl, [($C_1$-$C_4$)-alkoxy]carbonyl, [($C_1$-$C_4$)-haloalkoxy]carbonyl, ($C_3$-$C_6$)-cycloalkyl, ($C_3$-$C_6$)-cycloalkyl-($C_1$-$C_4$)-alkyl, phenyl, phenyl-($C_1$-$C_4$)-alkyl, where each of the 4 last-mentioned radicals is optionally substituted in the cycle by one or more identical or different radicals $R^{bb}$, or preferably H, ($C_1$-$C_4$)-alkyl, allyl, propargyl, ($C_1$-$C_4$)-alkoxy-($C_1$-$C_4$)-alkyl, formyl, acetyl, n-propanoyl, isopropanoyl, trifluoroacetyl, trichloroacetyl, methoxycarbonyl, ethoxycarbonyl, n- or i-propoxycarbonyl, n-, i-, sec-, t-butoxycarbonyl, [($C_1$-$C_4$)-haloalkoxy]-carbonyl, cyclopropyl, cyclobutyl, cyclopentyl, cyclohexyl, cyclopropylmethyl, phenyl, benzyl, 1- or 2-phenylethyl, R* and R** together with the nitrogen atom represent preferably saturated a 5- to 6-membered heterocycle which, in addition to the nitrogen atom, may contain one or two further ring heteroatoms from the group consisting of N, O and S and which may be unsubstituted or substituted by one or more radicals from the group consisting of ($C_1$-$C_4$)-alkyl, ($C_1$-$C_4$)-haloalkyl and oxo, preferably a 1-piperidine, 1-piperazine, 1-pyrrolidine, 1-pyrazolidine, 1-piperazolidine or 1-morpholine radical, $R^A$ represents halogen, cyano, hydroxy or ($C_1$-$C_6$)-alkoxy, $R^B$ represents halogen, cyano, hydroxy, oxo, nitro, ($C_1$-$C_4$)-alkyl, ($C_1$-$C_4$)-haloalkyl, cyano-($C_1$-$C_4$)-alkyl, hydroxy-($C_1$-$C_4$)-alkyl, nitro-($C_1$-$C_4$)-alkyl, ($C_2$-$C_4$)-alkenyl, ($C_2$-$C_4$)-alkynyl, ($C_1$-$C_4$)-alkoxy, ($C_2$-$C_4$)-alkenyloxy, ($C_2$-$C_4$)-alkynyloxy, ($C_1$-$C_4$)-haloalkoxy, ($C_1$-$C_4$)-alkoxy-($C_1$-$C_4$)-alkyl, ($C_1$-$C_4$)-alkoxy-($C_1$-$C_4$)-alkoxy, ($C_1$-$C_4$)-alkylthio, ($C_1$-$C_4$)-alkylsulphonyl, ($C_1$-$C_4$)-haloalkylsulphonyl, a radical of the formula $R^{aa}$—C(=O)— or $R^{aa}$—C(=O)—($C_1$-$C_6$)-alkyl, where the radicals R" are defined below, —NR*R**, where R* and R** are defined below, cyclopropyl, cyclopropylmethyl, phenyl, benzyl, 1- or 2-phenylethyl, phenoxy, 2-phenoxyethyl or a 5- or 6-membered monocyclic or 9- or 10-membered bicyclic heterocycle which contains 1, 2, 3 or 4 heteroatoms selected from the group consisting of O, N and S, where each of the 9 last-mentioned radicals is optionally substituted in the cyclic moiety by one or more identical or different radicals $R^{bb}$, $R^C$, $R^D$ are each independently of one another (also independently of radicals $R^C$, $R^D$ in other groups) hydrogen, ($C_1$-$C_6$)-alkyl, ($C_2$-$C_6$)-alkenyl or ($C_2$-$C_6$)-alkynyl, where each of the 3 last-mentioned radicals is unsubstituted or substituted by one or more radicals from the group consisting of halogen, cyano, nitro, hydroxy, ($C_1$-$C_4$)-alkoxy, ($C_2$-$C_4$)-alkenyloxy, ($C_2$-$C_4$)-alkynyloxy, ($C_1$-$C_4$)-haloalkoxy, ($C_1$-$C_4$)-alkoxy-($C_1$-$C_4$)- alkoxy, $(C_1-C_4)$-alkylthio, $(C_1-C_6)$-alkylsulphonyl and $(C_1-C_6)$-haloalkylsulphonyl, or $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_6)$-alkyl, phenyl-$(C_1-C_4)$-alkyl, phenoxy-$(C_1-C_4)$-alkyl or phenylamino-$(C_1-C_6)$-alkyl, radicals Het$^1$, Het$^1$-$(C_1-C_6)$-alkyl, Het$^1$-O-$(C_1-C_6)$-alkyl, where Het$^1$ has the meaning mentioned, where each of the 12 last-mentioned radicals is unsubstituted in the acyclic moiety or substituted by one or more identical or different radicals R$^A$ and is unsubstituted in the cyclic moiety or substituted by one or more identical or different radicals R$^B$, R$^{aa}$ independently of one another each represent hydrogen, OH, $(C_1-C_6)$-alkyl, $(C_1-C_4)$-haloalkyl, $(C_2-C_4)$-alkenyl, $(C_2-C_4)$-alkynyl, $(C_1-C_6)$-alkoxy, $(C_1-C_4)$-alkoxy-$(C_1-C_4)$-alkyl, $(C_1-C_4)$-alkoxy-$(C_1-C_4)$-alkyloxy, $(C_1-C_4)$-haloalkoxy, $(C_1-C_4)$-haloalkoxy-$(C_1-C_4)$-alkyl, $(C_1-C_4)$-haloalkoxy-$(C_1-C_4)$-alkoxy, —NR*R**, where R* and R** are as defined above, $(C_3-C_6)$-cycloalkyl, $(C_3-C_6)$-cycloalkoxy, $(C_3-C_6)$-cycloalkyl-$(C_1-C_6)$-alkyl, $(C_3-C_6)$-cycloalkyl-$(C_1-C_6)$-alkoxy, phenyl, phenyl-$(C_1-C_4)$-alkyl, phenyl-$(C_1-C_4)$-alkoxy, phenoxy, phenoxy-$(C_1-C_4)$-alkyl, phenoxy-$(C_1-C_4)$-alkoxy, phenylamino, phenylamino-$(C_1-C_4)$-alkyl, phenylamino-$(C_1-C_4)$-alkoxy or 5- or 6-membered monocyclic or 9- or 10-membered bicyclic heterocycle which is optionally attached via a $(C_1-C_4)$-alkylene group or a $(C_1-C_4)$-alkoxy group and contains 1, 2, 3 or 4 heteroatoms selected from the group consisting of O, N and S, where each of the 14 last-mentioned radicals is optionally substituted in the cyclic moiety by one or more identical or different radicals R$^{cc}$, R$^{bb}$ independently of one another each represent halogen, $(C_1-C_4)$-alkyl, $(C_1-C_4)$-haloalkyl, $(C_1-C_4)$-alkoxy or $(C_1-C_4)$-haloalkoxy, preferably halogen, methyl, CF$_3$, CCl$_3$, methoxy, ethoxy, OCH$_2$F, OCF$_2$H or OCF$_3$ and R$^{cc}$ independently of one another each represent halogen, $(C_1-C_4)$-alkyl, $(C_1-C_4)$-haloalkyl, $(C_1-C_4)$-alkoxy or $(C_1-C_4)$-haloalkoxy, preferably halogen, methyl, CF$_3$, CCl$_3$, methoxy, ethoxy, OCH$_2$F, OCF$_2$H or OCF$_3$.

More preference is here also given to compounds (I), preferably of the formula (Ia), or salts thereof in which R$^1$ represents H, $(C_1-C_6)$-alkyl, $(C_2-C_6)$-alkenyl, $(C_2-C_6)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, alkylsulphinyl, alkylsulphonyl, $(C_3-C_6)$-cycloalkyl which is unsubstituted or substituted by one or more radicals from the group consisting of halogen and $(C_1-C_4)$-alkyl, and phenyl, phenoxy, phenylthio, phenylsulphinyl, phenylsulphonyl, where the phenyl ring in the 5 last-mentioned radicals is in each case unsubstituted or substituted by one or more radicals from the group consisting of halogen, $(C_1-C_4)$-alkyl, $(C_1-C_4)$-alkoxy and $(C_1-C_4)$-haloalkyl, and a radical Het$^1$, preferably a saturated or partially unsaturated monocyclic heterocyclyl radical which has 5 or 6 ring atoms and contains 1, 2 or 3 heteroatoms selected from the group consisting of O, N and S and is unsubstituted or substituted by one or more radicals selected from the group consisting of halogen, $(C_1-C_4)$-alkyl, $(C_1-C_4)$-alkoxy and $(C_1-C_4)$-haloalkyl, or R$^1$ represents $(C_3-C_6)$-cycloalkyl which is unsubstituted or substituted by one or more radicals from the group consisting of $(C_1-C_4)$-alkyl, $(C_1-C_4)$-alkoxy and $(C_1-C_4)$-haloalkyl, or R$^1$ represents phenyl which is unsubstituted or substituted by one or more radicals from the group consisting of halogen, $(C_1-C_4)$-alkyl, $(C_1-C_4)$-alkoxy and $(C_1-C_4)$-haloalkyl.

Particular preference is here also given to compounds (I), preferably of the formula (Ia), or salts thereof in which R$^1$ represents H, $(C_1-C_4)$-alkyl, $(C_2-C_4)$-alkenyl or $(C_2-C_4)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two last-mentioned radicals is unsubstituted or substituted by one or more radicals from the group consisting of halogen and $(C_1-C_4)$-alkyl, and phenyl, phenylthio (=phenylsulphanyl), phenylsulphinyl, phenylsulphonyl, where each of the 4 last-mentioned radicals is unsubstituted or substituted by one or more radicals from the group consisting of halogen, $(C_1-C_4)$-alkyl, $(C_1-C_4)$-alkoxy and $(C_1-C_4)$-haloalkyl.

More preferably

R$^1$ also represents a polycyclic radical based on $(C_3-C_9)$-cycloalkyl, $(C_5-C_9)$-cycloalkenyl, $(C_5-C_9)$-cycloalkynyl or phenyl, where the base ring is condensed, preferably benzo-fused, with a carbocyclic or heterocyclic ring, preferably a 5- or 6-membered ring having 0 or 1 to 3 ring heteroatoms from the group consisting of N, O and S, and where the base ring or the polycyclic system is unsubstituted or substituted by one or more radicals from the group consisting of halogen, cyano, nitro, $(C_1-C_6)$-alkyl, $(C_1-C_6)$-haloalkyl, $(C_1-C_4)$-alkoxy-$(C_1-C_4)$-alkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_3-C_6)$-cycloalkyl, $(C_3-C_6)$-cycloalkoxy, [$(C_1-C_4)$-alkoxy]carbonyl and [$(C_1-C_4)$-haloalkoxy]carbonyl.

Preference is also given to compounds (I), preferably of the formula (Ia), or salts thereof in which R$^1$ represents a saturated, partially unsaturated or heteroaromatic heterocyclyl radical which has 3 to 9 ring atoms, preferably 5 or 6 ring atoms, which has 1 to 4 heteroatoms, preferably 1 to 3 ring heteroatoms from the group consisting of N, O and S and which is unsubstituted or substituted by one or more radicals from the group consisting of halogen, cyano, thio, nitro, hydroxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo.

Preference is also given to compounds (I), preferably of the formula (Ia), or salts thereof in which R$^1$ represents a radical of the formula SiR$^a$R$^b$R$^c$, —NR$^a$R$^b$ or —N=CR$^c$R$^d$, preferably of the formula —NR$^a$R$^b$ or —N=CR$^c$R$^d$, where in the 5 last-mentioned formulae each of the radicals R$^a$, R$^b$, R$^c$ and R$^d$ independently of the others represents hydrogen, $(C_1-C_4)$-alkyl, $(C_2-C_4)$-alkenyl, $(C_2-C_4)$-alkynyl, benzyl, substituted benzyl, phenyl or substituted phenyl, but where $SiH_3$ for $SiR^aR^bR^c$ is excluded, or $R^a$ and $R^b$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1-C_4)$-alkyl and $(C_1-C_4)$-haloalkyl, or $R^c$ and $R^d$ together with the carbon atom represent a 3- to 8-membered carbocyclic radical or heterocyclic radical which may contain 1 to 3 ring heteroatoms from the group consisting of N, O and S, where the carbocyclic or heterocyclic radical is unsubstituted or substituted by one or more radicals from the group consisting of $(C_1-C_4)$-alkyl and $(C_1-C_4)$-haloalkyl.

Particular preference is also given to compounds (I), preferably of the formula (Ia), or salts thereof in which
$R^1$ represents H, methyl, ethyl, n-propyl, i-propyl, n-butyl, s-butyl, i-butyl, t-butyl, allyl, ethynyl, propargyl (prop-2-yn-1-yl), prop-1-yn-1-yl, but-2-yn-1-yl, but-3-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, phenyl, 2-carboxyphenyl, 2-chlorophenyl, 3-chlorophenyl, 4-chlorophenyl, 2-fluorophenyl, 3-fluorophenyl, 4-fluorophenyl, 3-methoxyphenyl, 4-methoxyphenyl, 2-methoxyphenyl, 3-methoxyphenyl, 4-methoxyphenyl, benzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenylethyl, 1-phenylethyl, (4-chlorophenyl)methyl [i.e. =CH$_2$(4-Cl-Ph)=4-chlorobenzyl], (4-fluorophenyl)methyl [i.e. =CH$_2$(4-F-Ph)], (4-methoxyphenyl)methyl [i.e. =CH$_2$(4-OMe-Ph)], 2-phenoxyethyl, 2-phenylthioethyl [=2-(phenylsulphanyl)ethyl], 2-phenylsulphinylethyl, 2-phenylsulphonylethyl, trifluoromethyl, difluoromethyl, fluoromethyl, trichloromethyl, dichloromethyl, chloromethyl, methoxymethyl, 2-methoxyethyl, 2,2,2-trifluoroethyl, 1,1,1-trifluoroprop-2-yl, 2,2-difluoroethyl, 1,3-difluoroprop-2-yl, 2,3-dimethoxypropyl, 2,3-dimethoxyprop-2-yl, 2,2-dimethoxyeth-2-yl, 2-(2,2,2-trifluoroethoxyl)ethyl, 2-fluoroethyl, 2-chloroethyl, 2-bromoethyl, 2-iodoethyl, 2,2,3,3,3-pentafluoropropyl, 1-hydroxyprop-2-yl, 2-hydroxyprop-2-yl, 2-hydroxyprop-1-yl, 3-hydroxypropyl, 3-hydroxyprop-2-yl, (2-methoxyethoxy)methyl; 2-(2-methoxyethoxyl)ethyl; (2-ethoxyethoxy)methyl; 2-(2-ethoxyethoxyl)ethyl,
(acetoxy)methyl, (propanoyloxy)methyl, (2-methylpropanoyloxy)methyl, (2,2-dimethylpropanoyloxy)methyl, 1-(acetoxy)ethyl, 2-(acetoxy)ethyl, 2-(propanoyloxy)ethyl, 1-(propanoyloxy)ethyl, 1-(2-methylpropanoyloxy)eth-1-yl, 2-(2-methylpropanoyloxy)eth-1-yl, 2-(2,2-dimethylpropanoyloxyl)ethyl [i.e. 1-(t-butylcarbonyloxy)ethyl], 2-(2,2-dimethylpropanoyloxyl)ethyl;
1-(2,2-dimethylpropanoyloxy)-2-methylprop-1-yl, 1-(t-butylcarbonyloxy)-2-methylprop-1-yl, (methoxycarbonyl)methyl, (ethoxycarbonyl)methyl, (n-propoxycarbonyl)methyl, (i-propoxycarbonyl)methyl, (n-butoxycarbonyl)methyl, (s-butoxycarbonyl)methyl, (i-butoxycarbonyl)methyl, (t-butoxycarbonyl)methyl, 1-(methoxycarbonyl)ethyl, 2-(methoxycarbonyl)ethyl, 1-(ethoxycarbonyl)ethyl, 2-(ethoxycarbonyl)ethyl, 1-(n-propoxycarbonyl)ethyl, 2-(n-propoxycarbonyl)ethyl, 1-(i-propoxycarbonyl)ethyl, 2-(i-propoxycarbonyl)ethyl, 1-(n-butoxycarbonyl)ethyl, 2-(n-butoxycarbonyl)ethyl, 1-(s-butoxycarbonyl)ethyl, 2-(s-butoxycarbonyl)ethyl, 1-(i-butoxycarbonyl)ethyl, 2-(i-butoxycarbonyl)ethyl, 1-(t-butoxycarbonyl)ethyl, 2-(t-butoxycarbonyl)ethyl, (methoxycarbonyloxy)methyl, (ethoxycarbonyloxy)methyl, (n-propoxycarbonyloxy)methyl, (i-propoxycarbonyloxy)methyl, (n-butoxycarbonyloxy)methyl, (s-butoxycarbonyloxy)methyl, (i-butoxycarbonyloxy)methyl, (t-butoxycarbonyloxy)methyl, 1-(methoxycarbonyloxy)ethyl, 2-(methoxycarbonyloxy)ethyl, 1-(ethoxycarbonyloxy)ethyl, 2-(ethoxycarbonyloxy)ethyl, 1-(n-propoxycarbonyloxy)ethyl, 2-(n-propoxycarbonyloxy)ethyl, 1-(i-propoxycarbonyloxy)ethyl, 2-(i-propoxycarbonyloxy)ethyl, 1-(n-butoxycarbonyloxy)ethyl, 2-(n-butoxycarbonyloxy)ethyl, 1-(s-butoxycarbonyloxy)ethyl, 2-(s-butoxycarbonyloxy)ethyl, 1-(i-butoxycarbonyloxy)ethyl, 2-(i-butoxycarbonyloxy)ethyl, 1-(t-butoxycarbonyloxy)ethyl, 2-(t-butoxycarbonyloxy)ethyl, (cyclohexoxycarbonyloxy)methyl, 1-(cyclohexoxycarbonyloxy)eth-1-yl, 2-(cyclohexoxycarbonyloxy)eth-1-yl, (acetyl)methyl, 1-(acetyl)ethyl, 2-(acetyl)ethyl, 1-(acetyl)propyl, 2-(acetyl)propyl, 3-(acetyl)propyl, (propanoyl)methyl, 1-(propanoyl)ethyl, 2-(propanoyl)ethyl, 1-(propanoyl)propyl, 2-(propanoyl)propyl, 3-(propanoyl)propyl, 1-(propanoyl)-2-methylpropyl, 2-ethylthioethyl [=2-(ethylsulphanyl)ethyl], 2-(ethylsulphinyl)ethyl, 2-(ethylsulphonyl)ethyl, 2-(ethylideneaminooxy)ethyl, 2-(prop-2-ylideneaminooxy)ethyl, 2-(but-2-ylideneaminooxy)ethyl, 2-(pent-3-ylideneaminooxy)ethyl, (N,N-dimethylamino)methyl, 2-(N,N-dimethylamino)eth-1-yl, 1-(N,N-dimethylamino)eth-1-yl, 2-(N,N-diethylamino)eth-1-yl, 1-(N,N-diethylamino)eth-1-yl, (N,N-diethylamino)methyl, (N,N-dimethylaminocarbonyl)methyl, 1-(N,N-dimethylaminocarbonyl)ethyl, 2-(N,N-dimethylaminocarbonyl)ethyl, (N,N-diethylaminocarbonyl)methyl, 1-(N,N-diethylaminocarbonyl)ethyl, 2-(N,N-diethylaminocarbonyl)ethyl, 1-(dimethylamino)prop-2-yl [i.e. 2-(dimethylamino)-1-methylethyl], 1-(diethylamino)prop-2-yl, trimethylsilylmethyl, 1-(trimethylsilyl)ethyl, 2-(trimethylsilyl)ethyl, triethylsilylmethyl, 1-(triethylsilyl)ethyl, 2-(triethylsilyl)ethyl, cyclopropyl, cyclopropylmethyl, 1-cyclopropylethyl, 2-cyclopropylethyl, (1-methylcyclopropyl)methyl, 1-(1-methylcyclopropyl)ethyl, 2-(1-methylcyclopropyl)ethyl, (2,2-dichlorcyclopropyl)methyl, 1-(2,2-dichlorcyclopropyl)ethyl, 2-(2,2-dichlorcyclopropyl)ethyl, (2,2-dimethylcyclopropyl)methyl, 1-(2,2-dimethylcyclopropyl)ethyl, 2-(2,2-dimethylcyclopropyl)ethyl, cyclobutylmethyl, cyclopentylmethyl, cyclohexylmethyl or pyrid-2-yl, pyrid-3-yl, pyrid-4-yl, 2-chloropyrid-3-yl, 3-chloropyrid-2-yl, thien-2-yl, thien-3-yl, 2-chlorothien-3-yl, 3-chlorothien-2-yl, 4-chlorothien-2-yl, thietan-3-yl, (1-ethyl-5- methyl-1H-pyrazol-4-yl)methyl, 1-(1-ethyl-5-methyl-1H-pyrazol-4-yl)ethyl, 2-(1-ethyl-5-methyl-1H-pyrazol-4-yl)ethyl,
(1-ethyl-3-methyl-1H-pyrazol-4-yl)methyl, 1-(1-ethyl-3-methyl-1H-pyrazol-4-yl)ethyl, 2-(1-ethyl-3-methyl-1H-pyrazol-4-yl)ethyl,
tetrahydrofuran-2-yl, tetrahydrofuran-3-yl, tetrahydrofuran-2-ylmethyl, tetrahydrofuran-3-ylmethyl, (5-methyl-2-oxo-1,3-dioxol-4-yl)methyl;
oxetan-3-yl, (oxetan-3-yl)methyl, (oxetan-2-yl)methyl, (1,3-dioxolan-2-yl)methyl, (1,3-dioxolan-4-yl)methyl, 5-methyl-2-oxo-1,3-dioxolan-4-yl)methyl, (morpholin-4-yl)methyl; 1-(morpholin-4-yl)ethyl, 2-(morpholin-4-yl)ethyl, 2,3-dihydro-1H-inden-2-yl, dihydro-1H-inden-3-yl, dihydro-1H-inden-4-yl, dihydro-1H-inden-5-yl,
1H-inden-2-yl, 1H-inden-3-yl, 1H-inden-4-yl, 1H-inden-5-yl, 1H-inden-6-yl or 1H-inden-7-yl.

Here, very particular preference is given to compounds (I), preferably of the formula (Ia), and salts thereof in which $R^1$ represents H, methyl, ethyl, n-propyl, isopropyl, n-butyl, s-butyl, isobutyl, t-butyl, phenyl, benzyl, $CH_2$(4-Cl-Ph), i.e. (4-chlorophenyl)methyl, $CH_2$(4-F-Ph), i.e. (4-fluorophenyl)methyl, $CH_2$(4-OMe-Ph), i.e. (4-methoxyphenyl) methyl, 2-fluorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenoxyethyl, 2-ethylthioethyl, 2-ethylsulphinylethyl, 2-ethylsulphonylethyl, 2-phenylthioethyl, 2-phenylsulphinylethyl, 2-phenylsulphonylethyl, methoxymethyl, 2-methoxyethyl, tetrahydrofuran-2-ylmethyl, 2-(dimethylamino)ethyl, oxetan-3-yl, (3-methyloxetan-3-yl)methyl, thietan-3-yl, trifluoromethyl, difluoromethyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl) methyl, (2,2-dichlorocyclopropyl)methyl, (2,2-dimethylcyclopropyl)methyl, tetrahydrofuran-2-ylmethyl, allyl, ethynyl, propargyl (=prop-2-yn-1-yl), prop-1-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or 1-ethyl-5-methyl-1H-pyrazol-4-methyl, i.e. (1-ethyl-5-methyl-1H-pyrazol-4-yl)methyl.

Here, very particular preference is given to compounds (I), preferably of the formula (Ia), and salts thereof in which $R^1$ represents H, methyl, ethyl, n-propyl, isopropyl, n-butyl, s-butyl, isobutyl, t-butyl, allyl and propargyl, in particular methyl or ethyl.

Preference is also given to compounds (I) in which $(R^2)_n$ represents n substituents $R^2$,
where $R^2$, if n=1, or each of the substituents $R^2$, if n is greater than 1, independently of the others represents halogen, cyano, nitro, hydroxy, $(C_1-C_8)$-alkyl, $(C_2-C_6)$-alkenyl, $(C_3-C_6)$-cycloalkenyl, $(C_3-C_6)$-cycloalkyl-$(C_1-C_8)$-alkyl, $(C_3-C_6)$-cycloalkenyl-$(C_1-C_8)$-alkyl, $(C_2-C_6)$-alkynyl, $(C_1-C_8)$-alkoxy, $(C_1-C_8)$-alkylthio, $(C_1-C_8)$-alkylsulphinyl, $(C_1-C_8)$-alkylsulphonyl, $(C_1-C_6)$-haloalkyl, $(C_1-C_6)$-haloalkoxy, $(C_1-C_6)$-haloalkylthio, $(C_1-C_6)$-haloalkylsulphinyl, $(C_1-C_6)$-haloalkylsulphonyl, $(C_2-C_6)$-haloalkenyl, $(C_2-C_6)$-haloalkynyl, $(C_1-C_6)$-alkoxy-$(C_1-C_4)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^3$, $C(O)NR^4R^5$, $C(O)$-$Het^2$, $NR^6R^7$ or $Het^3$ or where in each case two groups $R^2$ located ortho at the ring together are a group of the formula $-Z^1-A^{**}-Z^2$ in which
$A^{**}$ represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy,
$Z^1$ represents a direct bond, O or S and
$Z^2$ represents a direct bond, O or S,
where the group $-Z^1-A^{**}-Z^2$ together with the carbon atoms, attached to the group, of the phenyl ring form a fused-on 5- or 6-membered ring,
$R^3$ represents hydrogen, $(C_1-C_6)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned below,
$R^4$, $R^5$, $R^6$ and $R^7$ independently of one another each represent hydrogen, $(C_1-C_6)$-alkyl, $(C_2-C_6)$-alkenyl or $(C_2-C_6)$-alkynyl, where each of the 3 last-mentioned radicals independently of the others is unsubstituted or substituted by one or more radicals from the group consisting of halogen, nitro, cyano and phenyl which is optionally substituted, or
$(C_3-C_6)$-cycloalkyl or phenyl, where each of the 2 last-mentioned radicals in each case independently of the other is unsubstituted or substituted by one or more radicals from the group consisting of halogen, nitro, cyano, $(C_1-C_4)$-alkyl, $(C_1-C_4)$-haloalkyl, phenyl and benzyl, where each of the 2 last-mentioned radicals is optionally substituted,
$Het^2$ and $Het^3$ independently of one another each represent a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo,
M represents an equivalent of a cation,
n represents 0, 1, 2, 3, 4 or 5, preferably 0, 1, 2, 3 or 4, in particular 0, 1, 2 or 3.

Here, more preference is given to compounds (I) in which $(R^2)_n$ represents n substituents $R^2$,
where $R^2$, if n=1, or each of the substituents $R^2$, if n is greater than 1, independently of one another represent halogen, cyano, nitro, hydroxy, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_1-$ $C_4$)-alkoxy-($C_1$-$C_4$)-alkyl, ($C_3$-$C_6$)-cycloalkyl, or a radical of the formula C(O)OR$^3$, C(O)NR$^4$R$^5$, C(O)-Het$^2$, NR$^6$R$^7$ or Het$^3$, or where in each case two groups R$^2$ located ortho at the ring together are a group of the formula —Z$^1$-A-Z$^2$ in which A represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, Z$^1$ represents a direct bond, O or S and Z$^2$ represents a direct bond, O or S, where the group —Z$^1$-A**-Z$^2$ together with the carbon atoms, attached to the group, of the phenyl ring form a fused-on 5- or 6-membered ring, R$^3$ represents hydrogen, ($C_1$-$C_4$)-alkyl or the group M mentioned, R$^4$, R$^5$, R$^6$, R$^7$, Het$^2$ and Het$^3$ have the meanings mentioned, preferably R$^4$, R$^5$, R$^6$ and R$^7$ independently of one another each represent hydrogen, ($C_1$-$C_4$)-alkyl, ($C_1$-$C_4$)-haloalkyl, benzyl, ($C_3$-$C_6$)-cycloalkyl or phenyl, Het$^2$ and Het$^3$ independently of one another each represent a morpholino, piperidino or pyrrolidino group and n represents 0, 1, 2, 3, 4 or 5, preferably 0, 1, 2, 3 or 4, in particular 0, 1, 2 or 3.

Here, more preference is given to compounds (I) in which (R$^2$)$_n$ represents n substituents R$^2$, where R$^2$, if n=1, or each of the substituents R$^2$, if n is greater than 1, independently of the others represents halogen, cyano, nitro, methyl, ethyl, methoxy, ethoxy, methylthio, ethylthio, ($C_1$-$C_2$)-alkylsulphinyl, ($C_1$-$C_2$)-alkylsulphonyl, ($C_1$-$C_2$)-haloalkyl, ($C_1$-$C_2$)-haloalkoxy, ($C_1$-$C_2$)-haloalkylthio, ($C_1$-$C_2$)-haloalkylsulphinyl, ($C_1$-$C_2$)-haloalkylsulphonyl or ($C_1$-$C_2$)-alkoxy-($C_1$-$C_2$)-alkyl, in particular each of the substituents R$^2$ independently of the others represents halogen, such as fluorine, chlorine, bromine or iodine, or cyano, nitro, methyl, methoxy, methylthio, methylsulphinyl, methylsulphonyl, trifluoromethyl, trifluoromethoxy, difluoromethoxy, trifluoroalkylthio, trifluoromethylsulphinyl or trifluoromethylsulphonyl, in particular cyano, nitro or halogen such as fluorine, chlorine or bromine, and n represents 0, 1, 2, 3, 4 or 5, preferably 0, 1, 2, 3 or 4, in particular 0, 1, 2 or 3.

More preference is given to compounds of the formula (I) or salts thereof in which (R$^2$)$_n$ represents 2-bromo, 3-bromo, 4-bromo, 2-chloro, 3-chloro, 4-chloro, 2-fluoro, 3-fluoro, 4-fluoro, 3-iodo, 2-cyano, 3-cyano, 4-cyano, 2-methyl, 3-methyl, 4-methyl, 2-ethyl, 3-ethyl, 4-ethyl, 2-CF$_3$, 3 CF$_3$, 4 CF$_3$, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-difluoromethoxy, 3-difluoromethoxy, 4-difluoromethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-NO$_2$-3-F), (3-Br-4-F), (3-CN-4-F), (3-NO$_2$-4-F), (3-CN-4-Cl), (3-NO$_2$-4-Cl), (S—CN-2-F), 2,3,4-trifluoro, 2,3,5-trifluoro, 2,3,6-trichloro, 2,4,6-trichloro, 3,4,5-trichloro, 2,3,4-trichloro, 2,3,5-trichloro, 2,3,6-trichloro, 2,4,6-trichloro, 3,4,5-trichloro or else (2,6-difluoro-4-Cl), 2,5-dicyano, 2,6-dicyano, (4-methoxy-3-F), where the numbering of the radicals refers to the position of the radical at the phenyl-1-yl radical in which the carbon atom attached to the 3-position at the butyric acid skeleton has the 1-position in the ring.

More preference is given to compounds of the formula (I) or salts thereof in which (R$^2$)$_n$ represents 2-cyano, 3-cyano, 4-cyano, 2-bromo, 3-bromo, 4-bromo, 2-chloro, 3-chloro, 4-chloro, 2-fluoro, 3-fluoro, 4-fluoro, 3-iodo, 2-nitro, 3-nitro, 4-nitro, 2-methoxy, 3-methoxy, 4-methoxy, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (3-Br-4-F), (3-CN-4-F), (4-Br-3-F), 2,3,4-trifluoro, 2,3,5-trifluoro, 2,3,6-trifluoro, trifluoro, 3,4,5-trifluoro, 2,3,4-trichloro, 2,3,5-trichloro, 2,3,6-trichloro, 2,4,6-trichloro, 3,4,5-trichloro, where the numbering of the radicals refers to the position of the radical at the phenyl-1-yl radical in which the carbon atom attached to the 3-position at the butyric acid skeleton has the 1-position in the ring.

More preference is here also given to compounds of the formula (I) or salts thereof in which (R$^2$)$_n$ represents 3-chloro, 4-chloro, 2-fluoro, 3-fluoro, 4-fluoro, 3-bromo, 4-bromo, 3-cyano, 4-cyano, 3-nitro, 2,3-difluoro, 2,4-difluoro, 2,5-difluoro, 2,6-difluoro, 3,4-difluoro, 3,5-difluoro, 3,4,5-trifluoro, 3,4-dichloro, 3,5-dichloro, (3-Cl-2-F), (3-Cl-4-F), (3-Cl-5-F), (3-Cl-6-F), (4-Cl-2-F), (4-Cl-3-F), (3-Br-4-F), (3-CN-4-F), (4-Br-3-F).

Particular preference is given to the substitution patterns in Table 1.

Very particularly preferred substitution patterns are:

Compounds of the formula (I) or salts thereof in which (R$^2$)$_n$ represents 3-chloro.

Compounds of the formula (I) or salts thereof in which (R$^2$)$_n$ represents 3-fluoro.

Compounds of the formula (I) or salts thereof in which (R$^2$)$_n$ represents 3,4-difluoro.

Compounds of the formula (I) or salts thereof in which (R$^2$)$_n$ represents (3-Cl-4-F).

Compounds of the formula (I) or salts thereof in which (R$^2$)$_n$ represents (4-Cl-3-F).

Compounds of the formula (I) or salts thereof in which (R$^2$)$_n$ represents (3-Br-4-F).

Compounds of the formula (I) or salts thereof in which (R$^2$)$_n$ represents (3-CN-4-F).

Compounds of the formula (I) or salts thereof in which (R$^2$)$_n$ represents (4-Br-3-F).

Preference is also given to compounds (I) in which (R$^{2''}$)$_m$ represents m substituents R$^{2''}$, where R$^{2''}$, if m=1, or each of the substituents R$^{2''}$, if m is greater than 1, independently of the others represents halogen, cyano, nitro, hydroxy, ($C_2$-$C_8$)-alkyl, ($C_2$-$C_6$)-alkenyl, ($C_3$-$C_6$)-cycloalkenyl, ($C_3$-$C_6$)-cycloalkyl-($C_1$-$C_8$)-alkyl, ($C_3$-$C_6$)-cycloalkenyl-($C_1$-$C_8$)-alkyl, ($C_2$-$C_6$)-alkynyl, ($C_2$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-

$C_6$)-haloalkyl, ($C_1$-$C_6$)-haloalkoxy, ($C_1$-$C_6$)-haloalkyl-thio, ($C_1$-$C_6$)-haloalkylsulphinyl, ($C_1$-$C_6$)-haloalkylsulphonyl, ($C_2$-$C_6$)-haloalkenyl, ($C_2$-$C_6$)-haloalkynyl, ($C_1$-$C_6$)-alkoxy-($C_1$-$C_4$)-alkyl, ($C_1$-$C_6$)-alkoxy-($C_1$-$C_4$)-alkoxy, ($C_1$-$C_6$)-haloalkoxy-($C_1$-$C_4$)-alkyl, ($C_1$-$C_6$)-haloalkoxy-($C_1$-$C_4$)-alkoxy, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)OR$^{3''}$, C(O)NR$^{4''}$R$^{5''}$, C(O)-Het$^{2''}$, NR$^{6''}$R$^{7''}$ or Het$^{3''}$ R$^{3''}$ represents hydrogen, ($C_1$-$C_6$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the group M mentioned below, R$^{4''}$, R$^{5''}$, R$^{6''}$ and R$^{7''}$ independently of one another each represent hydrogen, ($C_1$-$C_6$)-alkyl, ($C_2$-$C_6$)-alkenyl or ($C_2$-$C_6$)-alkynyl, where each of the 3 last-mentioned radicals independently of the others is unsubstituted or substituted by one or more radicals from the group consisting of halogen, nitro, cyano and phenyl which is optionally substituted, or ($C_3$-$C_6$)-cycloalkyl or phenyl, where each of the 2 last-mentioned radicals in each case independently of the other is unsubstituted or substituted by one or more radicals from the group consisting of halogen, nitro, cyano, ($C_1$-$C_4$)-alkyl, ($C_1$-$C_4$)-haloalkyl, phenyl and benzyl, where each of the 2 last-mentioned radicals is optionally substituted, Het$^{2''}$ and Het$^{3''}$ independently of one another each represent a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio and oxo, M represents an equivalent of a cation, m represents 1, 2, 3, 4 or 5, preferably 1, 2 or 3.

More preference is given to compounds of the formula (I) or salts thereof in which (R$^{2''}$)$_m$ represents m substituents R$^{2''}$, where R$^{2''}$, if m=1, or each of the substituents R$^{2''}$, if m is greater than 1, independently of the others represents fluorine, chlorine, bromine, iodine, cyano, nitro, ($C_2$-$C_8$)-alkyl which is in each case unsubstituted or substituted by at least one substituent selected from the group consisting of fluorine, chlorine, bromine, cyano and nitro, or ($C_2$-$C_8$)-alkoxy, and m represents 1, 2, 3 or 4.

More particular preference is given to compounds of the formula (I) or salts thereof in which (R$^{2''}$)$_m$ represents m substituents R$^2$, where R$^{2''}$, if m=1, or each of the substituents R$^{2''}$, if m is greater than 1, independently of the others represents fluorine, chlorine, bromine, iodine, cyano, nitro, ($C_2$-$C_4$)-alkyl which is in each case unsubstituted or substituted by at least one substituent selected from the group consisting of fluorine, chlorine, bromine, cyano and nitro, or ($C_2$-$C_4$)-alkoxy, and m represents 1, 2, 3 or 4.

More very particular preference is given to compounds of the formula (I) or salts thereof in which (R$^2$)$_m$ represents m substituents R$^{2''}$, where R$^{2''}$, if m=1, or each of the substituents R$^{2''}$, if m is greater than 1, independently of the others represents fluorine, chlorine, bromine, iodine, cyano, nitro, trifluoromethyl, trifluoromethoxy or difluoromethoxy, and m represents 1, 2 or 3.

Most preference is given to compounds of the formula (I) or salts thereof in which (R$^{2''}$)$_m$ represents m substituents R$^{2''}$, where R$^{2''}$, if m=1, or each of the substituents R$^{2''}$, if m is greater than 1, independently of the others represents fluorine, chlorine, bromine, cyano, nitro, or trifluoromethyl, and m represents 1 or 2.

Preferred, particularly preferred and especially preferred compounds according to the invention also include the compounds according to the invention mentioned in the experimental section, in particular the compounds mentioned in Tables Z1 and Z2.

The invention also includes all tautomers, such as keto and enol tautomers, and their mixtures and salts, if appropriate functional groups are present.

The compounds of the formula (I) and (Ia) according to the invention can be prepared by various alternative processes.

In the processes below, in some cases solvents are employed. In this context, "inert solvents" refers in each case to solvents which are inert under the particular reaction conditions, but which do not have to be inert under any reaction conditions.

In the processes below, the reactions described can alternatively also be carried out in a microwave oven.

The present invention also provides processes for preparing the compounds of the general formula (I) and/or their salts. This includes processes carried out analogously to known methods.

To prepare the compounds of the formula (I), it is possible to use initially the corresponding diastereomer mixtures in the form of their racemic mixtures. The preparation of the diastereomer mixtures of the cyanobutyrates is known in principle (see EP-A-5341, EP-A-266725, EPA 270830, JP 04/297454, JP 04/297455, JP 05/058979, WO 2011/003775, WO 2011/003776, WO 2011/042378, WO 2011/073143 and WO2011/098417 and also WO 2012/126764 A1 and WO 2012/126765 A1).

Analogously to the synthesis routes described in the publications cited, the compounds can be prepared by standard processes of organic chemistry.

Diastereomer mixtures of the compounds of the formula (I) comprising the compound (I) to be prepared are obtained, for example, in that (a) compounds of the formula (II) ("cyanomethylbenzenes"/"phenylacetonitriles")

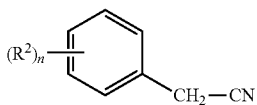

(II)

are reacted with compounds of the formula (III) (cinnamic acid derivatives) or salts thereof

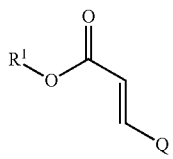

(III)

to give compounds of the formula (I') (diastereomers/racemic)

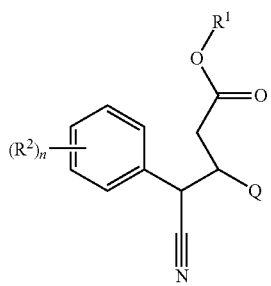

(I)

where $R^1$, $R^2$, Q and n in the compounds (II) and (III) are as defined in the respective compound of the general formula (I) to be prepared.

The starting materials of the formula (II) and the formula (III) required for preparing compounds of the formula (I) are known from the literature cited or can be prepared analogously to the literature cited.

The reaction according to variant (a) can be carried out, for example, according to methods and under conditions like those known for Michael additions. The reaction is carried out, for example, at temperatures of from −100° C. to 150° C., preferably from −78° C. to 100° C., in an organic or inorganic solvent, generally in the presence of a base or a catalyst or both [see also J. Chem. Soc. (1945), p. 438).

Suitable solvents are, for example, organic solvents such as:

aliphatic hydrocarbons such as pentane, hexane, cyclohexane or petroleum ether;
aromatic hydrocarbons such as toluene, o-, m- or p-xylene,
halogenated hydrocarbons such as methylene chloride, chloroform or chlorobenzene,
ethers, such as diethyl ether, diisopropyl ether, tert-butyl methyl ether, dioxane, anisole and tetrahydrofuran (THF),
nitriles such as acetonitrile or propionitrile,
ketones such as acetone, methyl ethyl ketone, diethyl ketone and tert-butyl methyl ketone,
alcohols such as methanol, ethanol, n-propanol, isopropanol, n-butanol and tert-butanol, and also
dimethyl sulphoxide, dimethylformamide, dimethylacetamide, sulpholane,
mixtures of the organic solvents mentioned.

In individual cases, it is also appropriate to use inorganic solvents such as water or mixtures of organic solvents with water.

Preferred solvents are THF and methanol and mixtures thereof with other organic solvents.

The reaction by preparation variant (a) is preferably carried out in the presence of a base, for example from the group of the inorganic compounds such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7ene (DBU).

Preferred organic bases are, for example, potassium tert-butoxide, lithium bis(trimethylsilyl)amide or 7-methyl-1,5,7-triazabicyclo[4.4.0]-dec-5-ene or 1,8-diazabicyclo[5.4.0] undec-7-ene (DBU).

The amount of base may generally be varied within wide limits. For example, it may be expedient to employ the base in catalytic amounts, in substoichiometric amounts, in equimolar amounts or in excess. A preferably liquid organic base may optionally also be used as solvent.

Suitable catalysts for the Michael addition according to variant (a) are acidic catalysts, for example from the group of the inorganic acids, for example Broensted acids, such as hydrofluoric acid, hydrochloric acid, hydrobromic acid, sulphuric acid or perchloric acid, or Lewis acids, such as boron trifluoride, aluminium trichloride, iron(III) chloride, tin(IV) chloride, titanium(IV) chloride, scandium(III) triflate or zinc(II) chloride, and also organic acids, for example formic acid, acetic acid, propionic acid, oxalic acid, toluenesulphonic acid, benzenesulphonic acid, camphorsulphonic acid, citric acid or trifluoroacetic acid.

The amount of acidic catalyst may generally be varied within wide limits. For example, it may be expedient to employ the acid in catalytic amounts, in substoichiometric amounts, in equimolar amounts or in excess. A preferably liquid acid may optionally also be used as solvent.

Variant (a1) for the preparation of intermediates of the formula (III):

Compounds of the formula (III) and their salts are also obtained, for example, by process [variant (a1)], characterized in that an aldehyde of the formula (IV) is reacted with phosphorylides of the formula (V) to give compounds (III) (Wittig reaction), where in the formula (V) the radical R represents a hydrocarbon radical, preferably $(C_1-C_6)$-alkyl, in particular methyl or ethyl. Instead of the phosphorylides (V), is also possible to use the corresponding phosphonate carbanions (Wittig-Horner reaction) in variant (a1).

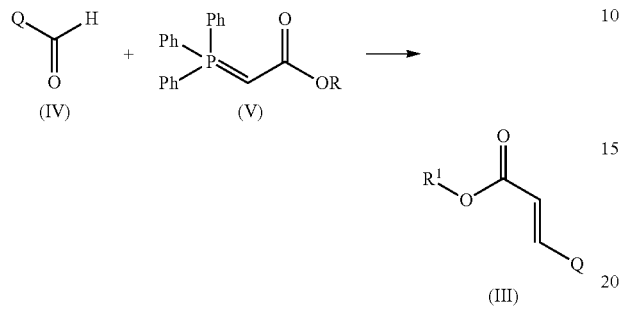

Wittig or Wittig-Horner reactions according to variant (a1) are known in principle to the person skilled in the art and described, for example, in *Journal of Heterocyclic Chemistry*, 1985, 22, 65-69; *Archiv der Pharmazie* (Weinheim, Germany), 1986, vol. 319, 4, 366-372; *Journal of Medicinal Chemistry*, 2002, 45, 16, 3549-3557; US2005/234033 A1, 2005; *Journal of Medicinal Chemistry*, 2007, 50, 25, 6303-6306; *Bioorganic and Medicinal Chemistry*, 2010, 18, 14, 5323-5338; *Journal of Medicinal Chemistry*, 2010, 53, 2, 787-797 and in the literature cited therein.

Diastereomer mixtures or racemic diastereomers of the compounds of the formula (I) can also be obtained according to variant (b) by transesterification, characterized in that (b) compounds of the formula (I*)

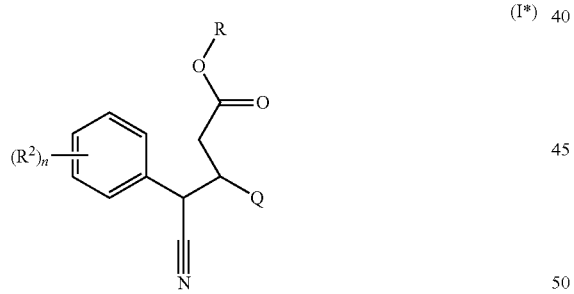

in which R represents a radical from the group of radicals possible for $R^1$ but is different from the radical $R^1$ in the compound (I) to be prepared are reacted with a compound of the formula $R^1$—OH in which $R^1$ is as defined in formula (I), to give the compound (I) where $R^2$, Q and n in the compound (I*) are as defined in the respective compound of the formula (I) to be prepared.

In a particular embodiment, according to variant (c) it is also possible to obtain, as compounds (I), stereochemically enriched compounds of the abovementioned formula (Ia), where variant (c) is characterized in that (c) stereochemically enriched compounds of the formula (Ia*), which correspond stereochemically (i.e. are at least as enriched as in the desired compound (Ia))

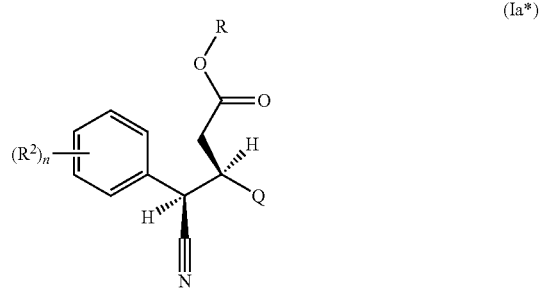

in which R is a radical from the group of the intended radicals possible for $R^1$, but different from the radical $R^1$ in the compound (Ia) to be prepared, is reacted with a compound of the formula $R^1$—OH in which $R^1$ is defined as in the compound of the formula (Ia) to be prepared.

The transesterifications (b) and (c) can be carried out, for example, using a suitable alcohol $R^1$—OH in the presence of a catalyst, optionally in the presence of an aprotic solvent.

Furthermore, in general, those conditions are advantageous where the chemical equilibrium is shifted to the side of the desired product, for example using a large excess of the alcohol $R^1$—OH under virtually anhydrous conditions, for example in the presence of a molecular sieve.

The reactions (transesterifications) can generally be carried out at temperatures of from 0° C. to 180° C., preferably from 20° C. to 100° C., in the presence of a Lewis or Broenstedt acid or an enzyme [cf. J. Org. Chem. 2002, 67, 431].

Suitable solvents are, for example, the following organic aprotic solvents:
  aliphatic hydrocarbons such as pentane, hexane, cyclohexane or petroleum ether;
  aromatic hydrocarbons such as toluene, o-, m- or p-xylene,
  halogenated hydrocarbons such as methylene chloride (dichloromethane), chloroform or chlorobenzene,
  ethers, such as diethyl ether, diisopropyl ether, tert-butyl methyl ether, dioxane, anisole or tetrahydrofuran (THF),
  nitriles such as acetonitrile or propionitrile,
  ketones such as acetone, methyl ethyl ketone, diethyl ketone and tert-butyl methyl ketone,
  dimethyl sulphoxide, dimethylformamide, dimethylacetamide or sulpholane or
  mixtures of the organic solvents mentioned.

The preferred solvent is the alcohol $R^1$—OH, which is at the same time used as reaction partner for the transesterification, optionally in combination with one of the aprotic organic solvents mentioned.

Alcohol is not included in the list of the aprotic solvents and is therefore to be considered more of an "alternative solvent".

Alternatively, it is also possible to obtain the desired ester from another ester in two steps by acidic or basic hydrolysis of the other esters to the free acid, i.e. to compounds (I*) or (Ia*), in which R is in each case H, and subsequent esterification with an alcohol $R^1$—OH.

The preparation of diastereomer mixtures or racemic diastereomers of the formula (I) according to variant (d) or optically active compounds (Ia) according to variant (e) is therefore characterized in that a free acid of the abovementioned formula (I*) or the formula (Ia*) in which the radicals R are each hydrogen is esterified with an alcohol of the formula R¹—OH by customary methods, if appropriate combined with a previous preparation (d-1) or (e-1) of the free acid from another ester of the formula (I*) or the formula (Ia*) in which the radicals R are each not hydrogen.

The esterification from the free acid of the formula (I*)/R=H or (Ia*)/R=H can be carried out, for example, analogously to customary methods, for example at temperatures of from 0° C. to 120° C., preferably from 20° C. to 50° C., optionally in the presence of a catalyst, in a substantially anhydrous medium or under conditions where the water including the water formed during the esterification is bound or otherwise removed. Suitable catalysts are anhydrous acids and bases, preferably organic acids or bases; see handbooks for chemical processes for esterifying carboxylic acids; see also, for example, J. Am. Chem. Soc. 2007, 129 (43), 13321; J. Org. Chem. 1984, 49 (22), 4287.

Suitable solvents for the esterification are the aprotic organic solvents mentioned above for process variants (b) and (c), including the alcohol R¹—OH which is at the same time used as a reaction partner for the esterification, optionally in combination with one of the aprotic organic solvents mentioned.

Suitable catalysts for the esterification are the bases or acidic or basic catalysts mentioned for process variant (a) (Michael addition), in anhydrous form or with a water content which is as low as possible. Preferred catalysts are the bases lithium hydroxide, potassium carbonate or organic amines such as pyridines, subsituted pyridines and DBU.

Any hydrolysis carried out before the esterification [process variants (d-1) and (e-1)] of other esters of the formula (I*) or the formula (Ia*), where R is in each case not H, can be carried out analogously to customary methods, for example at temperatures of from 0° C. to 120° C., preferably from 20° C. to 50° C., if appropriate in the presence of a catalyst, in a water-containing medium/solvent; see handbooks on chemical processes for hydrolysing carboxylic esters; see also, for example, J. Am. Chem. Soc. 2007, 129 (43), 13321; J. Org. Chem. 1984, 49 (22), 4287.

A suitable solvent for the hydrolysis, i.e. process variants (d-1) and (e-1), is water or a water-containing organic solvent, for example the organic solvent mentioned based on process variant (a) mentioned (Michael addition), preferably water or polar organic solvents containing water, such as THF.

Suitable catalysts for the hydrolysis are the acids, bases or acidic or basic catalysts mentioned for process variant (a) (Michael addition), in each case containing water. Preferred catalysts are aqueous acids and bases, in particular bases such as lithium hydroxide, sodium hydroxide, potassium carbonate, pyridines, substituted pyridines and DBU in the presence of organic solvents.

The catalysts for the esterification or the hydrolysis can generally be employed in catalytic amounts. In general, it is also possible to use relatively large amounts including equimolar amounts and a molar excess. Frequently, a use as solvent is also possible.

The reaction mixtures are worked up in a customary manner, for example by mixing with water, separating the phases and, if appropriate, chromatographic purification of the crude products. Some of the intermediates and end products are obtained in the form of colourless or slightly brownish viscous oils which are purified or freed from volatile components under reduced pressure and at moderately elevated temperature.

If the intermediates and end products are obtained as solids, the purification can also be carried out by recrystallization or digestion. If individual compounds (I) or (Ia) cannot be obtained by the routes described above, they can be prepared by derivatization of other compounds (I) or (Ia).

To prepare the threo compounds or optically active threo compounds (Ia) according to the invention from the diastereomer mixtures of the compounds (I), it is necessary to enrich the threo isomer or the stereoisomer (enantiomer) threo-2 from the mixture of the stereoisomers in an appropriate manner. Accordingly, an expedient process comprises the initial isolation of the threo isomers threo-1 and threo-2 from the diastereomer mixture of the compounds of the formula (I) which still comprises the erythro isomers, and the optional subsequent optical resolution with isolation or enrichment of the enantiomer threo-2 from the mixture with the enantiomer threo-1.

The isolation of the threo isomers as a racemic mixture can be carried out analogously to the customary separation and purification processes mentioned above (diastereomer separation).

Suitable for the subsequent preparation of compounds of the formula (Ia) are methods for optical resolution generally known to the person skilled in the art from analogous cases (cf. handbooks of stereochemistry), for example following processes for separating mixtures into diastereomers, for example by physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the diastereomer mixtures using optically active acids and, if appropriate, provided that acidic groups are present, using optically active bases.

Optically active acids which are suitable for optical resolution by crystallization of diastereomeric salts are, for example, camphorsulphonic acid, camphoric acid, bromocamphorsulphonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystallizate, by acidification or using a base.

Accordingly, the invention also provides the process for preparing the compounds (Ia), characterized in that compounds (I) or the threo compounds of the formula (I) are subjected to an optical resolution and the compound (Ia) is isolated in a stereochemical purity of from 60 to 100%, preferably from 70 to 100%, more preferably from 80 to 100%, in particular from 90 to 100%, based on the mixture of threo enantiomers present.

As an alternative to the optical resolution methods mentioned, enantioselective processes starting with stereochemically pure starting materials are in principle also suitable for preparing the threo-2 enantiomers (Ia).

The following acids are generally suitable for preparing the acid addition salts of the compounds of the formula (I): hydrohalic acids, such as hydrochloric acid or hydrobromic acid, furthermore phosphoric acid, nitric acid, sulphuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulphonic acids, such as p-toluenesulphonic acid and 1,5-naphthalenedisulphonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R"R"']$^+$OH$^-$.

What is meant by the "inert solvents" referred to in the above process variants are in each case solvents which are inert under the particular reaction conditions but need not be inert under all reaction conditions.

Collections of compounds of the formula (I) which can be synthesized by the aforementioned process can also be prepared in a parallel manner, it being possible for this to take place in a manual, partly automated or completely automated manner. In this connection, it is possible to automate the reaction procedure, the work-up or the purification of the products and/or intermediates. Overall, this is understood as meaning a procedure as described, for example, by S. H. DeWitt in "Annual Reports in Combinatorial Chemistry and Molecular Diversity: Automated Synthesis", Volume 1, Verlag Escom, 1997, pages 69 to 77.

For the parallelized reaction procedure and work-up it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleißheim, Germany. For the parallel purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described, the preparation of compounds of the formula (I) can take place completely or partially by solid-phase-supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example Barry A. Bunin in "The Combinatorial Index", Academic Press, 1998.

The use of solid-phase-supported synthesis methods permits a number of protocols, which are known from the literature and which for their part may be performed manually or in an automated manner. For example, the "teabag method" (Houghten, U.S. Pat. No. 4,631,211; Houghten et al., Proc. Natl. Acad. Sci, 1985, 82, 5131-5135) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The compounds of the formula (I) according to the invention (and/or their salts), above and hereinbelow also referred to together as "compounds according to the invention", "compounds (I) according to the invention" or in short as "compounds (I)", have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds), to the soil in or on which the plants grow (for example the soil of cropland or non-cropland) or to the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though there is no intention to restrict the enumeration to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca,*

*Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then they stop growing and ultimately die completely after three to four weeks have passed.

The compounds of the formula (I) according to the invention and/or their salts were found to be highly effective in the control of harmful plants such as *Alopecurus myosuroides, Avena fatua, Cyperus esculentus, Echinochloa crus-galli, Lolium multiflorum, Setaria viridis, Abutilon theophrasti, Amaranthus retroflexus, Matricaria inodora* (=*Tripleurospermum maritimum* subsp. inodorum), *Pharbitis purpurea, Polygonum convolvulus* (=*Fallopia convolvulus*), *Stellaria media, Viola tricolor, Veronica persica*, and *Pharbitis purpurea*.

The compounds according to the invention showed particularly good herbicidal activity against *Alopecurus myosuroides, Avena fatua, Echinochloa crus-galli, Lolium multiflorum, Setaria viridis, Amaranthus retroflexus, Pharbitis purpurea, Polygonum convolvulus, Viola tricolor* and *Veronica persica*.

If the active compounds are applied post-emergence to the green parts of the plants, growth stops after the treatment, and the harmful plants remain at the growth stage of the time of application, or they die completely after a certain time, such that competition by the weeds, which is harmful to the crop plants, is thus eliminated very early and in a lasting manner.

Although the compounds according to the invention have outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, will be damaged to a negligible extent only, if at all, depending on the structure of the particular compound according to the invention and its application rate. For these reasons, the present compounds are very suitable for selective control of unwanted plant growth in plant crops such as agriculturally useful plants or ornamental plants.

In addition, the compounds according to the invention (depending on their particular structure and the application rate deployed) have outstanding growth-regulating properties in crop plants. They intervene in the plants' own metabolism with regulatory effect, and can thus be used for controlled influencing of plant constituents and to facilitate harvesting, for example by triggering desiccation and stunted growth. Furthermore, they are also suitable for the general control and inhibition of unwanted vegetative growth without killing the plants in the process Inhibition of vegetative growth plays a major role for many mono- and dicotyledonous plants since, for example, this can reduce or completely prevent lodging.

By virtue of their herbicidal and plant growth regulatory properties, the active compounds can also be used to control harmful plants in crops of genetically modified plants or plants modified by conventional mutagenesis. In general, transgenic plants are notable for particular advantageous properties, for example for resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred with a view to transgenic crops to use the compounds according to the invention and/or their salts in economically important transgenic crops of useful plants and ornamentals, for example of cereals such as wheat, barley, rye, oats, millet, rice and maize or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant growth regulatory properties, the active compounds can also be used to control harmful plants in crops of genetically modified plants which are known or are yet to be developed. In general, the transgenic plants are notable for particular advantageous properties, for example for resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material. Other particular properties may be tolerance or resistance to abiotic stressors, for example heat, low temperatures, drought, salinity and ultraviolet radiation.

It is preferred to use the compounds of the formula (I) according to the invention or salts thereof in economically important transgenic crops of useful plants and ornamental plants, for example of cereals such as wheat, barley, rye, oats, sorghum and millet, rice, cassava and maize or else crops of sugar beet, cotton, soybean, oilseed rape, potato, tomato, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP-A-0221044, EP-A-0131624). For example, there have been descriptions in several cases of:

genetic modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulphonylureas (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants having reduced photorespiration, which have higher yields and higher stress tolerance (EPA 0305398), transgenic crop plants which produce pharmaceutically or diagnostically important proteins ("molecular pharming")

transgenic crop plants which feature higher yields or better quality, transgenic crop plants which feature a combination, for example, of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

For such recombinant manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulphonylureas, glyphosate, glufosinate or benzoylisoxazoles and analogous active compounds.

When the active compounds according to the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants.

Preference is given to the use by the pre- or post-emergence method in cereals such as wheat, barley, rye, oats, millet and rice, in particular in wheat by the post-emergence method.

Preference is also given to the use by the pre- or post-emergence method in maize, in particular by the pre-emergence method in maize Preference is also given to the use by the pre- or post-emergence method in soybeans, in particular by the post-emergence method in soybeans.

The use according to the invention for the control of harmful plants or for growth regulation of plants also includes the case in which the active compound of the formula (I) or its salt is not formed from a precursor substance ("prodrug") until after application on the plant, in the plant or in the soil.

The invention also provides the method (application method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd ed., Darland Books, Caldwell N.J.; H.v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Engineering], volume 7, C. Hanser Verlag Munich, 4th ed. 1986.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyethoxylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurate. To produce the wettable powders, the herbicidally active compounds are finely ground, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: alkylarylsulphonic calcium salts, such as
calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dustable powders are obtained by grinding the active compound with finely distributed solid substances, for example talc, natural clays such as kaolin, bentonite and pyrophyllite, or diatomaceous earth. Suspension concentrates may be water- or oil-based. They may be prepared, for example, by wet-grinding by means of commercial bead mills and optional addition of surfactants as have, for example, already been listed above for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be prepared either by spraying the active compound onto adsorptive granular inert material or by applying active compound concentrates to the surface of carriers, such as sand, kaolinites or granular inert material, by means of adhesives, for example polyvinyl alcohol, sodium polyacrylates or else mineral oils. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formula (I) and/or salts thereof.

In wettable powders, the active compound concentration is, for example, about 10 to 90% by weight, the remainder to 100% by weight consisting of customary formulation constituents. In emulsifiable concentrates, the active compound concentration may be about 1 to 90% and preferably 5 to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2006 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. These include, by way of example, one use form and in some cases also a plurality of use forms:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulphuron, aminocyclopyrachlor, aminocyclopyrachlor-potassium, aminocyclopyrachlor-methyl, aminopyralid, amitrole, ammonium sulphamate, ancymidol, anilofos, asulam, atrazine, azafenidin, azimsulphuron, aziprotryne, beflubutamid, benazolin, benazolin-ethyl, bencarbazone, benfluralin, benfuresate, bensulide, bensulphuron, bensulphuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulphuron, cinidon, cinidon-ethyl, cinmethylin, cinosulphuron, clethodim, clodinafop, clodinafop-propargyl, clofencet, clofencet-potassium, clomazone, clomeprop, cloprop, clopyralid, cloransulam, cloransulam-methyl, cumyluron, cyanamide, cyanazine, cyclanilide, cycloate, cyclosulphamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulphuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulphuron, ethametsulphuron-methyl, ethephon, ethidimuron, ethiozin, ethofumesate, ethoxyfen, ethoxyfen-ethyl, ethoxysulphuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulphonamide, F-7967, i.e. 3-[7-chloro-5-fluoro-2-(trifluoromethyl)-1H-benzimidazol-4-yl]-1-methyl-6-(trifluoromethyl)pyrimidine-2,4 (1H,3H)-dione, fenoprop, fenoxaprop, fenoxaprop-P, fenoxaprop-ethyl, fenoxaprop-P-ethyl, fenoxasulphone, fentrazamide, fenuron, flamprop, flamprop-M-isopropyl, flamprop-M-methyl, flazasulphuron, florasulam, fluazifop, fluazifop-P, fluazifop-butyl, fluazifop-P-butyl, fluazolate, flucarbazone, flucarbazone-sodium, flucetosulphuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulphuron, flupyrsulphuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulphuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulphuron, halosulphuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl(2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulphuron, inabenfide, indanofan, indaziflam, indoleacetic acid (IAA), 4-indol-3-ylbutyric acid (IBA), iodosulphuron, iodosulphuron-methyl-sodium, iofensulphuron, iofensulphuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]
methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulphuron, mesosulphuron-methyl, mesotrione, methabenzthiazuron, metam, metamifop, metamitron, metazachlor, metazasulphuron, methazole, methiopyrsulphuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulphuron, metsulphuron-methyl, molinate, monalide, monocarbamide, monocarbamide dihydrogensulphate, monolinuron, monosulphuron, monosulphuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulphuron, nipyraclofen, nitralin, nitrofen, nitrophenolate-sodium (isomer mixture), nitrofluorfen, nonanoic acid, norflurazon, orbencarb, orthosulphamuron, oryzalin, oxadiargyl, oxadiazon, oxasulphuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulphuron, primisulphuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulphuron, propyzamide, prosulphalin, prosulphocarb, prosulphuron, prynachlor, pyraclonil, pyraflufen, pyraflufen-ethyl, pyrasulphotole, pyrazolynate (pyrazolate), pyrazosulphuron, pyrazosulphuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulphan, pyrithiobac, pyrithiobac-sodium, pyroxasulphone, pyroxsulam, quinclorac, quinmerac, quinoclamine, quizalofop, quizalofop-ethyl, quizalofop-P, quizalofop-P-ethyl, quizalofop-P-tefuryl, rimsulphuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulphallate (CDEC), sulphentrazone, sulphometuron, sulphometuron-methyl, sulphosate (glyphosate-trimesium), sulphosulphuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulphuron, thifensulphuron-methyl, thiobencarb, tiocarbazil, topramezone, tralkoxydim, triafamone, triallate, triasulphuron, triaziflam, triazofenamide, tribenuron, tribenuron-methyl, trichloroacetic acid (TCA), triclopyr, tridiphane, trietazine, trifloxysulphuron, trifloxysulphuron-sodium, trifluralin, triflusulphuron, triflusulphuron-methyl, trimeturon, trinexapac, trinexapac-ethyl, tritosulphuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

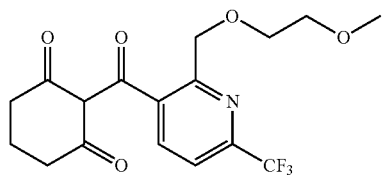

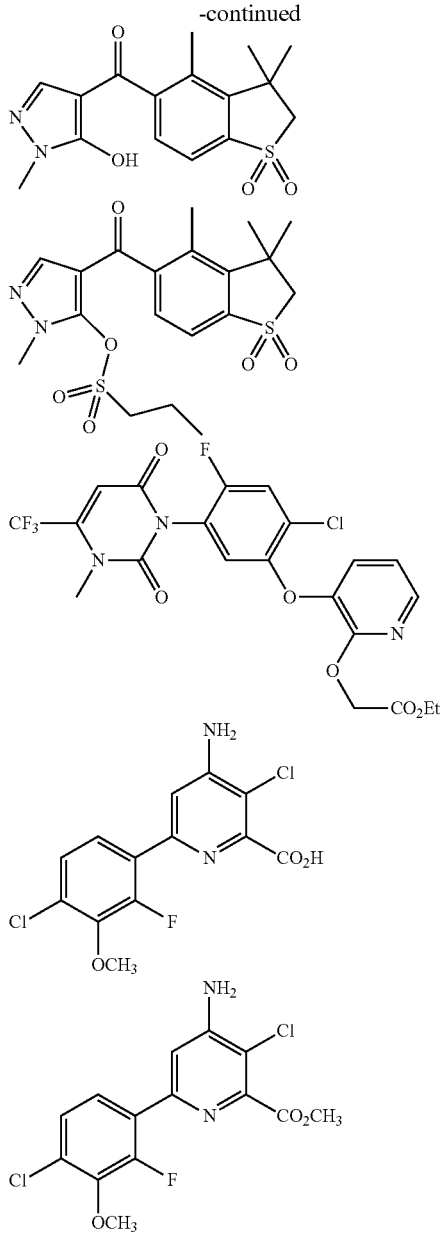

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners.

The safeners, which are used in an antidotically effective amount, reduce the phytotoxic side effects of the herbicides/pesticides employed, for example in economically important crops, such as cereals (wheat, barley, rye, maize, rice, millet), sugar beet, sugar cane, oilseed rape, cotton and soybeans, preferably cereals. The following groups of compounds are, for example, suitable for use as safeners for the compounds (I) and their combinations with further pesticides, including the stereoisomers possible in each case of the safeners, and including the agriculturally customary salts:

S1) compounds of the formula (S1)

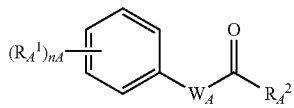
(S1)

where the symbols and indices are defined as follows:

$n_A$ is a natural number from 0 to 5, preferably from 0 to 3;
$R_A^1$ is halogen, $(C_1-C_4)$-alkyl, $(C_1-C_4)$-alkoxy, nitro or $(C_1-C_4)$-haloalkyl;
$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$;

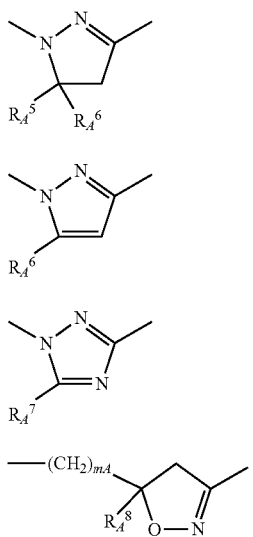

$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;
$R_A^3$ is hydrogen or an unsubstituted or substituted aliphatic hydrocarbon radical preferably having a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ is hydrogen, $(C_1-C_8)$-alkyl, $(C_1-C_8)$-haloalkyl, $(C_1-C_4)$-alkoxy-$(C_1-C_4)$-alkyl, hydroxyalkyl, $(C_3-C_{12})$-cycloalkyl or tri-$(C_1-C_4)$-alkylsilyl;
$R_A^6$, $R_A^7$, $R_A^8$ are identical or different and are each hydrogen, $(C_1-C_8)$-alkyl, $(C_1-C_8)$-haloalkyl, $(C_3-C_{12})$-cycloalkyl or substituted or unsubstituted phenyl;

preferably:
a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;
b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;
c) derivatives of 1,5-diphenylpyrazole-3-carboxylic acid (S1$^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;
d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;
e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

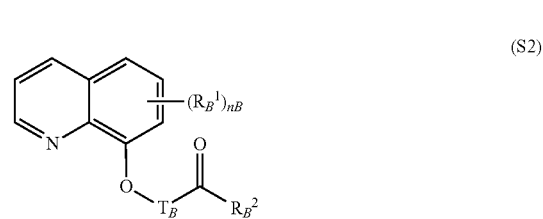
(S2)

where the symbols and indices are defined as follows:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably from 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ is hydrogen or an unsubstituted or substituted aliphatic hydrocarbon radical preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a ($C_1$ or $C_2$)-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type (S2$^a$), preferably
  1-methylhexyl(5-chloro-8-quinolinoxy)acetate ("cloquintocet-mexyl") (S2-1),
  1,3-dimethylbut-1-yl(5-chloro-8-quinolinoxy)acetate (S2-2),
  4-allyloxybutyl(5-chloro-8-quinolinoxy)acetate (S2-3),
  1-allyloxyprop-2-yl(5-chloro-8-quinolinoxy)acetate (S2-4),
  ethyl(5-chloro-8-quinolinoxy)acetate (S2-5),
  methyl 5-chloro-8-quinolinoxyacetate (S2-6),
  allyl(5-chloro-8-quinolinoxy)acetate (S2-7),
  2-(2-propylideneiminoxy)-1-ethyl(5-chloro-8-quinolinoxy)acetate (S2-8), 2-oxoprop-1-yl(5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminium, iron, ammonium, quaternary ammonium, sulphonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl(5-chloro-8-quinolinoxy)malonate, methyl ethyl(5-chloro-8-quinolinoxy)malonate and related compounds, as described in EP-A-0 582 198.

S3) Compounds of the formula (S3)

(S3)

where the symbols and indices are defined as follows:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and are each hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

Active compounds of the dichloroacetamide type, which are frequently used as pre-emergence safeners (soil-acting safeners), for example
  "dichlormid" (N,N-diallyl-2,2-dichloroacetamide) (S3-1),
  "R-29148" (3-dichloroacetyl-2,2,5-trimethyl-1,3-oxazolidine) from Stauffer (S3-2),
  "R-28725" (3-dichloroacetyl-2,2-dimethyl-1,3-oxazolidine) from Stauffer (S3-3),
  "benoxacor" (4-dichloroacetyl-3,4-dihydro-3-methyl-2H-1,4-benzoxazine) (S3-4),
  "PPG-1292" (N-allyl-N-[(1,3-dioxolan-2-yl)methyl]dichloroacetamide) from PPG Industries (S3-5),
  "DKA-24" (N-allyl-N-[(allylaminocarbonyl)methyl]dichloroacetamide) from Sagro-Chem (S3-6),
  "AD-67" or "MON 4660" (3-dichloroacetyl-1-oxa-3-azaspiro[4.5]decane) from Nitrokemia or Monsanto (53-7),
  "TI-35" (1-dichloroacetylazepane) from TRI-Chemical RT (S3-8),
  "Diclonon" (Dicyclonon) or "BAS145138" or "LAB145138" (S3-9)
  ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10), and the (R) isomer thereof (S3-11).

S4) N-acylsulphonamides of the formula (S4) and salts thereof, (S4)

where the symbols and indices are each defined as follows:

$A_D$ is $SO_2$—$NR_D^3$-CO or CO—$NR_D^3$-$SO_2$ $X_D$ is CH or N;

$R_D^1$ is CO—$NR_D^5R_D^6$ or NHCO—$R_D^7$;

$R_D^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D^3$ is hydrogen, $(C_1-C_4)$-alkyl, $(C_2-C_4)$-alkenyl or $(C_2-C_4)$-alkynyl;

$R_D^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group of nitrogen, oxygen and sulphur, where the seven last-mentioned radicals are substituted by $v_D$ substituents from the group of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1$-

$C_4$)-alkoxycarbonyl, ($C_1$-$C_4$)-alkylcarbonyl and phenyl and, in the case of cyclic radicals, also ($C_1$-$C_4$)-alkyl and ($C_1$-$C_4$)-haloalkyl;

$R_D^6$ is hydrogen, ($C_1$-$C_6$)-alkyl, ($C_2$-$C_6$)-alkenyl or ($C_2$-$C_6$)-alkynyl, where the three last-mentioned radicals are substituted by $v_D$ radicals from the group consisting of halogen, hydroxy, ($C_1$-$C_4$)-alkyl, ($C_1$-$C_4$)-alkoxy and ($C_1$-$C_4$)-alkylthio, or $R_D^5$ and $R_D^6$ together with the nitrogen atom carrying them form a pyrrolidinyl or piperidinyl radical;

$R_D^1$ is hydrogen, ($C_1$-$C_4$)-alkylamino, di-($C_1$-$C_4$)-alkylamino, ($C_1$-$C_6$)-alkyl, ($C_3$-$C_6$)-cycloalkyl, where the 2 last-mentioned radicals are substituted by $v_D$ substituents from the group consisting of halogen, ($C_1$-$C_4$)-alkoxy, ($C_1$-$C_6$)-haloalkoxy and ($C_1$-$C_4$)-alkylthio and, in the case of cyclic radicals, also ($C_1$-$C_4$)-alkyl and ($C_1$-$C_4$)-haloalkyl;

$n_D$ is 0, 1 or 2;
$m_D$ is 1 or 2;
$v_D$ is 0, 1, 2 or 3;

among these, preference is given to compounds of the N-acylsulphonamide type, for example of the formula (S4$^a$) below, which are known, for example, from WO-A-97/45016

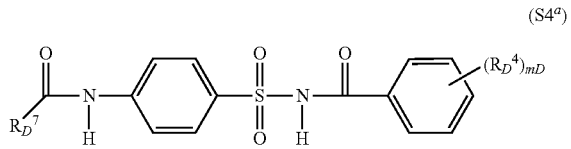

(S4$^a$)

in which
$R_D^7$ is ($C_1$-$C_6$)-alkyl, ($C_3$-$C_6$)-cycloalkyl, where the 2 latter radicals are substituted by vD substituents from the group consisting of halogen, ($C_1$-$C_4$)-alkoxy, ($C_1$-$C_6$)-haloalkoxy and ($C_1$-$C_4$)-alkylthio and, in the case of cyclic radicals, also ($C_1$-$C_4$)-alkyl and ($C_1$-$C_4$)-haloalkyl;

$R_D^4$ is halogen, ($C_1$-$C_4$)-alkyl, ($C_1$-$C_4$)-alkoxy, $CF_3$;
$m_D$ is 1 or 2;
$v_D$ is 0, 1, 2 or 3;
and
acylsulphamoylbenzamides, for example of the formula (S4$^b$) below, which are known, for example, from WO-A-99/16744,

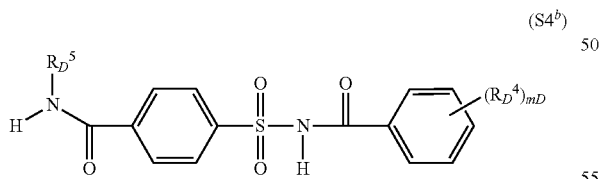

(S4$^b$)

for example those in which
$R_D^5$=cyclopropyl and ($R_D^4$)=2-OMe ("cyprosulphamide", S4-1),
$R_D^5$=cyclopropyl and ($R_D^4$)=5-Cl-2-OMe (S4-2),
$R_D^5$=ethyl and ($R_D^4$)=2-OMe (S4-3),
$R_D^5$=isopropyl and ($R_D^4$)=5-Cl-2-OMe (S4-4) and
$R_D^5$=isopropyl and ($R_D^4$)=2-OMe (S4-5)
and
compounds of the N-acylsulphamoylphenylurea type, of the formula (S4$^c$), which are known, for example, from EP-A-365484,

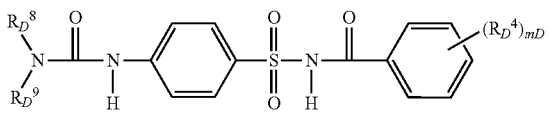

(S4$^c$)

in which
$R_D^8$ and $R_D^9$ independently of one another are hydrogen, ($C_1$-$C_8$)-alkyl, ($C_3$-$C_8$)-cycloalkyl, ($C_3$-$C_6$)-alkenyl, ($C_3$-$C_6$)-alkynyl,
$R_D^4$ is halogen, ($C_1$-$C_4$)-alkyl, ($C_1$-$C_4$)-alkoxy, $CF_3$
$m_D$ is 1 or 2;
for example
1-[4-(N-2-methoxybenzoylsulphamoyl)phenyl]-3-methylurea,
1-[4-(N-2-methoxybenzoylsulphamoyl)phenyl]-3,3-dimethylurea,
1-[4-(N-4,5-dimethylbenzoylsulphamoyl)phenyl]-3-methylurea,
and
N-phenylsulphonylterephthalamides, for example of the formula (S4$^d$) below, which are known, for example, from CN 101838227,

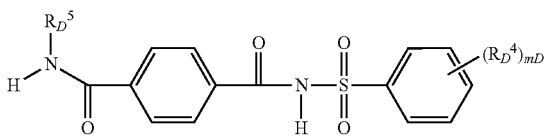

(S4$^d$)

for example those in which
$R_D^4$ is halogen, ($C_1$-$C_4$)-alkyl, ($C_1$-$C_4$)-alkoxy, $CF_3$
$m_D$ is 1 or 2;
$R_D^5$ is hydrogen, ($C_1$-$C_6$)-alkyl, ($C_3$-$C_6$)-cycloalkyl, ($C_2$-$C_6$)-alkenyl, ($C_2$-$C_6$)-alkynyl or ($C_5$-$C_6$)-cycloalkenyl.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydroquinoxalin-2-one, as described in WO-A-2005/112630.

S7) Compounds of the formula (S7), as described in WO-A-1998/38856,

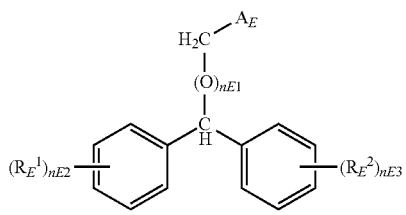

(S7)

where the symbols and indices are each defined as follows:

$R_E^1$, $R_E^2$ independently of one another are halogen, ($C_1$-$C_4$)-alkyl, ($C_1$-$C_4$)-alkoxy, ($C_1$-$C_4$)-haloalkyl, ($C_1$-$C_4$)-alkylamino, di-($C_1$-$C_4$)-alkylamino, nitro;

$A_E$ is $COOR_E^3$ or $COSR_E^4$ $R_E^3$, $R_E^4$ independently of one another are hydrogen, ($C_1$-$C_4$)-alkyl, ($C_2$-$C_6$)-alkenyl, ($C_2$-$C_4$)-alkynyl, cyanoalkyl, ($C_1$-$C_4$)-haloalkyl, phenyl, nitrophenyl, benzyl, halobenzyl, pyridinylalkyl and alkylammonium, $n_E^1$ is 0 or 1

$n_E^2$, $n_E^3$ independently of one another are 0, 1 or 2, preferably:
  diphenylmethoxyacetic acid,
  ethyl diphenylmethoxyacetate,
  methyl diphenylmethoxyacetate (CAS reg. no. 41858-19-9) (S7-1).

S8) Compounds of the formula (S8), as described in WO-A-98/27049,

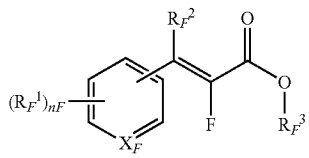

(S8)

in which $X_F$ is CH or N, $n_F$ in the case that $X_F$=N is an integer from 0 to 4 and in the case that $X_F$=CH is an integer from 0 to 5, $R_F^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy, nitro, ($C_1$-$C_4$)-alkylthio, ($C_1$-$C_4$)-alkylsulphonyl, ($C_1$-$C_4$)-alkoxycarbonyl, optionally substituted phenyl, optionally substituted phenoxy, $R_F^2$ is hydrogen or ($C_1$-$C_4$)-alkyl, $R_F^3$ is hydrogen, ($C_1$-$C_8$)-alkyl, ($C_2$-$C_4$)-alkenyl, ($C_2$-$C_4$)-alkynyl or aryl, where each of the carbon-containing radicals mentioned above is unsubstituted or substituted by one or more, preferably up to three, identical or different radicals from the group consisting of halogen and alkoxy, or salts thereof, preferably compounds in which $X_F$ is CH, $n_F$ is an integer from 0 to 2, $R_F^1$ is halogen, ($C_1$-$C_4$)-alkyl, ($C_1$-$C_4$)-haloalkyl, ($C_1$-$C_4$)-alkoxy, ($C_1$-$C_4$)-haloalkoxy, $R_F^2$ is hydrogen or ($C_1$-$C_4$)-alkyl, $R_F^3$ is hydrogen, ($C_1$-$C_8$)-alkyl, ($C_2$-$C_4$)-alkenyl, ($C_2$-$C_4$)-alkynyl, or aryl, where each of the aforementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example
  1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS reg. no. 95855-00-8), as described in WO-A-1999/000020.

S10) Compounds of the formula (S10$^a$) or (S10$^b$)
  as described in WO-A-2007/023719 and WO-A-2007/023764

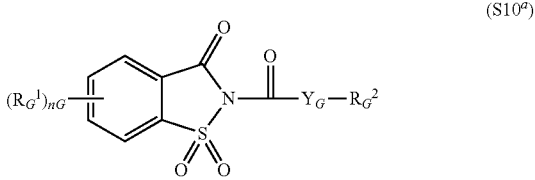

(S10$^a$)

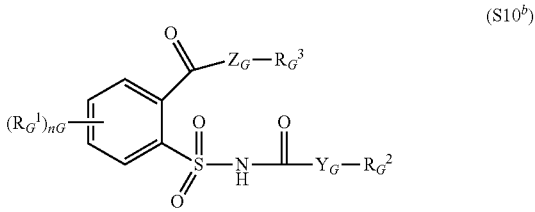

(S10$^b$)

in which $R_G^1$ is halogen, ($C_1$-$C_4$)-alkyl, methoxy, nitro, cyano, $CF_3$, $OCF_3$, $Y_G$, $Z_G$ independently of one another are O or S, $n_G$ is an integer from 0 to 4, $R_G^2$ is ($C_1$-$C_{16}$)-alkyl, ($C_2$-$C_6$)-alkenyl, ($C_3$-$C_6$)-cycloalkyl, aryl; benzyl, halobenzyl, $R_G^3$ is hydrogen or ($C_1$-$C_6$)-alkyl.

S11) Active compounds of the oxyimino compound type (S11), which are known as seed-dressing agents, for example
  "oxabetrinil" ((Z)-1,3-dioxolan-2-ylmethoxyimino(phenyl)acetonitrile) (S11-1), which is known as a seed-dressing safener for millet/sorghum against metolachlor damage,
  "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and
  "cyometrinil" or "CGA-43089" ((Z)-cyanomethoxyimino(phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4(3H)-ylidene)methoxy]acetate (CAS reg. no. 205121-04-6) (S12-1) and related compounds from WO-A-1998/13361.

S13) One or more compounds from group (S13):
  "naphthalic anhydride" (1,8-naphthalenedicarboxylic anhydride) (S13-1), which is known as a seed-dressing safener for maize against thiocarbamate herbicide damage,
  "fenclorim" (4,6-dichloro-2-phenylpyrimidine) (S13-2), which is known as a safener for pretilachlor in sown rice,
  "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS reg. no. 31541-57-8) (4-carboxy-3,4-dihydro-2H-1-benzopyran-4-acetic acid) (S13-4) from American Cyanamid, which is known as a safener for maize against damage by imidazolinones, "MG 191" (CAS reg. no. 96420-72-3) (2-dichloromethyl-2-methyl-1,3-dioxolane) (S13-5) from Nitrokemia, which is known as a safener for maize, "MG 838" (CAS reg. no. 133993-74-5) (2-propenyl 1-oxa-4-azaspiro[4.5]decane-4-carbodithioate) (S13-6) from Nitrokemia, "disulphoton" (0,0-diethyl S-2-ethylthioethyl phosphorodithioate) (S13-7), "dietholate" (0,0-diethyl 0-phenyl phosphorothioate) (S13-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY 93" (S-1-methyl 1-phenylethyl-piperidine-1-carbothioate), which is known as a safener for rice against damage by the herbicide molinate, "daimuron" or "SK 23" (1-(1-methyl-1-phenylethyl)-3-p-tolylurea), which is known as safener for rice against imazosulphuron herbicide damage, "cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as safener for rice against damage by some herbicides, "CSB" (1-bromo-4-(chloromethylsulphonyl)benzene) from Kumiai, (CAS reg. no. 54091-06-4), which is known as a safener against damage by some herbicides in rice.

S15) Compounds of the formula (S15) or tautomers thereof

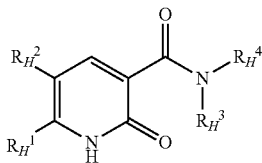

(S15)

as described in WO-A-2007/131861 and WO-A-2007/131860 in which $R_H^1$ is a $(C_1-C_6)$-haloalkyl radical and $R_H^2$ is hydrogen or halogen and $R_H^3$, $R_H^4$ independently of one another are hydrogen, $(C_1-C_{16})$-alkyl, $(C_2-C_{16})$-alkenyl or $(C_2-C_{16})$-alkynyl,
where each of the 3 last-mentioned radicals is unsubstituted or substituted by one or more radicals from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring,
where each of the 4 last-mentioned radicals is unsubstituted or substituted by one or more radicals from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl-3,6-dichloro-2-methoxybenzoate (lactidichlor-ethyl).

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tank mix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Dust-type formulations, granules for soil application or granules for scattering and sprayable solutions are not normally diluted further with other inert substances prior to application.

The required application rate of the compounds of the formula (I) and/or their salts varies according to the external conditions such as, inter alia, temperature, humidity and the type of herbicide used. It can vary within wide limits. For the application as herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as haulm stabilizer for crop plants like those mentioned above, preferably cereal plants, such as wheat, barley, rye, triticale, millet, rice or maize, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance (please check whether this should be mentioned). This applies both to application by the pre-emergence method and the post-emergence method, the post-emergence treatment generally being preferred.

The application as haulm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below. In the examples, the amounts (including percentages) refer to the weight, unless especially stated otherwise.

The symbols ">" and "<" mean "greater than" and "smaller than", respectively. The symbol ">" means "greater than or equal to", the symbol "<" means "smaller than or equal to".

If, in the context of the description and the examples, the terms "R" and "S" are given for the absolute configuration on a centre of chirality of the stereoisomers of the formula (I), this RS nomenclature follows, unless defined differently, the Cahn-Ingold-Prelog rule.

(A) SYNTHESIS EXAMPLES

Example A1 erythro- and threo-methyl 4-cyano-4-(3-cyanophenyl)-3-(3,5-difluoropyridin-4-yl)butanoate (Table 2, Examples erythro-Ibb1279 and threo-Ibb1279)

Under protective gas (Ar), 0.5 ml of N,N-dimethylformamide and 0.024 g (0.200 mmol) of potassium tert-butoxide were added to 0.181 g (0.910 mmol) of methyl 3-(3,5-difluoropyridin-4-yl)acrylate and 0.142 g (1.000 mmol) of (3-cyanophenyl)acetonitrile in 3.0 ml of toluene, and the mixture was stirred at 25° C. for 12 h and then at 50° C. for 8 h. The solvent was removed under reduced pressure and the residue was taken up in 10 ml of dichloromethane. The mixture was washed successively with 8 ml of 0.1 N aqueous hydrochloric acid and 8 ml of water and the organic phase was dried over sodium sulphate. Removal of the solvent under reduced pressure and chromatography of the residue on silica gel gave 0.137 g (36% of theory) of a mixture of erythro- and threo-methyl 4-cyano-4-(3-cyanophenyl)-3-(3,5-difluoropyridin-4-yl)butanoate (erythro-Ibb1279:threo-Ibb1279=50:50). The configuration was assigned by comparison of the chemical shifts of the respective CHCN signals at 4.20 ppm and 4.42 ppm, respectively, in the $^1$H-NMR (CDCl$_3$). The lower-field signal was assigned to the erythro-diastereomer, analogously to the literature. $^1$H-NMR in CDCl$_3$ see Table 2.

Example A2 erythro- and threo-methyl 4-cyano-4-(3,4-difluorophenyl)-3-(5-fluoropyridin-3-yl)butanoate (Table 2, Examples erythro-Ibb748 and threo-Ibb748)

Under protective gas (Ar), 5 ml of N,N-dimethylformamide and 0.067 g (1.244 mmol) of potassium tert-butoxide were added to 1.127 g (6.219 mmol) of methyl 3-(5-fluoropyridin-3-yl)acrylate and 1.000 g (6.530 mmol) of (3,4-difluorophenyl)acetonitrile in 15.0 ml of toluene, and the mixture was stirred at 70° C. for 5 h. The solvent was removed under reduced pressure and the residue was taken up in dichloromethane. The mixture was washed successively with water, 0.1 N aqueous hydrochloric acid and saturated aqueous sodium chloride solution and the organic phase was dried over sodium sulphate. Removal of the solvent under reduced pressure and chromatography of the residue on silica gel gave 1.008 g (46% of theory) of a mixture of erythro- and threo-methyl 4-cyano-4-(3,4-difluorophenyl)-3-(5-fluoropyridin-3-yl)butanoate (erythro-Ibb748:threo-Ibb748=60:40). The configuration was assigned by comparison of the chemical shifts of the respective CHCN doublets at 4.12 ppm and 4.48 ppm, respectively, in the $^1$H-NMR (CDCl$_3$). The lower-field signal was assigned to the erythro-diastereomer, analogously to the literature. $^1$H-NMR in CDCl$_3$ see Table 2.

Example A3

(3S,4S)-methyl 4-cyano-4-(3,4-difluorophenyl)-3-(5-fluoropyridin-3-yl)butanoate (Table 2, Example threo-1-Ibb748)

Preparative chromatography [(80 ml/min of n-heptane/2-propanol (80:20)] of the mixture, obtained in Example A2, of the diastereomeric methyl 4-cyano-4-(3,4-difluorophenyl)-3-(5-fluoropyridin-3-yl)butanoate on a chiral solid phase [Chiralpak IC, 20 μm, (250×50)-mm column] gave 0.130 g of (3S,4S)-methyl 4-cyano-4-(3,4-difluorophenyl)-3-(5-fluoropyridin-3-yl)butanoate, which was the second of the four stereoisomers to elute (retention time=20.0 min) For $^1$H-NMR in CDCl$_3$ and retention time in analytical HPLC: see Table 2.

Example A4

(3R,4R)-methyl 4-cyano-4-(3,4-difluorophenyl)-3-(5-fluoropyridin-3-yl)butanoate (Table 2, Example threo-2-Ibb748)

Preparative chromatography [(80 ml/min of n-heptane/2-propanol (80:20)] of the mixture, obtained in Example A3, of the diastereomeric methyl 4-cyano-4-(3,4-difluorophenyl)-3-(5-fluoropyridin-3-yl)butanoate on a chiral solid phase [Chiralpak IC, 20 μm, (250×50)-mm column] gave 0.134 g of (3R,4R)-methyl 4-cyano-4-(3,4-difluorophenyl)-3-(5-fluoropyridin-3-yl)butanoate, which was the last of the four stereoisomers to elute (retention time=26.7 min) For $^1$H-NMR in CDCl$_3$ and retention time in analytical HPLC: see Table 2.

The compounds described in the table below are obtained according to or analogously to the examples described above.

The compounds, described in the tables below, with the absolute configuration (3S,4S), (3S,4R), (3R,4S) and (3R, 4R) are obtained according to or analogously to the examples A3 and A4 described above.

In the tables:
Ex.=Example number
H=hydrogen (atom)
Me=methyl
rt=retention time
F, Cl, Br, I=fluorine, chlorine, bromine and iodine, respectively, in accordance with the conventional chemical atom symbols
CN=cyano
$NO_2$=nitro
MeO or OMe=methoxy
$CO_2Me$=methoxycarbonyl ("methylester group")
$CO_2H$=hydroxycarbonyl ("acid group")

The position of a substituent at the phenyl ring, for example in position 2, is stated as a prefix to the symbol or the abbreviation of the radical, for example
2-F=2-fluoro
3-Cl=3-chloro Numerations of the substituent positions for di- or trisubstituted substitution patterns are analogously stated as a prefix, for example
3,5-$F_2$=3,5-difluoro (e.g. as substitution at the phenyl ring)
2,6-$F_2$=2,6-difluoro (e.g. as substitution at the phenyl ring)

In addition, the customary chemical symbols and formulae apply, such as, for example, $CH_2$ for methylene or $CF_3$ for trifluoromethyl or OH for hydroxyl. Correspondingly, composite meanings are defined as composed of the abbreviations mentioned.

The retention times ("rt") given for the compounds of Tables 2a-2f were obtained by analytical HPLC of the compounds (I) on a chiral solid phase. At a concentration of 1 mg/ml, the compounds of the formula (I) were dissolved in dichloromethane p.a. and directly subjected to HPLC. The chromatographically purified compounds (I) have a stereochemical purity of >80%.

TABLE 1

Definitions of structural combinations of groups $(R^2)_n$ and Q for the tables of compounds of the general formula (I) according to the invention below

| No. | $(R^2)_n$ | Q |
| --- | --- | --- |
| 1 | H | 3-fluoropyridin-2-yl |
| 2 | 2-F | 3-fluoropyridin-2-yl |
| 3 | 3-F | 3-fluoropyridin-2-yl |
| 4 | 4-F | 3-fluoropyridin-2-yl |
| 5 | 3-Cl | 3-fluoropyridin-2-yl |
| 6 | 4-Cl | 3-fluoropyridin-2-yl |
| 7 | 3-Br | 3-fluoropyridin-2-yl |
| 8 | 4-Br | 3-fluoropyridin-2-yl |
| 9 | 3-I | 3-fluoropyridin-2-yl |
| 10 | 3-CN | 3-fluoropyridin-2-yl |
| 11 | 4-CN | 3-fluoropyridin-2-yl |
| 12 | 3-$NO_2$ | 3-fluoropyridin-2-yl |
| 13 | 3-Me | 3-fluoropyridin-2-yl |
| 14 | 4-Me | 3-fluoropyridin-2-yl |
| 15 | 2,3-$F_2$ | 3-fluoropyridin-2-yl |
| 16 | 2,4-$F_2$ | 3-fluoropyridin-2-yl |
| 17 | 2,5-$F_2$ | 3-fluoropyridin-2-yl |
| 18 | 2,6-$F_2$ | 3-fluoropyridin-2-yl |
| 19 | 3,4-$F_2$ | 3-fluoropyridin-2-yl |
| 20 | 3,5-$F_2$ | 3-fluoropyridin-2-yl |
| 21 | 3,4,5-$F_3$ | 3-fluoropyridin-2-yl |
| 22 | 3-F, 4-Cl | 3-fluoropyridin-2-yl |
| 23 | 3-F, 4-Br | 3-fluoropyridin-2-yl |
| 24 | 3-CN, 4-F | 3-fluoropyridin-2-yl |
| 25 | 3-Br, 4-F | 3-fluoropyridin-2-yl |
| 26 | 3-Cl, 4-F | 3-fluoropyridin-2-yl |
| 27 | 3,4-$Cl_2$ | 3-fluoropyridin-2-yl |
| 28 | H | 3-chloropyridin-2-yl |
| 29 | 2-F | 3-chloropyridin-2-yl |
| 30 | 3-F | 3-chloropyridin-2-yl |
| 31 | 4-F | 3-chloropyridin-2-yl |
| 32 | 3-Cl | 3-chloropyridin-2-yl |
| 33 | 4-Cl | 3-chloropyridin-2-yl |
| 34 | 3-Br | 3-chloropyridin-2-yl |
| 35 | 4-Br | 3-chloropyridin-2-yl |
| 36 | 3-I | 3-chloropyridin-2-yl |
| 37 | 3-CN | 3-chloropyridin-2-yl |
| 38 | 4-CN | 3-chloropyridin-2-yl |
| 39 | 3-$NO_2$ | 3-chloropyridin-2-yl |
| 40 | 3-Me | 3-chloropyridin-2-yl |
| 41 | 4-Me | 3-chloropyridin-2-yl |
| 42 | 2,3-$F_2$ | 3-chloropyridin-2-yl |
| 43 | 2,4-$F_2$ | 3-chloropyridin-2-yl |
| 44 | 2,5-$F_2$ | 3-chloropyridin-2-yl |
| 45 | 2,6-$F_2$ | 3-chloropyridin-2-yl |
| 46 | 3,4-$F_2$ | 3-chloropyridin-2-yl |
| 47 | 3,5-$F_2$ | 3-chloropyridin-2-yl |
| 48 | 3,4,5-$F_3$ | 3-chloropyridin-2-yl |
| 49 | 3-F, 4-Cl | 3-chloropyridin-2-yl |
| 50 | 3-F, 4-Br | 3-chloropyridin-2-yl |
| 51 | 3-CN, 4-F | 3-chloropyridin-2-yl |
| 52 | 3-Br, 4-F | 3-chloropyridin-2-yl |
| 53 | 3-Cl, 4-F | 3-chloropyridin-2-yl |
| 54 | 3,4-$Cl_2$ | 3-chloropyridin-2-yl |
| 55 | H | 3-cyanopyridin-2-yl |
| 56 | 2-F | 3-cyanopyridin-2-yl |
| 57 | 3-F | 3-cyanopyridin-2-yl |
| 58 | 4-F | 3-cyanopyridin-2-yl |
| 59 | 3-Cl | 3-cyanopyridin-2-yl |
| 60 | 4-Cl | 3-cyanopyridin-2-yl |
| 61 | 3-Br | 3-cyanopyridin-2-yl |
| 62 | 4-Br | 3-cyanopyridin-2-yl |
| 63 | 3-I | 3-cyanopyridin-2-yl |
| 64 | 3-CN | 3-cyanopyridin-2-yl |
| 65 | 4-CN | 3-cyanopyridin-2-yl |
| 66 | 3-$NO_2$ | 3-cyanopyridin-2-yl |
| 67 | 3-Me | 3-cyanopyridin-2-yl |
| 68 | 4-Me | 3-cyanopyridin-2-yl |
| 69 | 2,3-$F_2$ | 3-cyanopyridin-2-yl |
| 70 | 2,4-$F_2$ | 3-cyanopyridin-2-yl |
| 71 | 2,5-$F_2$ | 3-cyanopyridin-2-yl |
| 72 | 2,6-$F_2$ | 3-cyanopyridin-2-yl |
| 73 | 3,4-$F_2$ | 3-cyanopyridin-2-yl |
| 74 | 3,5-$F_2$ | 3-cyanopyridin-2-yl |
| 75 | 3,4,5-$F_3$ | 3-cyanopyridin-2-yl |
| 76 | 3-F, 4-Cl | 3-cyanopyridin-2-yl |
| 77 | 3-F, 4-Br | 3-cyanopyridin-2-yl |
| 78 | 3-CN, 4-F | 3-cyanopyridin-2-yl |
| 79 | 3-Br, 4-F | 3-cyanopyridin-2-yl |
| 80 | 3-Cl, 4-F | 3-cyanopyridin-2-yl |
| 81 | 3,4-$Cl_2$ | 3-cyanopyridin-2-yl |
| 82 | H | 4-fluoropyridin-2-yl |
| 83 | 2-F | 4-fluoropyridin-2-yl |
| 84 | 3-F | 4-fluoropyridin-2-yl |
| 85 | 4-F | 4-fluoropyridin-2-yl |
| 86 | 3-Cl | 4-fluoropyridin-2-yl |
| 87 | 4-Cl | 4-fluoropyridin-2-yl |
| 88 | 3-Br | 4-fluoropyridin-2-yl |
| 89 | 4-Br | 4-fluoropyridin-2-yl |
| 90 | 3-I | 4-fluoropyridin-2-yl |
| 91 | 3-CN | 4-fluoropyridin-2-yl |
| 92 | 4-CN | 4-fluoropyridin-2-yl |
| 93 | 3-$NO_2$ | 4-fluoropyridin-2-yl |
| 94 | 3-Me | 4-fluoropyridin-2-yl |
| 95 | 4-Me | 4-fluoropyridin-2-yl |
| 96 | 2,3-$F_2$ | 4-fluoropyridin-2-yl |
| 97 | 2,4-$F_2$ | 4-fluoropyridin-2-yl |
| 98 | 2,5-$F_2$ | 4-fluoropyridin-2-yl |
| 99 | 2,6-$F_2$ | 4-fluoropyridin-2-yl |
| 100 | 3,4-$F_2$ | 4-fluoropyridin-2-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 101 | 3,5-F$_2$ | 4-fluoropyridin-2-yl |
| 102 | 3,4,5-F$_3$ | 4-fluoropyridin-2-yl |
| 103 | 3-F, 4-Cl | 4-fluoropyridin-2-yl |
| 104 | 3-F, 4-Br | 4-fluoropyridin-2-yl |
| 105 | 3-CN, 4-F | 4-fluoropyridin-2-yl |
| 106 | 3-Br, 4-F | 4-fluoropyridin-2-yl |
| 107 | 3-Cl, 4-F | 4-fluoropyridin-2-yl |
| 108 | 3,4-Cl$_2$ | 4-fluoropyridin-2-yl |
| 109 | H | 4-chloropyridin-2-yl |
| 110 | 2-F | 4-chloropyridin-2-yl |
| 111 | 3-F | 4-chloropyridin-2-yl |
| 112 | 4-F | 4-chloropyridin-2-yl |
| 113 | 3-Cl | 4-chloropyridin-2-yl |
| 114 | 4-Cl | 4-chloropyridin-2-yl |
| 115 | 3-Br | 4-chloropyridin-2-yl |
| 116 | 4-Br | 4-chloropyridin-2-yl |
| 117 | 3-I | 4-chloropyridin-2-yl |
| 118 | 3-CN | 4-chloropyridin-2-yl |
| 119 | 4-CN | 4-chloropyridin-2-yl |
| 120 | 3-NO$_2$ | 4-chloropyridin-2-yl |
| 121 | 3-Me | 4-chloropyridin-2-yl |
| 122 | 4-Me | 4-chloropyridin-2-yl |
| 123 | 2,3-F$_2$ | 4-chloropyridin-2-yl |
| 124 | 2,4-F$_2$ | 4-chloropyridin-2-yl |
| 125 | 2,5-F$_2$ | 4-chloropyridin-2-yl |
| 126 | 2,6-F$_2$ | 4-chloropyridin-2-yl |
| 127 | 3,4-F$_2$ | 4-chloropyridin-2-yl |
| 128 | 3,5-F$_2$ | 4-chloropyridin-2-yl |
| 129 | 3,4,5-F$_3$ | 4-chloropyridin-2-yl |
| 130 | 3-F, 4-Cl | 4-chloropyridin-2-yl |
| 131 | 3-F, 4-Br | 4-chloropyridin-2-yl |
| 132 | 3-CN, 4-F | 4-chloropyridin-2-yl |
| 133 | 3-Br, 4-F | 4-chloropyridin-2-yl |
| 134 | 3-Cl, 4-F | 4-chloropyridin-2-yl |
| 135 | 3,4-Cl$_2$ | 4-chloropyridin-2-yl |
| 136 | H | 4-bromopyridin-2-yl |
| 137 | 2-F | 4-bromopyridin-2-yl |
| 138 | 3-F | 4-bromopyridin-2-yl |
| 139 | 4-F | 4-bromopyridin-2-yl |
| 140 | 3-Cl | 4-bromopyridin-2-yl |
| 141 | 4-Cl | 4-bromopyridin-2-yl |
| 142 | 3-Br | 4-bromopyridin-2-yl |
| 143 | 4-Br | 4-bromopyridin-2-yl |
| 144 | 3-I | 4-bromopyridin-2-yl |
| 145 | 3-CN | 4-bromopyridin-2-yl |
| 146 | 4-CN | 4-bromopyridin-2-yl |
| 147 | 3-NO$_2$ | 4-bromopyridin-2-yl |
| 148 | 3-Me | 4-bromopyridin-2-yl |
| 149 | 4-Me | 4-bromopyridin-2-yl |
| 150 | 2,3-F$_2$ | 4-bromopyridin-2-yl |
| 151 | 2,4-F$_2$ | 4-bromopyridin-2-yl |
| 152 | 2,5-F$_2$ | 4-bromopyridin-2-yl |
| 153 | 2,6-F$_2$ | 4-bromopyridin-2-yl |
| 154 | 3,4-F$_2$ | 4-bromopyridin-2-yl |
| 155 | 3,5-F$_2$ | 4-bromopyridin-2-yl |
| 156 | 3,4,5-F$_3$ | 4-bromopyridin-2-yl |
| 157 | 3-F, 4-Cl | 4-bromopyridin-2-yl |
| 158 | 3-F, 4-Br | 4-bromopyridin-2-yl |
| 159 | 3-CN, 4-F | 4-bromopyridin-2-yl |
| 160 | 3-Br, 4-F | 4-bromopyridin-2-yl |
| 161 | 3-Cl, 4-F | 4-bromopyridin-2-yl |
| 162 | 3,4-Cl$_2$ | 4-bromopyridin-2-yl |
| 163 | H | 5-fluoropyridin-2-yl |
| 164 | 2-F | 5-fluoropyridin-2-yl |
| 165 | 3-F | 5-fluoropyridin-2-yl |
| 166 | 4-F | 5-fluoropyridin-2-yl |
| 167 | 3-Cl | 5-fluoropyridin-2-yl |
| 168 | 4-Cl | 5-fluoropyridin-2-yl |
| 169 | 3-Br | 5-fluoropyridin-2-yl |
| 170 | 4-Br | 5-fluoropyridin-2-yl |
| 171 | 3-I | 5-fluoropyridin-2-yl |
| 172 | 3-CN | 5-fluoropyridin-2-yl |
| 173 | 4-CN | 5-fluoropyridin-2-yl |
| 174 | 3-NO$_2$ | 5-fluoropyridin-2-yl |
| 175 | 3-Me | 5-fluoropyridin-2-yl |
| 176 | 4-Me | 5-fluoropyridin-2-yl |
| 177 | 2,3-F$_2$ | 5-fluoropyridin-2-yl |
| 178 | 2,4-F$_2$ | 5-fluoropyridin-2-yl |
| 179 | 2,5-F$_2$ | 5-fluoropyridin-2-yl |
| 180 | 2,6-F$_2$ | 5-fluoropyridin-2-yl |
| 181 | 3,4-F$_2$ | 5-fluoropyridin-2-yl |
| 182 | 3,5-F$_2$ | 5-fluoropyridin-2-yl |
| 183 | 3,4,5-F$_3$ | 5-fluoropyridin-2-yl |
| 184 | 3-F, 4-Cl | 5-fluoropyridin-2-yl |
| 185 | 3-F, 4-Br | 5-fluoropyridin-2-yl |
| 186 | 3-CN, 4-F | 5-fluoropyridin-2-yl |
| 187 | 3-Br, 4-F | 5-fluoropyridin-2-yl |
| 188 | 3-Cl, 4-F | 5-fluoropyridin-2-yl |
| 189 | 3,4-Cl$_2$ | 5-fluoropyridin-2-yl |
| 190 | H | 5-chloropyridin-2-yl |
| 191 | 2-F | 5-chloropyridin-2-yl |
| 192 | 3-F | 5-chloropyridin-2-yl |
| 193 | 4-F | 5-chloropyridin-2-yl |
| 194 | 3-Cl | 5-chloropyridin-2-yl |
| 195 | 4-Cl | 5-chloropyridin-2-yl |
| 196 | 3-Br | 5-chloropyridin-2-yl |
| 197 | 4-Br | 5-chloropyridin-2-yl |
| 198 | 3-I | 5-chloropyridin-2-yl |
| 199 | 3-CN | 5-chloropyridin-2-yl |
| 200 | 4-CN | 5-chloropyridin-2-yl |
| 201 | 3-NO$_2$ | 5-chloropyridin-2-yl |
| 202 | 3-Me | 5-chloropyridin-2-yl |
| 203 | 4-Me | 5-chloropyridin-2-yl |
| 204 | 2,3-F$_2$ | 5-chloropyridin-2-yl |
| 205 | 2,4-F$_2$ | 5-chloropyridin-2-yl |
| 206 | 2,5-F$_2$ | 5-chloropyridin-2-yl |
| 207 | 2,6-F$_2$ | 5-chloropyridin-2-yl |
| 208 | 3,4-F$_2$ | 5-chloropyridin-2-yl |
| 209 | 3,5-F$_2$ | 5-chloropyridin-2-yl |
| 210 | 3,4,5-F$_3$ | 5-chloropyridin-2-yl |
| 211 | 3-F, 4-Cl | 5-chloropyridin-2-yl |
| 212 | 3-F, 4-Br | 5-chloropyridin-2-yl |
| 213 | 3-CN, 4-F | 5-chloropyridin-2-yl |
| 214 | 3-Br, 4-F | 5-chloropyridin-2-yl |
| 215 | 3-Cl, 4-F | 5-chloropyridin-2-yl |
| 216 | 3,4-Cl$_2$ | 5-chloropyridin-2-yl |
| 217 | H | 5-bromopyridin-2-yl |
| 218 | 2-F | 5-bromopyridin-2-yl |
| 219 | 3-F | 5-bromopyridin-2-yl |
| 220 | 4-F | 5-bromopyridin-2-yl |
| 221 | 3-Cl | 5-bromopyridin-2-yl |
| 222 | 4-Cl | 5-bromopyridin-2-yl |
| 223 | 3-Br | 5-bromopyridin-2-yl |
| 224 | 4-Br | 5-bromopyridin-2-yl |
| 225 | 3-I | 5-bromopyridin-2-yl |
| 226 | 3-CN | 5-bromopyridin-2-yl |
| 227 | 4-CN | 5-bromopyridin-2-yl |
| 228 | 3-NO$_2$ | 5-bromopyridin-2-yl |
| 229 | 3-Me | 5-bromopyridin-2-yl |
| 230 | 4-Me | 5-bromopyridin-2-yl |
| 231 | 2,3-F$_2$ | 5-bromopyridin-2-yl |
| 232 | 2,4-F$_2$ | 5-bromopyridin-2-yl |
| 233 | 2,5-F$_2$ | 5-bromopyridin-2-yl |
| 234 | 2,6-F$_2$ | 5-bromopyridin-2-yl |
| 235 | 3,4-F$_2$ | 5-bromopyridin-2-yl |
| 236 | 3,5-F$_2$ | 5-bromopyridin-2-yl |
| 237 | 3,4,5-F$_3$ | 5-bromopyridin-2-yl |
| 238 | 3-F, 4-Cl | 5-bromopyridin-2-yl |
| 239 | 3-F, 4-Br | 5-bromopyridin-2-yl |
| 240 | 3-CN, 4-F | 5-bromopyridin-2-yl |
| 241 | 3-Br, 4-F | 5-bromopyridin-2-yl |
| 242 | 3-Cl, 4-F | 5-bromopyridin-2-yl |
| 243 | 3,4-Cl$_2$ | 5-bromopyridin-2-yl |
| 244 | H | 5-cyanopyridin-2-yl |
| 245 | 2-F | 5-cyanopyridin-2-yl |
| 246 | 3-F | 5-cyanopyridin-2-yl |
| 247 | 4-F | 5-cyanopyridin-2-yl |
| 248 | 3-Cl | 5-cyanopyridin-2-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 249 | 4-Cl | 5-cyanopyridin-2-yl |
| 250 | 3-Br | 5-cyanopyridin-2-yl |
| 251 | 4-Br | 5-cyanopyridin-2-yl |
| 252 | 3-I | 5-cyanopyridin-2-yl |
| 253 | 3-CN | 5-cyanopyridin-2-yl |
| 254 | 4-CN | 5-cyanopyridin-2-yl |
| 255 | 3-NO$_2$ | 5-cyanopyridin-2-yl |
| 256 | 3-Me | 5-cyanopyridin-2-yl |
| 257 | 4-Me | 5-cyanopyridin-2-yl |
| 258 | 2,3-F$_2$ | 5-cyanopyridin-2-yl |
| 259 | 2,4-F$_2$ | 5-cyanopyridin-2-yl |
| 260 | 2,5-F$_2$ | 5-cyanopyridin-2-yl |
| 261 | 2,6-F$_2$ | 5-cyanopyridin-2-yl |
| 262 | 3,4-F$_2$ | 5-cyanopyridin-2-yl |
| 263 | 3,5-F$_2$ | 5-cyanopyridin-2-yl |
| 264 | 3,4,5-F$_3$ | 5-cyanopyridin-2-yl |
| 265 | 3-F, 4-Cl | 5-cyanopyridin-2-yl |
| 266 | 3-F, 4-Br | 5-cyanopyridin-2-yl |
| 267 | 3-CN, 4-F | 5-cyanopyridin-2-yl |
| 268 | 3-Br, 4-F | 5-cyanopyridin-2-yl |
| 269 | 3-Cl, 4-F | 5-cyanopyridin-2-yl |
| 270 | 3,4-Cl$_2$ | 5-cyanopyridin-2-yl |
| 271 | H | 5-nitropyridin-2-yl |
| 272 | 2-F | 5-nitropyridin-2-yl |
| 273 | 3-F | 5-nitropyridin-2-yl |
| 274 | 4-F | 5-nitropyridin-2-yl |
| 275 | 3-Cl | 5-nitropyridin-2-yl |
| 276 | 4% Cl: | 5-nitropyridin-2-yl |
| 277 | 3-Br | 5-nitropyridin-2-yl |
| 278 | 4-Br | 5-nitropyridin-2-yl |
| 279 | 3-I | 5-nitropyridin-2-yl |
| 280 | 3-CN | 5-nitropyridin-2-yl |
| 281 | 4-CN | 5-nitropyridin-2-yl |
| 282 | 3-NO$_2$ | 5-nitropyridin-2-yl |
| 283 | 3-Me | 5-nitropyridin-2-yl |
| 284 | 4-Me | 5-nitropyridin-2-yl |
| 285 | 2,3-F$_2$ | 5-nitropyridin-2-yl |
| 286 | 2,4-F$_2$ | 5-nitropyridin-2-yl |
| 287 | 2,5-F$_2$ | 5-nitropyridin-2-yl |
| 288 | 2,6-F$_2$ | 5-nitropyridin-2-yl |
| 289 | 3,4-F$_2$ | 5-nitropyridin-2-yl |
| 290 | 3,5-F$_2$ | 5-nitropyridin-2-yl |
| 291 | 3,4,5-F$_3$ | 5-nitropyridin-2-yl |
| 292 | 3-F, 4-Cl | 5-nitropyridin-2-yl |
| 293 | 3-F, 4-Br | 5-nitropyridin-2-yl |
| 294 | 3-CN, 4-F | 5-nitropyridin-2-yl |
| 295 | 3-Br, 4-F | 5-nitropyridin-2-yl |
| 296 | 3-Cl, 4-F | 5-nitropyridin-2-yl |
| 297 | 3,4-Cl$_2$ | 5-nitropyridin-2-yl |
| 298 | H | 6-fluoropyridin-2-yl |
| 299 | 2-F | 6-fluoropyridin-2-yl |
| 300 | 3-F | 6-fluoropyridin-2-yl |
| 301 | 4-F | 6-fluoropyridin-2-yl |
| 302 | 3-Cl | 6-fluoropyridin-2-yl |
| 303 | 4-Cl | 6-fluoropyridin-2-yl |
| 304 | 3-Br | 6-fluoropyridin-2-yl |
| 305 | 4-Br | 6-fluoropyridin-2-yl |
| 306 | 3-I | 6-fluoropyridin-2-yl |
| 307 | 3-CN | 6-fluoropyridin-2-yl |
| 308 | 4-CN | 6-fluoropyridin-2-yl |
| 309 | 3-NO$_2$ | 6-fluoropyridin-2-yl |
| 310 | 3-Me | 6-fluoropyridin-2-yl |
| 311 | 4-Me | 6-fluoropyridin-2-yl |
| 312 | 2,3-F$_2$ | 6-fluoropyridin-2-yl |
| 313 | 2,4-F$_2$ | 6-fluoropyridin-2-yl |
| 314 | 2,5-F$_2$ | 6-fluoropyridin-2-yl |
| 315 | 2,6-F$_2$ | 6-fluoropyridin-2-yl |
| 316 | 3,4-F$_2$ | 6-fluoropyridin-2-yl |
| 317 | 3,5-F$_2$ | 6-fluoropyridin-2-yl |
| 318 | 3,4,5-F$_3$ | 6-fluoropyridin-2-yl |
| 319 | 3-F, 4-Cl | 6-fluoropyridin-2-yl |
| 320 | 3-F, 4-Br | 6-fluoropyridin-2-yl |
| 321 | 3-CN, 4-F | 6-fluoropyridin-2-yl |
| 322 | 3-Br, 4-F | 6-fluoropyridin-2-yl |
| 323 | 3-Cl, 4-F | 6-fluoropyridin-2-yl |
| 324 | 3,4-Cl$_2$ | 6-fluoropyridin-2-yl |
| 325 | H | 6-chloropyridin-2-yl |
| 326 | 2-F | 6-chloropyridin-2-yl |
| 327 | 3-F | 6-chloropyridin-2-yl |
| 328 | 4-F | 6-chloropyridin-2-yl |
| 329 | 3-Cl | 6-chloropyridin-2-yl |
| 330 | 4-Cl | 6-chloropyridin-2-yl |
| 331 | 3-Br | 6-chloropyridin-2-yl |
| 332 | 4-Br | 6-chloropyridin-2-yl |
| 333 | 3-I | 6-chloropyridin-2-yl |
| 334 | 3-CN | 6-chloropyridin-2-yl |
| 335 | 4-CN | 6-chloropyridin-2-yl |
| 336 | 3-NO$_2$ | 6-chloropyridin-2-yl |
| 337 | 3-Me | 6-chloropyridin-2-yl |
| 338 | 4-Me | 6-chloropyridin-2-yl |
| 339 | 2,3-F$_2$ | 6-chloropyridin-2-yl |
| 340 | 2,4-F$_2$ | 6-chloropyridin-2-yl |
| 341 | 2,5-F$_2$ | 6-chloropyridin-2-yl |
| 342 | 2,6-F$_2$ | 6-chloropyridin-2-yl |
| 343 | 3,4-F$_2$ | 6-chloropyridin-2-yl |
| 344 | 3,5-F$_2$ | 6-chloropyridin-2-yl |
| 345 | 3,4,5-F$_3$ | 6-chloropyridin-2-yl |
| 346 | 3-F, 4-Cl | 6-chloropyridin-2-yl |
| 347 | 3-F, 4-Br | 6-chloropyridin-2-yl |
| 348 | 3-CN, 4-F | 6-chloropyridin-2-yl |
| 349 | 3-Br, 4-F | 6-chloropyridin-2-yl |
| 350 | 3-Cl, 4-F | 6-chloropyridin-2-yl |
| 351 | 3,4-Cl$_2$ | 6-chloropyridin-2-yl |
| 352 | H | 6-bromopyridin-2-yl |
| 353 | 2-F | 6-bromopyridin-2-yl |
| 354 | 3-F | 6-bromopyridin-2-yl |
| 355 | 4-F | 6-bromopyridin-2-yl |
| 356 | 3-Cl | 6-bromopyridin-2-yl |
| 357 | 4-Cl | 6-bromopyridin-2-yl |
| 358 | 3-Br | 6-bromopyridin-2-yl |
| 359 | 4-Br | 6-bromopyridin-2-yl |
| 360 | 3-I | 6-bromopyridin-2-yl |
| 361 | 3-CN | 6-bromopyridin-2-yl |
| 362 | 4-CN | 6-bromopyridin-2-yl |
| 363 | 3-NO$_2$ | 6-bromopyridin-2-yl |
| 364 | 3-Me | 6-bromopyridin-2-yl |
| 365 | 4-Me | 6-bromopyridin-2-yl |
| 366 | 2,3-F$_2$ | 6-bromopyridin-2-yl |
| 367 | 2,4-F$_2$ | 6-bromopyridin-2-yl |
| 368 | 2,5-F$_2$ | 6-bromopyridin-2-yl |
| 369 | 2,6-F$_2$ | 6-bromopyridin-2-yl |
| 370 | 3,4-F$_2$ | 6-bromopyridin-2-yl |
| 371 | 3,5-F$_2$ | 6-bromopyridin-2-yl |
| 372 | 3,4,5-F$_3$ | 6-bromopyridin-2-yl |
| 373 | 3-F, 4-Cl | 6-bromopyridin-2-yl |
| 374 | 3-F, 4-Br | 6-bromopyridin-2-yl |
| 375 | 3-CN, 4-F | 6-bromopyridin-2-yl |
| 376 | 3-Br, 4-F | 6-bromopyridin-2-yl |
| 377 | 3-Cl, 4-F | 6-bromopyridin-2-yl |
| 378 | 3,4-Cl$_2$ | 6-bromopyridin-2-yl |
| 379 | H | 4,5-difluoropyridin-2-yl |
| 380 | 2-F | 4,5-difluoropyridin-2-yl |
| 381 | 3-F | 4,5-difluoropyridin-2-yl |
| 382 | 4-F | 4,5-difluoropyridin-2-yl |
| 383 | 3-Cl | 4,5-difluoropyridin-2-yl |
| 384 | 4-Cl | 4,5-difluoropyridin-2-yl |
| 385 | 3-Br | 4,5-difluoropyridin-2-yl |
| 386 | 4-Br | 4,5-difluoropyridin-2-yl |
| 387 | 3-I | 4,5-difluoropyridin-2-yl |
| 388 | 3-CN | 4,5-difluoropyridin-2-yl |
| 389 | 4-CN | 4,5-difluoropyridin-2-yl |
| 390 | 3-NO$_2$ | 4,5-difluoropyridin-2-yl |
| 391 | 3-Me | 4,5-difluoropyridin-2-yl |
| 392 | 4-Me | 4,5-difluoropyridin-2-yl |
| 393 | 2,3-F$_2$ | 4,5-difluoropyridin-2-yl |
| 394 | 2,4-F$_2$ | 4,5-difluoropyridin-2-yl |
| 395 | 2,5-F$_2$ | 4,5-difluoropyridin-2-yl |
| 396 | 2,6-F$_2$ | 4,5-difluoropyridin-2-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 397 | 3,4-F$_2$ | 4,5-difluoropyridin-2-yl |
| 398 | 3,5-F$_2$ | 4,5-difluoropyridin-2-yl |
| 399 | 3,4,5-F$_3$ | 4,5-difluoropyridin-2-yl |
| 400 | 3-F, 4-Cl | 4,5-difluoropyridin-2-yl |
| 401 | 3-F, 4-Br | 4,5-difluoropyridin-2-yl |
| 402 | 3-CN, 4-F | 4,5-difluoropyridin-2-yl |
| 403 | 3-Br, 4-F | 4,5-difluoropyridin-2-yl |
| 404 | 3-Cl, 4-F | 4,5-difluoropyridin-2-yl |
| 405 | 3,4-Cl$_2$ | 4,5-difluoropyridin-2-yl |
| 406 | H | 5,6-difluoropyridin-2-yl |
| 407 | 2-F | 5,6-difluoropyridin-2-yl |
| 408 | 3-F | 5,6-difluoropyridin-2-yl |
| 409 | 4-F | 5,6-difluoropyridin-2-yl |
| 410 | 3-Cl | 5,6-difluoropyridin-2-yl |
| 411 | 4-Cl | 5,6-difluoropyridin-2-yl |
| 412 | 3-Br | 5,6-difluoropyridin-2-yl |
| 413 | 4-Br | 5,6-difluoropyridin-2-yl |
| 414 | 3-I | 5,6-difluoropyridin-2-yl |
| 415 | 3-CN | 5,6-difluoropyridin-2-yl |
| 416 | 4-CN | 5,6-difluoropyridin-2-yl |
| 417 | 3-NO$_2$ | 5,6-difluoropyridin-2-yl |
| 418 | 3-Me | 5,6-difluoropyridin-2-yl |
| 419 | 4-Me | 5,6-difluoropyridin-2-yl |
| 420 | 2,3-F$_2$ | 5,6-difluoropyridin-2-yl |
| 421 | 2,4-F$_2$ | 5,6-difluoropyridin-2-yl |
| 422 | 2,5-F$_2$ | 5,6-difluoropyridin-2-yl |
| 423 | 2,6-F$_2$ | 5,6-difluoropyridin-2-yl |
| 424 | 3,4-F$_2$ | 5,6-difluoropyridin-2-yl |
| 425 | 3,5-F$_2$ | 5,6-difluoropyridin-2-yl |
| 426 | 3,4,5-F$_3$ | 5,6-difluoropyridin-2-yl |
| 427 | 3-F, 4-Cl | 5,6-difluoropyridin-2-yl |
| 428 | 3-F, 4-Br | 5,6-difluoropyridin-2-yl |
| 429 | 3-CN, 4-F | 5,6-difluoropyridin-2-yl |
| 430 | 3-Br, 4-F | 5,6-difluoropyridin-2-yl |
| 431 | 3-Cl, 4-F | 5,6-difluoropyridin-2-yl |
| 432 | 3,4-Cl$_2$ | 5,6-difluoropyridin-2-yl |
| 433 | H | 2,4-difluoropyridin-3-yl |
| 434 | 2-F | 2,4-difluoropyridin-3-yl |
| 435 | 3-F | 2,4-difluoropyridin-3-yl |
| 436 | 4-F | 2,4-difluoropyridin-3-yl |
| 437 | 3-Cl | 2,4-difluoropyridin-3-yl |
| 438 | 4-Cl | 2,4-difluoropyridin-3-yl |
| 439 | 3-Br | 2,4-difluoropyridin-3-yl |
| 440 | 4-Br | 2,4-difluoropyridin-3-yl |
| 441 | 3-I | 2,4-difluoropyridin-3-yl |
| 442 | 3-CN | 2,4-difluoropyridin-3-yl |
| 443 | 4-CN | 2,4-difluoropyridin-3-yl |
| 444 | 3-NO$_2$ | 2,4-difluoropyridin-3-yl |
| 445 | 3-Me | 2,4-difluoropyridin-3-yl |
| 446 | 4-Me | 2,4-difluoropyridin-3-yl |
| 447 | 2,3-F$_2$ | 2,4-difluoropyridin-3-yl |
| 448 | 2,4-F$_2$ | 2,4-difluoropyridin-3-yl |
| 449 | 2,5-F$_2$ | 2,4-difluoropyridin-3-yl |
| 450 | 2,6-F$_2$ | 2,4-difluoropyridin-3-yl |
| 451 | 3,4-F$_2$ | 2,4-difluoropyridin-3-yl |
| 452 | 3,5-F$_2$ | 2,4-difluoropyridin-3-yl |
| 453 | 3,4,5-F$_3$ | 2,4-difluoropyridin-3-yl |
| 454 | 3-F, 4-Cl | 2,4-difluoropyridin-3-yl |
| 455 | 3-F, 4-Br | 2,4-difluoropyridin-3-yl |
| 456 | 3-CN, 4-F | 2,4-difluoropyridin-3-yl |
| 457 | 3-Br, 4-F | 2,4-difluoropyridin-3-yl |
| 458 | 3-Cl, 4-F | 2,4-difluoropyridin-3-yl |
| 459 | 3,4-Cl$_2$ | 2,4-difluoropyridin-3-yl |
| 460 | H | 5,6-difluoropyridin-3-yl |
| 461 | 2-F | 5,6-difluoropyridin-3-yl |
| 462 | 3-F | 5,6-difluoropyridin-3-yl |
| 463 | 4-F | 5,6-difluoropyridin-3-yl |
| 464 | 3-Cl | 5,6-difluoropyridin-3-yl |
| 465 | 4-Cl | 5,6-difluoropyridin-3-yl |
| 466 | 3-Br | 5,6-difluoropyridin-3-yl |
| 467 | 4-Br | 5,6-difluoropyridin-3-yl |
| 468 | 3-I | 5,6-difluoropyridin-3-yl |
| 469 | 3-CN | 5,6-difluoropyridin-3-yl |
| 470 | 4-CN | 5,6-difluoropyridin-3-yl |
| 471 | 3-NO$_2$ | 5,6-difluoropyridin-3-yl |
| 472 | 3-Me | 5,6-difluoropyridin-3-yl |
| 473 | 4-Me | 5,6-difluoropyridin-3-yl |
| 474 | 2,3-F$_2$ | 5,6-difluoropyridin-3-yl |
| 475 | 2,4-F$_2$ | 5,6-difluoropyridin-3-yl |
| 476 | 2,5-F$_2$ | 5,6-difluoropyridin-3-yl |
| 477 | 2,6-F$_2$ | 5,6-difluoropyridin-3-yl |
| 478 | 3,4-F$_2$ | 5,6-difluoropyridin-3-yl |
| 479 | 3,5-F$_2$ | 5,6-difluoropyridin-3-yl |
| 480 | 3,4,5-F$_3$ | 5,6-difluoropyridin-3-yl |
| 481 | 3-F, 4-Cl | 5,6-difluoropyridin-3-yl |
| 482 | 3-F, 4-Br | 5,6-difluoropyridin-3-yl |
| 483 | 3-CN, 4-F | 5,6-difluoropyridin-3-yl |
| 484 | 3-Br, 4-F | 5,6-difluoropyridin-3-yl |
| 485 | 3-Cl, 4-F | 5,6-difluoropyridin-3-yl |
| 486 | 3,4-Cl$_2$ | 5,6-difluoropyridin-3-yl |
| 487 | H | 5-fluoro-6-cyanopyridin-3-yl |
| 488 | 2-F | 5-fluoro-6-cyanopyridin-3-yl |
| 489 | 3-F | 5-fluoro-6-cyanopyridin-3-yl |
| 490 | 4-F | 5-fluoro-6-cyanopyridin-3-yl |
| 491 | 3-Cl | 5-fluoro-6-cyanopyridin-3-yl |
| 492 | 4-Cl | 5-fluoro-6-cyanopyridin-3-yl |
| 493 | 3-Br | 5-fluoro-6-cyanopyridin-3-yl |
| 494 | 4-Br | 5-fluoro-6-cyanopyridin-3-yl |
| 495 | 3-I | 5-fluoro-6-cyanopyridin-3-yl |
| 496 | 3-CN | 5-fluoro-6-cyanopyridin-3-yl |
| 497 | 4-CN | 5-fluoro-6-cyanopyridin-3-yl |
| 498 | 3-NO$_2$ | 5-fluoro-6-cyanopyridin-3-yl |
| 499 | 3-Me | 5-fluoro-6-cyanopyridin-3-yl |
| 500 | 4-Me | 5-fluoro-6-cyanopyridin-3-yl |
| 501 | 2,3-F$_2$ | 5-fluoro-6-cyanopyridin-3-yl |
| 502 | 2,4-F$_2$ | 5-fluoro-6-cyanopyridin-3-yl |
| 503 | 2,5-F$_2$ | 5-fluoro-6-cyanopyridin-3-yl |
| 504 | 2,6-F$_2$ | 5-fluoro-6-cyanopyridin-3-yl |
| 505 | 3,4-F$_2$ | 5-fluoro-6-cyanopyridin-3-yl |
| 506 | 3,5-F$_2$ | 5-fluoro-6-cyanopyridin-3-yl |
| 507 | 3,4,5-F$_3$ | 5-fluoro-6-cyanopyridin-3-yl |
| 508 | 3-F, 4-Cl | 5-fluoro-6-cyanopyridin-3-yl |
| 509 | 3-F, 4-Br | 5-fluoro-6-cyanopyridin-3-yl |
| 510 | 3-CN, 4-F | 5-fluoro-6-cyanopyridin-3-yl |
| 511 | 3-Br, 4-F | 5-fluoro-6-cyanopyridin-3-yl |
| 512 | 3-Cl, 4-F | 5-fluoro-6-cyanopyridin-3-yl |
| 513 | 3,4-Cl$_2$ | 5-fluoro-6-cyanopyridin-3-yl |
| 514 | H | 2-fluoropyridin-3-yl |
| 515 | 2-F | 2-fluoropyridin-3-yl |
| 516 | 3-F | 2-fluoropyridin-3-yl |
| 517 | 4-F | 2-fluoropyridin-3-yl |
| 518 | 3-Cl | 2-fluoropyridin-3-yl |
| 519 | 4-Cl | 2-fluoropyridin-3-yl |
| 520 | 3-Br | 2-fluoropyridin-3-yl |
| 521 | 4-Br | 2-fluoropyridin-3-yl |
| 522 | 3-I | 2-fluoropyridin-3-yl |
| 523 | 3-CN | 2-fluoropyridin-3-yl |
| 524 | 4-CN | 2-fluoropyridin-3-yl |
| 525 | 3-NO$_2$ | 2-fluoropyridin-3-yl |
| 526 | 3-Me | 2-fluoropyridin-3-yl |
| 527 | 4-Me | 2-fluoropyridin-3-yl |
| 528 | 2,3-F$_2$ | 2-fluoropyridin-3-yl |
| 529 | 2,4-F$_2$ | 2-fluoropyridin-3-yl |
| 530 | 2,5-F$_2$ | 2-fluoropyridin-3-yl |
| 531 | 2,6-F$_2$ | 2-fluoropyridin-3-yl |
| 532 | 3,4-F$_2$ | 2-fluoropyridin-3-yl |
| 533 | 3,5-F$_2$ | 2-fluoropyridin-3-yl |
| 534 | 3,4,5-F$_3$ | 2-fluoropyridin-3-yl |
| 535 | 3-F, 4-Cl | 2-fluoropyridin-3-yl |
| 536 | 3-F, 4-Br | 2-fluoropyridin-3-yl |
| 537 | 3-CN, 4-F | 2-fluoropyridin-3-yl |
| 538 | 3-Br, 4-F | 2-fluoropyridin-3-yl |
| 539 | 3-Cl, 4-F | 2-fluoropyridin-3-yl |
| 540 | 3,4-Cl$_2$ | 2-fluoropyridin-3-yl |
| 541 | H | 2-chloropyridin-3-yl |
| 542 | 2-F | 2-chloropyridin-3-yl |
| 543 | 3-F | 2-chloropyridin-3-yl |
| 544 | 4-F | 2-chloropyridin-3-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 545 | 3-Cl | 2-chloropyridin-3-yl |
| 546 | 4-Cl | 2-chloropyridin-3-yl |
| 547 | 3-Br | 2-chloropyridin-3-yl |
| 548 | 4-Br | 2-chloropyridin-3-yl |
| 549 | 3-I | 2-chloropyridin-3-yl |
| 550 | 3-CN | 2-chloropyridin-3-yl |
| 551 | 4-CN | 2-chloropyridin-3-yl |
| 552 | 3-NO$_2$ | 2-chloropyridin-3-yl |
| 553 | 3-Me | 2-chloropyridin-3-yl |
| 554 | 4-Me | 2-chloropyridin-3-yl |
| 555 | 2,3-F$_2$ | 2-chloropyridin-3-yl |
| 556 | 2,4-F$_2$ | 2-chloropyridin-3-yl |
| 557 | 2,5-F$_2$ | 2-chloropyridin-3-yl |
| 558 | 2,6-F$_2$ | 2-chloropyridin-3-yl |
| 559 | 3,4-F$_2$ | 2-chloropyridin-3-yl |
| 560 | 3,5-F$_2$ | 2-chloropyridin-3-yl |
| 561 | 3,4,5-F$_3$ | 2-chloropyridin-3-yl |
| 562 | 3-F, 4-Cl | 2-chloropyridin-3-yl |
| 563 | 3-F, 4-Br | 2-chloropyridin-3-yl |
| 564 | 3-CN, 4-F | 2-chloropyridin-3-yl |
| 565 | 3-Br, 4-F | 2-chloropyridin-3-yl |
| 566 | 3-Cl, 4-F | 2-chloropyridin-3-yl |
| 567 | 3,4-Cl$_2$ | 2-chloropyridin-3-yl |
| 568 | H | 2-cyanopyridin-3-yl |
| 569 | 2-F | 2-cyanopyridin-3-yl |
| 570 | 3-F | 2-cyanopyridin-3-yl |
| 571 | 4-F | 2-cyanopyridin-3-yl |
| 572 | 3-Cl | 2-cyanopyridin-3-yl |
| 573 | 4-Cl | 2-cyanopyridin-3-yl |
| 574 | 3-Br | 2-cyanopyridin-3-yl |
| 575 | 4-Br | 2-cyanopyridin-3-yl |
| 576 | 3-I | 2-cyanopyridin-3-yl |
| 577 | 3-CN | 2-cyanopyridin-3-yl |
| 578 | 4-CN | 2-cyanopyridin-3-yl |
| 579 | 3-NO$_2$ | 2-cyanopyridin-3-yl |
| 580 | 3-Me | 2-cyanopyridin-3-yl |
| 581 | 4-Me | 2-cyanopyridin-3-yl |
| 582 | 2,3-F$_2$ | 2-cyanopyridin-3-yl |
| 583 | 2,4-F$_2$ | 2-cyanopyridin-3-yl |
| 584 | 2,5-F$_2$ | 2-cyanopyridin-3-yl |
| 585 | 2,6-F$_2$ | 2-cyanopyridin-3-yl |
| 586 | 3,4-F$_2$ | 2-cyanopyridin-3-yl |
| 587 | 3,5-F$_2$ | 2-cyanopyridin-3-yl |
| 588 | 3,4,5-F$_3$ | 2-cyanopyridin-3-yl |
| 589 | 3-F, 4-Cl | 2-cyanopyridin-3-yl |
| 590 | 3-F, 4-Br | 2-cyanopyridin-3-yl |
| 591 | 3-CN, 4-F | 2-cyanopyridin-3-yl |
| 592 | 3-Br, 4-F | 2-cyanopyridin-3-yl |
| 593 | 3-Cl, 4-F | 2-cyanopyridin-3-yl |
| 594 | 3,4-Cl$_2$ | 2-cyanopyridin-3-yl |
| 595 | H | 2-bromopyridin-3-yl |
| 596 | 2-F | 2-bromopyridin-3-yl |
| 597 | 3-F | 2-bromopyridin-3-yl |
| 598 | 4-F | 2-bromopyridin-3-yl |
| 599 | 3-Cl | 2-bromopyridin-3-yl |
| 600 | 4-Cl | 2-bromopyridin-3-yl |
| 601 | 3-Br | 2-bromopyridin-3-yl |
| 602 | 4-Br | 2-bromopyridin-3-yl |
| 603 | 3-I | 2-bromopyridin-3-yl |
| 604 | 3-CN | 2-bromopyridin-3-yl |
| 605 | 4-CN | 2-bromopyridin-3-yl |
| 606 | 3-NO$_2$ | 2-bromopyridin-3-yl |
| 607 | 3-Me | 2-bromopyridin-3-yl |
| 608 | 4-Me | 2-bromopyridin-3-yl |
| 609 | 2,3-F$_2$ | 2-bromopyridin-3-yl |
| 610 | 2,4-F$_2$ | 2-bromopyridin-3-yl |
| 611 | 2,5-F$_2$ | 2-bromopyridin-3-yl |
| 612 | 2,6-F$_2$ | 2-bromopyridin-3-yl |
| 613 | 3,4-F$_2$ | 2-bromopyridin-3-yl |
| 614 | 3,5-F$_2$ | 2-bromopyridin-3-yl |
| 615 | 3,4,5-F$_3$ | 2-bromopyridin-3-yl |
| 616 | 3-F, 4-Cl | 2-bromopyridin-3-yl |
| 617 | 3-F, 4-Br | 2-bromopyridin-3-yl |
| 618 | 3-CN, 4-F | 2-bromopyridin-3-yl |
| 619 | 3-Br, 4-F | 2-bromopyridin-3-yl |
| 620 | 3-Cl, 4-F | 2-bromopyridin-3-yl |
| 621 | 3,4-Cl$_2$ | 2-bromopyridin-3-yl |
| 622 | H | 4-fluoropyridin-3-yl |
| 623 | 2-F | 4-fluoropyridin-3-yl |
| 624 | 3-F | 4-fluoropyridin-3-yl |
| 625 | 4-F | 4-fluoropyridin-3-yl |
| 626 | 3-Cl | 4-fluoropyridin-3-yl |
| 627 | 4-Cl | 4-fluoropyridin-3-yl |
| 628 | 3-Br | 4-fluoropyridin-3-yl |
| 629 | 4-Br | 4-fluoropyridin-3-yl |
| 630 | 3-I | 4-fluoropyridin-3-yl |
| 631 | 3-CN | 4-fluoropyridin-3-yl |
| 632 | 4-CN | 4-fluoropyridin-3-yl |
| 633 | 3-NO$_2$ | 4-fluoropyridin-3-yl |
| 634 | 3-Me | 4-fluoropyridin-3-yl |
| 635 | 4-Me | 4-fluoropyridin-3-yl |
| 636 | 2,3-F$_2$ | 4-fluoropyridin-3-yl |
| 637 | 2,4-F$_2$ | 4-fluoropyridin-3-yl |
| 638 | 2,5-F$_2$ | 4-fluoropyridin-3-yl |
| 639 | 2,6-F$_2$ | 4-fluoropyridin-3-yl |
| 640 | 3,4-F$_2$ | 4-fluoropyridin-3-yl |
| 641 | 3,5-F$_2$ | 4-fluoropyridin-3-yl |
| 642 | 3,4,5-F$_3$ | 4-fluoropyridin-3-yl |
| 643 | 3-F, 4-Cl | 4-fluoropyridin-3-yl |
| 644 | 3-F, 4-Br | 4-fluoropyridin-3-yl |
| 645 | 3-CN, 4-F | 4-fluoropyridin-3-yl |
| 646 | 3-Br, 4-F | 4-fluoropyridin-3-yl |
| 647 | 3-Cl, 4-F | 4-fluoropyridin-3-yl |
| 648 | 3,4-Cl$_2$ | 4-fluoropyridin-3-yl |
| 649 | H | 4-chloropyridin-3-yl |
| 650 | 2-F | 4-chloropyridin-3-yl |
| 651 | 3-F | 4-chloropyridin-3-yl |
| 652 | 4-F | 4-chloropyridin-3-yl |
| 653 | 3-Cl | 4-chloropyridin-3-yl |
| 654 | 4-Cl | 4-chloropyridin-3-yl |
| 655 | 3-Br | 4-chloropyridin-3-yl |
| 656 | 4-Br | 4-chloropyridin-3-yl |
| 657 | 3-I | 4-chloropyridin-3-yl |
| 658 | 3-CN | 4-chloropyridin-3-yl |
| 659 | 4-CN | 4-chloropyridin-3-yl |
| 660 | 3-NO$_2$ | 4-chloropyridin-3-yl |
| 661 | 3-Me | 4-chloropyridin-3-yl |
| 662 | 4-Me | 4-chloropyridin-3-yl |
| 663 | 2,3-F$_2$ | 4-chloropyridin-3-yl |
| 664 | 2,4-F$_2$ | 4-chloropyridin-3-yl |
| 665 | 2,5-F$_2$ | 4-chloropyridin-3-yl |
| 666 | 2,6-F$_2$ | 4-chloropyridin-3-yl |
| 667 | 3,4-F$_2$ | 4-chloropyridin-3-yl |
| 668 | 3,5-F$_2$ | 4-chloropyridin-3-yl |
| 669 | 3,4,5-F$_3$ | 4-chloropyridin-3-yl |
| 670 | 3-F, 4-Cl | 4-chloropyridin-3-yl |
| 671 | 3-F, 4-Br | 4-chloropyridin-3-yl |
| 672 | 3-CN, 4-F | 4-chloropyridin-3-yl |
| 673 | 3-Br, 4-F | 4-chloropyridin-3-yl |
| 674 | 3-Cl, 4-F | 4-chloropyridin-3-yl |
| 675 | 3,4-Cl$_2$ | 4-chloropyridin-3-yl |
| 676 | H | 4-cyanopyridin-3-yl |
| 677 | 2-F | 4-cyanopyridin-3-yl |
| 678 | 3-F | 4-cyanopyridin-3-yl |
| 679 | 4-F | 4-cyanopyridin-3-yl |
| 680 | 3-Cl | 4-cyanopyridin-3-yl |
| 681 | 4-Cl | 4-cyanopyridin-3-yl |
| 682 | 3-Br | 4-cyanopyridin-3-yl |
| 683 | 4-Br | 4-cyanopyridin-3-yl |
| 684 | 3-I | 4-cyanopyridin-3-yl |
| 685 | 3-CN | 4-cyanopyridin-3-yl |
| 686 | 4-CN | 4-cyanopyridin-3-yl |
| 687 | 3-NO$_2$ | 4-cyanopyridin-3-yl |
| 688 | 3-Me | 4-cyanopyridin-3-yl |
| 689 | 4-Me | 4-cyanopyridin-3-yl |
| 690 | 2,3-F$_2$ | 4-cyanopyridin-3-yl |
| 691 | 2,4-F$_2$ | 4-cyanopyridin-3-yl |
| 692 | 2,5-F$_2$ | 4-cyanopyridin-3-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 693 | 2,6-F$_2$ | 4-cyanopyridin-3-yl |
| 694 | 3,4-F$_2$ | 4-cyanopyridin-3-yl |
| 695 | 3,5-F$_2$ | 4-cyanopyridin-3-yl |
| 696 | 3,4,5-F$_3$ | 4-cyanopyridin-3-yl |
| 697 | 3-F, 4-Cl | 4-cyanopyridin-3-yl |
| 698 | 3-F, 4-Br | 4-cyanopyridin-3-yl |
| 699 | 3-CN, 4-F | 4-cyanopyridin-3-yl |
| 700 | 3-Br, 4-F | 4-cyanopyridin-3-yl |
| 701 | 3-Cl, 4-F | 4-cyanopyridin-3-yl |
| 702 | 3,4-Cl$_2$ | 4-cyanopyridin-3-yl |
| 703 | H | 4-trifluoromethylpyridin-3-yl |
| 704 | 2-F | 4-trifluoromethylpyridin-3-yl |
| 705 | 3-F | 4-trifluoromethylpyridin-3-yl |
| 706 | 4-F | 4-trifluoromethylpyridin-3-yl |
| 707 | 3-Cl | 4-trifluoromethylpyridin-3-yl |
| 708 | 4-Cl | 4-trifluoromethylpyridin-3-yl |
| 709 | 3-Br | 4-trifluoromethylpyridin-3-yl |
| 710 | 4-Br | 4-trifluoromethylpyridin-3-yl |
| 711 | 3-I | 4-trifluoromethylpyridin-3-yl |
| 712 | 3-CN | 4-trifluoromethylpyridin-3-yl |
| 713 | 4-CN | 4-trifluoromethylpyridin-3-yl |
| 714 | 3-NO$_2$ | 4-trifluoromethylpyridin-3-yl |
| 715 | 3-Me | 4-trifluoromethylpyridin-3-yl |
| 716 | 4-Me | 4-trifluoromethylpyridin-3-yl |
| 717 | 2,3-F$_2$ | 4-trifluoromethylpyridin-3-yl |
| 718 | 2,4-F$_2$ | 4-trifluoromethylpyridin-3-yl |
| 719 | 2,5-F$_2$ | 4-trifluoromethylpyridin-3-yl |
| 720 | 2,6-F$_2$ | 4-trifluoromethylpyridin-3-yl |
| 721 | 3,4-F$_2$ | 4-trifluoromethylpyridin-3-yl |
| 722 | 3,5-F$_2$ | 4-trifluoromethylpyridin-3-yl |
| 723 | 3,4,5-F$_3$ | 4-trifluoromethylpyridin-3-yl |
| 724 | 3-F, 4-Cl | 4-trifluoromethylpyridin-3-yl |
| 725 | 3-F, 4-Br | 4-trifluoromethylpyridin-3-yl |
| 726 | 3-CN, 4-F | 4-trifluoromethylpyridin-3-yl |
| 727 | 3-Br, 4-F | 4-trifluoromethylpyridin-3-yl |
| 728 | 3-Cl, 4-F | 4-trifluoromethylpyridin-3-yl |
| 729 | 3,4-Cl$_2$ | 4-trifluoromethylpyridin-3-yl |
| 730 | H | 5-fluoropyridin-3-yl |
| 731 | 2-F | 5-fluoropyridin-3-yl |
| 732 | 3-F | 5-fluoropyridin-3-yl |
| 733 | 4-F | 5-fluoropyridin-3-yl |
| 734 | 3-Cl | 5-fluoropyridin-3-yl |
| 735 | 4-Cl | 5-fluoropyridin-3-yl |
| 736 | 3-Br | 5-fluoropyridin-3-yl |
| 737 | 4-Br | 5-fluoropyridin-3-yl |
| 738 | 3-I | 5-fluoropyridin-3-yl |
| 739 | 3-CN | 5-fluoropyridin-3-yl |
| 740 | 4-CN | 5-fluoropyridin-3-yl |
| 741 | 3-NO$_2$ | 5-fluoropyridin-3-yl |
| 742 | 3-Me | 5-fluoropyridin-3-yl |
| 743 | 4-Me | 5-fluoropyridin-3-yl |
| 744 | 2,3-F$_2$ | 5-fluoropyridin-3-yl |
| 745 | 2,4-F$_2$ | 5-fluoropyridin-3-yl |
| 746 | 2,5-F$_2$ | 5-fluoropyridin-3-yl |
| 747 | 2,6-F$_2$ | 5-fluoropyridin-3-yl |
| 748 | 3,4-F$_2$ | 5-fluoropyridin-3-yl |
| 749 | 3,5-F$_2$ | 5-fluoropyridin-3-yl |
| 750 | 3,4,5-F$_3$ | 5-fluoropyridin-3-yl |
| 751 | 3-F, 4-Cl | 5-fluoropyridin-3-yl |
| 752 | 3-F, 4-Br | 5-fluoropyridin-3-yl |
| 753 | 3-CN, 4-F | 5-fluoropyridin-3-yl |
| 754 | 3-Br, 4-F | 5-fluoropyridin-3-yl |
| 755 | 3-Cl, 4-F | 5-fluoropyridin-3-yl |
| 756 | 3,4-Cl$_2$ | 5-fluoropyridin-3-yl |
| 757 | H | 5-chloropyridin-3-yl |
| 758 | 2-F | 5-chloropyridin-3-yl |
| 759 | 3-F | 5-chloropyridin-3-yl |
| 760 | 4-F | 5-chloropyridin-3-yl |
| 761 | 3-Cl | 5-chloropyridin-3-yl |
| 762 | 4-Cl | 5-chloropyridin-3-yl |
| 763 | 3-Br | 5-chloropyridin-3-yl |
| 764 | 4-Br | 5-chloropyridin-3-yl |
| 765 | 3-I | 5-chloropyridin-3-yl |
| 766 | 3-CN | 5-chloropyridin-3-yl |
| 767 | 4-CN | 5-chloropyridin-3-yl |
| 768 | 3-NO$_2$ | 5-chloropyridin-3-yl |
| 769 | 3-Me | 5-chloropyridin-3-yl |
| 770 | 4-Me | 5-chloropyridin-3-yl |
| 771 | 2,3-F$_2$ | 5-chloropyridin-3-yl |
| 772 | 2,4-F$_2$ | 5-chloropyridin-3-yl |
| 773 | 2,5-F$_2$ | 5-chloropyridin-3-yl |
| 774 | 2,6-F$_2$ | 5-chloropyridin-3-yl |
| 775 | 3,4-F$_2$ | 5-chloropyridin-3-yl |
| 776 | 3,5-F$_2$ | 5-chloropyridin-3-yl |
| 777 | 3,4,5-F$_3$ | 5-chloropyridin-3-yl |
| 778 | 3-F, 4-Cl | 5-chloropyridin-3-yl |
| 779 | 3-F, 4-Br | 5-chloropyridin-3-yl |
| 780 | 3-CN, 4-F | 5-chloropyridin-3-yl |
| 781 | 3-Br, 4-F | 5-chloropyridin-3-yl |
| 782 | 3-Cl, 4-F | 5-chloropyridin-3-yl |
| 783 | 3,4-Cl$_2$ | 5-chloropyridin-3-yl |
| 784 | H | 5-bromopyridin-3-yl |
| 785 | 2-F | 5-bromopyridin-3-yl |
| 786 | 3-F | 5-bromopyridin-3-yl |
| 787 | 4-F | 5-bromopyridin-3-yl |
| 788 | 3-Cl | 5-bromopyridin-3-yl |
| 789 | 4-Cl | 5-bromopyridin-3-yl |
| 790 | 3-Br | 5-bromopyridin-3-yl |
| 791 | 4-Br | 5-bromopyridin-3-yl |
| 792 | 3-I | 5-bromopyridin-3-yl |
| 793 | 3-CN | 5-bromopyridin-3-yl |
| 794 | 4-CN | 5-bromopyridin-3-yl |
| 795 | 3-NO$_2$ | 5-bromopyridin-3-yl |
| 796 | 3-Me | 5-bromopyridin-3-yl |
| 797 | 4-Me | 5-bromopyridin-3-yl |
| 798 | 2,3-F$_2$ | 5-bromopyridin-3-yl |
| 799 | 2,4-F$_2$ | 5-bromopyridin-3-yl |
| 800 | 2,5-F$_2$ | 5-bromopyridin-3-yl |
| 801 | 2,6-F$_2$ | 5-bromopyridin-3-yl |
| 802 | 3,4-F$_2$ | 5-bromopyridin-3-yl |
| 803 | 3,5-F$_2$ | 5-bromopyridin-3-yl |
| 804 | 3,4,5-F$_3$ | 5-bromopyridin-3-yl |
| 805 | 3-F, 4-Cl | 5-bromopyridin-3-yl |
| 806 | 3-F, 4-Br | 5-bromopyridin-3-yl |
| 807 | 3-CN, 4-F | 5-bromopyridin-3-yl |
| 808 | 3-Br, 4-F | 5-bromopyridin-3-yl |
| 809 | 3-Cl, 4-F | 5-bromopyridin-3-yl |
| 810 | 3,4-Cl$_2$ | 5-bromopyridin-3-yl |
| 811 | H | 5-cyanopyridin-3-yl |
| 812 | 2-F | 5-cyanopyridin-3-yl |
| 813 | 3-F | 5-cyanopyridin-3-yl |
| 814 | 4-F | 5-cyanopyridin-3-yl |
| 815 | 3-Cl | 5-cyanopyridin-3-yl |
| 816 | 4-Cl | 5-cyanopyridin-3-yl |
| 817 | 3-Br | 5-cyanopyridin-3-yl |
| 818 | 4-Br | 5-cyanopyridin-3-yl |
| 819 | 3-I | 5-cyanopyridin-3-yl |
| 820 | 3-CN | 5-cyanopyridin-3-yl |
| 821 | 4-CN | 5-cyanopyridin-3-yl |
| 822 | 3-NO$_2$ | 5-cyanopyridin-3-yl |
| 823 | 3-Me | 5-cyanopyridin-3-yl |
| 824 | 4-Me | 5-cyanopyridin-3-yl |
| 825 | 2,3-F$_2$ | 5-cyanopyridin-3-yl |
| 826 | 2,4-F$_2$ | 5-cyanopyridin-3-yl |
| 827 | 2,5-F$_2$ | 5-cyanopyridin-3-yl |
| 828 | 2,6-F$_2$ | 5-cyanopyridin-3-yl |
| 829 | 3,4-F$_2$ | 5-cyanopyridin-3-yl |
| 830 | 3,5-F$_2$ | 5-cyanopyridin-3-yl |
| 831 | 3,4,5-F$_3$ | 5-cyanopyridin-3-yl |
| 832 | 3-F, 4-Cl | 5-cyanopyridin-3-yl |
| 833 | 3-F, 4-Br | 5-cyanopyridin-3-yl |
| 834 | 3-CN, 4-F | 5-cyanopyridin-3-yl |
| 835 | 3-Br, 4-F | 5-cyanopyridin-3-yl |
| 836 | 3-Cl, 4-F | 5-cyanopyridin-3-yl |
| 837 | 3,4-Cl$_2$ | 5-cyanopyridin-3-yl |
| 838 | H | 6-nitropyridin-3-yl |
| 839 | 2-F | 6-nitropyridin-3-yl |
| 840 | 3-F | 6-nitropyridin-3-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 841 | 4-F | 6-nitropyridin-3-yl |
| 842 | 3-Cl | 6-nitropyridin-3-yl |
| 843 | 4-Cl | 6-nitropyridin-3-yl |
| 844 | 3-Br | 6-nitropyridin-3-yl |
| 845 | 4-Br | 6-nitropyridin-3-yl |
| 846 | 3-I | 6-nitropyridin-3-yl |
| 847 | 3-CN | 6-nitropyridin-3-yl |
| 848 | 4-CN | 6-nitropyridin-3-yl |
| 849 | 3-NO$_2$ | 6-nitropyridin-3-yl |
| 850 | 3-Me | 6-nitropyridin-3-yl |
| 851 | 4-Me | 6-nitropyridin-3-yl |
| 852 | 2,3-F$_2$ | 6-nitropyridin-3-yl |
| 853 | 2,4-F$_2$ | 6-nitropyridin-3-yl |
| 854 | 2,5-F$_2$ | 6-nitropyridin-3-yl |
| 855 | 2,6-F$_2$ | 6-nitropyridin-3-yl |
| 856 | 3,4-F$_2$ | 6-nitropyridin-3-yl |
| 857 | 3,5-F$_2$ | 6-nitropyridin-3-yl |
| 858 | 3,4,5-F$_3$ | 6-nitropyridin-3-yl |
| 859 | 3-F, 4-Cl | 6-nitropyridin-3-yl |
| 860 | 3-F, 4-Br | 6-nitropyridin-3-yl |
| 861 | 3-CN, 4-F | 6-nitropyridin-3-yl |
| 862 | 3-Br, 4-F | 6-nitropyridin-3-yl |
| 863 | 3-Cl, 4-F | 6-nitropyridin-3-yl |
| 864 | 3,4-Cl$_2$ | 6-nitropyridin-3-yl |
| 865 | H | 6-fluoropyridin-3-yl |
| 866 | 2-F | 6-fluoropyridin-3-yl |
| 867 | 3-F | 6-fluoropyridin-3-yl |
| 868 | 4-F | 6-fluoropyridin-3-yl |
| 869 | 3-Cl | 6-fluoropyridin-3-yl |
| 870 | 4-Cl | 6-fluoropyridin-3-yl |
| 871 | 3-Br | 6-fluoropyridin-3-yl |
| 872 | 4-Br | 6-fluoropyridin-3-yl |
| 873 | 3-I | 6-fluoropyridin-3-yl |
| 874 | 3-CN | 6-fluoropyridin-3-yl |
| 875 | 4-CN | 6-fluoropyridin-3-yl |
| 876 | 3-NO$_2$ | 6-fluoropyridin-3-yl |
| 877 | 3-Me | 6-fluoropyridin-3-yl |
| 878 | 4-Me | 6-fluoropyridin-3-yl |
| 879 | 2,3-F$_2$ | 6-fluoropyridin-3-yl |
| 880 | 2,4-F$_2$ | 6-fluoropyridin-3-yl |
| 881 | 2,5-F$_2$ | 6-fluoropyridin-3-yl |
| 882 | 2,6-F$_2$ | 6-fluoropyridin-3-yl |
| 883 | 3,4-F$_2$ | 6-fluoropyridin-3-yl |
| 884 | 3,5-F$_2$ | 6-fluoropyridin-3-yl |
| 885 | 3,4,5-F$_3$ | 6-fluoropyridin-3-yl |
| 886 | 3-F, 4-Cl | 6-fluoropyridin-3-yl |
| 887 | 3-F, 4-Br | 6-fluoropyridin-3-yl |
| 888 | 3-CN, 4-F | 6-fluoropyridin-3-yl |
| 889 | 3-Br, 4-F | 6-fluoropyridin-3-yl |
| 890 | 3-Cl, 4-F | 6-fluoropyridin-3-yl |
| 891 | 3,4-Cl$_2$ | 6-fluoropyridin-3-yl |
| 892 | H | 6-chloropyridin-3-yl |
| 893 | 2-F | 6-chloropyridin-3-yl |
| 894 | 3-F | 6-chloropyridin-3-yl |
| 895 | 4-F | 6-chloropyridin-3-yl |
| 896 | 3-Cl | 6-chloropyridin-3-yl |
| 897 | 4-Cl | 6-chloropyridin-3-yl |
| 898 | 3-Br | 6-chloropyridin-3-yl |
| 899 | 4-Br | 6-chloropyridin-3-yl |
| 900 | 3-I | 6-chloropyridin-3-yl |
| 901 | 3-CN | 6-chloropyridin-3-yl |
| 902 | 4-CN | 6-chloropyridin-3-yl |
| 903 | 3-NO$_2$ | 6-chloropyridin-3-yl |
| 904 | 3-Me | 6-chloropyridin-3-yl |
| 905 | 4-Me | 6-chloropyridin-3-yl |
| 906 | 2,3-F$_2$ | 6-chloropyridin-3-yl |
| 907 | 2,4-F$_2$ | 6-chloropyridin-3-yl |
| 908 | 2,5-F$_2$ | 6-chloropyridin-3-yl |
| 909 | 2,6-F$_2$ | 6-chloropyridin-3-yl |
| 910 | 3,4-F$_2$ | 6-chloropyridin-3-yl |
| 911 | 3,5-F$_2$ | 6-chloropyridin-3-yl |
| 912 | 3,4,5-F$_3$ | 6-chloropyridin-3-yl |
| 913 | 3-F, 4-Cl | 6-chloropyridin-3-yl |
| 914 | 3-F, 4-Br | 6-chloropyridin-3-yl |
| 915 | 3-CN, 4-F | 6-chloropyridin-3-yl |
| 916 | 3-Br, 4-F | 6-chloropyridin-3-yl |
| 917 | 3-Cl, 4-F | 6-chloropyridin-3-yl |
| 918 | 3,4-Cl$_2$ | 6-chloropyridin-3-yl |
| 919 | H | 6-bromopyridin-3-yl |
| 920 | 2-F | 6-bromopyridin-3-yl |
| 921 | 3-F | 6-bromopyridin-3-yl |
| 922 | 4-F | 6-bromopyridin-3-yl |
| 923 | 3-Cl | 6-bromopyridin-3-yl |
| 924 | 4-Cl | 6-bromopyridin-3-yl |
| 925 | 3-Br | 6-bromopyridin-3-yl |
| 926 | 4-Br | 6-bromopyridin-3-yl |
| 927 | 3-I | 6-bromopyridin-3-yl |
| 928 | 3-CN | 6-bromopyridin-3-yl |
| 929 | 4-CN | 6-bromopyridin-3-yl |
| 930 | 3-NO$_2$ | 6-bromopyridin-3-yl |
| 931 | 3-Me | 6-bromopyridin-3-yl |
| 932 | 4-Me | 6-bromopyridin-3-yl |
| 933 | 2,3-F$_2$ | 6-bromopyridin-3-yl |
| 934 | 2,4-F$_2$ | 6-bromopyridin-3-yl |
| 935 | 2,5-F$_2$ | 6-bromopyridin-3-yl |
| 936 | 2,6-F$_2$ | 6-bromopyridin-3-yl |
| 937 | 3,4-F$_2$ | 6-bromopyridin-3-yl |
| 938 | 3,5-F$_2$ | 6-bromopyridin-3-yl |
| 939 | 3,4,5-F$_3$ | 6-bromopyridin-3-yl |
| 940 | 3-F, 4-Cl | 6-bromopyridin-3-yl |
| 941 | 3-F, 4-Br | 6-bromopyridin-3-yl |
| 942 | 3-CN, 4-F | 6-bromopyridin-3-yl |
| 943 | 3-Br, 4-F | 6-bromopyridin-3-yl |
| 944 | 3-Cl, 4-F | 6-bromopyridin-3-yl |
| 945 | 3,4-Cl$_2$ | 6-bromopyridin-3-yl |
| 946 | H | 6-cyanopyridin-3-yl |
| 947 | 2-F | 6-cyanopyridin-3-yl |
| 948 | 3-F | 6-cyanopyridin-3-yl |
| 949 | 4-F | 6-cyanopyridin-3-yl |
| 950 | 3-Cl | 6-cyanopyridin-3-yl |
| 951 | 4-Cl | 6-cyanopyridin-3-yl |
| 952 | 3-Br | 6-cyanopyridin-3-yl |
| 953 | 4-Br | 6-cyanopyridin-3-yl |
| 954 | 3-I | 6-cyanopyridin-3-yl |
| 955 | 3-CN | 6-cyanopyridin-3-yl |
| 956 | 4-CN | 6-cyanopyridin-3-yl |
| 957 | 3-NO$_2$ | 6-cyanopyridin-3-yl |
| 958 | 3-Me | 6-cyanopyridin-3-yl |
| 959 | 4-Me | 6-cyanopyridin-3-yl |
| 960 | 2,3-F$_2$ | 6-cyanopyridin-3-yl |
| 961 | 2,4-F$_2$ | 6-cyanopyridin-3-yl |
| 962 | 2,5-F$_2$ | 6-cyanopyridin-3-yl |
| 963 | 2,6-F$_2$ | 6-cyanopyridin-3-yl |
| 964 | 3,4-F$_2$ | 6-cyanopyridin-3-yl |
| 965 | 3,5-F$_2$ | 6-cyanopyridin-3-yl |
| 966 | 3,4,5-F$_3$ | 6-cyanopyridin-3-yl |
| 967 | 3-F, 4-Cl | 6-cyanopyridin-3-yl |
| 968 | 3-F, 4-Br | 6-cyanopyridin-3-yl |
| 969 | 3-CN, 4-F | 6-cyanopyridin-3-yl |
| 970 | 3-Br, 4-F | 6-cyanopyridin-3-yl |
| 971 | 3-Cl, 4-F | 6-cyanopyridin-3-yl |
| 972 | 3,4-Cl$_2$ | 6-cyanopyridin-3-yl |
| 973 | H | 6-trifluoromethylpyridin-3-yl |
| 974 | 2-F | 6-trifluoromethylpyridin-3-yl |
| 975 | 3-F | 6-trifluoromethylpyridin-3-yl |
| 976 | 4-F | 6-trifluoromethylpyridin-3-yl |
| 977 | 3-Cl | 6-trifluoromethylpyridin-3-yl |
| 978 | 4-Cl | 6-trifluoromethylpyridin-3-yl |
| 979 | 3-Br | 6-trifluoromethylpyridin-3-yl |
| 980 | 4-Br | 6-trifluoromethylpyridin-3-yl |
| 981 | 3-I | 6-trifluoromethylpyridin-3-yl |
| 982 | 3-CN | 6-trifluoromethylpyridin-3-yl |
| 983 | 4-CN | 6-trifluoromethylpyridin-3-yl |
| 984 | 3-NO$_2$ | 6-trifluoromethylpyridin-3-yl |
| 985 | 3-Me | 6-trifluoromethylpyridin-3-yl |
| 986 | 4-Me | 6-trifluoromethylpyridin-3-yl |
| 987 | 2,3-F$_2$ | 6-trifluoromethylpyridin-3-yl |
| 988 | 2,4-F$_2$ | 6-trifluoromethylpyridin-3-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 989 | 2,5-$F_2$ | 6-trifluoromethylpyridin-3-yl |
| 990 | 2,6-$F_2$ | 6-trifluoromethylpyridin-3-yl |
| 991 | 3,4-$F_2$ | 6-trifluoromethylpyridin-3-yl |
| 992 | 3,5-$F_2$ | 6-trifluoromethylpyridin-3-yl |
| 993 | 3,4,5-$F_3$ | 6-trifluoromethylpyridin-3-yl |
| 994 | 3-F, 4-Cl | 6-trifluoromethylpyridin-3-yl |
| 995 | 3-F, 4-Br | 6-trifluoromethylpyridin-3-yl |
| 996 | 3-CN, 4-F | 6-trifluoromethylpyridin-3-yl |
| 997 | 3-Br, 4-F | 6-trifluoromethylpyridin-3-yl |
| 998 | 3-Cl, 4-F | 6-trifluoromethylpyridin-3-yl |
| 999 | 3,4-$Cl_2$ | 6-trifluoromethylpyridin-3-yl |
| 1000 | H | 2-fluoropyridin-4-yl |
| 1001 | 2-F | 2-fluoropyridin-4-yl |
| 1002 | 3-F | 2-fluoropyridin-4-yl |
| 1003 | 4-F | 2-fluoropyridin-4-yl |
| 1004 | 3-Cl | 2-fluoropyridin-4-yl |
| 1005 | 4-Cl | 2-fluoropyridin-4-yl |
| 1006 | 3-Br | 2-fluoropyridin-4-yl |
| 1007 | 4-Br | 2-fluoropyridin-4-yl |
| 1008 | 3-I | 2-fluoropyridin-4-yl |
| 1009 | 3-CN | 2-fluoropyridin-4-yl |
| 1010 | 4-CN | 2-fluoropyridin-4-yl |
| 1011 | 3-$NO_2$ | 2-fluoropyridin-4-yl |
| 1012 | 3-Me | 2-fluoropyridin-4-yl |
| 1013 | 4-Me | 2-fluoropyridin-4-yl |
| 1014 | 2,3-$F_2$ | 2-fluoropyridin-4-yl |
| 1015 | 2,4-$F_2$ | 2-fluoropyridin-4-yl |
| 1016 | 2,5-$F_2$ | 2-fluoropyridin-4-yl |
| 1017 | 2,6-$F_2$ | 2-fluoropyridin-4-yl |
| 1018 | 3,4-$F_2$ | 2-fluoropyridin-4-yl |
| 1019 | 3,5-$F_2$ | 2-fluoropyridin-4-yl |
| 1020 | 3,4,5-$F_3$ | 2-fluoropyridin-4-yl |
| 1021 | 3-F, 4-Cl | 2-fluoropyridin-4-yl |
| 1022 | 3-F, 4-Br | 2-fluoropyridin-4-yl |
| 1023 | 3-CN, 4-F | 2-fluoropyridin-4-yl |
| 1024 | 3-Br, 4-F | 2-fluoropyridin-4-yl |
| 1025 | 3-Cl, 4-F | 2-fluoropyridin-4-yl |
| 1026 | 3,4-$Cl_2$ | 2-fluoropyridin-4-yl |
| 1027 | H | 2-chloropyridin-4-yl |
| 1028 | 2-F | 2-chloropyridin-4-yl |
| 1029 | 3-F | 2-chloropyridin-4-yl |
| 1030 | 4-F | 2-chloropyridin-4-yl |
| 1031 | 3-Cl | 2-chloropyridin-4-yl |
| 1032 | 4-Cl | 2-chloropyridin-4-yl |
| 1033 | 3-Br | 2-chloropyridin-4-yl |
| 1034 | 4-Br | 2-chloropyridin-4-yl |
| 1035 | 3-I | 2-chloropyridin-4-yl |
| 1036 | 3-CN | 2-chloropyridin-4-yl |
| 1037 | 4-CN | 2-chloropyridin-4-yl |
| 1038 | 3-$NO_2$ | 2-chloropyridin-4-yl |
| 1039 | 3-Me | 2-chloropyridin-4-yl |
| 1040 | 4-Me | 2-chloropyridin-4-yl |
| 1041 | 2,3-$F_2$ | 2-chloropyridin-4-yl |
| 1042 | 2,4-$F_2$ | 2-chloropyridin-4-yl |
| 1043 | 2,5-$F_2$ | 2-chloropyridin-4-yl |
| 1044 | 2,6-$F_2$ | 2-chloropyridin-4-yl |
| 1045 | 3,4-$F_2$ | 2-chloropyridin-4-yl |
| 1046 | 3,5-$F_2$ | 2-chloropyridin-4-yl |
| 1047 | 3,4,5-$F_3$ | 2-chloropyridin-4-yl |
| 1048 | 3-F, 4-Cl | 2-chloropyridin-4-yl |
| 1049 | 3-F, 4-Br | 2-chloropyridin-4-yl |
| 1050 | 3-CN, 4-F | 2-chloropyridin-4-yl |
| 1051 | 3-Br, 4-F | 2-chloropyridin-4-yl |
| 1052 | 3-Cl, 4-F | 2-chloropyridin-4-yl |
| 1053 | 3,4-$Cl_2$ | 2-chloropyridin-4-yl |
| 1054 | H | 2-bromopyridin-4-yl |
| 1055 | 2-F | 2-bromopyridin-4-yl |
| 1056 | 3-F | 2-bromopyridin-4-yl |
| 1057 | 4-F | 2-bromopyridin-4-yl |
| 1058 | 3-Cl | 2-bromopyridin-4-yl |
| 1059 | 4-Cl | 2-bromopyridin-4-yl |
| 1060 | 3-Br | 2-bromopyridin-4-yl |
| 1061 | 4-Br | 2-bromopyridin-4-yl |
| 1062 | 3-I | 2-bromopyridin-4-yl |
| 1063 | 3-CN | 2-bromopyridin-4-yl |
| 1064 | 4-CN | 2-bromopyridin-4-yl |
| 1065 | 3-$NO_2$ | 2-bromopyridin-4-yl |
| 1066 | 3-Me | 2-bromopyridin-4-yl |
| 1067 | 4-Me | 2-bromopyridin-4-yl |
| 1068 | 2,3-$F_2$ | 2-bromopyridin-4-yl |
| 1069 | 2,4-$F_2$ | 2-bromopyridin-4-yl |
| 1070 | 2,5-$F_2$ | 2-bromopyridin-4-yl |
| 1071 | 2,6-$F_2$ | 2-bromopyridin-4-yl |
| 1072 | 3,4-$F_2$ | 2-bromopyridin-4-yl |
| 1073 | 3,5-$F_2$ | 2-bromopyridin-4-yl |
| 1074 | 3,4,5-$F_3$ | 2-bromopyridin-4-yl |
| 1075 | 3-F, 4-Cl | 2-bromopyridin-4-yl |
| 1076 | 3-F, 4-Br | 2-bromopyridin-4-yl |
| 1077 | 3-CN, 4-F | 2-bromopyridin-4-yl |
| 1078 | 3-Br, 4-F | 2-bromopyridin-4-yl |
| 1079 | 3-Cl, 4-F | 2-bromopyridin-4-yl |
| 1080 | 3,4-$Cl_2$ | 2-bromopyridin-4-yl |
| 1081 | H | 2-cyanopyridin-4-yl |
| 1082 | 2-F | 2-cyanopyridin-4-yl |
| 1083 | 3-F | 2-cyanopyridin-4-yl |
| 1084 | 4-F | 2-cyanopyridin-4-yl |
| 1085 | 3-Cl | 2-cyanopyridin-4-yl |
| 1086 | 4-Cl | 2-cyanopyridin-4-yl |
| 1087 | 3-Br | 2-cyanopyridin-4-yl |
| 1088 | 4-Br | 2-cyanopyridin-4-yl |
| 1089 | 3-I | 2-cyanopyridin-4-yl |
| 1090 | 3-CN | 2-cyanopyridin-4-yl |
| 1091 | 4-CN | 2-cyanopyridin-4-yl |
| 1092 | 3-$NO_2$ | 2-cyanopyridin-4-yl |
| 1093 | 3-Me | 2-cyanopyridin-4-yl |
| 1094 | 4-Me | 2-cyanopyridin-4-yl |
| 1095 | 2,3-$F_2$ | 2-cyanopyridin-4-yl |
| 1096 | 2,4-$F_2$ | 2-cyanopyridin-4-yl |
| 1097 | 2,5-$F_2$ | 2-cyanopyridin-4-yl |
| 1098 | 2,6-$F_2$ | 2-cyanopyridin-4-yl |
| 1099 | 3,4-$F_2$ | 2-cyanopyridin-4-yl |
| 1100 | 3,5-$F_2$ | 2-cyanopyridin-4-yl |
| 1101 | 3,4,5-$F_3$ | 2-cyanopyridin-4-yl |
| 1102 | 3-F, 4-Cl | 2-cyanopyridin-4-yl |
| 1103 | 3-F, 4-Br | 2-cyanopyridin-4-yl |
| 1104 | 3-CN, 4-F | 2-cyanopyridin-4-yl |
| 1105 | 3-Br, 4-F | 2-cyanopyridin-4-yl |
| 1106 | 3-Cl, 4-F | 2-cyanopyridin-4-yl |
| 1107 | 3,4-$Cl_2$ | 2-cyanopyridin-4-yl |
| 1108 | H | 3-fluoropyridin-4-yl |
| 1109 | 2-F | 3-fluoropyridin-4-yl |
| 1110 | 3-F | 3-fluoropyridin-4-yl |
| 1111 | 4-F | 3-fluoropyridin-4-yl |
| 1112 | 3-Cl | 3-fluoropyridin-4-yl |
| 1113 | 4-Cl | 3-fluoropyridin-4-yl |
| 1114 | 3-Br | 3-fluoropyridin-4-yl |
| 1115 | 4-Br | 3-fluoropyridin-4-yl |
| 1116 | 3-I | 3-fluoropyridin-4-yl |
| 1117 | 3-CN | 3-fluoropyridin-4-yl |
| 1118 | 4-CN | 3-fluoropyridin-4-yl |
| 1119 | 3-$NO_2$ | 3-fluoropyridin-4-yl |
| 1120 | 3-Me | 3-fluoropyridin-4-yl |
| 1121 | 4-Me | 3-fluoropyridin-4-yl |
| 1122 | 2,3-$F_2$ | 3-fluoropyridin-4-yl |
| 1123 | 2,4-$F_2$ | 3-fluoropyridin-4-yl |
| 1124 | 2,5-$F_2$ | 3-fluoropyridin-4-yl |
| 1125 | 2,6-$F_2$ | 3-fluoropyridin-4-yl |
| 1126 | 3,4-$F_2$ | 3-fluoropyridin-4-yl |
| 1127 | 3,5-$F_2$ | 3-fluoropyridin-4-yl |
| 1128 | 3,4,5-$F_3$ | 3-fluoropyridin-4-yl |
| 1129 | 3-F, 4-Cl | 3-fluoropyridin-4-yl |
| 1130 | 3-F, 4-Br | 3-fluoropyridin-4-yl |
| 1131 | 3-CN, 4-F | 3-fluoropyridin-4-yl |
| 1132 | 3-Br, 4-F | 3-fluoropyridin-4-yl |
| 1133 | 3-Cl, 4-F | 3-fluoropyridin-4-yl |
| 1134 | 3,4-$Cl_2$ | 3-fluoropyridin-4-yl |
| 1135 | H | 3-chloropyridin-4-yl |
| 1136 | 2-F | 3-chloropyridin-4-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 1137 | 3-F | 3-chloropyridin-4-yl |
| 1138 | 4-F | 3-chloropyridin-4-yl |
| 1139 | 3-Cl | 3-chloropyridin-4-yl |
| 1140 | 4-Cl | 3-chloropyridin-4-yl |
| 1141 | 3-Br | 3-chloropyridin-4-yl |
| 1142 | 4-Br | 3-chloropyridin-4-yl |
| 1143 | 3-I | 3-chloropyridin-4-yl |
| 1144 | 3-CN | 3-chloropyridin-4-yl |
| 1145 | 4-CN | 3-chloropyridin-4-yl |
| 1146 | 3-NO$_2$ | 3-chloropyridin-4-yl |
| 1147 | 3-Me | 3-chloropyridin-4-yl |
| 1148 | 4-Me | 3-chloropyridin-4-yl |
| 1149 | 2,3-F$_2$ | 3-chloropyridin-4-yl |
| 1150 | 2,4-F$_2$ | 3-chloropyridin-4-yl |
| 1151 | 2,5-F$_2$ | 3-chloropyridin-4-yl |
| 1152 | 2,6-F$_2$ | 3-chloropyridin-4-yl |
| 1153 | 3,4-F$_2$ | 3-chloropyridin-4-yl |
| 1154 | 3,5-F$_2$ | 3-chloropyridin-4-yl |
| 1155 | 3,4,5-F$_3$ | 3-chloropyridin-4-yl |
| 1156 | 3-F, 4-Cl | 3-chloropyridin-4-yl |
| 1157 | 3-F, 4-Br | 3-chloropyridin-4-yl |
| 1158 | 3-CN, 4-F | 3-chloropyridin-4-yl |
| 1159 | 3-Br, 4-F | 3-chloropyridin-4-yl |
| 1160 | 3-Cl, 4-F | 3-chloropyridin-4-yl |
| 1161 | 3,4-Cl$_2$ | 3-chloropyridin-4-yl |
| 1162 | H | 3-bromopyridin-4-yl |
| 1163 | 2-F | 3-bromopyridin-4-yl |
| 1164 | 3-F | 3-bromopyridin-4-yl |
| 1165 | 4-F | 3-bromopyridin-4-yl |
| 1166 | 3-Cl | 3-bromopyridin-4-yl |
| 1167 | 4-Cl | 3-bromopyridin-4-yl |
| 1168 | 3-Br | 3-bromopyridin-4-yl |
| 1169 | 4-Br | 3-bromopyridin-4-yl |
| 1170 | 3-I | 3-bromopyridin-4-yl |
| 1171 | 3-CN | 3-bromopyridin-4-yl |
| 1172 | 4-CN | 3-bromopyridin-4-yl |
| 1173 | 3-NO$_2$ | 3-bromopyridin-4-yl |
| 1174 | 3-Me | 3-bromopyridin-4-yl |
| 1175 | 4-Me | 3-bromopyridin-4-yl |
| 1176 | 2,3-F$_2$ | 3-bromopyridin-4-yl |
| 1177 | 2,4-F$_2$ | 3-bromopyridin-4-yl |
| 1178 | 2,5-F$_2$ | 3-bromopyridin-4-yl |
| 1179 | 2,6-F$_2$ | 3-bromopyridin-4-yl |
| 1180 | 3,4-F$_2$ | 3-bromopyridin-4-yl |
| 1181 | 3,5-F$_2$ | 3-bromopyridin-4-yl |
| 1182 | 3,4,5-F$_3$ | 3-bromopyridin-4-yl |
| 1183 | 3-F, 4-Cl | 3-bromopyridin-4-yl |
| 1184 | 3-F, 4-Br | 3-bromopyridin-4-yl |
| 1185 | 3-CN, 4-F | 3-bromopyridin-4-yl |
| 1186 | 3-Br, 4-F | 3-bromopyridin-4-yl |
| 1187 | 3-Cl, 4-F | 3-bromopyridin-4-yl |
| 1188 | 3,4-Cl$_2$ | 3-bromopyridin-4-yl |
| 1189 | H | 3-cyanopyridin-4-yl |
| 1190 | 2-F | 3-cyanopyridin-4-yl |
| 1191 | 3-F | 3-cyanopyridin-4-yl |
| 1192 | 4-F | 3-cyanopyridin-4-yl |
| 1193 | 3-Cl | 3-cyanopyridin-4-yl |
| 1194 | 4-Cl | 3-cyanopyridin-4-yl |
| 1195 | 3-Br | 3-cyanopyridin-4-yl |
| 1196 | 4-Br | 3-cyanopyridin-4-yl |
| 1197 | 3-I | 3-cyanopyridin-4-yl |
| 1198 | 3-CN | 3-cyanopyridin-4-yl |
| 1199 | 4-CN | 3-cyanopyridin-4-yl |
| 1200 | 3-NO$_2$ | 3-cyanopyridin-4-yl |
| 1201 | 3-Me | 3-cyanopyridin-4-yl |
| 1202 | 4-Me | 3-cyanopyridin-4-yl |
| 1203 | 2,3-F$_2$ | 3-cyanopyridin-4-yl |
| 1204 | 2,4-F$_2$ | 3-cyanopyridin-4-yl |
| 1205 | 2,5-F$_2$ | 3-cyanopyridin-4-yl |
| 1206 | 2,6-F$_2$ | 3-cyanopyridin-4-yl |
| 1207 | 3,4-F$_2$ | 3-cyanopyridin-4-yl |
| 1208 | 3,5-F$_2$ | 3-cyanopyridin-4-yl |
| 1209 | 3,4,5-F$_3$ | 3-cyanopyridin-4-yl |
| 1210 | 3-F, 4-Cl | 3-cyanopyridin-4-yl |
| 1211 | 3-F, 4-Br | 3-cyanopyridin-4-yl |
| 1212 | 3-CN, 4-F | 3-cyanopyridin-4-yl |
| 1213 | 3-Br, 4-F | 3-cyanopyridin-4-yl |
| 1214 | 3-Cl, 4-F | 3-cyanopyridin-4-yl |
| 1215 | 3,4-Cl$_2$ | 3-cyanopyridin-4-yl |
| 1216 | H | 5-fluoropyridin-4-yl |
| 1217 | 2-F | 5-fluoropyridin-4-yl |
| 1218 | 3-F | 5-fluoropyridin-4-yl |
| 1219 | 4-F | 5-fluoropyridin-4-yl |
| 1220 | 3-Cl | 5-fluoropyridin-4-yl |
| 1221 | 4-Cl | 5-fluoropyridin-4-yl |
| 1222 | 3-Br | 5-fluoropyridin-4-yl |
| 1223 | 4-Br | 5-fluoropyridin-4-yl |
| 1224 | 3-I | 5-fluoropyridin-4-yl |
| 1225 | 3-CN | 5-fluoropyridin-4-yl |
| 1226 | 4-CN | 5-fluoropyridin-4-yl |
| 1227 | 3-NO$_2$ | 5-fluoropyridin-4-yl |
| 1228 | 3-Me | 5-fluoropyridin-4-yl |
| 1229 | 4-Me | 5-fluoropyridin-4-yl |
| 1230 | 2,3-F$_2$ | 5-fluoropyridin-4-yl |
| 1231 | 2,4-F$_2$ | 5-fluoropyridin-4-yl |
| 1232 | 2,5-F$_2$ | 5-fluoropyridin-4-yl |
| 1233 | 2,6-F$_2$ | 5-fluoropyridin-4-yl |
| 1234 | 3,4-F$_2$ | 5-fluoropyridin-4-yl |
| 1235 | 3,5-F$_2$ | 5-fluoropyridin-4-yl |
| 1236 | 3,4,5-F$_3$ | 5-fluoropyridin-4-yl |
| 1237 | 3-F, 4-Cl | 5-fluoropyridin-4-yl |
| 1238 | 3-F, 4-Br | 5-fluoropyridin-4-yl |
| 1239 | 3-CN, 4-F | 5-fluoropyridin-4-yl |
| 1240 | 3-Br, 4-F | 5-fluoropyridin-4-yl |
| 1241 | 3-Cl, 4-F | 5-fluoropyridin-4-yl |
| 1242 | 3,4-Cl$_2$ | 5-fluoropyridin-4-yl |
| 1243 | H | 5-chloropyridin-4-yl |
| 1244 | 2-F | 5-chloropyridin-4-yl |
| 1245 | 3-F | 5-chloropyridin-4-yl |
| 1246 | 4-F | 5-chloropyridin-4-yl |
| 1247 | 3-Cl | 5-chloropyridin-4-yl |
| 1248 | 4-Cl | 5-chloropyridin-4-yl |
| 1249 | 3-Br | 5-chloropyridin-4-yl |
| 1250 | 4-Br | 5-chloropyridin-4-yl |
| 1251 | 3-I | 5-chloropyridin-4-yl |
| 1252 | 3-CN | 5-chloropyridin-4-yl |
| 1253 | 4-CN | 5-chloropyridin-4-yl |
| 1254 | 3-NO$_2$ | 5-chloropyridin-4-yl |
| 1255 | 3-Me | 5-chloropyridin-4-yl |
| 1256 | 4-Me | 5-chloropyridin-4-yl |
| 1257 | 2,3-F$_2$ | 5-chloropyridin-4-yl |
| 1258 | 2,4-F$_2$ | 5-chloropyridin-4-yl |
| 1259 | 2,5-F$_2$ | 5-chloropyridin-4-yl |
| 1260 | 2,6-F$_2$ | 5-chloropyridin-4-yl |
| 1261 | 3,4-F$_2$ | 5-chloropyridin-4-yl |
| 1262 | 3,5-F$_2$ | 5-chloropyridin-4-yl |
| 1263 | 3,4,5-F$_3$ | 5-chloropyridin-4-yl |
| 1264 | 3-F, 4-Cl | 5-chloropyridin-4-yl |
| 1265 | 3-F, 4-Br | 5-chloropyridin-4-yl |
| 1266 | 3-CN, 4-F | 5-chloropyridin-4-yl |
| 1267 | 3-Br, 4-F | 5-chloropyridin-4-yl |
| 1268 | 3-Cl, 4-F | 5-chloropyridin-4-yl |
| 1269 | 3,4-Cl$_2$ | 5-chloropyridin-4-yl |
| 1270 | H | 3,5-difluoropyridin-4-yl |
| 1271 | 2-F | 3,5-difluoropyridin-4-yl |
| 1272 | 3-F | 3,5-difluoropyridin-4-yl |
| 1273 | 4-F | 3,5-difluoropyridin-4-yl |
| 1274 | 3-Cl | 3,5-difluoropyridin-4-yl |
| 1275 | 4-Cl | 3,5-difluoropyridin-4-yl |
| 1276 | 3-Br | 3,5-difluoropyridin-4-yl |
| 1277 | 4-Br | 3,5-difluoropyridin-4-yl |
| 1278 | 3-I | 3,5-difluoropyridin-4-yl |
| 1279 | 3-CN | 3,5-difluoropyridin-4-yl |
| 1280 | 4-CN | 3,5-difluoropyridin-4-yl |
| 1281 | 3-NO$_2$ | 3,5-difluoropyridin-4-yl |
| 1282 | 3-Me | 3,5-difluoropyridin-4-yl |
| 1283 | 4-Me | 3,5-difluoropyridin-4-yl |
| 1284 | 2,3-F$_2$ | 3,5-difluoropyridin-4-yl |

TABLE 1-continued

Definitions of structural combinations of groups $(R^2)_n$ and Q for the tables of compounds of the general formula (I) according to the invention below

| No. | $(R^2)_n$ | Q |
|---|---|---|
| 1285 | 2,4-F$_2$ | 3,5-difluoropyridin-4-yl |
| 1286 | 2,5-F$_2$ | 3,5-difluoropyridin-4-yl |
| 1287 | 2,6-F$_2$ | 3,5-difluoropyridin-4-yl |
| 1288 | 3,4-F$_2$ | 3,5-difluoropyridin-4-yl |
| 1289 | 3,5-F$_2$ | 3,5-difluoropyridin-4-yl |
| 1290 | 3,4,5-F$_3$ | 3,5-difluoropyridin-4-yl |
| 1291 | 3-F, 4-Cl | 3,5-difluoropyridin-4-yl |
| 1292 | 3-F, 4-Br | 3,5-difluoropyridin-4-yl |
| 1293 | 3-CN, 4-F | 3,5-difluoropyridin-4-yl |
| 1294 | 3-Br, 4-F | 3,5-difluoropyridin-4-yl |
| 1295 | 3-Cl, 4-F | 3,5-difluoropyridin-4-yl |
| 1296 | 3,4-Cl$_2$ | 3,5-difluoropyridin-4-yl |
| 1297 | H | 3,5-dichloropyridin-4-yl |
| 1298 | 2-F | 3,5-dichloropyridin-4-yl |
| 1299 | 3-F | 3,5-dichloropyridin-4-yl |
| 1300 | 4-F | 3,5-dichloropyridin-4-yl |
| 1301 | 3-Cl | 3,5-dichloropyridin-4-yl |
| 1302 | 4-Cl | 3,5-dichloropyridin-4-yl |
| 1303 | 3-Br | 3,5-dichloropyridin-4-yl |
| 1304 | 4-Br | 3,5-dichloropyridin-4-yl |
| 1305 | 3-I | 3,5-dichloropyridin-4-yl |
| 1306 | 3-CN | 3,5-dichloropyridin-4-yl |
| 1307 | 4-CN | 3,5-dichloropyridin-4-yl |
| 1308 | 3-NO$_2$ | 3,5-dichloropyridin-4-yl |
| 1309 | 3-Me | 3,5-dichloropyridin-4-yl |
| 1310 | 4-Me | 3,5-dichloropyridin-4-yl |
| 1311 | 2,3-F$_2$ | 3,5-dichloropyridin-4-yl |
| 1312 | 2,4-F$_2$ | 3,5-dichloropyridin-4-yl |
| 1313 | 2,5-F$_2$ | 3,5-dichloropyridin-4-yl |
| 1314 | 2,6-F$_2$ | 3,5-dichloropyridin-4-yl |
| 1315 | 3,4-F$_2$ | 3,5-dichloropyridin-4-yl |
| 1316 | 3,5-F$_2$ | 3,5-dichloropyridin-4-yl |
| 1317 | 3,4,5-F$_3$ | 3,5-dichloropyridin-4-yl |
| 1318 | 3-F, 4-Cl | 3,5-dichloropyridin-4-yl |
| 1319 | 3-F, 4-Br | 3,5-dichloropyridin-4-yl |
| 1320 | 3-CN, 4-F | 3,5-dichloropyridin-4-yl |
| 1321 | 3-Br, 4-F | 3,5-dichloropyridin-4-yl |
| 1322 | 3-Cl, 4-F | 3,5-dichloropyridin-4-yl |
| 1323 | 3,4-Cl$_2$ | 3,5-dichloropyridin-4-yl |
| 1324 | H | 2,6-difluoropyridin-4-yl |
| 1325 | 2-F | 2,6-difluoropyridin-4-yl |
| 1326 | 3-F | 2,6-difluoropyridin-4-yl |
| 1327 | 4-F | 2,6-difluoropyridin-4-yl |
| 1328 | 3-Cl | 2,6-difluoropyridin-4-yl |
| 1329 | 4-Cl | 2,6-difluoropyridin-4-yl |
| 1330 | 3-Br | 2,6-difluoropyridin-4-yl |
| 1331 | 4-Br | 2,6-difluoropyridin-4-yl |
| 1332 | 3-I | 2,6-difluoropyridin-4-yl |
| 1333 | 3-CN | 2,6-difluoropyridin-4-yl |
| 1334 | 4-CN | 2,6-difluoropyridin-4-yl |
| 1335 | 3-NO$_2$ | 2,6-difluoropyridin-4-yl |
| 1336 | 3-Me | 2,6-difluoropyridin-4-yl |
| 1337 | 4-Me | 2,6-difluoropyridin-4-yl |
| 1338 | 2,3-F$_2$ | 2,6-difluoropyridin-4-yl |
| 1339 | 2,4-F$_2$ | 2,6-difluoropyridin-4-yl |
| 1340 | 2,5-F$_2$ | 2,6-difluoropyridin-4-yl |
| 1341 | 2,6-F$_2$ | 2,6-difluoropyridin-4-yl |
| 1342 | 3,4-F$_2$ | 2,6-difluoropyridin-4-yl |
| 1343 | 3,5-F$_2$ | 2,6-difluoropyridin-4-yl |
| 1344 | 3,4,5-F$_3$ | 2,6-difluoropyridin-4-yl |
| 1345 | 3-F, 4-Cl | 2,6-difluoropyridin-4-yl |
| 1346 | 3-F, 4-Br | 2,6-difluoropyridin-4-yl |
| 1347 | 3-CN, 4-F | 2,6-difluoropyridin-4-yl |
| 1348 | 3-Br, 4-F | 2,6-difluoropyridin-4-yl |
| 1349 | 3-Cl, 4-F | 2,6-difluoropyridin-4-yl |
| 1350 | 3,4-Cl$_2$ | 2,6-difluoropyridin-4-yl |
| 1351 | H | 2,6-dichloropyridin-4-yl |
| 1352 | 2-F | 2,6-dichloropyridin-4-yl |
| 1353 | 3-F | 2,6-dichloropyridin-4-yl |
| 1354 | 4-F | 2,6-dichloropyridin-4-yl |
| 1355 | 3-Cl | 2,6-dichloropyridin-4-yl |
| 1356 | 4-Cl | 2,6-dichloropyridin-4-yl |
| 1357 | 3-Br | 2,6-dichloropyridin-4-yl |
| 1358 | 4-Br | 2,6-dichloropyridin-4-yl |
| 1359 | 3-I | 2,6-dichloropyridin-4-yl |
| 1360 | 3-CN | 2,6-dichloropyridin-4-yl |
| 1361 | 4-CN | 2,6-dichloropyridin-4-yl |
| 1362 | 3-NO$_2$ | 2,6-dichloropyridin-4-yl |
| 1363 | 3-Me | 2,6-dichloropyridin-4-yl |
| 1364 | 4-Me | 2,6-dichloropyridin-4-yl |
| 1365 | 2,3-F$_2$ | 2,6-dichloropyridin-4-yl |
| 1366 | 2,4-F$_2$ | 2,6-dichloropyridin-4-yl |
| 1367 | 2,5-F$_2$ | 2,6-dichloropyridin-4-yl |
| 1368 | 2,6-F$_2$ | 2,6-dichloropyridin-4-yl |
| 1369 | 3,4-F$_2$ | 2,6-dichloropyridin-4-yl |
| 1370 | 3,5-F$_2$ | 2,6-dichloropyridin-4-yl |
| 1371 | 3,4,5-F$_3$ | 2,6-dichloropyridin-4-yl |
| 1372 | 3-F, 4-Cl | 2,6-dichloropyridin-4-yl |
| 1373 | 3-F, 4-Br | 2,6-dichloropyridin-4-yl |
| 1374 | 3-CN, 4-F | 2,6-dichloropyridin-4-yl |
| 1375 | 3-Br, 4-F | 2,6-dichloropyridin-4-yl |
| 1376 | 3-Cl, 4-F | 2,6-dichloropyridin-4-yl |
| 1377 | 3,4-Cl$_2$ | 2,6-dichloropyridin-4-yl |

Definition of the Examples in Tables 2 to 2f Below:

For reference purposes, specific numbers (=Example Numbers) have been assigned to the individual compounds in Tables 2 to 2f below, where the Example Number in question is composed of the number of the chemical formula assigned to the respective table and a "row number" (row number) which refers to the same number in the row of the first column of Table 1. The chemical structure of the Example No. "(formula number)(row number)" is thus defined unambiguously by the formula above the respective table by formula number and row number of Table 1, for example:

The example of No. "Iba1" from Table 2 is the compound of the formula (Ib) in which $R^1$=H (=hydrogen) [=formula (Iba)] and $(R^2)_n$=H (=hydrogen) and Q=3-fluoropyridin-2-yl, defined according to row 1 of Table 1.

The example of No. "Ibd1201" from Table 2 is the compound of the formula (Ib) in which $R^1$=n-propyl [=formula (Ibd)] and $(R^2)_n$=3-methyl and Q=3-cyanopyridin-4-yl, defined according to row 1201 of Table 1.

This applies correspondingly to the assignment of racemic or optically active threo stereoisomers or erythro stereoisomers. For example, for reference purposes, specific numbers (=Example Numbers) have been assigned to the compounds of Table 2a, where the number "threo-Iba(row number)" refers to the racemic mixture of the threo enantiomers having the chemical structure of the formulae (threo-1-Iba) and (threo-2-Iba), each of which has the structural combination of groups $(R^2)_n$ and Q according to the row number of Table 1.

Table 2: Compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby) and (Ibz) where $(R^2)_n$ and Q are each as defined in Table 1

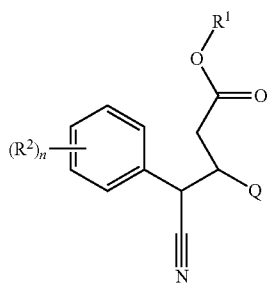

(Ib)

For definitions of subformulae of formula (Ib), see Table U1 below:

TABLE U1

| Formula | Radical R¹ in formula (Ib) |
|---|---|
| (Iba) | H (hydrogen atom) |
| (Ibb) | methyl |
| (Ibc) | ethyl |
| (Ibd) | n-propyl |
| (Ibe) | i-propyl (=isopropyl) |
| (Ibf) | 2,2-difluoroethyl |
| (Ibg) | 2,2,2-trifluoroethyl |
| (Ibh) | 2-methoxyethyl |
| (Ibi) | cyclopropylmethyl |
| (Ibj) | (1-methylcyclopropyl)methyl |
| (Ibk) | allyl |
| (Ibl) | prop-2-yn-1-yl |
| (Ibm) | ethynyl |
| (Ibn) | prop-1-yn-1-yl |
| (Ibo) | benzyl |
| (Ibp) | 4-chlorobenzyl |
| (Ibq) | phenyl |
| (Ibr) | methoxymethyl |
| (Ibs) | difluoromethyl |
| (Ibt) | oxetan-3-yl |
| (Ibu) | thietan-3-yl |
| (Ibv) | 2-(phenylsulphanyl)ethyl |
| (Ibw) | 2-(phenylsulphinyl)ethyl |
| (Ibx) | 2-(ethylsulphanyl)ethyl |
| (Iby) | 2-(ethylsulphinyl)ethyl |
| (Ibz) | tetrahydrofuran-2-ylmethyl |

According to the invention, preference is given here to the compounds of the formula (Ib) in which which R¹ represents hydrogen, alkyl, alkenyl, alkynyl or cycloalkyl, from among these preferably hydrogen, alkyl having 1 to 12 carbon atoms, alkenyl having 2 to 12 carbon atoms or alkynyl having 2 to 12 carbon atoms, from among these in turn with preference hydrogen, alkyl having 1 to 6 carbon atoms, alkenyl having 2 to 6 carbon atoms or alkynyl having 2 to 6 carbon atoms.

Particular preference according to the invention is given to the compounds of the formulae Iba, Ibb and Ibc (i.e. compounds of the formula (Ib) in which R¹ represents hydrogen, methyl or ethyl), from among these in turn with preference the compounds Ibc1029, Ibc1029, Ibb1029, Ibc894, Ibc894, Ibb894, Ibb748, Ibc895, Ibc892, Ibc901, Ibc896, Ibc910, Ibc1045, Ibc1036, Ibb1045, Ibb748, Ibb734, Ibb730, Ibb1027, Ibb755, Ibb1052, Ibb1036, Ibb1049, Ibb751, Ibb1048, Ibb208, Ibb192, Ibb732, Ibb10, Ibb37, Ibb361, Ibb118, Ibb334, Ibb1279, Ibb3, Ibb30, Ibb354, Ibb111, Ibb327, Ibb1272, Ibb22, Ibb49, Ibb373, Ibb130, Ibb346, Ibb1291, Ibb5, Ibb356, Ibb113, Ibb329, Ibb1274, Ibb109, Ibb1270, Ibb19, Ibb46, Ibb370, Ibb127, Ibb343, Ibb1288, Ibb4, Ibb355, Ibb328, Ibb1273, Ibc916, Ibb194, Ibb211, Ibb190, Ibb210, Ibb215, Ibb212, Ibb193, Ibb451, Ibb1018, Ibb435, Ibb1002, Ibb458, Ibb1025, Ibb454, Ibb1021 and Ibb1031.

Erythro/threo mixtures of the formulae (Iba) to (Ibz):

Examples of compounds of the formulae (Iba) to (Ibz) are the compounds of the respective formulae (Iba) to (Ibz), in each case in the form of a racemic erythro/threo mixture (ratio 70:30 to 30:70), where the structural combination of groups (R²)ₙ and Q is defined according to a row number of Table 1. The numeration is carried out according to "(formula)(row number)" without any brackets, for example Iba200=compound of the formula (Iba) having the structural combination of row 200 of Table 1.

Tables 2a, 2b and 2c:

Threo, threo-1 and threo-2 compounds of the compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr), (Ibs), (Ibt), (Ibu), (Iby), (Ibw), (Ibx), (Iby) and (Ibz) where (R²)ₙ and Q are each as defined in Table 1

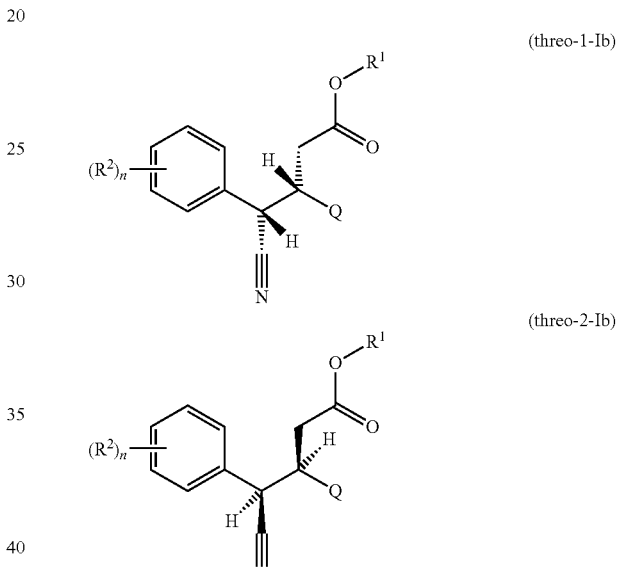

(threo-1-Ib)

(threo-2-Ib)

(threo-Ib)=(threo-1-Ib)+(threo-2-Ib)(50:50)=(rac.)

For definitions of subformulae of formulae (threo-Ib), (threo-1-Ib) and (threo-2-Ib), see Table U2 below:

TABLE U2

| Formula | Radical R¹ in formula (threo-Ib) |
|---|---|
| (threo-Iba) | H (hydrogen atom) |
| (threo-1-Iba) | H (hydrogen atom) |
| (threo-2-Iba) | H (hydrogen atom) |
| (threo-Ibb) | methyl |
| (threo-1-Ibb) | methyl |
| (threo-2-Ibb) | methyl |
| (threo-Ibc) | ethyl |
| (threo-1-Ibc) | ethyl |
| (threo-2-Ibc) | ethyl |
| (threo-Ibd) | n-propyl |
| (threo-1-Ibd) | n-propyl |
| (threo-2-Ibd) | n-propyl |
| (threo-Ibe) | i-propyl (=isopropyl) |
| (threo-1-Ibe) | i-propyl |
| (threo-2-Ibe) | i-propyl |
| (threo-Ibf) | 2,2-difluoroethyl |
| (threo-1-Ibf) | 2,2-difluoroethyl |
| (threo-2-Ibf) | 2,2-difluoroethyl |
| (threo-Ibg) | 2,2,2-trifluoroethyl |

TABLE U2-continued

| Formula | Radical $R^1$ in formula (threo-Ib) |
|---|---|
| (threo-1-Ibg) | 2,2,2-trifluoroethyl |
| (threo-2-Ibg) | 2,2,2-trifluoroethyl |
| (threo-Ibh) | 2-methoxyethyl |
| (threo-1-Ibh) | 2-methoxyethyl |
| (threo-2-Ibh) | 2-methoxyethyl |
| (threo-Ibi) | cyclopropylmethyl |
| (threo-1-Ibi) | cyclopropylmethyl |
| (threo-2-Ibi) | cyclopropylmethyl |
| (threo-Ibj) | (1-methylcyclopropyl)methyl |
| (threo-1-Ibj) | (1-methylcyclopropyl)methyl |
| (threo-2-Ibj) | (1-methylcyclopropyl)methyl |
| (threo-Ibk) | allyl |
| (threo-1-Ibk) | allyl |
| (threo-2-Ibk) | allyl |
| (threo-Ibl) | prop-2-yn-1-yl |
| (threo-1-Ibl) | prop-2-yn-1-yl |
| (threo-2-Ibl) | prop-2-yn-1-yl |
| (threo-Ibm) | ethynyl |
| (threo-1-Ibm) | ethynyl |
| (threo-2-Ibm) | ethynyl |
| (threo-Ibn) | prop-1-yn-1-yl |
| (threo-1-Ibn) | prop-1-yn-1-yl |
| (threo-2-Ibn) | prop-1-yn-1-yl |
| (threo-Ibo) | benzyl |
| (threo-1-Ibo) | benzyl |
| (threo-2-Ibo) | benzyl |
| (threo-Ibp) | 4-chlorobenzyl |
| (threo-1-Ibp) | 4-chlorobenzyl |
| (threo-2-Ibp) | 4-chlorobenzyl |
| (threo-Ibq) | phenyl |
| (threo-1-Ibq) | phenyl |
| (threo-2-Ibq) | phenyl |
| (threo-Ibr) | methoxymethyl |
| (threo-1-Ibr) | methoxymethyl |
| (threo-2-Ibr) | methoxymethyl |
| (threo-Ibs) | difluoromethyl |
| (threo-1-Ibs) | difluoromethyl |
| (threo-2-Ibs) | difluoromethyl |
| (threo-Ibt) | oxetan-3-yl |
| (threo-1-Ibt) | oxetan-3-yl |
| (threo-2-Ibt) | oxetan-3-yl |
| (threo-Ibu) | thietan-3-yl |
| (threo-1-Ibu) | thietan-3-yl |
| (threo-2-Ibu) | thietan-3-yl |
| (threo-Ibv) | 2-(phenylsulphanyl)ethyl |
| (threo-1-Ibv) | 2-(phenylsulphanyl)ethyl |
| (threo-2-Ibv) | 2-(phenylsulphanyl)ethyl |
| (threo-Ibw) | 2-(phenylsulphinyl)ethyl |
| (threo-1-Ibw) | 2-(phenylsulphinyl)ethyl |
| (threo-2-Ibw) | 2-(phenylsulphinyl)ethyl |
| (threo-Ibx) | 2-(ethylsulphanyl)ethyl |
| (threo-1-Ibx) | 2-(ethylsulphanyl)ethyl |
| (threo-2-Ibx) | 2-(ethylsulphanyl)ethyl |
| (threo-Iby) | 2-(ethylsulphinyl)ethyl |
| (threo-1-Iby) | 2-(ethylsulphinyl)ethyl |
| (threo-2-Iby) | 2-(ethylsulphinyl)ethyl |
| (threo-Ibz) | tetrahydrofuran-2-ylmethyl |
| (threo-1-Ibz) | tetrahydrofuran-2-ylmethyl |
| (threo-2-Ibz) | tetrahydrofuran-2-ylmethyl |

Table 2a (Threo Racemates), Examples:

Examples of the compounds of the formulae (threo-Iba) to (threo-Ibz) (see Table U2) are the compounds of the formulae in question in the form of the racemic mixture of the threo isomers where the structural combination of groups $(R^2)_n$ and Q is defined according to a row number of Table 1.

The numeration is carried out according to "(formula) (row number)" without any brackets, for example threo-Iba200=compound of the formula (threo-Iba) having the structural combination of row 200 of Table 1.

Table 2b (Optically Active Threo-2 Enantiomers): Examples:

Examples of the compounds of the formulae (threo-2-Iba) to (threo-2-Ibz) (see Table U2) are the optically active threo-2 compounds of the formulae in question in enriched form [=(3R,4R)-form having more than 80% ee] where the structural combination of groups $(R^2)_n$ and Q is defined according to a row number of Table 1.

Compounds are numbered "(formula)(row number)", without any brackets. For example, No. threo-2-Iba789 refers to the compound of the formula (threo-2-Iba) in which $(R^2)_n$=4-chloro and Q=5-bromopyridin-3-yl.

Table 2c (Optically Active Threo-1 Enantiomers): Examples:

Examples of the compounds of the formulae (threo-1-Iba) to (threo-1-Ibz) (see Table U2) are the optically active threo-1 compounds of the formulae in question in enriched form [=(3S,4S)-form having more than 80% ee] where the structural combination of groups $(R^2)_n$ and Q is defined according to a row number of Table 1.

Compounds are numbered "(formula)(row number)", without any brackets. For example, No. threo-1-Ibb5 refers to the compound of the formula (threo-1-Ibb) in which $(R^2)_n$=3-chloro and Q=3-fluoropyridin-2-yl.

Tables 2d, 2e and 2f:

Erythro, erythro-1 and erythro-2 compounds of the compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby) and (Ibz) where $(R^2)_n$ and Q are each as defined in Table 1

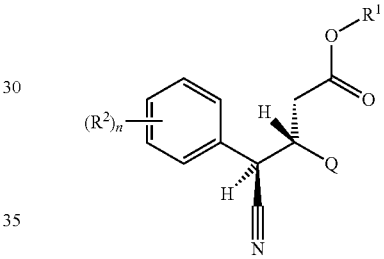

(erythro-1-Ib)

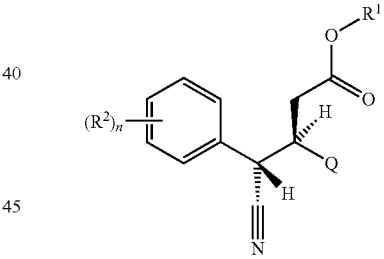

(erythro-2-Ib)

(erythro-Ib)=(erythro-1-Ib)+(erythro-2-Ib)(50:50)= (rac.)

For definitions of subformulae of formulae (erythro-Ib), (erythro-1-Ib) and (erythro-2-Ib), see Table U3 below:

TABLE U3

| Formula | Radical $R^1$ in formula (erythro-Ib) |
|---|---|
| (erythro-Iba) | H (hydrogen atom) |
| (erythro-1-Iba) | H (hydrogen atom) |
| (erythro-2-Iba) | H (hydrogen atom) |
| (erythro-Ibb) | methyl |
| (erythro-1-Ibb) | methyl |
| (erythro-2-Ibb) | methyl |
| (erythro-Ibc) | ethyl |
| (erythro-1-Ibc) | ethyl |
| (erythro-2-Ibc) | ethyl |
| (erythro-Ibd) | n-propyl |
| (erythro-1-Ibd) | n-propyl |

TABLE U3-continued

| Formula | Radical R$^1$ in formula (erythro-Ib) |
|---|---|
| (erythro-2-Ibd) | n-propyl |
| (erythro-Ibe) | i-propyl (=isopropyl) |
| (erythro-1-Ibe) | i-propyl |
| (erythro-2-Ibe) | i-propyl |
| (erythro-Ibf) | 2,2-difluoroethyl |
| (erythro-1-Ibf) | 2,2-difluoroethyl |
| (erythro-2-Ibf) | 2,2-difluoroethyl |
| (erythro-Ibg) | 2,2,2-trifluoroethyl |
| (erythro-1-Ibg) | 2,2,2-trifluoroethyl |
| (erythro-2-Ibg) | 2,2,2-trifluoroethyl |
| (erythro-Ibh) | 2-methoxyethyl |
| (erythro-1-Ibh) | 2-methoxyethyl |
| (erythro-2-Ibh) | 2-methoxyethyl |
| (erythro-Ibi) | cyclopropylmethyl |
| (erythro-1-Ibi) | cyclopropylmethyl |
| (erythro-2-Ibi) | cyclopropylmethyl |
| (erythro-Ibj) | (1-methylcyclopropyl)methyl |
| (erythro-1-Ibj) | (1-methylcyclopropyl)methyl |
| (erythro-2-Ibj) | (1-methylcyclopropyl)methyl |
| (erythro-Ibk) | allyl |
| (erythro-1-Ibk) | allyl |
| (erythro-2-Ibk) | allyl |
| (erythro-Ibl) | prop-2-yn-1-yl |
| (erythro-1-Ibl) | prop-2-yn-1-yl |
| (erythro-2-Ibl) | prop-2-yn-1-yl |
| (erythro-Ibm) | ethynyl |
| (erythro-1-Ibm) | ethynyl |
| (erythro-2-Ibm) | ethynyl |
| (erythro-Ibn) | prop-1-yn-1-yl |
| (erythro-1-Ibn) | prop-1-yn-1-yl |
| (erythro-2-Ibn) | prop-1-yn-1-yl |
| (erythro-Ibo) | benzyl |
| (erythro-1-Ibo) | benzyl |
| (erythro-2-Ibo) | benzyl |
| (erythro-Ibp) | 4-chlorobenzyl |
| (erythro-1-Ibp) | 4-chlorobenzyl |
| (erythro-2-Ibp) | 4-chlorobenzyl |
| (erythro-Ibq) | phenyl |
| (erythro-1-Ibq) | phenyl |
| (erythro-2-Ibq) | phenyl |
| (erythro-Ibr) | methoxymethyl |
| (erythro-1-Ibr) | methoxymethyl |
| (erythro-2-Ibr) | methoxymethyl |
| (erythro-Ibs) | difluoromethyl |
| (erythro-1-Ibs) | difluoromethyl |
| (erythro-2-Ibs) | difluoromethyl |
| (erythro-Ibt) | oxetan-3-yl |
| (erythro-1-Ibt) | oxetan-3-yl |
| (erythro-2-Ibt) | oxetan-3-yl |
| erythro-Ibu) | thietan-3-yl |
| (erythro-1-Ibu) | thietan-3-yl |
| (erythro-2-Ibu) | thietan-3-yl |
| (erythro-Ibv) | 2-(phenylsulphanyl)ethyl |
| (erythro-1-Ibv) | 2-(phenylsulphanyl)ethyl |
| (erythro-2-Ibv) | 2-(phenylsulphanyl)ethyl |
| (erythro-Ibw) | 2-(phenylsulphinyl)ethyl |
| (erythro-1-Ibw) | 2-(phenylsulphinyl)ethyl |
| (erythro-2-Ibw) | 2-(phenylsulphinyl)ethyl |
| (erythro-Ibx) | 2-(ethylsulphanyl)ethyl |
| (erythro-1-Ibx) | 2-(ethylsulphanyl)ethyl |
| (erythro-2-Ibx) | 2-(ethylsulphanyl)ethyl |
| (erythro-Iby) | 2-(ethylsulphinyl)ethyl |
| (erythro-1-Iby) | 2-(ethylsulphinyl)ethyl |
| (erythro-2-Iby) | 2-(ethylsulphinyl)ethyl |
| (erythro-Ibz) | tetrahydrofuran-2-ylmethyl |
| (erythro-1-Ibz) | tetrahydrofuran-2-ylmethyl |
| (erythro-2-Ibz) | tetrahydrofuran-2-ylmethyl |

Table 2d (Erythro Racemates), Examples:

Examples of the compounds of the formulae (erythro-Iba) to (erythro-Ibz) (see Table U3) are the compounds of the formulae in question in the form of the racemic mixture of the erythro isomers where the structural combination of groups $(R^2)_n$ and Q is defined according to a row number of Table 1.

The numeration is carried out according to "(formula) (row number)" without any brackets, for example erythro-Iba200=compound of the formula (erythro-Iba) having the structural combination of row 200 of Table 1.

Table 2e (Optically Active Erythro-2 Enantiomers): Examples:

Examples of the compounds of the formulae (erythro-2-Iba) to (erythro-2-Ibz) (see Table U3) are the optically active erythro-2 compounds of the formulae in question in enriched form [=(3R,4S)-form having more than 80% ee] where the structural combination of groups $(R^2)_n$ and Q is defined according to a row number of Table 1.

Compounds are numbered "(formula)(row number)", without any brackets. For example, No. erythro-2-Iba789 refers to the compound of the formula (erythro-2-Iba) in which $(R^2)_n$=4-chloro and Q=5-bromopyridin-3-yl.

Table 2f (Optically Active Erythro-1 Enantiomers): Examples:

Examples of the compounds of the formulae (erythro-1-Iba) to (erythro-1-Ibz) (see Table U3) are the optically active erythro-1 compounds of the formulae in question in enriched form [=(3S,4R)-form having more than 80% ee] where the structural combination of groups $(R^2)_n$ and Q is defined according to a row number of Table 1.

Compounds are numbered "(formula)(row number)", without any brackets. For example, No. erythro-1-Ibb5 refers to the compound of the formula (erythro-1-Ibb) in which $(R^2)_n$=3-chloro and Q=3-fluoropyridin-2-yl.

According to the invention, particular preference is given to the racemic threo compounds threo-Ib mentioned in Table Z1 below.

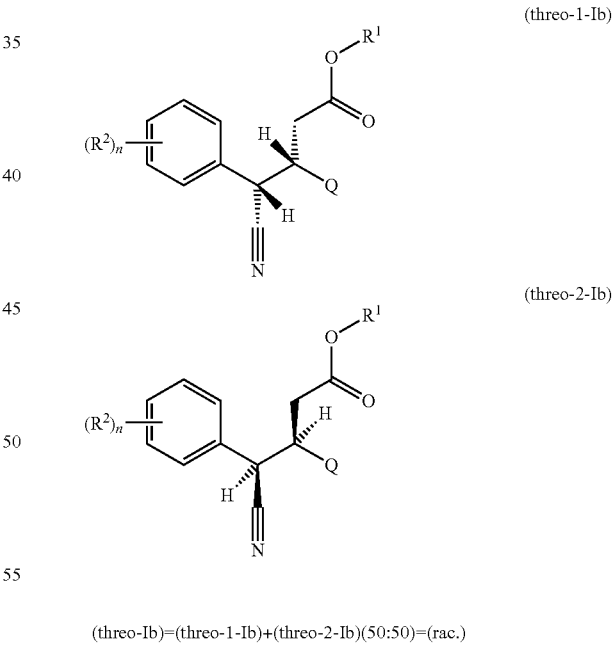

(threo-Ib)=(threo-1-Ib)+(threo-2-Ib)(50:50)=(rac.)

TABLE Z1

| Example number | R$^1$ | $(R^2)_n$ | Q |
|---|---|---|---|
| threo-Iba3 | H | 3-F | 3-fluoropyridin-2-yl |
| threo-Ibb3 | Me | 3-F | 3-fluoropyridin-2-yl |
| threo-Ibc3 | Et | 3-F | 3-fluoropyridin-2-yl |
| threo-Iba19 | H | 3,4-F$_2$ | 3-fluoropyridin-2-yl |
| threo-Ibb19 | Me | 3,4-F$_2$ | 3-fluoropyridin-2-yl |

TABLE Z1-continued

| Example number | R¹ | (R²)ₙ | Q |
|---|---|---|---|
| threo-Ibc19 | Et | 3,4-F₂ | 3-fluoropyridin-2-yl |
| threo-Iba24 | H | 3-CN, 4-F | 3-fluoropyridin-2-yl |
| threo-Ibb24 | Me | 3-CN, 4-F | 3-fluoropyridin-2-yl |
| threo-Ibc24 | Et | 3-CN, 4-F | 3-fluoropyridin-2-yl |
| threo-Iba25 | H | 3-Br, 4-F | 3-fluoropyridin-2-yl |
| threo-Ibb25 | Me | 3-Br, 4-F | 3-fluoropyridin-2-yl |
| threo-Ibc25 | Et | 3-Br, 4-F | 3-fluoropyridin-2-yl |
| threo-Iba26 | H | 3-Cl, 4-F | 3-fluoropyridin-2-yl |
| threo-Ibb26 | Me | 3-Cl, 4-F | 3-fluoropyridin-2-yl |
| threo-Ibc26 | Et | 3-Cl, 4-F | 3-fluoropyridin-2-yl |
| threo-Iba111 | H | 3-F | 4-chloropyridin-2-yl |
| threo-Ibb111 | Me | 3-F | 4-chloropyridin-2-yl |
| threo-Ibc111 | Et | 3-F | 4-chloropyridin-2-yl |
| threo-Iba127 | H | 3,4-F₂ | 4-chloropyridin-2-yl |
| threo-Ibb127 | Me | 3,4-F₂ | 4-chloropyridin-2-yl |
| threo-Ibc127 | Et | 3,4-F₂ | 4-chloropyridin-2-yl |
| threo-Iba132 | H | 3-CN, 4-F | 4-chloropyridin-2-yl |
| threo-Ibb132 | Me | 3-CN, 4-F | 4-chloropyridin-2-yl |
| threo-Ibc132 | Et | 3-CN, 4-F | 4-chloropyridin-2-yl |
| threo-Iba133 | H | 3-Br, 4-F | 4-chloropyridin-2-yl |
| threo-Ibb133 | Me | 3-Br, 4-F | 4-chloropyridin-2-yl |
| threo-Ibc133 | Et | 3-Br, 4-F | 4-chloropyridin-2-yl |
| threo-Iba134 | H | 3-Cl, 4-F | 4-chloropyridin-2-yl |
| threo-Ibb134 | Me | 3-Cl, 4-F | 4-chloropyridin-2-yl |
| threo-Ibc134 | Et | 3-Cl, 4-F | 4-chloropyridin-2-yl |
| threo-Iba192 | H | 3-F | 5-chloropyridin-2-yl |
| threo-Ibb192 | Me | 3-F | 5-chloropyridin-2-yl |
| threo-Ibc192 | Et | 3-F | 5-chloropyridin-2-yl |
| threo-Iba208 | H | 3,4-F₂ | 5-chloropyridin-2-yl |
| threo-Ibb208 | Me | 3,4-F₂ | 5-chloropyridin-2-yl |
| threo-Ibc208 | Et | 3,4-F₂ | 5-chloropyridin-2-yl |
| threo-Iba213 | H | 3-CN, 4-F | 5-chloropyridin-2-yl |
| threo-Ibb213 | Me | 3-CN, 4-F | 5-chloropyridin-2-yl |
| threo-Ibc213 | Et | 3-CN, 4-F | 5-chloropyridin-2-yl |
| threo-Iba214 | H | 3-Br, 4-F | 5-chloropyridin-2-yl |
| threo-Ibb214 | Me | 3-Br, 4-F | 5-chloropyridin-2-yl |
| threo-Ibc214 | Et | 3-Br, 4-F | 5-chloropyridin-2-yl |
| threo-Iba215 | H | 3-Cl, 4-F | 5-chloropyridin-2-yl |
| threo-Ibb215 | Me | 3-Cl, 4-F | 5-chloropyridin-2-yl |
| threo-Ibc215 | Et | 3-Cl, 4-F | 5-chloropyridin-2-yl |
| threo-Iba435 | H | 3-F | 2,4-difluoropyridin-3-yl |
| threo-Ibb435 | Me | 3-F | 2,4-difluoropyridin-3-yl |
| threo-Ibc435 | Et | 3-F | 2,4-difluoropyridin-3-yl |
| threo-Iba451 | H | 3,4-F₂ | 2,4-difluoropyridin-3-yl |
| threo-Ibb451 | Me | 3,4-F₂ | 2,4-difluoropyridin-3-yl |
| threo-Ibc451 | Et | 3,4-F₂ | 2,4-difluoropyridin-3-yl |
| threo-Iba456 | H | 3-CN, 4-F | 2,4-difluoropyridin-3-yl |
| threo-Ibb456 | Me | 3-CN, 4-F | 2,4-difluoropyridin-3-yl |
| threo-Ibc456 | Et | 3-CN, 4-F | 2,4-difluoropyridin-3-yl |
| threo-Iba457 | H | 3-Br, 4-F | 2,4-difluoropyridin-3-yl |
| threo-Ibb457 | Me | 3-Br, 4-F | 2,4-difluoropyridin-3-yl |
| threo-Ibc457 | Et | 3-Br, 4-F | 2,4-difluoropyridin-3-yl |
| threo-Iba458 | H | 3-Cl, 4-F | 2,4-difluoropyridin-3-yl |
| threo-Ibb458 | Me | 3-Cl, 4-F | 2,4-difluoropyridin-3-yl |
| threo-Ibc458 | Et | 3-Cl, 4-F | 2,4-difluoropyridin-3-yl |
| threo-Iba732 | H | 3-F | 5-fluoropyridin-3-yl |
| threo-Ibb732 | Me | 3-F | 5-fluoropyridin-3-yl |
| threo-Ibc732 | Et | 3-F | 5-fluoropyridin-3-yl |
| threo-Iba748 | H | 3,4-F₂ | 5-fluoropyridin-3-yl |
| threo-Ibb748 | Me | 3,4-F₂ | 5-fluoropyridin-3-yl |
| threo-Ibc748 | Et | 3,4-F₂ | 5-fluoropyridin-3-yl |
| threo-Iba753 | H | 3-CN, 4-F | 5-fluoropyridin-3-yl |
| threo-Ibb753 | Me | 3-CN, 4-F | 5-fluoropyridin-3-yl |
| threo-Ibc753 | Et | 3-CN, 4-F | 5-fluoropyridin-3-yl |
| threo-Iba754 | H | 3-Br, 4-F | 5-fluoropyridin-3-yl |
| threo-Ibb754 | Me | 3-Br, 4-F | 5-fluoropyridin-3-yl |
| threo-Ibc754 | Et | 3-Br, 4-F | 5-fluoropyridin-3-yl |
| threo-Iba755 | H | 3-Cl, 4-F | 5-fluoropyridin-3-yl |
| threo-Ibb755 | Me | 3-Cl, 4-F | 5-fluoropyridin-3-yl |
| threo-Ibc755 | Et | 3-Cl, 4-F | 5-fluoropyridin-3-yl |
| threo-Iba759 | H | 3-F | 5-chloropyridin-3-yl |
| threo-Ibb759 | Me | 3-F | 5-chloropyridin-3-yl |
| threo-Ibc759 | Et | 3-F | 5-chloropyridin-3-yl |
| threo-Iba775 | H | 3,4-F₂ | 5-chloropyridin-3-yl |
| threo-Ibb775 | Me | 3,4-F₂ | 5-chloropyridin-3-yl |
| threo-Ibc775 | Et | 3,4-F₂ | 5-chloropyridin-3-yl |
| threo-Iba780 | H | 3-CN, 4-F | 5-chloropyridin-3-yl |
| threo-Ibb780 | Me | 3-CN, 4-F | 5-chloropyridin-3-yl |
| threo-Ibc780 | Et | 3-CN, 4-F | 5-chloropyridin-3-yl |
| threo-Iba781 | H | 3-Br, 4-F | 5-chloropyridin-3-yl |
| threo-Ibb781 | Me | 3-Br, 4-F | 5-chloropyridin-3-yl |
| threo-Ibc781 | Et | 3-Br, 4-F | 5-chloropyridin-3-yl |
| threo-Iba782 | H | 3-Cl, 4-F | 5-chloropyridin-3-yl |
| threo-Ibb782 | Me | 3-Cl, 4-F | 5-chloropyridin-3-yl |
| threo-Ibc782 | Et | 3-Cl, 4-F | 5-chloropyridin-3-yl |
| threo-Iba894 | H | 3-F | 6-chloropyridin-3-yl |
| threo-Ibb894 | Me | 3-F | 6-chloropyridin-3-yl |
| threo-Ibc894 | Et | 3-F | 6-chloropyridin-3-yl |
| threo-Iba910 | H | 3,4-F₂ | 6-chloropyridin-3-yl |
| threo-Ibb910 | Me | 3,4-F₂ | 6-chloropyridin-3-yl |
| threo-Ibc910 | Et | 3,4-F₂ | 6-chloropyridin-3-yl |
| threo-Iba915 | H | 3-CN, 4-F | 6-chloropyridin-3-yl |
| threo-Ibb915 | Me | 3-CN, 4-F | 6-chloropyridin-3-yl |
| threo-Ibc915 | Et | 3-CN, 4-F | 6-chloropyridin-3-yl |
| threo-Iba916 | H | 3-Br, 4-F | 6-chloropyridin-3-yl |
| threo-Ibb916 | Me | 3-Br, 4-F | 6-chloropyridin-3-yl |
| threo-Ibc916 | Et | 3-Br, 4-F | 6-chloropyridin-3-yl |
| threo-Iba917 | H | 3-Cl, 4-F | 6-chloropyridin-3-yl |
| threo-Ibb917 | Me | 3-Cl, 4-F | 6-chloropyridin-3-yl |
| threo-Ibc917 | Et | 3-Cl, 4-F | 6-chloropyridin-3-yl |
| threo-Iba1002 | H | 3-F | 2-fluoropyridin-4-yl |
| threo-Ibb1002 | Me | 3-F | 2-fluoropyridin-4-yl |
| threo-Ibc1002 | Et | 3-F | 2-fluoropyridin-4-yl |
| threo-Iba1018 | H | 3,4-F₂ | 2-fluoropyridin-4-yl |
| threo-Ibb1018 | Me | 3,4-F₂ | 2-fluoropyridin-4-yl |
| threo-Ibc1018 | Et | 3,4-F₂ | 2-fluoropyridin-4-yl |
| threo-Iba1023 | H | 3-CN, 4-F | 2-fluoropyridin-4-yl |
| threo-Ibb1023 | Me | 3-CN, 4-F | 2-fluoropyridin-4-yl |
| threo-Ibc1023 | Et | 3-CN, 4-F | 2-fluoropyridin-4-yl |
| threo-Iba1024 | H | 3-Br, 4-F | 2-fluoropyridin-4-yl |
| threo-Ibb1024 | Me | 3-Br, 4-F | 2-fluoropyridin-4-yl |
| threo-Ibc1024 | Et | 3-Br, 4-F | 2-fluoropyridin-4-yl |
| threo-Iba1025 | H | 3-Cl, 4-F | 2-fluoropyridin-4-yl |
| threo-Ibb1025 | Me | 3-Cl, 4-F | 2-fluoropyridin-4-yl |
| threo-Ibc1025 | Et | 3-Cl, 4-F | 2-fluoropyridin-4-yl |
| threo-Iba1029 | H | 3-F | 2-chloropyridin-4-yl |
| threo-Ibb1029 | Me | 3-F | 2-chloropyridin-4-yl |
| threo-Ibc1029 | Et | 3-F | 2-chloropyridin-4-yl |
| threo-Iba1045 | H | 3,4-F₂ | 2-chloropyridin-4-yl |
| threo-Ibb1045 | Me | 3,4-F₂ | 2-chloropyridin-4-yl |
| threo-Ibc1045 | Et | 3,4-F₂ | 2-chloropyridin-4-yl |
| threo-Iba1050 | H | 3-CN, 4-F | 2-chloropyridin-4-yl |
| threo-Ibb1050 | Me | 3-CN, 4-F | 2-chloropyridin-4-yl |
| threo-Ibc1050 | Et | 3-CN, 4-F | 2-chloropyridin-4-yl |
| threo-Iba1051 | H | 3-Br, 4-F | 2-chloropyridin-4-yl |
| threo-Ibb1051 | Me | 3-Br, 4-F | 2-chloropyridin-4-yl |
| threo-Ibc1051 | Et | 3-Br, 4-F | 2-chloropyridin-4-yl |
| threo-Iba1052 | H | 3-Cl, 4-F | 2-chloropyridin-4-yl |
| threo-Ibb1052 | Me | 3-Cl, 4-F | 2-chloropyridin-4-yl |
| threo-Ibc1052 | Et | 3-Cl, 4-F | 2-chloropyridin-4-yl |
| threo-Iba1110 | H | 3-F | 3-fluoropyridin-4-yl |
| threo-Ibb1110 | Me | 3-F | 3-fluoropyridin-4-yl |
| threo-Ibc1110 | Et | 3-F | 3-fluoropyridin-4-yl |
| threo-Iba1126 | H | 3,4-F₂ | 3-fluoropyridin-4-yl |
| threo-Ibb1126 | Me | 3,4-F₂ | 3-fluoropyridin-4-yl |
| threoIbc1126 | Et | 3,4-F₂ | 3-fluoropyridin-4-yl |
| threo-Iba1131 | H | 3-CN, 4-F | 3-fluoropyridin-4-yl |
| threo-Ibb1131 | Me | 3-CN, 4-F | 3-fluoropyridin-4-yl |
| threo-Ibc1131 | Et | 3-CN, 4-F | 3-fluoropyridin-4-yl |
| threo-Iba1132 | H | 3-Br, 4-F | 3-fluoropyridin-4-yl |
| threo-Ibb1132 | Me | 3-Br, 4-F | 3-fluoropyridin-4-yl |
| threo-Ibc1132 | Et | 3-Br, 4-F | 3-fluoropyridin-4-yl |
| threo-Iba1133 | H | 3-Cl, 4-F | 3-fluoropyridin-4-yl |
| threo-Ibb1133 | Me | 3-Cl, 4-F | 3-fluoropyridin-4-yl |
| threo-Ibc1133 | Et | 3-Cl, 4-F | 3-fluoropyridin-4-yl |
| threo-Iba1272 | H | 3-F | 3,5-difluoropyridin-4-yl |
| threo-Ibb1272 | Me | 3-F | 3,5-difluoropyridin-4-yl |
| threo-Ibc1272 | Et | 3-F | 3,5-difluoropyridin-4-yl |
| threo-Iba1288 | H | 3,4-F₂ | 3,5-difluoropyridin-4-yl |
| threo-Ibb1288 | Me | 3,4-F₂ | 3,5-difluoropyridin-4-yl |
| threo-Ibc1288 | Et | 3,4-F₂ | 3,5-difluoropyridin-4-yl |
| threo-Iba1293 | H | 3-CN, 4-F | 3,5-difluoropyridin-4-yl |
| threo-Ibb1293 | Me | 3-CN, 4-F | 3,5-difluoropyridin-4-yl |
| threo-Ibc1293 | Et | 3-CN, 4-F | 3,5-difluoropyridin-4-yl |
| threo-Iba1294 | H | 3-Br, 4-F | 3,5-difluoropyridin-4-yl |
| threo-Ibb1294 | Me | 3-Br, 4-F | 3,5-difluoropyridin-4-yl |

TABLE Z1-continued

| Example number | R¹ | (R²)ₙ | Q |
|---|---|---|---|
| threo-Ibc1294 | Et | 3-Br, 4-F | 3,5-difluoropyridin-4-yl |
| threo-Iba1295 | H | 3-Cl, 4-F | 3,5-difluoropyridin-4-yl |
| threo-Ibb1295 | Me | 3-Cl, 4-F | 3,5-difluoropyridin-4-yl |
| threo-Ibc1295 | Et | 3-Cl, 4-F | 3,5-difluoropyridin-4-yl |

According to the invention, particular preference is given to the optically active threo-2 enantiomers threo-2-Ib [(=3R, 4R)-form with more than 80% ee] mentioned in Table Z2 below.

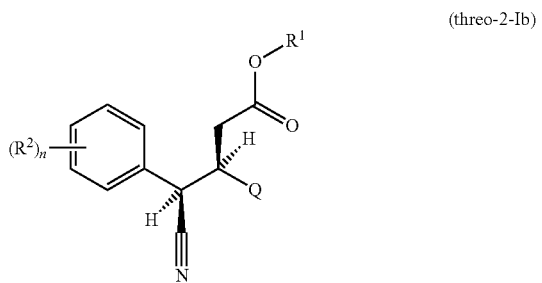

(threo-2-Ib)

TABLE Z2

| Example number | R¹ | (R²)ₙ | Q |
|---|---|---|---|
| threo-2-Iba3 | H | 3-F | 3-fluoropyridin-2-yl |
| threo-2-Ibb3 | Me | 3-F | 3-fluoropyridin-2-yl |
| threo-2-Ibc3 | Et | 3-F | 3-fluoropyridin-2-yl |
| threo-2-Iba19 | H | 3,4-F₂ | 3-fluoropyridin-2-yl |
| threo-2-Ibb19 | Me | 3,4-F₂ | 3-fluoropyridin-2-yl |
| threo-2-Ibc19 | Et | 3,4-F₂ | 3-fluoropyridin-2-yl |
| threo-2-Iba24 | H | 3-CN, 4-F | 3-fluoropyridin-2-yl |
| threo-2-Ibb24 | Me | 3-CN, 4-F | 3-fluoropyridin-2-yl |
| threo-2-Ibc24 | Et | 3-CN, 4-F | 3-fluoropyridin-2-yl |
| threo-2-Iba25 | H | 3-Br, 4-F | 3-fluoropyridin-2-yl |
| threo-2-Ibb25 | Me | 3-Br, 4-F | 3-fluoropyridin-2-yl |
| threo-2-Ibc25 | Et | 3-Br, 4-F | 3-fluoropyridin-2-yl |
| threo-2-Iba26 | H | 3-Cl, 4-F | 3-fluoropyridin-2-yl |
| threo-2-Ibb26 | Me | 3-Cl, 4-F | 3-fluoropyridin-2-yl |
| threo-2-Ibc26 | Et | 3-Cl, 4-F | 3-fluoropyridin-2-yl |
| threo-2-Iba111 | H | 3-F | 4-chloropyridin-2-yl |
| threo-2-Ibb111 | Me | 3-F | 4-chloropyridin-2-yl |
| threo-2-Ibc111 | Et | 3-F | 4-chloropyridin-2-yl |
| threo-2-Iba127 | H | 3,4-F₂ | 4-chloropyridin-2-yl |
| threo-2-Ibb127 | Me | 3,4-F₂ | 4-chloropyridin-2-yl |
| threo-2-Ibc127 | Et | 3,4-F₂ | 4-chloropyridin-2-yl |
| threo-2-Iba132 | H | 3-CN, 4-F | 4-chloropyridin-2-yl |
| threo-2-Ibb132 | Me | 3-CN, 4-F | 4-chloropyridin-2-yl |
| threo-2-Ibc132 | Et | 3-CN, 4-F | 4-chloropyridin-2-yl |
| threo-2-Iba133 | H | 3-Br, 4-F | 4-chloropyridin-2-yl |
| threo-2-Ibb133 | Me | 3-Br, 4-F | 4-chloropyridin-2-yl |
| threo-2-Ibc133 | Et | 3-Br, 4-F | 4-chloropyridin-2-yl |
| threo-2-Iba134 | H | 3-Cl, 4-F | 4-chloropyridin-2-yl |
| threo-2-Ibb134 | Me | 3-Cl, 4-F | 4-chloropyridin-2-yl |
| threo-2-Ibc134 | Et | 3-Cl, 4-F | 4-chloropyridin-2-yl |
| threo-2-Iba192 | H | 3-F | 5-chloropyridin-2-yl |
| threo-2-Ibb192 | Me | 3-F | 5-chloropyridin-2-yl |
| threo-2-Ibc192 | Et | 3-F | 5-chloropyridin-2-yl |
| threo-2-Iba208 | H | 3,4-F₂ | 5-chloropyridin-2-yl |
| threo-2-Ibb208 | Me | 3,4-F₂ | 5-chloropyridin-2-yl |
| threo-2-Ibc208 | Et | 3,4-F₂ | 5-chloropyridin-2-yl |
| threo-2-Iba213 | H | 3-CN, 4-F | 5-chloropyridin-2-yl |
| threo-2-Ibb213 | Me | 3-CN, 4-F | 5-chloropyridin-2-yl |
| threo-2-Ibc213 | Et | 3-CN, 4-F | 5-chloropyridin-2-yl |
| threo-2-Iba214 | H | 3-Br, 4-F | 5-chloropyridin-2-yl |
| threo-2-Ibb214 | Me | 3-Br, 4-F | 5-chloropyridin-2-yl |
| threo-2-Ibc214 | Et | 3-Br, 4-F | 5-chloropyridin-2-yl |
| threo-2-Iba215 | H | 3-Cl, 4-F | 5-chloropyridin-2-yl |
| threo-2-Ibb215 | Me | 3-Cl, 4-F | 5-chloropyridin-2-yl |

TABLE Z2-continued

| Example number | R¹ | (R²)ₙ | Q |
|---|---|---|---|
| threo-2-Ibc215 | Et | 3-Cl, 4-F | 5-chloropyridin-2-yl |
| threo-2-Iba435 | H | 3-F | 2,4-difluoropyridin-3-yl |
| threo-2-Ibb435 | Me | 3-F | 2,4-difluoropyridin-3-yl |
| threo-2-Ibc435 | Et | 3-F | 2,4-difluoropyridin-3-yl |
| threo-2-Iba451 | H | 3,4-F₂ | 2,4-difluoropyridin-3-yl |
| threo-2-Ibb451 | Me | 3,4-F₂ | 2,4-difluoropyridin-3-yl |
| threo-2-Ibc451 | Et | 3,4-F₂ | 2,4-difluoropyridin-3-yl |
| threo-2-Iba456 | H | 3-CN, 4-F | 2,4-difluoropyridin-3-yl |
| threo-2-Ibb456 | Me | 3-CN, 4-F | 2,4-difluoropyridin-3-yl |
| threo-2-Ibc456 | Et | 3-CN, 4-F | 2,4-difluoropyridin-3-yl |
| threo-2-Iba457 | H | 3-Br, 4-F | 2,4-difluoropyridin-3-yl |
| threo-2-Ibb457 | Me | 3-Br, 4-F | 2,4-difluoropyridin-3-yl |
| threo-2-Ibc457 | Et | 3-Br, 4-F | 2,4-difluoropyridin-3-yl |
| threo-2-Iba458 | H | 3-Cl, 4-F | 2,4-difluoropyridin-3-yl |
| threo-2-Ibb458 | Me | 3-Cl, 4-F | 2,4-difluoropyridin-3-yl |
| threo-2-Ibc458 | Et | 3-Cl, 4-F | 2,4-difluoropyridin-3-yl |
| threo-2-Iba732 | H | 3-F | 5-fluoropyridin-3-yl |
| threo-2-Ibb732 | Me | 3-F | 5-fluoropyridin-3-yl |
| threo-2-Ibc732 | Et | 3-F | 5-fluoropyridin-3-yl |
| threo-2-Iba748 | H | 3,4-F₂ | 5-fluoropyridin-3-yl |
| threo-2-Ibb748 | Me | 3,4-F₂ | 5-fluoropyridin-3-yl |
| threo-2-Ibc748 | Et | 3,4-F₂ | 5-fluoropyridin-3-yl |
| threo-2-Iba753 | H | 3-CN, 4-F | 5-fluoropyridin-3-yl |
| threo-2-Ibb753 | Me | 3-CN, 4-F | 5-fluoropyridin-3-yl |
| threo-2-Ibc753 | Et | 3-CN, 4-F | 5-fluoropyridin-3-yl |
| threo-2-Iba754 | H | 3-Br, 4-F | 5-fluoropyridin-3-yl |
| threo-2-Ibb754 | Me | 3-Br, 4-F | 5-fluoropyridin-3-yl |
| threo-2-Ibc754 | Et | 3-Br, 4-F | 5-fluoropyridin-3-yl |
| threo-2-Iba755 | H | 3-Cl, 4-F | 5-fluoropyridin-3-yl |
| threo-2-Ibb755 | Me | 3-Cl, 4-F | 5-fluoropyridin-3-yl |
| threo-2-Ibc755 | Et | 3-Cl, 4-F | 5-fluoropyridin-3-yl |
| threo-2-Iba759 | H | 3-F | 5-chloropyridin-3-yl |
| threo-2-Ibb759 | Me | 3-F | 5-chloropyridin-3-yl |
| threo-2-Ibc759 | Et | 3-F | 5-chloropyridin-3-yl |
| threo-2-Iba775 | H | 3,4-F₂ | 5-chloropyridin-3-yl |
| threo-2-Ibb775 | Me | 3,4-F₂ | 5-chloropyridin-3-yl |
| threo-2-Ibc775 | Et | 3,4-F₂ | 5-chloropyridin-3-yl |
| threo-2-Iba780 | H | 3-CN, 4-F | 5-chloropyridin-3-yl |
| threo-2-Ibb780 | Me | 3-CN, 4-F | 5-chloropyridin-3-yl |
| threo-2-Ibc780 | Et | 3-CN, 4-F | 5-chloropyridin-3-yl |
| threo-2-Iba781 | H | 3-Br, 4-F | 5-chloropyridin-3-yl |
| threo-2-Ibb781 | Me | 3-Br, 4-F | 5-chloropyridin-3-yl |
| threo-2-Ibc781 | Et | 3-Br, 4-F | 5-chloropyridin-3-yl |
| threo-2-Iba782 | H | 3-Cl, 4-F | 5-chloropyridin-3-yl |
| threo-2-Ibb782 | Me | 3-Cl, 4-F | 5-chloropyridin-3-yl |
| threo-2-Ibc782 | Et | 3-Cl, 4-F | 5-chloropyridin-3-yl |
| threo-2-Iba894 | H | 3-F | 6-chloropyridin-3-yl |
| threo-2-Ibb894 | Me | 3-F | 6-chloropyridin-3-yl |
| threo-2-Ibc894 | Et | 3-F | 6-chloropyridin-3-yl |
| threo-2-Iba910 | H | 3,4-F₂ | 6-chloropyridin-3-yl |
| threo-2-Ibb910 | Me | 3,4-F₂ | 6-chloropyridin-3-yl |
| threo-2-Ibc910 | Et | 3,4-F₂ | 6-chloropyridin-3-yl |
| threo-2-Iba915 | H | 3-CN, 4-F | 6-chloropyridin-3-yl |
| threo-2-Ibb915 | Me | 3-CN, 4-F | 6-chloropyridin-3-yl |
| threo-2-Ibc915 | Et | 3-CN, 4-F | 6-chloropyridin-3-yl |
| threo-2-Iba916 | H | 3-Br, 4-F | 6-chloropyridin-3-yl |
| threo-2-Ibb916 | Me | 3-Br, 4-F | 6-chloropyridin-3-yl |
| threo-2-Ibc916 | Et | 3-Br, 4-F | 6-chloropyridin-3-yl |
| threo-2-Iba917 | H | 3-Cl, 4-F | 6-chloropyridin-3-yl |
| threo-2-Ibb917 | Me | 3-Cl, 4-F | 6-chloropyridin-3-yl |
| threo-2-Ibc917 | Et | 3-Cl, 4-F | 6-chloropyridin-3-yl |
| threo-2-Iba1002 | H | 3-F | 2-fluoropyridin-4-yl |
| threo-2-Ibb1002 | Me | 3-F | 2-fluoropyridin-4-yl |
| threo-2-Ibc1002 | Et | 3-F | 2-fluoropyridin-4-yl |
| threo-2-Iba1018 | H | 3,4-F₂ | 2-fluoropyridin-4-yl |
| threo-2-Ibb1018 | Me | 3,4-F₂ | 2-fluoropyridin-4-yl |
| threo-2-Ibc1018 | Et | 3,4-F₂ | 2-fluoropyridin-4-yl |
| threo-2-Iba1023 | H | 3-CN, 4-F | 2-fluoropyridin-4-yl |
| threo-2-Ibb1023 | Me | 3-CN, 4-F | 2-fluoropyridin-4-yl |
| threo-2-Ibc1023 | Et | 3-CN, 4-F | 2-fluoropyridin-4-yl |
| threo-2-Iba1024 | H | 3-Br, 4-F | 2-fluoropyridin-4-yl |
| threo-2-Ibb1024 | Me | 3-Br, 4-F | 2-fluoropyridin-4-yl |
| threo-2-Ibc1024 | Et | 3-Br, 4-F | 2-fluoropyridin-4-yl |
| threo-2-Iba1025 | H | 3-Cl, 4-F | 2-fluoropyridin-4-yl |
| threo-2-Ibb1025 | Me | 3-Cl, 4-F | 2-fluoropyridin-4-yl |
| threo-2-Ibc1025 | Et | 3-Cl, 4-F | 2-fluoropyridin-4-yl |
| threo-2-Iba1029 | H | 3-F | 2-chloropyridin-4-yl |
| threo-2-Ibb1029 | Me | 3-F | 2-chloropyridin-4-yl |

TABLE Z2-continued

| Example number | R[1] | (R[2])$_n$ | Q |
|---|---|---|---|
| threo-2-Ibc1029 | Et | 3-F | 2-chloropyridin-4-yl |
| threo-2-Iba1045 | H | 3,4-F$_2$ | 2-chloropyridin-4-yl |
| threo-2-Ibb1045 | Me | 3,4-F$_2$ | 2-chloropyridin-4-yl |
| threo-2-Ibc1045 | Et | 3,4-F$_2$ | 2-chloropyridin-4-yl |
| threo-2-Iba1050 | H | 3-CN, 4-F | 2-chloropyridin-4-yl |
| threo-2-Ibb1050 | Me | 3-CN, 4-F | 2-chloropyridin-4-yl |
| threo-2-Ibc1050 | Et | 3-CN, 4-F | 2-chloropyridin-4-yl |
| threo-2-Iba1051 | H | 3-Br, 4-F | 2-chloropyridin-4-yl |
| threo-2-Ibb1051 | Me | 3-Br, 4-F | 2-chloropyridin-4-yl |
| threo-2-Ibc1051 | Et | 3-Br, 4-F | 2-chloropyridin-4-yl |
| threo-2-Iba1052 | H | 3-Cl, 4-F | 2-chloropyridin-4-yl |
| threo-2-Ibb1052 | Me | 3-Cl, 4-F | 2-chloropyridin-4-yl |
| threo-2-Ibc1052 | Et | 3-Cl, 4-F | 2-chloropyridin-4-yl |
| threo-2-Iba1110 | H | 3-F | 3-fluoropyridin-4-yl |
| threo-2-Ibb1110 | Me | 3-F | 3-fluoropyridin-4-yl |
| threo-2-Ibc1110 | Et | 3-F | 3-fluoropyridin-4-yl |
| threo-2-Iba1126 | H | 3,4-F$_2$ | 3-fluoropyridin-4-yl |
| threo-2-Ibb1126 | Me | 3,4-F$_2$ | 3-fluoropyridin-4-yl |
| threo-2-Ibc1126 | Et | 3,4-F$_2$ | 3-fluoropyridin-4-yl |
| threo-2-Iba1131 | H | 3-CN, 4-F | 3-fluoropyridin-4-yl |
| threo-2-Ibb1131 | Me | 3-CN, 4-F | 3-fluoropyridin-4-yl |
| threo-2-Ibc1131 | Et | 3-CN, 4-F | 3-fluoropyridin-4-yl |
| threo-2-Iba1132 | H | 3-Br, 4-F | 3-fluoropyridin-4-yl |
| threo-2-Ibb1132 | Me | 3-Br, 4-F | 3-fluoropyridin-4-yl |
| threo-2-Ibc1132 | Et | 3-Br, 4-F | 3-fluoropyridin-4-yl |
| threo-2-Iba1133 | H | 3-Cl, 4-F | 3-fluoropyridin-4-yl |
| threo-2-Ibb1133 | Me | 3-Cl, 4-F | 3-fluoropyridin-4-yl |
| threo-2-Ibc1133 | Et | 3-Cl, 4-F | 3-fluoropyridin-4-yl |
| threo-2-Iba1272 | H | 3-F | 3,5-difluoropyridin-4-yl |
| threo-2-Ibb1272 | Me | 3-F | 3,5-difluoropyridin-4-yl |
| threo-2-Ibc1272 | Et | 3-F | 3,5-difluoropyridin-4-yl |
| threo-2-Iba1288 | H | 3,4-F$_2$ | 3,5-difluoropyridin-4-yl |
| threo-2-Ibb1288 | Me | 3,4-F$_2$ | 3,5-difluoropyridin-4-yl |
| threo-2-Ibc1288 | Et | 3,4-F$_2$ | 3,5-difluoropyridin-4-yl |
| threo-2-Iba1293 | H | 3-CN, 4-F | 3,5-difluoropyridin-4-yl |
| threo-2-Ibb1293 | Me | 3-CN, 4-F | 3,5-difluoropyridin-4-yl |
| threo-2-Ibc1293 | Et | 3-CN, 4-F | 3,5-difluoropyridin-4-yl |
| threo-2-Iba1294 | H | 3-Br, 4-F | 3,5-difluoropyridin-4-yl |
| threo-2-Ibb1294 | Me | 3-Br, 4-F | 3,5-difluoropyridin-4-yl |
| threo-2-Ibc1294 | Et | 3-Br, 4-F | 3,5-difluoropyridin-4-yl |
| threo-2-Iba1295 | H | 3-Cl, 4-F | 3,5-difluoropyridin-4-yl |
| threo-2-Ibb1295 | Me | 3-Cl, 4-F | 3,5-difluoropyridin-4-yl |
| threo-2-Ibc1295 | Et | 3-Cl, 4-F | 3,5-difluoropyridin-4-yl |

Physical Data for Tables 2a-2f:
Test Methods:
1) NMR=$^1$H-NMR data (400 MHz, CDCl$_3$); characteristic chemical shifts [in ppm] are indicated for the example in question,
2) MS=mass spectrum, measured using a quadrupole instrument; electrospray ionization (+−), mass range 100-1000; molecular peak M or [M+H]+ or [M−1]+ or [M−2]+ or [M+1]+ indicated for the example in question,
3) HPLC=High Performance Liquid Chromatography, column: Zorbax Eclipse, 50×3.0, C18 1.8 ym, mobile phase: water+0.06% formic acid/acrylonitrile+0.06% formic acid, gradient: 90:10, after 2 min 5:95; detector: DAD (210-400 nm); retention time (Rt) indicated for the example in question,
4) chiral HPLC=HPLC on a chiral column, column: Chiralpak IC, 250×4.6 mm, 5 μm DAIC 83325, detector wavelength: 210 nm; column temperature 25° C.,
   mobile phase a: (n-heptane:2-propanol), (60:40), Chromasolv, flow rate: 1.0 ml/min
   mobile phase b: (n-heptane:2-propanol), (70:30), Chromasolv, flow rate: 1.0 ml/min
   mobile phase c: (n-heptane:2-propanol), (80:20), Chromasolv, flow rate: 1.0 ml/min
   mobile phase d: (n-heptane:2-propanol), (90:10), Chromasolv, flow rate: 0.6 ml/min
   mobile phase e: (n-heptane:2-propanol), (90:10), Chromasolv, flow rate: 1.0 ml/min Ex. Ibb3 (diastereomer mixture of erythro-Ibb3 and threo-Ibb3), NMR: 2.67 (dd, 1H, erythro-Ibb3), 2.95 (dd, 1H, erythro-Ibb3), 3.05 (dd, 1H, threo-Ibb3), 3.33 (dd, 1H, threo-Ibb3), 3.54 (s, 3H, erythro-Ibb3), 3.58 (s, 3H, threo-Ibb3), 4.27 (d, 1H, threo-Ibb3), 4.33 (d, 1H, erythro-Ibb3), 8.38 (m, 1H, threo-Ibb3), 8.44 (m, 1H, erythro-Ibb3)

Ex. Ibb4 (diastereomer mixture of erythro-Ibb4 and threo-Ibb4), NMR: 2.66 (dd, 1H, erythro-Ibb4), 2.94 (dd, 1H, erythro-Ibb4), 3.06 (dd, 1H, threo-Ibb4), 3.31 (dd, 1H, threo-Ibb4), 3.53 (s, 3H, erythro-Ibb4), 3.57 (s, 3H, threo-Ibb4), 4.24 (d, 1H, threo-Ibb4), 4.31 (d, 1H, erythro-Ibb4), 6.92 (t, 2H), 7.08 (t, 2H), 8.38 (m, 1H, threo-Ibb4), 8.43 (m, 1H, erythro-Ibb4)

Ex. Ibb5 (diastereomer mixture of erythro-Ibb5 and threo-Ibb5), NMR: 2.67 (dd, 1H), 2.95 (dd, 1H), 3.04 (dd, 1H), 3.30 (dd, 1H), 3.54 (s, 3H), 3.58 (s, 3H), 4.25 (d, 1H), 4.31 (d, 1H), 8.39 (m, 1H), 8.43 (m, 1H)

Ex. Ibb10 (diastereomer mixture of erythro-Ibb10 and threo-Ibb10), NMR: 2.75 (dd, 1H, erythro-Ibb10), 2.96 (dd, 1H, erythro-Ibb10), 3.09 (dd, 1H, threo-Ibb10), 3.30 (dd, 1H, threo-Ibb10), 3.58 (s, 3H, erythro-Ibb10), 3.59 (s, 3H, threo-Ibb10), 8.40 (m, 1H, threo-Ibb10), 8.44 (m, 1H, erythro-Ibb10)

Ex. Ibb19 (diastereomer mixture of erythro-Ibb19 and threo-Ibb19), NMR: 2.71 (dd, 1H), 2.94 (dd, 1H), 3.06 (dd, 1H), 3.28 (dd, 1H), 3.56 (s, 3H), 3.59 (s, 3H), 4.25 (d, 1H), 4.35 (d, 1H), 8.38 (m, 1H), 8.43 (m, 1H)

Ex. erythro-Ibb19, NMR: 2.71 (dd, 1H), 2.94 (dd, 1H), 3.56 (s, 3H), 4.13 (m, 1H), 4.35 (d, 1H), 7.05 (m, 1H), 7.23 (m, 1H), 7.38 (m, 1H), 8.43 (m, 1H)

Ex. threo-Ibb19, NMR: 3.06 (dd, 1H), 3.28 (dd, 1H), 3.59 (s, 3H), 4.13 (m, 1H), 4.25 (d, 1H), 6.89 (m, 1H), 6.96 (m, 1H), 7.03 (m, 1H), 7.18 (m, 1H), 8.38 (m, 1H)

Ex. Ibb22 (diastereomer mixture of erythro-Ibb22 and threo-Ibb22), NMR: 2.71 (dd, 1H), 2.94 (dd, 1H), 3.06 (dd, 1H), 3.28 (dd, 1H), 3.56 (s, 3H), 3.59 (s, 3H), 4.27 (d, 1H), 4.37 (d, 1H), 8.38 (m, 1H), 8.43 (m, 1H)

Ex. Ibb28 (diastereomer mixture of erythro-Ibb28 and threo-Ibb28), NMR: 2.60 (dd, 1H, erythro-Ibb28), 2.95 (dd, 1H, erythro-Ibb28), 3.96 (dd, 1H, threo-Ibb28), 3.40 (dd, 1H, threo-Ibb28), 3.49 (s, 3H, erythro-Ibb28), 3.54 (s, 3H, threo-Ibb28), 7.10 (dd, 1H, threo-Ibb28), 7.18 (dd, 1H, erythro-Ibb28), 7.53 (dd, 1H, erythro-Ibb28), 7.70 (dd, 1H, erythro-Ibb28), 8.51 (m, 1H, threo-Ibb28), 8.52 (m, 1H, erythro-Ibb28)

Ex. Ibb30 (diastereomer mixture of erythro-Ibb30 and threo-Ibb30), NMR: 2.65 (dd, 1H, erythro-Ibb30), 2.96 (dd, 1H, erythro-Ibb30), 2.93 (dd, 1H, threo-Ibb30), 3.37 (dd, 1H, threo-Ibb30), 3.53 (s, 3H, erythro-Ibb30), 3.55 (s, 3H, threo-Ibb30), 7.55 (dd, 1H), 7.70 (dd, 1H), 8.51 (m, 1H), 8.52 (m, 1H)

Ex. Ibb32 (diastereomer mixture of erythro-Ibb32 and threo-Ibb32), NMR: 2.63 (dd, 1H, erythro-Ibb32), 2.93 (dd, 1H, erythro-Ibb32), 2.99 (dd, 1H, threo-Ibb32), 3.35 (dd, 1H, threo-Ibb32), 3.52 (s, 3H, erythro-Ibb32), 3.56 (s, 3H, threo-Ibb32), 6.94 (t, 2H, threo-Ibb32), 7.53 (dd, 1H, threo-Ibb32), 7.70 (dd, 1H, erythro-Ibb32), 8.49 (m, 1H, threo-Ibb32), 8.51 (m, 1H, erythro-Ibb32)

Ex. Ibb37 (diastereomer mixture of erythro-Ibb37 and threo-Ibb37), NMR: 2.73 (dd, 1H, erythro-Ibb37), 2.96 (dd, 1H, erythro-Ibb37), 3.02 (dd, 1H, threo-Ibb37), 3.35 (dd, 1H, threo-Ibb37), 3.58 (s, 3H, erythro-Ibb37), 3.59 (s, 3H, threo-Ibb37), 7.13 (dd, 1H, threo-Ibb37), 7.20 (dd, 1H, erythro-Ibb37), 8.51 (m, 1H, threo-Ibb37), 8.52 (m, 1H, erythro-Ibb37)

Ex. Ibb46 (diastereomer mixture of erythro-Ibb46 and threo-Ibb46), NMR: 3.55 (s, 3H), 3.57 (s, 3H), 7.54 (dd, 1H, threo-Ibb46), 7.70 (dd, 1H, erythro-Ibb46), 8.50 (m, 1H, threo-Ibb46), 8.52 (m, 1H, erythro-Ibb46)

Ex. Ibb49 (diastereomer mixture of erythro-Ibb49 and threo-Ibb49), NMR: 3.55 (s, 3H), 3.57 (s, 3H), 7.27 (m, 1H, threo-Ibb49), 7.38 (m, 1H, erythro-Ibb49), 7.57 (dd, 1H, threo-Ibb49), 7.70 (dd, 1H, erythro-Ibb49), 8.50 (m, 1H, threo-Ibb49), 8.52 (m, 1H, erythro-Ibb49)

Ex. Ibb109 (diastereomer mixture of erythro-Ibb109 and threo-Ibb109), NMR: 2.57 (dd, 1H, erythro-Ibb109), 2.88 (dd, 1H, erythro-Ibb109), 3.05 (dd, 1H, threo-Ibb109), 3.20 (dd, 1H, threo-Ibb109), 3.52 (s, 3H, erythro-Ibb109), 3.58 (s, 3H, threo-Ibb109), 4.29 (d, 1H), 4.31 (d, 1H), 8.45 (d, 1H, threo-Ibb109), 8.50 (d, 1H, erythro-Ibb109)

Ex. Ibb111 (diastereomer mixture of erythro-Ibb111 and threo-Ibb111), NMR: 2.59 (dd, 1H, erythro-Ibb111), 2.86 (dd, 1H, erythro-Ibb111), 3.06 (dd, 1H, threo-Ibb111), 3.16 (dd, 1H, threo-Ibb111), 3.52 (s, 3H, erythro-Ibb111), 3.59 (s, 3H, threo-Ibb111), 8.45 (d, 1H, threo-Ibb111), 8.50 (d, 1H, erythro-Ibb111)

Ex. Ibb113 (diastereomer mixture of erythro-Ibb113 and threo-Ibb113), NMR: 2.60 (dd, 1H, erythro-Ibb113), 2.87 (dd, 1H, erythro-Ibb113), 3.03 (dd, 1H, threo-Ibb113), 3.16 (dd, 1H, threo-Ibb113), 3.54 (s, 3H, erythro-Ibb113), 3.60 (s, 3H, threo-Ibb113), 4.32 (d, 1H), 4.34 (d, 1H), 8.47 (d, 1H, threo-Ibb113), 8.51 (d, 1H, erythro-Ibb113)

Ex. Ibb118 (diastereomer mixture of erythro-Ibb118 and threo-Ibb118), NMR: 2.65 (dd, 1H, erythro-Ibb118), 2.88 (dd, 1H, erythro-Ibb118), 3.07 (dd, 1H, threo-Ibb118), 3.15 (dd, 1H, threo-Ibb118), 3.57 (s, 3H, erythro-Ibb118), 3.61 (s, 3H, threo-Ibb118), 8.48 (d, 1H, threo-Ibb118), 8.50 (d, 1H, erythro-Ibb118)

Ex. Ibb127 (diastereomer mixture of erythro-Ibb127 and threo-Ibb127), NMR: 2.62 (dd, 1H, erythro-Ibb127), 2.86 (dd, 1H, erythro-Ibb127), 3.09 (m, 2H, threo-Ibb127), 3.56 (s, 3H, erythro-Ibb127), 3.60 (s, 3H, threo-Ibb127), 8.46 (d, 1H, threo-Ibb127), 8.50 (d, 1H, erythro-Ibb127)

Ex. erythro-Ibb127, NMR: 2.62 (dd, 1H), 2.86 (dd, 1H), 3.56 (s, 3H), 3.66 (m, 1H), 4.34 (d, 1H), 7.05 (m, 1H), 8.50 (d, 1H)

Ex. threo-Ibb127, NMR: 3.09 (m, 2H), 3.60 (s, 3H), 3.66 (m, 1H), 4.37 (d, 1H), 6.86 (m, 1H), 6.95 (m, 2H), 7.05 (m, 1H), 7.15 (dd, 1H), 8.46 (d, 1H)

Ex. Ibb130 (diastereomer mixture of erythro-Ibb130 and threo-Ibb130), NMR: 2.62 (dd, 1H, erythro-Ibb130), 2.86 (dd, 1H, erythro-Ibb130), 3.09 (m, 2H, threo-Ibb130), 3.56 (s, 3H, erythro-Ibb130), 3.60 (s, 3H, threo-Ibb130), 4.36 (d, 1H), 4.40 (d, 1H), 8.45 (d, 1H, threo-Ibb130), 8.50 (d, 1H, erythro-Ibb130)

Ex. Ibb190 (diastereomer mixture of erythro-Ibb190 and threo-Ibb190), NMR: 2.56 (dd, 1H, erythro-Ibb190), 2.88 (dd, 1H, erythro-Ibb190), 3.07 (dd, 1H, threo-Ibb190), 3.18 (dd, 1H, threo-Ibb190), 3.51 (s, 3H, erythro-Ibb190), 3.57 (s, 3H, threo-Ibb190), 6.81 (d, 1H, threo-Ibb190), 7.61 (dd, 1H, erythro-Ibb190), 8.52 (d, 1H, threo-Ibb190), 8.56 (d, 1H, erythro-Ibb190)

Ex. Ibb192 (diastereomer mixture of erythro-Ibb192 and threo-Ibb192), NMR: 2.59 (dd, 1H, erythro-Ibb192), 2.90 (dd, 1H, erythro-Ibb192), 3.07 (dd, 1H, threo-Ibb192), 3.15 (dd, 1H, threo-Ibb192), 3.54 (s, 3H, erythro-Ibb192), 3.58 (s, 3H, threo-Ibb192), 7.44 (dd, 1H, threo-Ibb192), 7.61 (dd, 1H, erythro-Ibb192), 8.52 (d, 1H, threo-Ibb192), 8.55 (d, 1H, erythro-Ibb192)

Ex. Ibb193 (diastereomer mixture of erythro-Ibb193 and threo-Ibb193), NMR: 2.58 (dd, 1H, erythro-Ibb193), 2.89 (dd, 1H, erythro-Ibb193), 3.08 (dd, 1H, threo-Ibb193), 3.19 (dd, 1H, threo-Ibb193), 3.53 (s, 3H, erythro-Ibb193), 3.58 (s, 3H, threo-Ibb193), 6.82 (d, 1H, threo-Ibb193), 7.15 (d, 1H, erythro-Ibb193), 7.43 (dd, 1H, threo-Ibb193), 7.61 (dd, 1H, erythro-Ibb193), 8.51 (d, 1H, threo-Ibb193), 8.55 (d, 1H, erythro-Ibb193)

Ex. threo-Ibb193, NMR: 3.08 (dd, 1H), 3.19 (dd, 1H), 3.58 (s, 3H), 3.69 (m, 1H), 4.29 (d, 1H), 6.82 (d, 1H), 6.95 (m, 2H), 7.07 (m, 2H), 7.43 (dd, 1H), 8.51 (d, 1H)

Ex. Ibb194 (diastereomer mixture of erythro-Ibb194 and threo-Ibb194), NMR: 2.59 (dd, 1H, erythro-Ibb194), 2.88 (dd, 1H, erythro-Ibb194), 3.06 (dd, 1H, threo-Ibb194), 3.15 (dd, 1H, threo-Ibb194), 3.54 (s, 3H, erythro-Ibb194), 3.58 (s, 3H, threo-Ibb194), 7.45 (dd, 1H, threo-Ibb194), 7.62 (dd, 1H, erythro-Ibb194), 8.52 (d, 1H, threo-Ibb194), 8.56 (d, 1H, erythro-Ibb194)

Ex. Ibb208 (diastereomer mixture of erythro-Ibb208 and threo-Ibb208), NMR, [D$_6$]-DMSO: 3.41 (s, 3H, erythro-Ibb208), 3.47 (s, 3H, threo-Ibb208), 7.27 (d, 1H, threo-Ibb208), 7.33 (d, 1H, erythro-Ibb208), 7.81 (dd, 1H, threo-Ibb208), 7.90 (dd, 1H, erythro-Ibb208), 8.55 (d, 1H, threo-Ibb208), 8.64 (d, 1H, erythro-Ibb208)

Ex. erythro-Ibb208, NMR: 2.60 (dd, 1H), 2.86 (dd, 1H), 3.56 (s, 3H), 3.68 (m, 1H), 4.31 (d, 1H), 7.05 (m, 1H), 7.14 (d, 1H), 7.62 (dd, 1H), 8.56 (d, 1H)

Ex. threo-Ibb208, NMR: 3.10 (m, 2H), 3.59 (s, 3H), 3.69 (m, 1H), 4.32 (d, 1H), 6.82 (m, 1H), 6.87 (d, 1H), 6.97 (m, 1H), 7.03 (m, 1H), 7.46 (dd, 1H), 8.51 (d, 1H)

Ex. threo-1-Ibb208, NMR: 3.10 (m, 2H), 3.59 (s, 3H), 3.69 (m, 1H), 4.32 (d, 1H), 6.82 (m, 1H), 6.87 (d, 1H), 6.97 (m, 1H), 7.03 (m, 1H), 7.46 (dd, 1H), 8.51 (d, 1H); chiral HPLC: 7.6 min, mobile phase c Ex. threo-2-Ibb208, NMR: 3.10 (m, 2H), 3.59 (s, 3H), 3.69 (m, 1H), 4.32 (d, 1H), 6.82 (m, 1H), 6.87 (d, 1H), 6.97 (m, 1H), 7.03 (m, 1H), 7.46 (dd, 1H), 8.51 (d, 1H); chiral HPLC: 8.7 min, mobile phase c Ex. Ibb210 (diastereomer mixture of erythro-Ibb210 and threo-Ibb210), NMR: 2.63 (dd, 1H, erythro-Ibb210), 2.86 (dd, 1H, erythro-Ibb210), 3.07 (m, 2H, threo-Ibb210), 3.58 (s, 3H, erythro-Ibb210), 3.60 (s, 3H, threo-Ibb210), 6.78 (dd, 2H, threo-Ibb210), 6.92 (d, 1H, threo-Ibb210), 6.98 (dd, 2H, erythro-Ibb210), 7.15 (d, 1H, erythro-Ibb210), 7.50 (dd, 1H, threo-Ibb210), 7.63 (dd, 1H, erythro-Ibb210), 8.52 (d, 1H, threo-Ibb210), 8.56 (d, 1H, erythro-Ibb210)

Ex. threo-Ibb210, NMR: 3.07 (m, 2H), 3.60 (s, 3H), 3.69 (m, 1H), 4.34 (d, 1H), 6.78 (dd, 2H), 6.92 (d, 1H), 7.50 (dd, 1H), 8.52 (d, 1H)

Ex. Ibb211 (diastereomer mixture of erythro-Ibb211 and threo-Ibb211), NMR: 2.59 (dd, 1H, erythro-Ibb211), 2.88 (dd, 1H, erythro-Ibb211), 3.08 (m, 2H, threo-Ibb211), 3.56 (s, 3H, erythro-Ibb211), 3.59 (s, 3H, threo-Ibb211), 7.48 (dd, 1H, threo-Ibb211), 7.62 (dd, 1H, erythro-Ibb211), 8.52 (d, 1H, threo-Ibb211), 8.56 (d, 1H, erythro-Ibb211)

Ex. threo-Ibb211, NMR: 3.08 (m, 2H), 3.59 (s, 3H), 3.69 (m, 1H), 4.34 (d, 1H), 6.83 (m, 1H), 6.89 (d, 1H), 6.95 (dd, 1H), 7.29 (m, 1H), 7.48 (dd, 1H), 8.52 (d, 1H)

Ex. Ibb212 (diastereomer mixture of erythro-Ibb212 and threo-Ibb212), NMR: 2.62 (dd, 1H, erythro-Ibb212), 2.87 (dd, 1H, erythro-Ibb212), 3.09 (m, 2H, threo-Ibb212), 3.56 (s, 3H, erythro-Ibb212), 3.59 (s, 3H, threo-Ibb212), 7.10 (dd, 1H, erythro-Ibb212), 7.15 (d, 1H, erythro-Ibb212), 7.48 (dd, 1H, threo-Ibb212), 7.62 (dd, 1H, erythro-Ibb212), 8.52 (d, 1H, threo-Ibb212), 8.56 (d, 1H, erythro-Ibb212)

Ex. threo-Ibb212, NMR: 3.09 (m, 2H), 3.59 (s, 3H), 3.70 (m, 1H), 4.34 (d, 1H), 6.78 (m, 1H), 6.90 (d, 1H), 6.93 (dd, 1H), 7.43 (dd, 1H), 7.48 (dd, 1H), 8.52 (d, 1H)

Ex. Ibb215 (diastereomer mixture of erythro-Ibb215 and threo-Ibb215), NMR: 2.61 (dd, 1H, erythro-Ibb215), 2.86 (dd, 1H, erythro-Ibb215), 3.08 (m, 2H, threo-Ibb215), 3.55 (s, 3H, erythro-Ibb215), 3.59 (s, 3H, threo-Ibb215), 7.47

(dd, 1H, threo-Ibb215), 7.62 (dd, 1H, erythro-Ibb215), 8.52 (d, 1H, threo-Ibb215), 8.56 (d, 1H, erythro-Ibb215)

Ex. threo-Ibb215, NMR: 3.08 (m, 2H), 3.59 (s, 3H), 3.69 (m, 1H), 4.31 (d, 1H), 6.87 (d, 1H), 6.95 (m, 1H), 7.01 (t, 1H), 7.20 (m, 1H), 7.47 (dd, 1H), 8.52 (d, 1H)

Ex. Ibb325 (diastereomer mixture of erythro-Ibb325 and threo-Ibb325), NMR: 2.50 (dd, 1H, erythro-Ibb325), 2.86 (dd, 1H, erythro-Ibb325), 3.10 (dd, 1H, threo-Ibb325), 3.18 (dd, 1H, threo-Ibb325), 3.50 (s, 3H, erythro-Ibb325), 3.58 (s, 3H, threo-Ibb325), 4.26 (d, 1H), 4.34 (d, 1H), 6.79 (d.1H, threo-Ibb325), 7.62 (m, 1H, erythro-Ibb325)

Ex. Ibb327 (diastereomer mixture of erythro-Ibb327 and threo-Ibb327), NMR: 2.53 (dd, 1H, erythro-Ibb327), 2.88 (dd, 1H, erythro-Ibb327), 3.09 (dd, 1H, threo-Ibb327), 3.17 (dd, 1H, threo-Ibb327), 3.53 (s, 3H, erythro-Ibb327), 3.60 (s, 3H, threo-Ibb327), 4.29 (d, 1H, threo-Ibb327), 4.37 (d, 1H, erythro-Ibb327), 7.40 (m.1H, threo-Ibb327), 7.63 (m, 1H, erythro-Ibb327)

Ex. Ibb328 (diastereomer mixture of erythro-Ibb328 and threo-Ibb328), NMR: 2.51 (dd, 1H, erythro-Ibb328), 2.85 (dd, 1H, erythro-Ibb328), 3.09 (dd, 1H, threo-Ibb328), 3.16 (dd, 1H, threo-Ibb328), 3.52 (s, 3H, erythro-Ibb328), 3.60 (s, 3H, threo-Ibb328), 4.29 (d, 1H), 4.37 (d, 1H), 6.79 (d, 1H), 6.93 (t, 2H), 7.40 (m.1H, threo-Ibb328), 7.63 (m, 1H, erythro-Ibb328)

Ex. Ibb329 (diastereomer mixture of erythro-Ibb329 and threo-Ibb329), NMR: 2.52 (dd, 1H), 2.87 (dd, 1H), 3.05 (dd, 1H), 3.10 (dd, 1H), 3.53 (s, 3H), 3.60 (s, 3H), 4.27 (d, 1H), 4.35 (d, 1H), 6.83 (d, 1H), 7.00 (m, 1H), 7.43 (m.1H), 7.63 (m, 1H)

Ex. Ibb334 (diastereomer mixture of erythro-Ibb334 and threo-Ibb334), NMR: 2.57 (dd, 1H, erythro-Ibb334), 2.86 (dd, 1H, erythro-Ibb334), 3.10 (m, 2H, threo-Ibb334), 3.56 (s, 3H, erythro-Ibb334), 3.67 (s, 3H, threo-Ibb334), 6.83 (d, 1H, threo-Ibb334)

Ex. Ibb343 (diastereomer mixture of erythro-Ibb343 and threo-Ibb343), NMR: 2.55 (dd, 1H, erythro-Ibb343), 2.85 (dd, 1H, erythro-Ibb343), 3.10 (m, 2H, threo-Ibb343), 3.55 (s, 3H, erythro-Ibb343), 3.61 (s, 3H, threo-Ibb343), 4.31 (d, 1H), 4.36 (d, 1H), 7.44 (m, 1H), 7.63 (m, 1H)

Ex. Ibb346 (diastereomer mixture of erythro-Ibb346 and threo-Ibb346), NMR: 2.55 (dd, 1H, erythro-Ibb346), 2.85 (dd, 1H, erythro-Ibb346), 3.10 (m, 2H, threo-Ibb346), 3.55 (s, 3H, erythro-Ibb346), 3.61 (s, 3H, threo-Ibb346), 4.32 (d, 1H), 4.39 (d, 1H), 7.44 (m, 1H), 7.63 (m, 1H)

Ex. Ibb352 (diastereomer mixture of erythro-Ibb352 and threo-Ibb352), NMR: 2.50 (dd, 1H, erythro-Ibb352), 2.86 (dd, 1H, erythro-Ibb352), 3.07 (dd, 1H, threo-Ibb352), 3.17 (dd, 1H, threo-Ibb352), 3.51 (s, 3H, erythro-Ibb352), 3.59 (s, 3H, threo-Ibb352), 4.26 (d, 1H), 4.35 (d, 1H), 6.83 (m, 1H)

Ex. Ibb354 (diastereomer mixture of erythro-Ibb354 and threo-Ibb354), NMR: 2.54 (dd, 1H, erythro-Ibb354), 2.86 (dd, 1H, erythro-Ibb354), 3.06 (dd, 1H, threo-Ibb354), 3.15 (dd, 1H, threo-Ibb354), 3.54 (s, 3H, erythro-Ibb354), 3.60 (s, 3H, threo-Ibb354), 4.29 (d, 1H), 4.37 (d, 1H), 7.42 (d, 1H), 7.50 (d, 1H)

Ex. Ibb355 (diastereomer mixture of erythro-Ibb355 and threo-Ibb355), NMR: 2.52 (dd, 1H, erythro-Ibb355), 2.85 (dd, 1H, erythro-Ibb355), 3.08 (dd, 1H, threo-Ibb355), 3.13 (dd, 1H, threo-Ibb355), 3.53 (s, 3H, erythro-Ibb355), 3.60 (s, 3H, threo-Ibb355), 4.29 (d, 1H), 4.36 (d, 1H), 6.96 (t, 2H), 7.41 (d, 1H), 7.51 (m, 1H)

Ex. Ibb356 (diastereomer mixture of erythro-Ibb356 and threo-Ibb356), NMR: 2.52 (dd, 1H), 2.87 (dd, 1H), 3.08 (dd, 1H), 3.13 (dd, 1H), 3.54 (s, 3H), 3.60 (s, 3H), 4.27 (d, 1H), 4.36 (d, 1H)

Ex. Ibb361 (diastereomer mixture of erythro-Ibb361 and threo-Ibb361), NMR: 2.57 (dd, 1H, erythro-Ibb361), 2.85 (dd, 1H, erythro-Ibb361), 3.10 (m, 2H, threo-Ibb361), 3.57 (s, 3H, erythro-Ibb361), 3.62 (s, 3H, threo-Ibb361), 4.43 (d, 1H), 4.47 (d, 1H)

Ex. Ibb370 (diastereomer mixture of erythro-Ibb370 and threo-Ibb370), NMR: 2.55 (dd, 1H, erythro-Ibb370), 2.84 (dd, 1H, erythro-Ibb370), 3.09 (m, 2H, threo-Ibb370), 3.56 (s, 3H, erythro-Ibb370), 3.61 (s, 3H, threo-Ibb370), 4.31 (d, 1H), 4.37 (d, 1H), 7.41 (m, 1H), 7.52 (m, 1H)

Ex. Ibb373 (diastereomer mixture of erythro-Ibb373 and threo-Ibb373), NMR: 2.56 (dd, 1H, erythro-Ibb373), 2.85 (dd, 1H, erythro-Ibb373), 3.09 (m, 2H, threo-Ibb373), 3.56 (s, 3H, erythro-Ibb373), 3.61 (s, 3H, threo-Ibb373), 4.32 (d, 1H), 4.39 (d, 1H)

Ex. Ibb435 (diastereomer mixture of erythro-Ibb435 and threo-Ibb435), NMR: 2.70 (dd, 1H, erythro-Ibb435), 2.84 (dd, 1H, erythro-Ibb435), 3.11 (dd, 1H, threo-Ibb435), 3.22 (dd, 1H, threo-Ibb435), 3.56 (s, 3H, erythro-Ibb435), 3.62 (s, 3H, threo-Ibb435), 4.12 (m, 1H, threo-Ibb435), 4.25 (d, 1H, erythro-Ibb435), 6.81 (dd, 1H, threo-Ibb435), 8.02 (dd, 1H, threo-Ibb435), 8.17 (m, 1H, erythro-Ibb435)

Ex. Ibb451 (diastereomer mixture of erythro-Ibb451 and threo-Ibb451), NMR: 2.74 (dd, 1H, erythro-Ibb451), 2.84 (dd, 1H, erythro-Ibb451), 3.09 (dd, 1H, threo-Ibb451), 3.21 (dd, 1H, threo-Ibb451), 3.59 (s, 3H, erythro-Ibb451), 3.63 (s, 3H, threo-Ibb451), 4.10 (m, 2H, threo-Ibb451), 4.26 (d, 1H, erythro-Ibb451), 6.84 (dd, 1H, threo-Ibb451), 8.04 (dd, 1H, threo-Ibb451), 8.18 (m, 1H, erythro-Ibb451)

Ex. erythro-Ibb451, NMR: 2.74 (dd, 1H), 2.84 (dd, 1H), 3.59 (s, 3H), 4.02 (q, 1H), 4.26 (d, 1H), 7.09 (m, 2H), 7.21 (m, 2H), 8.18 (dd, 1H)

Ex. erythro-2-Ibb451, NMR: 2.74 (dd, 1H), 2.84 (dd, 1H), 3.59 (s, 3H), 4.02 (q, 1H), 4.26 (d, 1H), 7.09 (m, 2H), 7.21 (m, 2H), 8.18 (dd, 1H); chiral HPLC: 16.9 min, mobile phase c Ex. threo-1-Ibb451, NMR: 3.09 (dd, 1H), 3.21 (dd, 1H), 3.63 (s, 3H), 4.10 (m, 2H), 6.84 (dd, 1H), 6.92 (m, 1H), 7.06 (m, 2H), 8.04 (dd, 1H); chiral HPLC: 11.5 min, mobile phase c Ex. threo-2-Ibb451, NMR: 3.09 (dd, 1H), 3.21 (dd, 1H), 3.63 (s, 3H), 4.10 (m, 2H), 6.84 (dd, 1H), 6.92 (m, 1H), 7.06 (m, 2H), 8.04 (dd, 1H); chiral HPLC: 14.9 min, mobile phase c Ex. Ibb454 (diastereomer mixture of erythro-Ibb454 and threo-Ibb454), NMR: 2.75 (dd, 1H, erythro-Ibb454), 2.84 (dd, 1H, erythro-Ibb454), 3.09 (dd, 1H, threo-Ibb454), 3.22 (dd, 1H, threo-Ibb454), 3.58 (s, 3H, erythro-Ibb454), 3.63 (s, 3H, threo-Ibb454), 4.12 (m, 1H, threo-Ibb454), 4.27 (d, 1H, erythro-Ibb454), 6.85 (dd, 1H, threo-Ibb454), 7.45 (dd, 1H), 8.05 (dd, 1H, threo-Ibb454), 8.18 (m, 1H, erythro-Ibb454)

Ex. Ibb458 (diastereomer mixture of erythro-Ibb458 and threo-Ibb458), NMR: 2.73 (dd, 1H, erythro-Ibb458), 2.84 (dd, 1H, erythro-Ibb458), 3.10 (dd, 1H, threo-Ibb458), 3.21 (dd, 1H, threo-Ibb458), 3.58 (s, 3H, erythro-Ibb458), 3.63 (s, 3H, threo-Ibb458), 4.10 (m, 1H, threo-Ibb458), 4.24 (d, 1H, erythro-Ibb458), 6.84 (dd, 1H, threo-Ibb458), 8.05 (dd, 1H, threo-Ibb458), 8.19 (m, 1H, erythro-Ibb458)

Ex. Ibb730 (diastereomer mixture of erythro-Ibb730 and threo-Ibb730), NMR: 2.84 (dd, 1H, erythro-Ibb730), 2.93 (dd, 2H, threo-Ibb730), 3.03 (dd, 1H, erythro-Ibb730), 3.58 (s, 3H, threo-Ibb730), 3.68 (s, 3H, erythro-Ibb730), 3.73 (q, 1H, threo-Ibb730), 4.12 (d, 1H, threo-Ibb730), 4.41 (d, 1H, erythro-Ibb730), 7.11 (m, 2H, erythro-Ibb730), 7.19 (m, 2H, threo-Ibb730), 7.94 (m, 1H, erythro-Ibb730), 8.22 (m, 1H, threo-Ibb730)

Ex. Ibb732 (diastereomer mixture of erythro-Ibb732 and threo-Ibb732), NMR: 2.85 (dd, 1H, erythro-Ibb732), 2.92 (d, 2H, threo-Ibb732), 3.05 (dd, 1H, erythro-Ibb732), 3.59 (s, 3H, threo-Ibb732), 3.70 (s, 3H, erythro-Ibb732), 4.13 (d, 1H, threo-Ibb732), 4.47 (d, 1H, erythro-Ibb732), 7.94 (t, 1H, erythro-Ibb732), 8.24 (t, 1H, threo-Ibb732)

Ex. erythro-1-Ibb732, NMR: 2.85 (dd, 1H), 3.05 (dd, 1H), 3.65 (q, 1H), 3.70 (s, 3H), 4.46 (d, 1H), 6.87 (m, 1H), 7.00 (m, 1H), 7.04 (m, 1H), 7.29 (m, 2H), 7.94 (s, 1H), 8.40 (d, 1H); chiral HPLC: 9.1 min, mobile phase b Ex. erythro-2-Ibb732, NMR: 2.85 (dd, 1H), 3.05 (dd, 1H), 3.65 (q, 1H), 3.70 (s, 3H), 4.46 (d, 1H), 6.87 (m, 1H), 7.00 (m, 1H), 7.04 (m, 1H), 7.29 (m, 2H), 7.94 (s, 1H), 8.40 (d, 1H); chiral HPLC: 11.6 min, mobile phase b Ex. threo-Ibb732, NMR: 2.92 (m, 2H), 3.59 (s, 3H), 3.71 (q, 1H), 4.13 (d, 1H), 6.95 (m, 1H), 6.97 (m, 1H), 7.15 (m, 1H), 7.27 (m, 1H), 8.24 (bs, 1H), 8.40 (bs, 1H); chiral HPLC: 10.5 min, mobile phase b Ex. Ibb734 (diastereomer mixture of erythro-Ibb734 and threo-Ibb734), NMR: 2.84 (dd, 1H, erythro-Ibb734), 2.92 (m, 2H, threo-Ibb734), 3.04 (dd, 1H, erythro-Ibb734), 3.59 (s, 3H, threo-Ibb734), 3.70 (s, 3H, erythro-Ibb734), 4.11 (d, 1H, threo-Ibb734), 4.44 (d, 1H, erythro-Ibb734), 7.94 (m, 1H, erythro-Ibb734), 8.24 (m, 1H, threo-Ibb734)

Ex. erythro-2-Ibb734, NMR: 2.84 (dd, 1H), 3.04 (dd, 1H), 3.64 (q, 1H), 3.70 (s, 3H), 4.44 (d, 1H), 6.98 (m, 1H), 7.17 (m, 1H), 7.28 (m, 1H), 7.31 (m, 1H), 7.94 (m, 1H), 8.40 (m, 1H); chiral HPLC: 20.0 min, mobile phase c Ex. threo-2-Ibb734, NMR: 2.92 (m, 2H), 3.59 (s, 3H), 3.72 (q, 1H), 4.11 (d, 1H), 7.06 (m, 1H), 7.22 (m, 1H), 7.29 (m, 1H), 7.33 (m, 1H), 8.24 (m, 1H), 8.41 (m, 1H); chiral HPLC: 17.0 min, mobile phase c Ex. Ibb739 (diastereomer mixture of erythro-Ibb739 and threo-Ibb739), NMR: 2.87 (dd, 1H, erythro-Ibb739), 2.93 (d, 2H, threo-Ibb739), 3.09 (dd, 1H, erythro-Ibb739), 3.61 (s, 3H, threo-Ibb739), 3.73 (s, 3H, erythro-Ibb739), 4.21 (d, 1H, threo-Ibb739), 4.60 (d, 1H, erythro-Ibb739), 7.86 (m, 1H, erythro-Ibb739), 8.20 (m, 1H, threo-Ibb739)

Ex. Ibb748 (diastereomer mixture of erythro-Ibb748 and threo-Ibb748), NMR: 2.84 (dd, 1H, erythro-Ibb748), 3.05 (dd, 1H, erythro-Ibb748), 3.61 (s, 3H, threo-Ibb748), 3.71 (s, 3H, erythro-Ibb748), 4.12 (d, 1H, threo-Ibb748), 4.48 (d, 1H, erythro-Ibb748), 7.93 (t, 1H, erythro-Ibb748), 8.22 (t, 1H, threo-Ibb748)

Ex. erythro-1-Ibb748, NMR: 2.84 (dd, 1H), 3.05 (dd, 1H), 3.61 (m, 1H), 3.71 (s, 3H), 4.48 (d, 1H), 6.87 (m, 1H), 6.99 (m, 1H), 7.14 (m, 1H), 7.29 (m, 1H), 7.93 (s, 1H), 8.41 (d, 1H); chiral HPLC: 10.8 min, mobile phase c Ex. erythro-2-Ibb748, NMR: 2.84 (dd, 1H), 3.05 (dd, 1H), 3.61 (m, 1H), 3.71 (s, 3H), 4.48 (d, 1H), 6.87 (m, 1H), 6.99 (m, 1H), 7.14 (m, 1H), 7.29 (m, 1H), 7.93 (s, 1H), 8.41 (d, 1H); chiral HPLC: 14.3 min, mobile phase c Ex. threo-1-Ibb748, NMR: 2.92 (m, 2H), 3.61 (s, 3H), 3.70 (q, 1H), 4.12 (d, 1H), 6.92 (m, 1H), 7.05 (m, 1H), 7.15 (m, 1H), 7.26 (m, 1H), 8.22 (t, 1H), 8.41 (d, 1H); chiral HPLC: 12.3 min, mobile phase c Ex. threo-2-Ibb748, NMR: 2.92 (m, 2H), 3.61 (s, 3H), 3.70 (q, 1H), 4.12 (d, 1H), 6.92 (m, 1H), 7.05 (m, 1H), 7.15 (m, 1H), 7.26 (m, 1H), 8.22 (bs, 1H), 8.41 (bs, 1H); chiral HPLC: 15.8 min, mobile phase c Ex. Ibb751 (diastereomer mixture of erythro-Ibb751 and threo-Ibb751), NMR: 2.84 (dd, 1H, erythro-Ibb751), 2.92 (m, 2H, threo-Ibb751), 3.05 (dd, 1H, erythro-Ibb751), 3.60 (s, 3H, threo-Ibb751), 3.72 (s, 3H, erythro-Ibb751), 4.14 (d, 1H, threo-Ibb751), 4.48 (d, 1H, erythro-Ibb751)

Ex. erythro-Ibb751, NMR: 2.84 (dd, 1H), 3.05 (dd, 1H), 3.62 (m, 1H), 3.72 (s, 3H), 4.48 (d, 1H), 6.86 (m, 1H), 6.96 (m, 1H), 7.30 (m, 1H), 7.36 (m, 1H), 7.93 (s, 1H), 8.41 (d, 1H)

Ex. threo-1-Ibb751, NMR: 2.92 (m, 2H), 3.60 (s, 3H), 3.72 (q, 1H), 4.14 (d, 1H), 6.92 (m, 1H), 7.02 (m, 1H), 7.28 (m, 1H), 7.39 (m, 1H), 8.22 (bs, 1H), 8.42 (bs, 1H); chiral HPLC: 40.0 min, mobile phase d Ex. threo-2-Ibb751, NMR: 2.92 (m, 2H), 3.60 (s, 3H), 3.72 (q, 1H), 4.14 (d, 1H), 6.92 (m, 1H), 7.02 (m, 1H), 7.28 (m, 1H), 7.39 (m, 1H), 8.22 (bs, 1H), 8.42 (bs, 1H); chiral HPLC: 47.0 min, mobile phase d Ex. Ibb752 (diastereomer mixture of erythro-Ibb752 and threo-Ibb752), NMR: 2.84 (dd, 1H, erythro-Ibb752), 2.92 (d, 2H, threo-Ibb752), 3.05 (dd, 1H, erythro-Ibb752), 3.60 (s, 3H, threo-Ibb752), 3.71 (s, 3H, erythro-Ibb752), 4.14 (d, 1H, threo-Ibb752), 4.48 (d, 1H, erythro-Ibb752), 6.81 (dd, 1H, erythro-Ibb752), 6.86 (dd, 1H, threo-Ibb752), 6.95 (dd, 1H, erythro-Ibb752), 7.00 (dd, 1H, threo-Ibb752), 7.93 (m, 1H, erythro-Ibb752), 8.23 (m, 1H, threo-Ibb752)

Ex. Ibb755 (diastereomer mixture of erythro-Ibb755 and threo-Ibb755), NMR: 2.84 (dd, 1H, erythro-Ibb755), 2.92 (m, 2H, threo-Ibb755), 3.05 (dd, 1H, erythro-Ibb755), 3.60 (s, 3H, threo-Ibb755), 3.71 (s, 3H, erythro-Ibb755), 4.11 (d, 1H, threo-Ibb755), 4.46 (d, 1H, erythro-Ibb755), 7.93 (m, 1H, erythro-Ibb755), 8.23 (m, 1H, threo-Ibb755)

Ex. erythro-1-Ibb755, NMR: 2.84 (dd, 1H), 3.05 (dd, 1H), 3.61 (m, 1H), 3.71 (s, 3H), 4.46 (d, 1H), 6.97 (m, 1H), 7.09 (m, 1H), 7.22 (m, 1H), 7.29 (m, 1H), 7.93 (bs, 1H), 8.41 (bs, 1H); chiral HPLC: 12.0 min, mobile phase c Ex. erythro-2-Ibb755, NMR: 2.84 (dd, 1H), 3.05 (dd, 1H), 3.61 (m, 1H), 3.71 (s, 3H), 4.46 (d, 1H), 6.97 (m, 1H), 7.09 (m, 1H), 7.22 (m, 1H), 7.29 (m, 1H), 7.93 (bs, 1H), 8.41 (bs, 1H); chiral HPLC: 15.7 min, mobile phase c Ex. threo-1-Ibb755, NMR: 2.92 (m, 2H), 3.60 (s, 3H), 3.70 (q, 1H), 4.11 (d, 1H), 7.06 (m, 1H), 7.13 (m, 1H), 7.28 (m, 2H), 8.22 (bs, 1H), 8.42 (bs, 1H); chiral HPLC: 13.0 min, mobile phase c Ex. threo-2-Ibb755, NMR: 2.92 (m, 2H), 3.60 (s, 3H), 3.70 (q, 1H), 4.11 (d, 1H), 7.06 (m, 1H), 7.13 (m, 1H), 7.28 (m, 2H), 8.22 (bs, 1H), 8.42 (bs, 1H); chiral HPLC: 14.7 min, mobile phase c Ex. Ibc892 (diastereomer mixture of erythro-Ibc892 and threo-Ibc892), NMR: 1.14 (t, 3H, threo-Ibc892), 1.22 (t, 3H, erythro-Ibc892), 2.83 (dd, 1H, erythro-Ibc892), 2.86 (m, 2H, threo-Ibc892), 3.02 (dd, 1H, erythro-Ibc892), 3.60 (m, 1H, erythro-Ibc892), 3.69 (m, 1H, threo-Ibc892), 7.84 (d, 1H, erythro-Ibc892), 8.13 (d, 1H, threo-Ibc892)

Ex. Ibb894 (diastereomer mixture of erythro-Ibb894 and threo-Ibb894), NMR: 2.83 (dd, 1H, erythro-Ibb894), 2.87 (m, 2H, threo-Ibb894), 3.03 (dd, 1H, erythro-Ibb894), 3.58 (s, 3H, threo-Ibb894), 3.70 (s, 3H, erythro-Ibb894), 7.88 (d, 1H, erythro-Ibb894), 8.15 (d, 1H, threo-Ibb894)

Ex. Ibc894 (diastereomer mixture of erythro-Ibc894 and threo-Ibc894), NMR: 1.15 (t, 3H, threo-Ibc894), 1.24 (t, 3H, erythro-Ibc894), 2.83 (dd, 1H, erythro-Ibc894), 2.88 (d, 2H, threo-Ibc894), 3.01 (dd, 1H, erythro-Ibc894), 3.60 (m, 1H, erythro-Ibc894), 3.68 (m, 1H, threo-Ibc894), 7.86 (d, 1H, erythro-Ibc894), 8.15 (d, 1H, threo-Ibc894)

Ex. erythro-1-Ibc894, NMR: 1.24 (t, 3H), 2.83 (dd, 1H), 3.01 (dd, 1H), 3.60 (m, 1H), 4.14 (q, 2H), 4.44 (d, 1H), 6.88 (m, 2H), 7.03 (m, 1H), 7.31 (m, 2H), 7.50 (dd, 1H), 7.86 (d, 1H); chiral HPLC: 17.4 min, mobile phase c Ex. erythro-2-Ibc894, NMR: 1.24 (t, 3H), 2.83 (dd, 1H), 3.01 (dd, 1H), 3.60 (m, 1H), 4.14 (q, 2H), 4.44 (d, 1H), 6.88 (m, 2H), 7.03 (m, 1H), 7.31 (m, 2H), 7.50 (dd, 1H), 7.86 (d, 1H); chiral HPLC: 21.8 min, mobile phase c Ex. threo-1-Ibc894, NMR: 1.15 (t, 3H), 2.88 (m, 2H), 3.68 (m, 1H), 4.03 (m, 2H), 4.12 (d, 1H), 6.94 (m, 2H), 7.06 (m, 1H), 7.33 (m, 2H), 7.50 (dd, 1H), 8.15 (d, 1H); chiral HPLC: 22.4 min, mobile phase c Ex. threo-2-Ibc894, NMR: 1.15 (t, 3H), 2.88 (m, 2H), 3.68 (m, 1H), 4.03 (m, 2H), 4.12 (d, 1H), 6.94 (m, 2H), 7.06 (m, 1H), 7.33 (m, 2H), 7.50 (dd, 1H), 8.15 (d, 1H); chiral HPLC: 26.4 min, mobile phase c Ex. Ibc895 (diastereomer mixture of erythro-Ibc895 and threo-Ibc895), NMR: 1.15 (t, 3H, threo-Ibc895), 1.23 (t, 3H, erythro-Ibc895), 2.82 (dd, 1H, erythro-Ibc895), 2.89 (m, 2H, threo-Ibc895), 3.03 (dd, 1H, erythro-Ibc895), 3.56 (m, 1H, erythro-Ibc895), 3.68 (m, 1H, threo-Ibc895), 4.03 (m, 2H, threo-Ibc895), 7.85 (m, 1H, erythro-Ibc895), 8.13 (m, 1H, threo-Ibc895)

Ex. erythro-Ibc895, NMR: 1.23 (t, 3H), 2.82 (dd, 1H), 3.03 (dd, 1H), 3.56 (m, 1H), 4.15 (q, 2H), 4.43 (d, 1H), 7.05 (m, 4H), 7.28 (m, 1H), 7.49 (m, 1H), 7.85 (m, 1H)

Ex. Ibc896 (diastereomer mixture of erythro-Ibc896 and threo-Ibc896), NMR: 1.15 (t, 3H, threo-Ibc896), 1.23 (t, 3H, erythro-Ibc896), 2.82 (dd, 1H, erythro-Ibc896), 2.87 (d, 2H, threo-Ibc896), 3.02 (dd, 1H, erythro-Ibc896), 7.88 (d, 1H, erythro-Ibc896), 8.17 (d, 1H, threo-Ibc896)

Ex. erythro-Ibc896, NMR: 1.23 (t, 3H), 2.82 (dd, 1H), 3.02 (dd, 1H), 3.59 (m, 1H), 4.14 (q, 2H), 4.42 (d, 1H), 6.96 (m, 1H), 7.17 (m, 1H), 7.27 (m, 3H), 7.49 (m, 1H), 7.88 (d, 1H)

Ex. erythro-1-Ibc896, NMR: 1.23 (t, 3H), 2.82 (dd, 1H), 3.02 (dd, 1H), 3.59 (m, 1H), 4.14 (q, 2H), 4.42 (d, 1H), 6.96 (m, 1H), 7.17 (m, 1H), 7.27 (m, 3H), 7.49 (dd, 1H), 7.88 (d, 1H); chiral HPLC: 18.3 min, mobile phase c Ex. erythro-2-Ibc896, NMR: 1.23 (t, 3H), 2.82 (dd, 1H), 3.02 (dd, 1H), 3.59 (m, 1H), 4.14 (q, 2H), 4.42 (d, 1H), 6.96 (m, 1H), 7.17 (m, 1H), 7.27 (m, 3H), 7.49 (dd, 1H), 7.88 (d, 1H); chiral HPLC: 20.8 min, mobile phase c Ex. threo-1-Ibc896, NMR: 1.15 (t, 3H), 2.87 (m, 2H), 3.68 (q, 1H), 4.03 (m, 2H), 4.09 (d, 1H), 7.04 (m, 1H), 7.22 (m, 1H), 7.29 (m, 3H), 7.50 (dd, 1H), 8.17 (d, 1H); chiral HPLC: 23.2 min, mobile phase c Ex. threo-2-Ibc896, NMR: 1.15 (t, 3H), 2.87 (m, 2H), 3.68 (q, 1H), 4.03 (m, 2H), 4.09 (d, 1H), 7.04 (m, 1H), 7.22 (m, 1H), 7.29 (m, 3H), 7.50 (dd, 1H), 8.17 (d, 1H); chiral HPLC: 27.2 min, mobile phase c Ex. erythro-Ibc901, NMR: 1.26 (t, 3H), 2.86 (dd, 1H), 3.07 (dd, 1H), 3.58 (m, 1H), 4.17 (q, 2H), 4.57 (d, 1H), 7.32 (m, 2H), 7.48 (m, 3H), 7.65 (m, 1H), 7.81 (d, 1H)

Ex. threo-Ibc901, NMR: 1.16 (t, 3H), 2.88 (m, 2H), 3.70 (q, 1H), 4.04 (m, 2H), 4.19 (d, 1H), 7.30 (d, 1H), 7.41 (m, 1H), 7.49 (m, 3H), 7.66 (m, 1H), 8.14 (d, 1H)

Ex. Ibc910 (diastereomer mixture of erythro-Ibc910 and threo-Ibc910), NMR: 1.16 (t, 3H, threo-Ibc910), 1.24 (t, 3H, erythro-Ibc910), 2.82 (dd, 1H, erythro-Ibc910), 2.88 (m, 2H, threo-Ibc910), 3.03 (dd, 1H, erythro-Ibc910), 3.55 (m, 1H, erythro-Ibc910), 3.67 (m, 1H, threo-Ibc910), 4.05 (m, 2H, threo-Ibc910), 7.88 (d, 1H, erythro-Ibc910), 8.15 (d, 1H, threo-Ibc910)

Ex. erythro-Ibc910, NMR: 1.24 (t, 3H), 2.82 (dd, 1H), 3.03 (dd, 1H), 3.55 (m, 1H), 4.15 (q, 2H), 4.45 (d, 1H), 6.85 (m, 1H), 6.98 (m, 1H), 7.12 (m, 1H), 7.31 (d, 1H), 7.50 (dd, 1H), 7.88 (d, 1H)

Ex. erythro-1-Ibc910, NMR: 1.24 (t, 3H), 2.82 (dd, 1H), 3.03 (dd, 1H), 3.55 (m, 1H), 4.15 (q, 2H), 4.45 (d, 1H), 6.85 (m, 1H), 6.98 (m, 1H), 7.12 (m, 1H), 7.31 (d, 1H), 7.50 (dd, 1H), 7.88 (d, 1H); chiral HPLC: 16.7 min, mobile phase c Ex. erythro-2-Ibc910, NMR: 1.24 (t, 3H), 2.82 (dd, 1H), 3.03 (dd, 1H), 3.55 (m, 1H), 4.15 (q, 2H), 4.45 (d, 1H), 6.85 (m, 1H), 6.98 (m, 1H), 7.12 (m, 1H), 7.31 (d, 1H), 7.50 (dd, 1H), 7.88 (d, 1H); chiral HPLC: 22.1 min, mobile phase c Ex. threo-Ibc910, NMR: 1.16 (t, 3H), 2.88 (m, 2H), 3.67 (m, 1H), 4.05 (m, 2H), 4.11 (d, 1H), 6.90 (m, 1H), 7.04 (m, 1H), 7.15 (m, 1H), 7.30 (d, 1H), 7.50 (dd, 1H), 8.15 (d, 1H)

Ex. threo-1-Ibc910, NMR: 1.16 (t, 3H), 2.88 (m, 2H), 3.67 (m, 1H), 4.05 (m, 2H), 4.11 (d, 1H), 6.90 (m, 1H), 7.04 (m, 1H), 7.15 (m, 1H), 7.30 (d, 1H), 7.50 (dd, 1H), 8.15 (d, 1H); chiral HPLC: 12.0 min, mobile phase c Ex. Ibc916 (diastereomer mixture of erythro-Ibc916 and threo-Ibc916), NMR: 1.16 (t, 3H, threo-Ibc916), 1.24 (t, 3H, erythro-Ibc916), 2.82 (dd, 1H, erythro-Ibc916), 2.87 (m, 2H, threo-Ibc916), 3.03 (dd, 1H, erythro-Ibc916), 3.55 (m, 1H, erythro-Ibc916), 3.67 (q, 1H, threo-Ibc916), 4.03 (m, 2H, threo-Ibc916), 4.10 (d, 1H, threo-Ibc916), 4.15 (q, 2H, erythro-Ibc916), 4.44 (d, 1H, erythro-Ibc916), 7.41 (dd, 1H, threo-Ibc916), 7.89 (d, 1H, erythro-Ibc916), 8.16 (d, 1H, threo-Ibc916)

Ex. erythro-Ibc916, NMR: 1.24 (t, 3H), 2.82 (dd, 1H), 3.03 (dd, 1H), 3.55 (m, 1H), 4.15 (q, 2H), 4.44 (d, 1H), 6.98 (m, 1H), 7.08 (d, 1H), 7.30 (d, 1H), 7.37 (dd, 1H), 7.49 (dd, 1H), 7.89 (d, 1H)

Ex. Ibb1002 (diastereomer mixture of erythro-Ibb1002 and threo-Ibb1002), NMR: 2.84 (dd, 1H, erythro-Ibb1002), 2.92 (m, 2H, threo-Ibb1002), 3.01 (dd, 1H, erythro-Ibb1002), 3.60 (s, 3H, threo-Ibb1002), 3.70 (s, 3H, erythro-Ibb1002), 4.12 (d, 1H, threo-Ibb1002), 4.45 (d, 1H, erythro-Ibb1002), 6.60 (m, 1H, erythro-Ibb1002), 6.74 (m, 1H, threo-Ibb1002), 8.13 (d, 1H, erythro-Ibb1002), 8.17 (d, 1H, threo-Ibb1002)

Ex. Ibb1018 (diastereomer mixture of erythro-Ibb1018 and threo-Ibb1018), NMR: 2.83 (dd, 1H, erythro-Ibb1018), 2.92 (m, 2H, threo-Ibb1018), 3.01 (dd, 1H, erythro-Ibb1018), 3.61 (s, 3H, threo-Ibb1018), 3.70 (s, 3H, erythro-Ibb1018), 4.11 (d, 1H, threo-Ibb1018), 4.45 (d, 1H, erythro-Ibb1018), 6.61 (m, 1H, erythro-Ibb1018), 6.74 (m, 1H, threo-Ibb1018), 8.14 (d, 1H, erythro-Ibb1018), 8.18 (d, 1H, threo-Ibb1018)

Ex. erythro-Ibb1018, NMR: 2.83 (dd, 1H), 3.01 (dd, 1H), 3.57 (q, 1H), 3.70 (s, 3H), 4.45 (d, 1H), 6.61 (m, 1H), 6.88 (m, 2H), 7.01 (m, 1H), 7.13 (m, 1H), 8.14 (d, 1H)

Ex. erythro-1-Ibb1018, NMR: 2.83 (dd, 1H), 3.01 (dd, 1H), 3.57 (q, 1H), 3.70 (s, 3H), 4.45 (d, 1H), 6.61 (m, 1H), 6.88 (m, 2H), 7.01 (m, 1H), 7.13 (m, 1H), 8.14 (d, 1H); chiral HPLC: 9.8 min, mobile phase a Ex. erythro-2-Ibb1018, NMR: 2.83 (dd, 1H), 3.01 (dd, 1H), 3.57 (q, 1H), 3.70 (s, 3H), 4.45 (d, 1H), 6.61 (m, 1H), 6.88 (m, 2H), 7.01 (m, 1H), 7.13 (m, 1H), 8.14 (d, 1H); chiral HPLC: 29.2 min, mobile phase a Ex. threo-1-Ibb1018, NMR: 2.92 (m, 2H), 3.61 (s, 3H), 3.67 (q, 1H), 4.11 (d, 1H), 6.74 (m, 1H), 6.93 (m, 1H), 7.00 (m, 1H), 7.08 (m, 1H), 7.18 (m, 1H), 8.18 (d, 1H); chiral HPLC: 8.4 min, mobile phase a Ex. threo-2-Ibb1018, NMR: 2.92 (m, 2H), 3.61 (s, 3H), 3.67 (q, 1H), 4.11 (d, 1H), 6.74 (m, 1H), 6.93 (m, 1H), 7.00 (m, 1H), 7.08 (m, 1H), 7.18 (m, 1H), 8.18 (d, 1H); chiral HPLC: 10.4 min, mobile phase a Ex. Ibb1021 (diastereomer mixture of erythro-Ibb1021 and threo-Ibb1021), NMR: 2.83 (dd, 1H, erythro-Ibb1021), 2.92 (m, 2H, threo-Ibb1021), 3.01 (dd, 1H, erythro-Ibb1021), 3.61 (s, 3H, threo-Ibb1021), 3.71 (s, 3H, erythro-Ibb1021), 4.13 (d, 1H, threo-Ibb1021), 4.46 (d, 1H, erythro-Ibb1021), 6.63 (m, 1H, erythro-Ibb1021), 6.75 (m, 1H, threo-Ibb1021), 8.14 (d, 1H, erythro-Ibb1021), 8.19 (d, 1H, threo-Ibb1021)

Ex. Ibb1025 (diastereomer mixture of erythro-Ibb1025 and threo-Ibb1025), NMR: 2.83 (dd, 1H, erythro-Ibb1025), 2.91 (m, 2H, threo-Ibb1025), 3.01 (dd, 1H, erythro-Ibb1025), 3.57 (q, 1H, erythro-Ibb1025), 3.58 (s, 3H, threo-Ibb1025), 3.66 (q, 1H, threo-Ibb1025), 3.70 (s, 3H, erythro-Ibb1025), 4.11 (d, 1H, threo-Ibb1025), 4.44 (d, 1H, erythro-Ibb1025), 6.62 (m, 1H, erythro-Ibb1025), 6.75 (m, 1H, threo-Ibb1025), 7.24 (m, 1H, erythro-Ibb1025), 7.29 (m, 1H, threo-Ibb1025), 8.15 (d, 1H, erythro-Ibb1025), 8.19 (d, 1H, threo-Ibb1025)

Ex. Ibb1027 (diastereomer mixture of erythro-Ibb1027 and threo-Ibb1027), NMR: 3.59 (s, 3H, threo-Ibb1027), 3.67 (s, 3H, erythro-Ibb1027), 4.10 (d, 1H, threo-Ibb1027), 4.37 (d, 1H, erythro-Ibb1027), 8.28 (d, 1H, erythro-Ibb1027), 8.31 (d, 1H, threo-Ibb1027)

Ex. erythro-1-Ibb1027, NMR: 2.82 (dd, 1H), 2.98 (dd, 1H), 3.57 (m, 1H), 3.67 (s, 3H), 4.37 (d, 1H), 6.93 (m, 1H), 6.95 (s, 1H), 7.13 (m, 2H), 7.35 (m, 3H), 8.28 (d, 1H)

Ex. erythro-2-Ibb1027, NMR: 2.82 (dd, 1H), 2.98 (dd, 1H), 3.57 (m, 1H), 3.67 (s, 3H), 4.37 (d, 1H), 6.93 (m, 1H), 6.95 (s, 1H), 7.13 (m, 2H), 7.35 (m, 3H), 8.28 (d, 1H)

Ex. threo-Ibb1027, NMR: 2.91 (d, 2H), 3.59 (s, 3H), 3.64 (q, 1H), 4.10 (d, 1H), 7.04 (m, 1H), 7.11 (s, 1H), 7.19 (m, 2H), 7.37 (m, 3H), 8.31 (d, 1H)

Ex. Iba1029 (diastereomer mixture of erythro-Iba1029 and threo-Iba1029), NMR: 3.53 (q, 1H, erythro-Iba1029), 3.61 (q, 1H, threo-Iba1029), 4.10 (d, 1H, threo-Iba1029), 4.41 (d, 1H, erythro-Iba1029), 8.30 (d, 1H, erythro-Iba1029), 8.37 (d, 1H, threo-Iba1029)

Ex. Ibb1029 (diastereomer mixture of erythro-Ibb1029 and threo-Ibb1029), NMR: 3.59 (s, 3H, threo-Ibb1029), 3.70 (s, 3H, erythro-Ibb1029), 4.11 (d, 1H, threo-Ibb1029), 4.42 (d, 1H, erythro-Ibb1029), 8.30 (d, 1H, erythro-Ibb1029), 8.32 (d, 1H, threo-Ibb1029)

Ex. erythro-1-Ibb1029, NMR: 2.71 (dd, 1H), 3.00 (dd, 1H), 3.55 (q, 1H), 3.70 (s, 3H), 4.42 (d, 1H), 6.91 (m, 3H), 6.97 (s, 1H), 7.06 (dt, 1H), 7.31 (m, 1H), 8.30 (d, 1H)

Ex. erythro-2-Ibb1029, NMR: 2.71 (dd, 1H), 3.00 (dd, 1H), 3.55 (q, 1H), 3.70 (s, 3H), 4.42 (d, 1H), 6.91 (m, 3H), 6.97 (s, 1H), 7.06 (dt, 1H), 7.31 (m, 1H), 8.30 (d, 1H)

Ex. threo-Ibb1029, NMR: 2.90 (m, 2H), 3.59 (s, 3H), 3.62 (m, 1H), 4.11 (d, 1H), 6.96 (m, 2H), 7.06 (m, 2H), 7.13 (s, 1H), 7.35 (m, 1H), 8.32 (d, 1H)

Ex. Ibc1029 (diastereomer mixture of erythro-Ibc1029 and threo-Ibc1029), NMR: 1.18 (t, 3H, threo-Ibc1029), 1.22 (t, 3H, erythro-Ibc1029), 3.55 (q, 1H, erythro-Ibc1029), 3.62 (m, 1H, threo-Ibc1029), 4.42 (d, 1H, erythro-Ibc1029), 8.30 (d, 1H, erythro-Ibc1029), 8.32 (d, 1H, threo-Ibc1029)

Ex. erythro-1-Ibc1029, NMR: 1.22 (t, 3H), 2.71 (dd, 1H), 2.99 (dd, 1H), 3.55 (q, 1H), 4.15 (q, 2H), 4.42 (d, 1H), 6.91 (m, 3H), 6.99 (s, 1H), 7.06 (dt, 1H), 7.31 (m, 1H), 8.30 (d, 1H); chiral HPLC: 15.3 min, mobile phase c Ex. erythro-2-Ibc1029, NMR: 1.22 (t, 3H), 2.71 (dd, 1H), 2.99 (dd, 1H), 3.55 (q, 1H), 4.15 (q, 2H), 4.42 (d, 1H), 6.91 (m, 3H), 6.99 (s, 1H), 7.06 (dt, 1H), 7.31 (m, 1H), 8.30 (d, 1H); chiral HPLC: 21.0 min, mobile phase c Ex. threo-Ibc1029, NMR: 1.18 (t, 3H), 2.89 (m, 2H), 3.62 (m, 1H), 4.04 (m, 2H), 4.12 (d, 1H), 6.98 (m, 2H), 7.05 (m, 2H), 7.13 (s, 1H), 7.35 (m, 1H), 8.32 (d, 1H)

Ex. threo-1-Ibc1029, chiral HPLC: 11.0 min, mobile phase c

Ex. threo-2-Ibc1029, chiral HPLC: 11.5 min, mobile phase c

Ex. Ibb1031 (diastereomer mixture of erythro-Ibb1031 and threo-Ibb1031), NMR: 2.81 (dd, 1H, erythro-Ibb1031), 2.89 (m, 2H, threo-Ibb1031), 2.98 (dd, 1H, erythro-Ibb1031), 3.54 (q, 1H, erythro-Ibb1031), 3.60 (s, 3H, threo-Ibb1031), 3.63 (m, 1H, threo-Ibb1031), 3.69 (s, 3H, erythro-Ibb1031), 4.09 (d, 1H, threo-Ibb1031), 4.40 (d, 1H, erythro-Ibb1031), 8.30 (d, 1H, erythro-Ibb1031), 8.34 (d, 1H, threo-Ibb1031)

Ex. Ibb1036 (diastereomer mixture of erythro-Ibb1036 and threo-Ibb1036), NMR: 3.61 (s, 3H, threo-Ibb1036), 3.72 (s, 3H, erythro-Ibb1036), 4.19 (d, 1H, threo-Ibb1036), 4.56 (d, 1H, erythro-Ibb1036), 8.30 (d, 1H, erythro-Ibb1036), 8.35 (d, 1H, threo-Ibb1036)

Ex. erythro-Ibb1036, NMR: 2.84 (dd, 1H), 3.03 (dd, 1H), 3.54 (m, 1H), 3.72 (s, 3H), 4.56 (d, 1H), 6.90 (m, 1H), 6.94 (s, 1H), 7.35 (m, 1H), 7.48 (t, 1H), 7.52 (m, 1H), 7.67 (m, 1H), 8.30 (d, 1H)

Ex. erythro-1-Ibb1036, NMR: 2.84 (dd, 1H), 3.03 (dd, 1H), 3.54 (m, 1H), 3.72 (s, 3H), 4.56 (d, 1H), 6.90 (m, 1H), 6.94 (s, 1H), 7.35 (m, 1H), 7.48 (t, 1H), 7.52 (m, 1H), 7.67 (m, 1H), 8.30 (d, 1H)

Ex. erythro-2-Ibb1036, NMR: 2.84 (dd, 1H), 3.03 (dd, 1H), 3.54 (m, 1H), 3.72 (s, 3H), 4.56 (d, 1H), 6.90 (m, 1H), 6.94 (s, 1H), 7.35 (m, 1H), 7.48 (t, 1H), 7.52 (m, 1H), 7.67 (m, 1H), 8.30 (d, 1H)

Ex. threo-1-Ibb1036, NMR: 2.90 (m, 2H), 3.61 (s, 3H), 3.66 (m, 1H), 4.19 (d, 1H), 7.03 (m, 1H), 7.12 (s, 1H), 7.42 (m, 1H), 7.53 (t, 1H), 7.56 (m, 1H), 7.68 (m, 1H), 8.35 (d, 1H)

Ex. threo-2-Ibb1036, NMR: 2.90 (m, 2H), 3.61 (s, 3H), 3.66 (m, 1H), 4.19 (d, 1H), 7.03 (m, 1H), 7.12 (s, 1H), 7.42 (m, 1H), 7.53 (t, 1H), 7.56 (m, 1H), 7.68 (m, 1H), 8.35 (d, 1H)

Ex. Ibc1036 (diastereomer mixture of erythro-Ibc1036 and threo-Ibc1036), NMR: 1.17 (t, 3H, threo-Ibc1036), 1.25 (t, 3H, erythro-Ibc1036), 3.53 (m, 1H, erythro-Ibc1036), 3.63 (m, 1H, threo-Ibc1036), 4.04 (dq, 2H, threo-Ibc1036), 4.16 (q, 2H, erythro-Ibc1036), 4.19 (d, 1H, threo-Ibc1036), 4.55 (d, 1H, erythro-Ibc1036), 8.31 (d, 1H, erythro-Ibc1036), 8.36 (d, 1H, threo-Ibc1036)

Ex. Ibb1045 (diastereomer mixture of erythro-Ibb1045 and threo-Ibb1045), NMR: 3.60 (s, 3H, threo-Ibb1045), 3.70 (s, 3H, erythro-Ibb1045), 4.10 (d, 1H, threo-Ibb1045), 4.44 (d, 1H, erythro-Ibb1045), 8.31 (d, 1H, erythro-Ibb1045), 8.34 (d, 1H, threo-Ibb1045)

Ex. erythro-Ibb1045, NMR: 2.82 (dd, 1H), 2.98 (dd, 1H), 3.52 (q, 1H), 3.70 (s, 3H), 4.44 (d, 1H), 6.88 (m, 1H), 6.92 (m, 1H), 6.99 (s, 1H), 7.02 (m, 1H), 7.14 (m, 1H), 8.31 (d, 1H)

Ex. erythro-1-Ibb1045, NMR: 2.82 (dd, 1H), 2.98 (dd, 1H), 3.52 (q, 1H), 3.70 (s, 3H), 4.44 (d, 1H), 6.88 (m, 1H), 6.92 (m, 1H), 6.99 (s, 1H), 7.02 (m, 1H), 7.14 (m, 1H), 8.31 (d, 1H); chiral HPLC: 15.3 min, mobile phase b Ex. erythro-2-Ibb1045, NMR: 2.82 (dd, 1H), 2.98 (dd, 1H), 3.52 (q, 1H), 3.70 (s, 3H), 4.44 (d, 1H), 6.88 (m, 1H), 6.92 (m, 1H), 6.99 (s, 1H), 7.02 (m, 1H), 7.14 (m, 1H), 8.31 (d, 1H); chiral HPLC: 29.0 min, mobile phase b Ex. threo-1-Ibb1045, NMR: 2.90 (m, 2H,), 3.60 (m, 1H), 3.61 (s, 3H), 4.10 (d, 1H), 6.93 (m, 1H), 7.03 (m, 1H), 7.07 (m, 1H), 7.13 (s, 1H), 7.16 (m, 1H), 8.34 (d, 1H); chiral HPLC: 10.7 min, mobile phase b Ex. threo-2-Ibb1045, NMR: 2.90 (m, 2H,), 3.60 (m, 1H), 3.61 (s, 3H), 4.10 (d, 1H), 6.93 (m, 1H), 7.03 (m, 1H), 7.07 (m, 1H), 7.13 (s, 1H), 7.16 (m, 1H), 8.34 (d, 1H); chiral HPLC: 12.1 min, mobile phase b Ex. Ibc1045 (diastereomer mixture of erythro-Ibc1045 and threo-Ibc1045), NMR: 1.16 (t, 3H, threo-Ibc1045), 1.24 (t, 3H, erythro-Ibc1045), 2.88 (m, 2H, threo-Ibc1045), 3.51 (q, 1H, erythro-Ibc1045), 3.61 (q, 1H, threo-Ibc1045), 4.05 (dq, 2H, threo-Ibc1045), 4.12 (d, 1H, threo-Ibc1045), 4.43 (d, 1H, erythro-Ibc1045), 8.31 (d, 1H, erythro-Ibc1045), 8.35 (d, 1H, threo-Ibc1045)

Ex. erythro-Ibc1045, NMR: 1.24 (t, 3H), 2.80 (dd, 1H), 2.98 (dd, 1H), 3.51 (q, 1H), 4.15 (q, 2H), 4.43 (d, 1H), 6.87 (m, 1H), 6.92 (dd, 1H), 7.00 (s, 1H), 7.03 (m, 1H), 7.14 (m, 1H), 8.31 (d, 1H)

Ex. Ibb1048 (diastereomer mixture of erythro-Ibb1048 and threo-Ibb1048), NMR: 3.61 (s, 3H, threo-Ibb1048), 3.71 (s, 3H, erythro-Ibb1048), 4.11 (d, 1H, threo-Ibb1048), 4.45 (d, 1H, erythro-Ibb1048), 8.31 (d, 1H, erythro-Ibb1048), 8.35 (d, 1H, threo-Ibb1048)

Ex. erythro-Ibb1048, NMR: 2.82 (dd, 1H), 3.00 (dd, 1H), 3.52 (q, 1H), 3.71 (s, 3H), 4.45 (d, 1H), 6.87 (m, 1H), 6.90 (m, 1H), 6.98 (m, 1H), 7.00 (s, 1H), 7.38 (m, 1H), 8.31 (d, 1H)

Ex. erythro-2-Ibb1048, NMR: 2.82 (dd, 1H), 3.00 (dd, 1H), 3.52 (q, 1H), 3.71 (s, 3H), 4.45 (d, 1H), 6.87 (m, 1H), 6.90 (m, 1H), 6.98 (m, 1H), 7.00 (s, 1H), 7.38 (m, 1H), 8.31 (d, 1H); chiral HPLC: 41.2 min, mobile phase d Ex. threo-1-Ibb1048, NMR: 2.89 (m, 2H),), 3.61 (s, 3H), 3.62 (m, 1H), 4.11 (d, 1H), 6.92 (m, 1H), 7.05 (m, 2H), 7.15 (s, 1H), 7.40 (m, 1H), 8.35 (d, 1H); chiral HPLC: 25.8 min, mobile phase d Ex. threo-2-Ibb1048, NMR: 2.89 (m, 2H),), 3.61 (s, 3H), 3.62 (m, 1H), 4.11 (d, 1H), 6.92 (m, 1H), 7.05 (m, 2H), 7.15 (s, 1H), 7.40 (m, 1H), 8.35 (d, 1H); chiral HPLC: 29.6 min, mobile phase d Ex. Ibb1049 (diastereomer mixture of erythro-Ibb1049 and threo-Ibb1049), NMR: 2.82 (dd, 1H, erythro-Ibb1049), 2.89 (m, 2H, threo-Ibb1049), 2.99 (dd, 1H, erythro-Ibb1049), 3.53 (m, 1H, erythro-Ibb1049), 3.60 (s, 3H, threo-Ibb1049), 3.61 (m, 1H, threo-Ibb1049), 3.70 (s, 3H, erythro-Ibb1049), 4.12 (d, 1H, threo-Ibb1049), 4.44 (d, 1H, erythro-Ibb1049), 6.82 (m, 1H, erythro-Ibb1049), 6.87 (m, 1H, threo-Ibb1049), 7.01 (s, 1H, erythro-Ibb1049), 7.16 (s, 1H, threo-Ibb1049), 8.31 (d, 1H, erythro-Ibb1049), 8.35 (d, 1H, threo-Ibb1049)

Ex. Ibb1052 (diastereomer mixture of erythro-Ibb1052 and threo-Ibb1052), NMR: 3.62 (s, 3H, threo-Ibb1052), 3.70 (s, 3H, erythro-Ibb1052), 4.09 (d, 1H, threo-Ibb1052), 4.42 (d, 1H, erythro-Ibb1052), 8.31 (d, 1H, erythro-Ibb1052), 8.35 (d, 1H, threo-Ibb1052)

Ex. erythro-1-Ibb1052, NMR: 2.81 (dd, 1H), 2.99 (dd, 1H), 3.51 (q, 1H), 3.70 (s, 3H), 4.42 (d, 1H), 6.90 (m, 1H), 6.99 (m, 2H), 7.11 (t, 1H), 8.31 (d, 1H); chiral HPLC: 10.8 min, mobile phase a Ex. erythro-2-Ibb1052, NMR: 2.81 (dd, 1H), 2.99 (dd, 1H), 3.51 (q, 1H), 3.70 (s, 3H), 4.42 (d, 1H), 6.90 (m, 1H), 6.99 (m, 2H), 7.11 (t, 1H), 8.31 (d, 1H); chiral HPLC: 20.4 min, mobile phase a Ex. threo-1-Ibb1052, NMR: 2.89 (m, 2H),), 3.61 (m, 1H), 3.62 (s, 3H), 4.09 (d, 1H), 7.03 (m, 2H), 7.14 (m, 2H), 7.29 (m, 1H), 8.35 (d, 1H); HPLC-Chiral: 8.3 min, mobile phase a Ex. threo-2-Ibb1052, NMR: 2.89 (m, 2H),), 3.61 (m, 1H), 3.62 (s, 3H), 4.09 (d, 1H), 7.03 (m, 2H), 7.14 (m, 2H), 7.29 (m, 1H), 8.35 (d, 1H); chiral HPLC: 8.9 min, mobile phase a Ex. Ibb1270 (diastereomer mixture of erythro-Ibb1270 and threo-Ibb1270), NMR: 3.54 (s, 3H, erythro-Ibb1270), 3.65 (s, 3H, threo-Ibb1270), 4.15 (d, 1H, threo-Ibb1270), 4.25 (d, 1H, erythro-Ibb1270), 8.28 (s, 2H, threo-Ibb1270), 8.36 (s, 2H, erythro-Ibb1270)

Ex. erythro-Ibb1270, NMR: 2.73 (dd, 1H), 2.86 (dd, 1H), 3.54 (s, 3H), 4.11 (m, 1H), 4.25 (d, 1H), 7.36 (m, 5H), 8.36 (s, 2H)

Ex. threo-Ibb1270, NMR: 3.07 (dd, 1H), 3.30 (m, 1H), 3.65 (s, 3H), 4.15 (d, 1H), 7.39 (m, 5H), 8.28 (s, 2H)

Ex. Ibb1272 (diastereomer mixture of erythro-Ibb1272 and threo-Ibb1272), NMR: 3.58 (s, 3H, erythro-Ibb1272), 3.63 (s, 3H, threo-Ibb1272), 4.16 (m, 1H, threo-Ibb1272), 4.29 (d, 1H, erythro-Ibb1272), 8.21 (s, 2H, threo-Ibb1272), 8.37 (s, 2H, erythro-Ibb1272)

Ex. erythro-Ibb1272, NMR: 2.78 (dd, 1H), 2.88 (dd, 1H), 3.58 (s, 3H), 4.10 (q, 1H), 4.29 (d, 1H), 7.10 (m, 1H), 7.14 (m, 2H), 7.39 (m, 1H), 8.37 (s, 2H)

Ex. threo-1-Ibb1272, NMR: 3.19 (m, 2H), 3.63 (s, 3H), 4.16 (m, 1H), 4.17 (m, 1H), 6.97 (m, 3H), 7.23 (m, 1H), 8.21 (s, 2H); chiral HPLC: 16.2 min, mobile phase d Ex. threo-2-Ibb1272, NMR: 3.19 (m, 2H), 3.63 (s, 3H), 4.16 (m, 1H), 4.17 (m, 1H), 6.97 (m, 3H), 7.23 (m, 1H), 8.21 (s, 2H); chiral HPLC: 18.3 min, mobile phase d Ex. Ibb1273 (diastereomer mixture of erythro-Ibb1273 and threo-Ibb1273), NMR: 3.57 (s, 3H), 3.62 (s, 3H), 4.15 (m, 1H, threo-Ibb1273), 4.29 (d, 1H, erythro-Ibb1273), 6.96 (t, 2H), 7.11 (t, 2H), 8.20 (s, 2H), 8.36 (s, 2H)

Ex. erythro-Ibb1273, NMR: 2.76 (dd, 1H), 2.84 (dd, 1H), 3.57 (s, 3H), 4.08 (q, 1H), 4.29 (d, 1H), 7.11 (t, 2H), 7.33 (m, 2H), 8.36 (s, 2H)

Ex. threo-1-Ibb1273, NMR: 3.15 (m, 1H), 3.23 (m, 1H), 3.62 (s, 3H), 4.15 (m, 1H), 4.16 (m, 1H), 6.96 (t, 2H), 7.17 (m, 2H), 8.20 (s, 2H); chiral HPLC: 11.2 min, mobile phase c Ex. threo-2-Ibb1273, NMR: 3.15 (m, 1H), 3.23 (m, 1H), 3.62 (s, 3H), 4.15 (m, 1H), 4.16 (m, 1H), 6.96 (t, 2H), 7.17 (m, 2H), 8.20 (s, 2H); chiral HPLC: 12.3 min, mobile phase c Ex. Ibb1274 (diastereomer mixture of erythro-Ibb1274 and threo-Ibb1274), NMR: 3.57 (s, 3H, erythro-Ibb1274), 3.63 (s, 3H, threo-Ibb1274), 4.14 (m, 1H, threo-Ibb1274), 4.27 (d, 1H, erythro-Ibb1274), 8.22 (s, 2H, threo-Ibb1274), 8.37 (s, 2H, erythro-Ibb1274)

Ex. Ibb1279 (diastereomer mixture of erythro-Ibb1279 and threo-Ibb1279), NMR: 3.61 (s, 3H), 3.64 (s, 3H), 4.20 (m, 1H, threo-Ibb1279), 4.42 (d, 1H, erythro-Ibb1279), 8.23 (s, 2H), 8.37 (s, 2H)

Ex. Ibb1288 (diastereomer mixture of erythro-Ibb1288 and threo-Ibb1288), NMR: 3.60 (s, 3H), 3.63 (s, 3H), 4.14 (m, 1H, threo-Ibb1288), 4.31 (d, 1H, erythro-Ibb1288), 8.23 (s, 2H), 8.37 (s, 2H)

Ex. erythro-Ibb1288, NMR: 2.85 (m, 2H), 3.60 (s, 3H), 4.07 (q, 1H), 4.31 (d, 1H), 7.08 (m, 1H), 7.21 (m, 2H), 8.37 (s, 2H)

Ex. threo-Ibb1288, NMR: 3.18 (m, 2H), 3.63 (s, 3H), 4.14 (m, 1H), 4.16 (m, 1H), 6.91 (m, 1H), 7.07 (m, 2H), 8.23 (s, 2H)

Ex. threo-1-Ibb1288, NMR: 3.18 (m, 2H), 3.63 (s, 3H), 4.14 (m, 1H), 4.16 (m, 1H), 6.91 (m, 1H), 7.07 (m, 2H), 8.23 (s, 2H); chiral HPLC: 23.6 min, mobile phase d Ex. threo-2-Ibb1288, NMR: 3.18 (m, 2H), 3.63 (s, 3H), 4.14 (m, 1H), 4.16 (m, 1H), 6.91 (m, 1H), 7.07 (m, 2H), 8.23 (s, 2H); chiral HPLC: 27.0 min, mobile phase d Ex. Ibb1291 (diastereomer mixture of erythro-Ibb1291 and threo-Ibb1291), NMR: 4.32 (d, 1H, erythro-Ibb1291), 8.24 (s, 2H, threo-Ibb1291), 8.37 (s, 2H, erythro-Ibb1291)

Ex. erythro-1-Ibb-1291, NMR: 2.85 (m, 2H), 3.60 (s, 3H), 4.08 (q, 1H), 4.32 (d, 1H), 7.09 (m, 1H), 7.18 (m, 1H), 7.45 (m, 1H), 8.37 (s, 2H); chiral HPLC: 21.5 min, mobile phase e Ex. erythro-2-Ibb-1291, NMR: 2.85 (m, 2H), 3.60 (s, 3H), 4.08 (q, 1H), 4.32 (d, 1H), 7.09 (m, 1H), 7.18 (m, 1H), 7.45 (m, 1H), 8.37 (s, 2H); chiral HPLC: 28.0 min, mobile phase e Ex. threo-1-Ibb1291, NMR: 3.18 (m, 2H), 3.63 (s, 3H), 4.15 (m, 2H), 6.92 (m, 1H), 7.04 (m, 1H), 7.31 (m, 1H), 8.24 (s, 2H); chiral HPLC: 15.7 min, mobile phase e Ex. threo-2-Ibb1291, NMR: 3.18 (m, 2H), 3.63 (s, 3H), 4.15 (m, 2H), 6.92 (m, 1H), 7.04 (m, 1H), 7.31 (m, 1H), 8.24 (s, 2H); chiral HPLC: 18.1 min, mobile phase e (B) FORMULATION EXAMPLES a) A dust is obtained by mixing 10 parts by weight of a compound of the formula (I) and 90 parts by weight of talc as inert substance and comminuting the mixture in a hammer mill.
b) A wettable powder which is readily dispersible in water is obtained by mixing 25 parts by weight of a compound of the formula (I), 64 parts by weight of kaolin-containing quartz as inert substance, 10 parts by weight of potassium lignosulphonate and 1 part by weight of sodium oleoyl-methyltaurate as wetting agent and dispersant, and grinding the mixture in a pinned-disk mill.
c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.
d) An emulsifiable concentrate is obtained from 15 parts by weight of a compound of the formula (I), 75 parts by weight of cyclohexanone as solvent and 10 parts by weight of oxyethylated nonylphenol as emulsifier.
e) Water-dispersible granules are obtained by mixing
75 parts by weight of a compound of the formula (I),
10 parts by weight of calcium lignosulphonate,
5 parts by weight of sodium laurylsulphate,
3 parts by weight of polyvinyl alcohol and
7 parts by weight of kaolin,
grinding the mixture in a pinned-disk mill, and granulating the powder in a fluidized bed by spray application of water as a granulating liquid.
f) Water-dispersible granules are also obtained by homogenizing and precomminuting, in a colloid mill,
25 parts by weight of a compound of the formula (I),
5 parts by weight of sodium 2,2'-dinaphthylmethane-6,6'-disulphonate,
2 parts by weight of sodium oleoylmethyltaurate,
1 part by weight of polyvinyl alcohol,
17 parts by weight of calcium carbonate and
50 parts by weight of water,
then grinding the mixture in a bead mill and atomizing and drying the resulting suspension in a spray tower by means of a one-phase nozzle.

(C) BIOLOGICAL EXAMPLES

1. Herbicidal Pre-Emergence Action

Seeds of monocotyledonous and dicotyledonous weed plants and crop plants were placed in wood-fibre pots in sandy loam and covered with soil. The compounds (I) according to the invention, formulated in the form of wettable powders (WP), were then applied as aqueous suspension or emulsion at a water application rate of 600 l/ha (converted) with the addition of 0.2% of wetting agent to the surface of the covering soil.

After the treatment, the pots were placed in a greenhouse and kept under good growth conditions for the test plants. After about 3 weeks, the effect of the preparations was scored visually in comparison with untreated controls as percentages. For example, 100% activity=the plants have died, 50% herbicidal activity or damage=the plants have been reduced by 50% or the plant mass has been reduced by 50%, 0% activity=like control plants.

Compounds (I) according to the invention such as, for example, the compounds Nos. Ibc1029, threo-Ibc1029, erythro-1-Ibc1029, threo-Ibb1029, erythro-2-Ibc894, Ibb748,
erythro-Ibc910, threo-Ibc910, Ibc910, Ibc1045, erythro-Ibc896, threo-2-Ibb1045, threo-2-Ibb748, Ibb1045, Ibb1027, Ibb1052, Ibb208, Ibb192, threo-Ibb732 from Tables 2 to 2f above have good herbicidal efficacy (70% to 100% activity) against a plurality of harmful plants at an application rate of 320 g or less of active substance per hectare when applied by the pre-emergence method.

Here, for example, the compounds Nos. Ibc1029, Ibb1029, Ibc894, threo-Ibc1029, erythro-1-Ibc1029, threo-Ibb1029, erythro-2-Ibc894, Ibc896, erythro-Ibc910, threo-Ibc910, Ibc910, Ibc1045, erythro-Ibc896, threo-2-Ibb1045, erythro-1-Ibb1045,
erythro-2-Ibb748, threo-2-Ibb748, Ibb1045, Ibb734, Ibb755, Ibb1052, Ibb739, Ibb208,
Ibb192, threo-Ibb732 from Tables 2 to 2f above have very good activity (90-100%) against harmful plants such as *Echinochloa crus-galli* when applied by the pre-emergence method at an application rate of 0.32 kg of active substance per hectare.

For example, the compounds Ibc1029, Ibb1029, threo-Ibc1029, threo-Ibb1029, erythro-Ibc910, threo-Ibc910, Ibc910, Ibc1045, threo-2-Ibb1045,
threo-2-Ibb748, Ibb1045, Ibb734, Ibb1027, Ibb1052, Ibb208 from Tables 2 to 2f above have very good activity (90-100%) against harmful plants such as *Lolium multiflorum* when applied by the pre-emergence method at an application rate of 0.32 kg of active substance per hectare.

For example, the compounds Nos. Ibc1029, threo-Ibc910, threo-2-Ibb1045, threo-2-Ibb748, Ibb734, Ibb1027, Ibb755, Ibb208, Ibb192 from Tables 2 to 2f above have very good activity (90-100%) against harmful plants such as *Viola tricolor* when applied by the pre-emergence method at an application rate of 0.32 kg of active substance per hectare.

2. Herbicidal Post-Emergence Action

Seeds of monocotyledonous and dicotyledonous weeds and crop plants were placed in sandy loam in wood-fibre pots, covered with soil and cultivated in a greenhouse under good growth conditions. 2 to 3 weeks after sowing, the test plants were treated at the one-leaf stage, where the compounds (I) according to the invention, formulated in the form of wettable powders (WP), were applied by spraying as aqueous suspension or emulsion at a water application rate of 600 l/ha (converted) with the addition of 0.2% of wetting agent to the green parts of the plants. After the test plants had been kept in the greenhouse under optimum growth conditions for about 3 weeks, the activity of the preparations was rated visually in comparison to untreated controls in per cent (%). For example, 100% activity=the plants have died, 50% herbicidal activity or damage=the plants have been reduced by 50% or the plant mass has been reduced by 50%, 0% activity=like control plants.

As shown by the results, compounds (I) according to the invention, for example the compounds Nos. Ibc1029, Ibb1029, Ibc894, threo-Ibc1029, erythro-1-Ibc1029, threo- Ibb1029, erythro-1-Ibb1029, Iba894, erythro-2-Ibc894, Ibb748, Ibc895, erythro-Ibc895, Ibc892, Ibc896, erythro-Ibc896, erythro-Ibc910,
threo-Ibc910, Ibc910, Ibc1045, Ibc1036, erythro-Ibc896, threo-1-Ibb1045, threo-2-Ibb1045, erythro-1-Ibb1045, threo-1-Ibb748, erythro-2-Ibb748, threo-2-Ibb748, Ibb1045, Ibb734, Ibb1027, Ibb755,
Ibb1052, Ibb1036, Ibb1049, Ibb751, Ibb1048, Ibb208, Ibb192, threo-Ibb732, erythro-2-Ibb732 from Tables 2 to 2f above have good herbicidal efficacy (70% to 100% activity) against a plurality of harmful plants at an application rate of 320 g or less of active substance per hectare when applied by the post-emergence method.

Here, for example, the compounds Nos. Ibb1029, erythro-2-Ibc894, Ibc895,
erythro-Ibc895, Ibc892, Ibc896, erythro-Ibc910, threo-Ibc910, Ibc910, Ibc1029, threo-1-Ibb1045, threo-2-Ibb1045, erythro-1-Ibb1045, erythro-2-Ibb748, threo-2-Ibb748, Ibb734, Ibb1027, Ibb755, Ibb1052, Ibb1049, Ibb751, Ibb1048, Ibb208, threo-Ibb732,
erythro-2-Ibb732 from Tables 2 to 2f above have very good activity (90-100%) against harmful plants such as *Alopecurus myosuroides* and *Avena fatua* when applied by the post-emergence method at an application rate of 0.32 kg of active substance per hectare.

Here, for example, the compounds Nos. erythro-2-Ibc894, Ibc895, Ibc892,
erythro-Ibc896, threo-1-Ibb1045, erythro-2-Ibb748, Ibb755, Ibb1052, Ibb1048, Ibb192, threo-Ibb732 from Tables 2 to 2f above have very good activity (90-100%) against harmful plants such as *Polygonum* convulvus when applied by the post-emergence method at an application rate of 0.32 kg of active substance per hectare.

For example, the compounds Ibc895, Ibc892, threo-Ibc901, Ibc896, erythro-Ibc910, threo-Ibc910, Ibc910, Ibc1029, Ibc1045, threo-2-Ibb1045,
erythro-1-Ibb1045, erythro-2-Ibb748, threo-2-Ibb748, Ibb755, Ibb1052, Ibb1049, Ibb751, Ibb1048, Ibb208, Ibb192 from Tables 2 to 2f above have good activity (90-100%) against harmful plants such as *Setaria viridis* when applied by the post-emergence method at an application rate of 0.32 kg of active substance per hectare.

3. Herbicidal Pre-Emergence and Post-Emergence Action

Further biological tests by the pre-emergence method and the post-emergence method were in each case carried out separately with the compounds according to the invention below:

Ibc1029, Iba1029, Ibb1029, Ibc894, threo-Ibc1029, erythro-1-Ibc1029, threo-Ibb1029, erythro-1-Ibb1029, Iba894, erythro-2-Ibc894, Ibb894, Ibb748, Ibc895, erythro-Ibc895, Ibc892, erythro-Ibc901, Ibc896, erythro-Ibc896, erythro-Ibc910, threo-Ibc910, Ibc910, Ibc1045, Ibc1036, erythro-2-Ibc910, threo-1-Ibb1045, threo-2-Ibb1045, erythro-1-Ibb1045, erythro-2-Ibb1045, threo-1-Ibb748, erythro-2-Ibb748, threo-2-Ibb748, Ibb1045, Ibb734, Ibb730, Ibb1027, Ibb755, Ibb1052, Ibb1036, Ibb1049, Ibb751, Ibb1048, Ibb208, Ibb192, threo-Ibb732, erythro-2-Ibb732, Ibb10, Ibb37, Ibb361, Ibb118, Ibb334, Ibb1279, Ibb3, Ibb30, Ibb354, Ibb111, Ibb327, Ibb1272, Ibb22, Ibb49, Ibb373, Ibb130, Ibb346, Ibb1291, Ibb5, Ibb356, Ibb113, Ibb329, Ibb1274, Ibb109, Ibb1270, Ibb19, Ibb46, Ibb370, Ibb127, Ibb343, Ibb1288, Ibb4, Ibb355, Ibb111, Ibb328, Ibb1273, threo-1-Ibb1036, threo-2-Ibb1036, erythro-Ibb1036, erythro-1-Ibb1027, threo-Ibb1027, threo-1-Ibc894, threo-2-Ibc894, erythro-1-Ibc896, threo-2-Ibc896, erythro-Ibb1048, erythro-1-Ibb1052, erythro-2-Ibb1052, threo-2-Ibb1052, threo-1-Ibb1052, erythro-Ibb751, threo-1-Ibb751, threo-1-Ibb1048, threo-2-Ibb1048, erythro-2-Ibb1048, threo-2-Ibb755, erythro-2-Ibb755, Ibc916, erythro-Ibc916, erythro-Ibb208, threo-1-Ibb208, threo-2-Ibb208, Ibb194, Ibb211, threo-Ibb211, Ibb190, Ibb210, Ibb215, threo-Ibb215, threo-Ibb212, Ibb193, threo-Ibb193, erythro-2-Ibb734, threo-2-Ibb734, Ibb451, Ibb1018, Ibb435, Ibb1002, Ibb458, Ibb1025, Ibb454, Ibb1021, Ibb1031, threo-Ibb19, erythro-Ibb127, threo-Ibb127, erythro-Ibb1288, threo-2-Ibb1288, threo-1-Ibb1272, erythro-Ibb1272, threo-2-Ibb1272, erythro-Ibb1273, threo-1-Ibb1273, threo-2-Ibb1273, erythro-1-Ibb1291, threo-2-Ibb1291, erythro-Ibb451 and erythro-Ibb1018.

Here, the compounds according to the invention were in each case employed in the biological tests as a component of a wettable powder (WP formulation) or an emulsion concentrate (EC).

At an application rate of 320 g/ha, all the compounds according to the invention mentioned showed 80% to 100% herbicidal activity in the biological tests, against one, more than one or all of the harmful plants below:

ALOMY=*Alopecurus myosuroides*
AVEFA=*Avena fatua*
CYPES=*Cyperus esculentus*
ECHCG=*Echinochloa crus-galli*
LOLMU=*Lolium multiflorum*
SETVI=*Setaria viridis*
ABUTH=*Abutilon theophrasti*
AMARE=*Amaranthus retroflexus*
MATIN=*Matricaria inodora* (=*Tripleurospermum maritimum* subsp. inodorum)
PHBPU=*Pharbitis purpurea*
POLCO=*Polygonum convolvulus* (=*Fallopia convolvulus*)
STEME=*Stellaria media*
VIOTR=*Viola tricolor*
VERPE=*Veronica persica*

What was determined was the respective herbicidal activity, in each case at the same point in time after application of the formulation in question. i.e. the damage to the respective harmful plant in %.

The compounds according to the invention showed particularly good herbicidal activity against ALOMY=*Alopecurus myosuroides*, AVEFA=*Avena fatua*, ECHCG=*Echinochloa crus-galli*, LOLMU=*Lolium multiflorum*, SETVI=*Setaria viridis*, AMARE=*Amaranthus retroflexus*, PHBPU=*Pharbitis purpurea*, POLCO=*Polygonum convolvulus*, VIOTR=*Viola tricolor* and VERPE=*Veronica persica*.

Furthermore, the compounds according to the invention mentioned above were applied to the following useful plants, in each case at the application rates mentioned:

ORYSA=*Oryza sativa* (common rice)
TRZAS=*Triticum aestivum* (spring) (summer wheat)
ZEAMX=*Zea mays* (maize)
BRSNW=*Brassica napus* subsp. *napus* (winter) (winter oilseed rape)

Here, the observed damage to the respective useful plants was within the acceptable range and was generally assessed as low (generally in a range from 0 to 20%).

The invention claimed is:
1. A 4-cyano-3-(pyridyl)-4-phenylbutanoate of formula (I) and/or a salt thereof

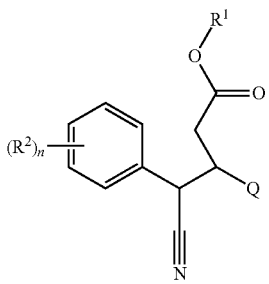

(I)

in which
R$^1$ represents hydrogen or a hydrolyzable radical that is
(a) a saturated or unsaturated aliphatic, cycloaliphatic, or aromatic monocyclic hydrocarbon radical having a total, including any carbon atoms in any substituents attached thereto, of 1 to 30 carbon atoms, a saturated or partially unsaturated heterocyclyl radical having at least one heterocyclic ring having 3 to 9 ring atoms and 1 to 4 ring heteroatoms selected from the group consisting of N, O, and S and having a total, including any carbon atoms in any substituents attached thereto, of 2 to 30 carbon atoms, or a heteroaromatic radical having 5 or 6 ring atoms and 1 to 4 ring heteroatoms selected from the group consisting of N, O, and S and having a total, including any carbon atoms in any substituents attached thereto, of 2 to 30 carbon atoms, wherein each such hydrolyzable radical is optionally substituted with (i) one or more substituents selected from the group consisting of amino, hydroxyl, halogen, nitro, cyano, mercapto, carboxyl, carbonamide, SF$_5$, amino-sulphonyl, alkyl, haloalkyl, cycloalkyl, halocycloalkyl, alkenyl, haloalkenyl, cycloalkenyl, halocycloalkenyl, alkynyl, haloalkynyl, monoalkylamino, dialkyl-amino, N-alkanoylamino, alkoxy, haloalkoxy, alkenyloxy, haloalkenyloxy, alkynyloxy, haloalkynyloxy, alkoxyalkoxy, cycloalkoxy, cycloalkoxyalkoxy, halocycloalkoxy, cycloalkenyloxy, halocycloalkenyloxy, alkoxycarbonyl, alkenyloxycarbonyl, alkynyloxycarbonyl, aryloxycarbonyl, alkanoyl, alkenyl-carbonyl, alkynylcarbonyl, arylcarbonyl, alkylthio, cycloalkylthio, alkenylthio, cycloalkenylthio, alkynylthio, alkylsulphinyl, alkylsulphonyl, monoalkylamino-sulphonyl, dialkylaminosulphonyl, N-alkylaminocarbonyl, N,N-dialkylamino-carbonyl, N-alkanoylaminocarbonyl, N-alkanoyl-N-alkylaminocarbonyl, aryl, aryloxy, benzyl, benzyloxy, benzylthio, arylthio, arylamino, and benzylamino, wherein aryl represents phenyl, naphthyl, tetrahydronaphthyl, indenyl, indanyl, pentalenyl, fluorenyl, or biphenylyl and/or (ii) two substituents that together form a fused-on saturated or unsaturated hydrocarbon bridge in which one or more bridge carbon atoms are optionally replaced by N or O, or (b) a radical of formula SiR$^a$R$^b$R$^c$, —NR$^a$R$^b$ or —N=CR$^c$R$^d$, where R$^a$, R$^b$, R$^c$ and R$^d$ independently of the others each represents hydrogen or an optionally substituted hydrocarbon radical having 1 to 30 carbon atoms, with the proviso that SiR$^a$R$^b$R$^c$ is not SiH$_3$, or where R$^a$ and R$^b$ together with the nitrogen atom of the group —NR$^a$R$^b$ represent an optionally substituted 3- to 8-membered heterocycle that, in addition to the nitrogen atom, optionally contains one or two further ring heteroatoms selected from the group consisting of N, O, and S, or where R$^c$ and R$^d$ together with the carbon atom of the group —N=CR$^c$R$^d$ represent an optionally substituted 3- to 8-membered carbocyclic radical or a heterocyclic radical that optionally contains 1 to 3 ring heteroatoms selected from the group consisting of N, O, and S, where each R$^a$, R$^b$, R$^c$, and R$^d$ is optionally substituted with (C$_1$-C$_4$)-alkyl or (C$_1$-C$_4$)-haloalkyl, or (c) a radical of formula —C(=O)—R$^e$ or —P(=O)(R$^f$)$_2$ where R$^e$ and R$^f$ independently of one another each represent hydrogen, OH, (C$_1$-C$_8$)-alkyl, (C$_1$-C$_4$)-haloalkyl, (C$_2$-C$_8$)-alkenyl, (C$_2$-C$_8$)-alkynyl, (C$_1$-C$_6$)-alkoxy, (C$_1$-C$_6$)-alkoxy-(C$_1$-C$_8$)-alkyl, (C$_1$-C$_6$)-alkoxy-(C$_1$-C$_8$)-alkoxy, (C$_1$-C$_4$)-haloalkoxy, (C$_1$-C$_4$)-haloalkoxy-(C$_1$-C$_8$)-alkyl, (C$_1$-C$_4$)-haloalkoxy-(C$_1$-C$_8$)-alkoxy, (C$_3$-C$_8$)-alkenyloxy, (C$_3$-C$_8$)-alkenyl-oxy-(C$_1$-C$_8$)-alkyl, (C$_3$-C$_8$)-alkenyloxy-(C$_1$-C$_8$)-alkoxy, (C$_3$-C$_8$)-alkynyloxy, (C$_3$-C$_8$)-alkynyloxy-(C$_1$-C$_8$)-alkyl, (C$_3$-C$_8$)-alkynyloxy-(C$_1$-C$_8$)-alkoxy, —NR*R**, tri-[(C$_1$-C$_4$)-alkyl]silyl, tri-[(C$_1$-C$_4$)-alkyl]silyl-(C$_1$-C$_8$)-alkyl, (C$_3$-C$_6$)-cycloalkyl, (C$_3$-C$_6$)-cycloalkyl-(C$_1$-C$_8$)-alkyl, (C$_3$-C$_6$)-cycloalkyl-(C$_1$-C$_8$)-alkoxy, (C$_5$-C$_6$)-cycloalkenyl, (C$_5$-C$_6$)-cycloalkenyl-(C$_1$-C$_8$)-alkyl, (C$_5$-C$_6$)-cycloalkenyl-(C$_1$-C$_8$)-alkoxy, (C$_5$-C$_6$)-cycloalkynyl, (C$_5$-C$_6$)-cycloalkynyl-(C$_1$-C$_8$)-alkyl, (C$_5$-C$_6$)-cycloalkynyl-(C$_1$-C$_8$)-alkoxy, phenyl, phenyl-(C$_1$-C$_8$)-alkyl, phenyl-(C$_1$-C$_8$)-alkoxy, phenoxy, phenoxy-(C$_1$-C$_8$)-alkyl, phenoxy-(C$_1$-C$_8$)-alkoxy, phenylamino, phenylamino-(C$_1$-C$_8$)-alky, phenylamino-(C$_1$-C$_8$)-alkoxy, a radical Het$^1$, Het$^1$—(C$_1$-C$_6$)-alkyl, Het$^1$—(C$_1$-C$_6$)-alkoxy, Het$^1$—O—(C$_1$-C$_6$)-alkoxy, where each of the 23 last-mentioned radicals is unsubstituted in the acyclic moiety or substituted by one or more identical or different radicals R$^A$ and is unsubstituted in the cyclic moiety or substituted by one or more identical or different radicals R$^B$, Het$^1$ independently represents a saturated, partially unsaturated or heteroaromatic monocyclic heterocyclyl radical having 3 to 9 ring atoms or a 9- or 10-membered bicyclic hetero-cycle, each containing 1, 2, 3 or 4 heteroatoms selected from the group consisting of O, N, and S, R* and R** independently of one another and independently of other radicals NR*R** represent H, (C$_1$-C$_8$)-alkyl, (C$_2$-C$_8$)-alkenyl, (C$_2$-C$_8$)-alkynyl, (C$_1$-C$_4$)-alkoxy-(C$_1$-C$_4$)-alkyl, (C$_1$-C$_6$)-alkanoyl, [(C$_1$-C$_4$)-haloalkyl]carbonyl, [(C$_1$-C$_4$)-alkoxy]carbonyl, [(C$_1$-C$_4$)-haloalkoxy]carbonyl, (C$_3$-C$_6$)-cycloalkyl, (C$_3$-C$_6$)-cycloalkyl-(C$_1$-C$_4$)-alkyl, (C$_3$-C$_6$)-cycloalkyl-(C$_1$-C$_4$)-alkylcarbonyl, phenyl, phenylcarbonyl, phenyl-(C$_1$-C$_4$)-alkyl, phenyl-(C$_1$-C$_4$)-alkylcarbonyl, where each of the 7 last-mentioned radicals is optionally substituted in the cycle by one or more identical or different radicals selected from the group consisting of halogen, ($C_1$-$C_4$)-alkyl, ($C_1$-C4)-haloalkyl, ($C_1$-$C_4$)-alkoxy and ($C_1$-$C_4$)-haloalkoxy or, in the case of saturated cyclic base groups, also oxo, or R* and R** together with the nitrogen atom represent a 3- to 8-membered heterocycle which, in addition to the nitrogen atom, optionally contains one or two further ring heteroatoms selected from the group consisting of N, O, and S and which is optionally substituted by one or more radicals selected from the group consisting of ($C_1$-$C_4$)-alkyl, ($C_1$-$C_4$)-halo-alkyl, and oxo, $R^A$ represents halogen, cyano, hydroxy or ($C_1$-$C_6$)-alkoxy, $R^B$ represents halogen, cyano, hydroxy, oxo, nitro, ($C_1$-$C_8$)-alkyl, ($C_1$-$C_6$)-haloalkyl, cyano-($C_1$-$C_6$)-alkyl, hydroxy-($C_1$-$C_6$)-alkyl, nitro-($C_1$-$C_6$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_6$)-alkoxy-($C_1$-$C_6$)-alkyl, ($C_1$-$C_6$)-alkoxy-($C_1$-$C_4$)-alkoxy, ($C_1$-$C_6$)-haloalkoxy-($C_1$-$C_4$)-alkyl, ($C_1$-$C_6$)-haloalkoxy-($C_1$-$C_4$)-alkoxy, ($C_1$-$C_8$alkylthio, ($C_2$-$C_6$)-alkenylthio, ($C_2$-$C_6$)-alkynylthio, ($C_1$-$C_8$)-alkylsulphinyl, ($C_1$-$C_6$)-haloalkylsulphinyl, ($C_1$-$C_8$)-alkylsulphonyl, ($C_1$-$C_6$)-haloalkylsulphonyl, a radical of the formula $R^{aa}$—C(=O)—, $R^{aa}$—C(=O)—($C_1$-$C_6$)-alkyl, —NR*R**, tri [($C_1C_4$) alkyl]silyl, tri-[($C_1$-$C_4$)-alkyl]silyl-($C_1$-$C_6$)-alkyl, ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, phenyl, phenyl-($C_1$-$C_8$)-alkyl, phenoxy, phenoxy-($C_1$-$C_8$)-alkyl, phenylamino, phenylamino-($C_1$-$C_8$)-alkyl or a 5-or 6-membered monocyclic or 9- or 10-membered bicyclic heterocycle which contains 1, 2, 3, or 4 heteroatoms selected from the group consisting of O, N, and S, where each of the 11 last-mentioned radicals is optionally substituted in the cyclic moiety by one or more identical or different radicals $R^{bb}$, $R^{aa}$ independently of one another represent hydrogen, OH, ($C_1$-$C_8$)-alkyl, ($C_1$-$C_6$)-haloalkyl, ($C_2$-$C_8$)-alkenyl, ($C_2$-$C_8$)-alkynyl, ($C_1$-$C_8$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_6$)-haloalkoxy, ($C_1$-$C_6$)-haloalkoxy-($C_1$-$C_6$)-alkyl, ($C_1$-$C_6$)-haloalkoxy-($C_1$-$C_6$)-alkoxy, ($C_3$-$C_8$)-alkenyloxy, ($C_3$-$C_8$)-alkenyloxy-($C_1$-$C_6$)-alkyl, ($C_3$-$C_8$)-alkenyloxy-($C_1$-$C_6$)-alkoxy, ($C_3$-$C_8$)-alkynyloxy, ($C_3$-$C_8$)-alkynyloxy-($C_1$-$C_6$)-alkyl, ($C_3$-$C_8$)-alkynyloxy-($C_1$-$C_6$)-alkoxy, —NR*R**, tri-[($C_1$-$C_4$)-alkyl]silyl, tri-[($C_1$-$C_4$)-alkyl]silyl-($C_1$-$C_6$)-alkyl, tri-[($C_1$-$C_4$)-alkyl]silyl-($C_1$-$C_6$)-alkoxy, ($C_3$-$C_8$)-cycloalkyl, ($C_3$-$C_8$)-cycloalkoxy, ($C_3$-$C_8$)-cycloalkyl-($C_1$-$C_8$)-alkyl, ($C_3$-$C_8$)-cycloalkyl-($C_1$-$C_8$)-alkoxy, ($C_5$-$C_8$)-cycloalkenyl, ($C_5$-$C_8$)-cycloalkenyl-($C_1$-$C_6$)-alkyl, ($C_5$-$C_8$)-cyclo-alkenyloxy, ($C_5$-$C_8$)-cycloalkynyl, ($C_5$-$C_8$)-cycloalkynyl-($C_1$-$C_6$)-alkyl, ($C_5$-$C_8$)-cycloalkynyl-($C_1$-$C_6$)-alkoxy, phenyl, phenyl-($C_1$-$C_8$)-alkyl, phenyl-($C_1$-$C_8$)-alkoxy, phenoxy, phenoxy-($C_1$-$C_8$)-alkyl, phenoxy-($C_1$-$C_8$)alkoxy, phenylamino, phenylamino-($C_1$-$C_8$)-alkyl, phenylamino-($C_1$-$C_8$)-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N, and S, where each of the 20 last-mentioned radicals is optionally substituted in the cyclic moiety by one or more identical or different radicals $R^{cc}$, $R^{bb}$ and $R^{cc}$ independently of one another represent halogen, ($C_1$-$C_4$)-alkyl, ($C_1$-$C_4$)-haloalkyl, ($C_1$-$C_4$)-alkoxy or ($C_1$-$C_4$)-haloalkoxy or, in the case of saturated or partially unsaturated cyclic base groups, also represent oxo, $(R^2)_n$ represents n substituents $R^2$,
where $R^2$, if n=1, or each of the substituents $R^2$, if n is greater than 1, independently of the others represents halogen, n represents 0, 1, or 2, and Q represents pyridin-2-yl (Q1), pyridin-3-yl (Q2) or pyridin-4-yl (Q3)

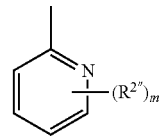

(Q1)

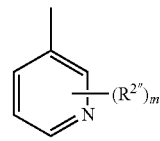

(Q2)

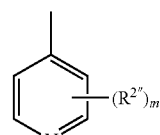

(Q3)

where $(R^{2''})$, represents m substituents $R^{2''}$, where $R^{2''}$, if m=1, or each of the substituents $R^{2''}$, if m is greater than 1, independently of the others represents fluorine, chlorine, bromine, cyano, nitro, or trifluoromethyl, and m represents 1 or 2.

2. The compound or salt thereof according to claim 1, wherein $R^1$ represents hydrogen or a hydrolyzable radical that is
(a) an alkyl, alkenyl, alkynyl, cycloalkyl, cycloalkenyl, cycloalkynyl, or phenyl radical having a total, including any carbon atoms in any substituents attached thereto, of 1 to 30 carbon atoms or a heterocyclyl radical having 3 to 9 ring atoms and 1 to 4 heteroatoms selected from the group consisting of N, O, and S and having a total, including any carbon atoms in any substituents attached thereto, of 2 to 30 carbon atoms, wherein each such hydrolyzable radical is optionally substituted with amino, hydroxyl, halogen, nitro, cyano, mercapto, carboxyl, carbonamide, $SF_5$, aminosulphonyl, alkyl, haloalkyl, cycloalkyl, halocycloalkyl, alkenyl, haloalkenyl, cycloalkenyl, halocycloalkenyl, alkynyl, haloalkynyl, monoalkylamino, dialkylamino, N-alkanoylamino, alkoxy, haloalkoxy, alkenyl-oxy, haloalkenyloxy, alkynyloxy, haloalkynyloxy, alkoxyalkoxy, cycloalkoxy, cycloalkoxyalkoxy, halocycloalkoxy, cycloalkenyloxy, halocycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkyl-thio, alkenylthio, cycloalkenylthio, alkynylthio, alkylsulphinyl, alkylsulphonyl, monoalkylaminosulphonyl, dialkylaminosulphonyl, N-alkylaminocarbonyl, N,N-dialkylaminocarbonyl, N-alkanoylaminocarbonyl, N-alkanoyl-N-alkyl-aminocarbonyl, aryl, aryloxy, benzyl, benzyloxy, benzylthio, arylthio, arylamino, and benzylamino, wherein aryl represents phenyl, naphthyl, tetrahydronaphthyl, indenyl, indanyl, pentalenyl, fluorenyl, or biphenylyl and/or (ii) two substituents that together form a fused-on saturated or unsaturated hydrocarbon bridge in which one or more bridge carbon atoms are optionally replaced by N or O, or (b) a radical of formula $SiR^aR^bR^c$, $-NR^aR^b$ or $-N=CR^cR^d$, where each of the radicals $R^a$, $R^b$, $R^c$ and $R^d$ independently of the others represents hydrogen, alkyl, alkenyl, alkynyl, benzyl, or phenyl, where, however, $SiR^aR^bR^c$ is not $SiH_3$, or $R^a$ and $R^b$ together with the nitrogen atom of the group $-NR^aR^b$ represent a 3- to 8-membered heterocycle which, in addition to the nitrogen atom, optionally contains one or two further ring heteroatoms selected from the group consisting of N, O and S and is optionally substituted with $(C_1-C_4)$-alkyl or $(C_1-C_4)$-haloalkyl, or $R^c$ and $R^d$ together with the carbon atom of the group $-N=CR^cR^d$ represent a 3- to 8-membered carbocyclic radical or a heterocyclic radical which optionally contains 1 to 3 ring heteroatoms selected from the group consisting of N, O and S and is optionally substituted with $(C_1-C_4)$-alkyl or $(C_1-C_4)$-haloalkyl, where each of the radicals $R^a$, $R^b$, $R^c$ and $R^d$, including substituents attached thereto, has up to 30 carbon atoms, or (c) a radical of formula $-C(=O)-R^e$ or $-P(=O)(R^f)_2$ where $R^e$ and $R^f$ independently of one another each represent hydrogen, OH, $(C_1-C_8)$-alkyl, $(C_1-C_4)$-haloalkyl, $(C_2-C_8)$-alkenyl, $(C_2-C_8)$-alkynyl, $(C_1-C_6)$-alkoxy, $(C_1-C_6)$-alkoxy-$(C_1-C_8)$-alkyl, $(C_1-C_6)$-alkoxy-$(C_1-C_8)$-alkoxy, $(C_1-C_4)$-haloalkoxy, $(C_1-C_4)$-haloalkoxy-$(C_1-C_8)$-alkyl, $(C_1-C_4)$-haloalkoxy-$(C_1-C_8)$-alkoxy, $(C_3-C_8)$-alkenyloxy, $(C_3-C_8)$-alkenyloxy-$(C_1-C_8)$-alkyl, $(C_3-C_8)$-alkenyloxy-$(C_1-C_8)$-alkoxy, $(C_3-C_8)$-alkynyloxy, $(C_3-C_8)$-alkynyloxy-$(C_1-C_8)$-alkyl, $(C_3-C_8)$-alkynyl-oxy-$(C_1-C_8)$-alkoxy, $-NR^*R^{**}$, tri-$[(C_1-C_4)$-alkyl]silyl, tri-$[(C_1-C_4)$-alkyl]silyl-$(C_1-C_8)$-alkyl, $(C_3-C_6)$-cycloalkyl, $(C_3-C_6)$-cycloalkyl-$(C_1-C_8)$-alkyl, $(C_3-C_6)$-cycloalkyl-$(C_1-C_8)$-alkoxy, $(C_5-C_6)$-cycloalkenyl, $(C_5-C_6)$-cycloalkenyl-$(C_1-C_8)$-alkyl, $(C_5-C_6)$-cycloalkenyl-$(C_1-C_8)$-alkoxy, $(C_5-C_6)$-cycloalkynyl, $(C_5-C_6)$-cyclo-alkynyl-$(C_1-C_8)$-alkyl, $(C_5-C_6)$-cycloalkynyl-$(C_1-C_8)$-alkoxy, phenyl, phenyl-$(C_1-C_8)$-alkyl, phenyl-$(C_1-C_8)$-alkoxy, phenoxy, phenoxy-$(C_1-C_8)$-alkyl, phenoxy-$(C_1-C_8)$-alkoxy, phenylamino, phenylamino-$(C_1-C_8)$-alkyl, phenylamino-$(C_1-C_8)$-alkoxy, a radical $Het^1$, $Het^1$-$(C_1-C_6)$-alkyl, $Het^1-(C_1-C_6)$-alkoxy, $Het^1-O-(C_1-C_6)$-alkyl or $Het^1-O-(C_1-C_6)$-alkoxy, where each of the 23 last-mentioned radicals is unsubstituted in the acyclic moiety or substituted by one or more identical or different radicals $R^A$ and is unsubstituted in the cyclic moiety or substituted by one or more identical or different radicals $R^B$, $Het^1$ independently of the others in each case represents a saturated, partially unsaturated or heteroaromatic monocyclic heterocyclyl radical having 3 to 9 ring atoms or a 9- or 10-membered bicyclic heterocycle, each containing 1, 2, 3 or 4 heteroatoms selected from the group consisting of O, N and S, $R^*$ and $R^{**}$ independently of one another and also independently of other radicals $NR^*R^{**}$ represent H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]carbonyl, $[(C_1-C_4)$-alkoxy]carbonyl, $[(C_1-C_4)$-haloalkoxy]carbonyl, $(C_3-C_6)$-cycloalkyl, $(C_3-C_6)$-cycloalkyl-$(C_1-C_4)$-alkyl, $(C_3-C_6)$-cycloalkyl-$(C_1-C_4)$-alkylcarbonyl, phenyl, phenylcarbonyl, phenyl-$(C_1-C_4)$-alkyl, phenyl-$(C_1-C_4)$-alkylcarbonyl, where each of the 7 last-mentioned radicals is optionally substituted in the cycle by one or more identical or different radicals selected from the group consisting of halogen, $(C_1-C_4)$-alkyl, $(C_1-C_4)$-haloalkyl, $(C_1-C_4)$-alkoxy and $(C_1-C_4)$-haloalkoxy or, in the case of saturated cyclic base groups, also oxo, or $R^*$ and $R^{**}$ together with the nitrogen atom represent a 3- to 8-membered heterocycle which, in addition to the nitrogen atom, optionally contains one or two further ring heteroatoms selected from the group consisting of N, O and S and which is optionally substituted by one or more radicals selected from the group consisting of $(C_1-C_4)$-alkyl, $(C_1-C_4)$-haloalkyl and oxo, $R^A$ represents halogen, cyano, hydroxy or $(C_1-C_6)$-alkoxy, $R^B$ represents halogen, cyano, hydroxy, oxo, nitro, $(C_1-C_8)$-alkyl, $(C_1-C_6)$-haloalkyl, cyano-$(C_1-C_6)$-alkyl, hydroxy-$(C_1-C_6)$-alkyl, nitro-$(C_1-C_6)$-alkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy, $(C_2-C_8)$-alkenyloxy, $(C_2-C_8)$-alkynyloxy, $(C_1-C_8)$-haloalkoxy, $(C_1-C_6)$-alkoxy-$(C_1-C_6)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_1-C_8)$-alkylthio, $(C_2-C_6)$-alkenylthio, $(C_2-C_6)$-alkynylthio, $(C_1-C_8)$-alkylsulphinyl, $(C_1-C_6)$-haloalkylsulphinyl, $(C_1-C_8)$-alkylsulphonyl, $(C_1-C_6)$-haloalkylsulphonyl, a radical of the formula $R^{aa}-C(=O)-$, $R^{aa}-C(=O)-(C_1-C_6)$-alkyl, $-NR^*R^{**}$, tri-$[(C_1-C_4)$-alkyl]silyl, tri-$[(C_1-C_4)$-alkyl]silyl-$(C_1-C_6)$-alkyl, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, phenyl, phenyl-$(C_1-C_8)$-alkyl, phenoxy, phenoxy-$(C_1-C_8)$-alkyl, phenylamino, phenylamino-$(C_1-C_8)$-alkyl or a 5-or 6-membered monocyclic or 9- or 10-membered bicyclic heterocycle which contains 1, 2, 3 or 4 heteroatoms selected from the group consisting of O, N and S, where each of the 11 last-mentioned radicals is optionally substituted in the cyclic moiety by one or more identical or different radicals $R^{bb}$, $R^{aa}$ independently of one another each represent hydrogen, OH, $(C_1-C_8)$-alkyl, $(C_1-C_6)$-haloalkyl, $(C_2-C_8)$-alkenyl, $(C_2-C_8)$-alkynyl, $(C_1-C_8)$-alkoxy, $(C_1-C_6)$-alkoxy-$(C_1-C_6)$-alkyl, $(C_1-C_6)$-alkoxy-$(C_1-C_6)$-alkyloxy, $(C_1-C_6)$-haloalkoxy, $(C_1-C_6)$-haloalkoxy-$(C_1-C_6)$-alkyl, $(C_1-C_6)$-haloalkoxy-$(C_1-C_6)$-alkoxy, $(C_3-C_8)$-alkenyloxy, $(C_3-C_8)$-alkenyloxy-$(C_1-C_6)$-alkyl, $(C_3-C_8)$-alkenyloxy-$(C_1-C_6)$-alkoxy, $(C_3-C_8)$-alkynyloxy, $(C_3-C_8)$-alkynyl-oxy-$(C_1-C_6)$-alkyl, $(C_3-C_8)$-alkynyloxy-$(C_1-C_6)$-alkoxy, $-NR^*R^{**}$, tri-$[(C_1-C_4)$-alkyl]silyl, tri-$[(C_1-C_4)$-alkyl]silyl-$(C_1-C_6)$-alkyl, tri-$[(C_1-C_4)$-alkyl]silyl-$(C_1-C_6)$-alkoxy, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, $(C_5-C_8)$-cycloalkenyl, $(C_5-C_8)$-cycloalkenyl-$(C_1-C_6)$-alkyl, $(C_5-C_8)$-cycloalkenyloxy, $(C_5-C_8)$-cycloalkynyl, $(C_5-C_8)$-cycloalkynyl-$(C_1-C_6)$-alkyl, $(C_5-C_8)$-cycloalkynyl-$(C_1-C_6)$-alkoxy, phenyl, phenyl-$(C_1-C_8)$-alkyl, phenyl-$(C_1-C_8)$-alkoxy, phenoxy, phenoxy-$(C_1-$ $C_8$)-alkyl, phenoxy-($C_1$-$C_8$)-alkoxy, phenylamino, phenylamino-($C_1$-$C_8$)-alkyl, phenylamino-($C_1$-$C_8$)-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the 20 last-mentioned radicals is optionally substituted in the cyclic moiety by one or more identical or different radicals $R^{cc}$, and $R^{bb}$ and $R^{cc}$ independently of one another each represent halogen, ($C_1$-$C_4$)-alkyl, ($C_1$-$C_4$)-haloalkyl, ($C_1$-$C_4$)-alkoxy or ($C_1$-$C_4$)-haloalkoxy or, in the case of saturated or partially unsaturated cyclic base groups, also represent oxo.

3. The compound or salt thereof according to claim 1, wherein $R^1$ represents H, or $R^1$ represents ($C_1$-$C_{18}$)-alkyl, ($C_2$-$C_{18}$)-alkenyl or ($C_2$-$C_{18}$)-alkynyl that is optionally substituted with one or more
  (i) halogen, cyano, thio, nitro, hydroxy, carboxy, ($C_1$-$C_6$)-alkoxy, ($C_2$-$C_6$)-alkenyl-oxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_1$-$C_6$)-haloalkylthio, ($C_2$-$C_6$)-haloalkenylthio ($C_2$-$C_6$)haloalkynylthio ($C_1$-$C_6$)alkylsulphinyl, ($C_2$-$C_6$)-alkenylsulphinyl, ($C_2$-$C_6$)-alkynylsulphinyl, ($C_1$-$C_6$)-haloalkylsulphinyl, ($C_2$-$C_6$)-haloalkenylsulphinyl, ($C_2$-$C_6$)-haloalkynylsulphinyl, ($C_1$-$C_6$)-alkyl-sulphonyl, ($C_2$-$C_6$)-alkenylsulphonyl, ($C_2$-$C_6$)-alkynylsulphonyl, ($C_1$-$C_6$)-halo-alkylsulphonyl, ($C_2$-$C_6$)-haloalkenylsulphonyl, ($C_2$-$C_6$)-haloalkynylsulphonyl, radicals of the formula —NR*R**, ($C_3$-$C_6$)-cycloalkyl, ($C_5$-$C_6$)-cycloalkenyl, ($C_5$-$C_6$)-cycloalkynyl, ($C_3$-$C_6$)-cycloalkyl-($C_1$-$C_4$)-alkoxy, ($C_5$-$C_6$)-cycloalkenyl-($C_1$-$C_4$)-alkoxy, ($C_5$-$C_6$)-cycloalkynyl-($C_1$-$C_4$)-alkoxy, ($C_3$-$C_6$)-cycloalkoxy, ($C_5$-$C_6$)-cycloalkenyloxy, ($C_5$-$C_6$)-cycloalkynyloxy, ($C_3$-$C_6$)-cycloalkoxy-($C_1$-$C_4$)-alkoxy, phenyl, phenyl-($C_1$-$C_6$)-alkoxy, phenoxy, phenoxy-($C_1$-$C_4$)-alkoxy, phenyl-S(O)$_p$—, phenyl-($C_1$-$C_6$)-alkyl-S(O)$_p$—, phenyloxy-($C_1$-$C_6$)-alkyl-S(O)$_p$—, a radical Het$^1$, Het$^1$—($C_1$-$C_6$)-alkoxy, Het$^1$—O—, Het$^1$-O—($C_1$-$C_4$)-alkoxy, Het$^1$—($C_1$-$C_6$)-alkoxy, Het$^1$-S(O)$_p$—, or Het$^1$—O—($C_1$-$C_4$)-alkyl-S(O)$_p$—, where each of the 24 last-mentioned radicals is optionally substituted in the acyclic moiety by one or more identical or different radicals $R^A$ and is optionally substituted in the cyclic moiety by one or more identical or different radicals $R^B$ and p independently of the others in each case represents 0, 1, or 2,
  (ii) a radical of the formula —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$), or —O—P(=O)(O$R^C$)(O$R^D$),
  (iii) a radical of the formula -SiR'$_3$, —O—SiR'$_3$, (R')$_3$Si-($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others represents H, ($C_1$-$C_4$)-alkyl, or phenyl that is optionally substituted by one or more halogen, ($C_1$-$C_4$)-alkyl, ($C_1$-$C_4$)-alkoxy, ($C_1$-$C_4$)-haloalkyl, ($C_1$-$C_4$)-haloalkoxy, or nitro or is substituted at two adjacent positions by a ($C_2$-$C_6$)-alkylene bridge, and where q represents an integer from 0 to 6, or
  (iv) a radical of the formula R"O—CHR'"CH(OR")-($C_1$-$C_6$)-alkoxy, in which each of the radicals R" independently of the others represents H or ($C_1$-$C_4$)-alkyl or together the radicals represent a ($C_1$-$C_6$)-alkylene group and R'" represents H or ($C_1$-$C_4$)-alkyl, or $R^1$ represents ($C_3$-$C_9$)-cycloalkyl, ($C_5$-$C_9$)-cycloalkenyl, ($C_5$-$C_9$)-cycloalkynyl or phenyl that is optionally substituted with one or more
  (i) halogen, cyano, thio, nitro, hydroxy, carboxy, ($C_1$-$C_6$)-alkyl, ($C_1$-$C_6$)-haloalkyl, ($C_1$-$C_4$)-alkoxy-($C_1$-$C_4$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkyl-thio, ($C_2$-$C_6$)-alkenylthio, ($C_2$-$C_6$)-alkynylthio or a radical of the formula —NR*R**,
  (ii) a radical of the formula —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$), or —O—P(=O)(O$R^C$)(O$R^D$),
  (iii) a radical of the formula —SiR'$_3$, —O—SiR'$_3$, (R')$_3$Si-($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others represents H, ($C_1$-$C_4$)-alkyl, or phenyl that is substituted by one or more halogen, ($C_1$-$C_4$)-alkyl, ($C_1$-$C_4$)-alkoxy, ($C_1$-$C_4$)-haloalkyl, ($C_1$-$C_4$)-haloalkoxy, or nitro or is substituted at two adjacent positions by a ($C_2$-$C_6$)-alkylene bridge, and where q represents an integer from 0 to 6, and
  (iv) a radical of the formula R"O——CHR'"(OR")-($C_1$-$C_6$)-alkoxy, in which each of the radicals R" independently of the others represents H or ($C_1$-$C_4$)-alkyl or together the radicals represent a ($C_1$-$C_6$)-alkylene group and R'" represents H or ($C_1$-$C_4$)-alkyl, and
  (v) a radical of the formula Het$^1$ which is optionally substituted by one or more identical or different radicals $R^B$, Het$^1$ independently of the others represents a saturated, partially unsaturated or heteroaromatic monocyclic heterocyclyl radical having 3 to 9 ring atoms or a 9- or 10-membered bicyclic heterocycle, each containing 1, 2, 3, or 4 heteroatoms selected from the group consisting of O, N, and S, R* and R** independently of one another and independently of other radicals NR*R** represent H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]carbonyl, [($C_1$-$C_4$)-alkoxy]carbonyl, [($C_1$-$C_4$)-haloalkoxy]carbonyl, ($C_3$-$C_6$)-cycloalkyl, ($C_3$-$C_6$)-cycloalkyl-($C_1$-$C_4$)-alkyl, ($C_3$-$C_6$)-cycloalkyl-($C_1$-$C_4$)-alkylcarbonyl, phenyl, phenylcarbonyl, phenyl-($C_1$-$C_4$)-alkyl, phenyl-($C_1$-$C_4$)-alkylcarbonyl, where each of the 7 last-mentioned radicals is optionally substituted in the cycle by one or more identical or different radicals selected from the group consisting of halogen, $(C_1-C_4)$-alkyl, $(C_1-C_4)$-haloalkyl, $(C_1-C_4)$-alkoxy, and $(C_1-C_4)$-haloalkoxy or, in the case of saturated cyclic base groups, also oxo, or R* and R** together with the nitrogen atom represent a 3- to 8-membered heterocycle which, in addition to the nitrogen atom, optionally contains one or two further ring heteroatoms selected from the group consisting of N, O, and S and which is optionally substituted by one or more radicals selected from the group consisting of $(C_1-C_4)$-alkyl, $(C_1-C_4)$-halo-alkyl, and oxo, $R^A$ represents halogen, cyano, hydroxy, or $(C_1-C_6)$-alkoxy, $R^B$ represents halogen, cyano, hydroxy, oxo, nitro, $(C_1-C_8)$-alkyl, $(C_1-C_6)$-haloalkyl, cyano-$(C_1-C_6)$-alkyl, hydroxy-$(C_1-C_6)$-alkyl, nitro-$(C_1-C_6)$-alkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy, $(C_2-C_8)$-alkenyloxy, $(C_2-C_8)$-alkynyloxy, $(C_1-C_8)$-haloalkoxy, $(C_1-C_6)$-alkoxy-$(C_1-C_6)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_1-C_8)$alkylthio, $(C_2-C_6)$-alkenylthio, $(C_2-C_6)$-alkynylthio, $(C_1-C_8)$-alkylsulphinyl, $(C_1-C_6)$-haloalkylsulphinyl, $(C_1-C_8)$-alkylsulphonyl, $(C_1-C_6)$-haloalkylsulphonyl, a radical of the formula $R^{aa}-C(=O)-$, $R^{aa}-C(=O)-(C_1-C_6)$-alkyl, $-NR^*R^{**}$, tri $[(C_1-C_4)$-alkyl]silyl, tri-$[(C_1-C_4)$-alkyl]silyl-$(C_1-C_6)$-alkyl, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8$-alkoxy, phenyl, phenyl-$(C_1-C_8)$-alkyl, phenoxy, phenoxy-$(C_1-C_8)$-alkyl, phenylamino, phenylamino-$(C_1-C_8)$-alkyl or a 5-or 6-membered monocyclic or 9- or 10-membered bicyclic heterocycle which contains 1, 2, 3, or 4 heteroatoms selected from the group consisting of O, N, and S, where each of the 11 last-mentioned radicals is optionally substituted in the cyclic moiety by one or more identical or different radicals $R^{bb}$, $R^C$ and $R^D$ each independently of one another represent hydrogen, $(C_1-C_8)$-alkyl, $(C_2-C_8)$-alkenyl or $(C_2-C_8)$-alkynyl, where each of the 3 last-mentioned radicals is unsubstituted or substituted by one or more radicals from the group consisting of halogen, cyano, nitro, hydroxy, $(C_1-C_6)$-alkoxy, $(C_2-C_6)$-alkenyloxy, $(C_2-C_6)$-alkynyloxy, $(C_1-C_8)$-haloalkoxy, $(C_1-C_4)$-alkoxy-$(C_1-C_4)$-alkoxy, $(C_1-C_8)$-alkylthio, $(C_1-C_8)$-haloalkylthio, $(C_1-C_8)$-alkylsulphinyl, $(C_1-C_8)$-haloalkylsulphinyl, $(C_1-C_8)$-alkylsulphonyl, $(C_1-C_8)$-haloalkylsulphonyl and tri-$[(C_1-C_4)$-alkyl]silyl, or $(C_3-C_8)$-cycloalkyl, $(C_5-C_8)$-cycloalkenyl, $(C_5-C_8)$-cycloalkynyl, phenyl, $(C_3-C_8)$-cycloalkyl-$(C_1-C_6)$-alkyl, $(C_5-C_8)$-cycloalkenyl-$(C_1-C_6)$-alkyl, $(C_5-C_8)$-cycloalkynyl-$(C_1-C_6)$-alkyl, phenyl-$(C_1-C_6)$-alkyl, $(C_3-C_8)$-cycloalkyloxy-$(C_1-C_6)$-alkyl, $(C_3-C_8)$-cycloalkyl-$S(O)_p$—$(C_1-C_6)$-alkyl, $(C_5-C_8)$-cycloalkenyloxy-$(C_1-C_6)$-alkyl, $(C_5-C_8)$-cycloalkynyloxy-$(C_1-C_6)$-alkyl, phenoxy-$(C_1-C_6)$-alkyl, phenyl-$S(O)_p$—$(C_1-C_6)$-alkyl, $(C_3-C_8)$-cycloalkylamino-$(C_1-C_6)$-alkyl, $(C_5-C_8)$-cycloalkenylamino-$(C_1-C_6)$-alkyl, $(C_5-C_8)$-cycloalkynylamino-$(C_1-C_6)$-alkyl, phenylamino-$(C_1-C_6)$-alkyl, $Het^1$, $Het^1$—$(C_1-C_6)$-alkyl, $Het^1$—O—$(C_1-C_6)$-alkyl or $Het^1$-$S(O)_p$—$(C_1-C_6)$-alkyl, where each of the 22 last-mentioned radicals is unsubstituted in the acyclic moiety or substituted by one or more identical or different radicals $R^A$ and is unsubstituted in the cyclic moiety or substituted by one or more identical or different radicals $R^B$ and p independently of the others in each case represents 0, 1 or 2, $R^{aa}$ independently of one another each represent hydrogen, OH, $(C_1-C_8)$-alkyl, $(C_1-C_6)$-haloalkyl, $(C_2-C_8)$-alkenyl, $(C_2-C_8)$-alkynyl, $(C_1-C_8)$-alkoxy, $(C_1-C_6)$-alkoxy-$(C_1-C_6)$-alkyl, $(C_1-C_6)$-alkoxy-$(C_1-C_6)$-alkyloxy, $(C_1-C_6)$-haloalkoxy, $(C_1-C_6)$-haloalkoxy-$(C_1-C_6)$-alkyl, $(C_1-C_6)$-haloalkoxy-$(C_1-C_6)$-alkoxy, $(C_3-C_8)$-alkenyloxy, $(C_3-C_8)$-alkenyloxy-$(C_1-C_6)$-alkyl, $(C_3-C_8)$-alkenyloxy-$(C_1-C_6)$-alkoxy, $(C_3-C_8)$-alkynyloxy, $(C_3-C_8)$-alkynyl-oxy-$(C_1-C_6)$-alkyl, $(C_3-C_8)$-alkynyloxy-$(C_1-C_6)$-alkoxy, $-NR^*R^{**}$, tri $[(C_1-C_4)$ alkyl]silyl, tri-$[(C_1-C_4)$-alkyl]silyl-$(C_1-C_6)$-alkyl, tri-$[(C_1-C_4)$-alkyl]silyl-$(C_1-C_6)$-alkoxy, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, $(C_5-C_8)$-cycloalkenyl, $(C_5-C_8)$-cycloalkenyl-$(C_1-C_6)$-alkyl, $(C_5-C_8)$-cycloalkenyloxy, $(C_5-C_8)$-cycloalkynyl, $(C_5-C_8)$-cycloalkynyl-$(C_1-C_6)$-alkyl, $(C_5-C_8)$-cycloalkynyl-$(C_1-C_6)$-alkoxy, phenyl, phenyl-$(C_1-C_8)$-alkyl, phenyl-$(C_1-C_8)$-alkoxy, phenoxy, phenoxy-$(C_1-C_8)$-alkyl, phenoxy-$(C_1-C_8)$-alkoxy, phenylamino, phenylamino-$(C_1-C_8)$-alkyl, phenylamino-$(C_1-C_8)$-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the 20 last-mentioned radicals is optionally substituted in the cyclic moiety by one or more identical or different radicals $R^{cc}$, and $R^{bb}$ and $R^{cc}$ independently of one another each represent halogen, $(C_1-C_4)$-alkyl, $(C_1-C_4)$-haloalkyl, $(C_1-C_4$-alkoxy or $(C_1-C_4)$-haloalkoxy or, in the case of saturated or partially unsaturated cyclic base groups, also represent oxo.

4. The compound or salt thereof according to claim 1, wherein $(R^2)_n$ represents n substituents $R^2$, where $R^2$, if n=1, or each of the substituents $R^2$, if n is greater than 1, independently of the others represents fluorine, chlorine, bromine, or iodine, and n represents 0, 1, or 2.

5. A process for preparing a compound of formula (I) as defined in claim 1, or a salt thereof, comprising (a) reacting a compound of formula (II)

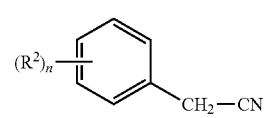

with a compound of formula (III) or a salt thereof

to give a compound of formula (I)

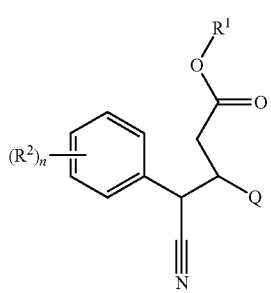

where $R^1$, $R^2$, Q and n in the compounds (II) and (III) are as defined in the respective compound of formula (I) to be prepared, or (b) reacting a compound of formula (I*)

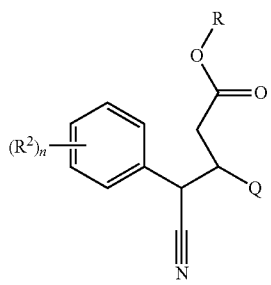

in which R represents a radical selected from the group of radicals possible for $R^1$ but is different from the radical $R^1$ in the compound (I) to be prepared, with a compound of the formula $R^1$—OH in which $R^1$ is as defined in formula (I), to give the compound (I), where $R^2$, Q and n in the compound (I*) are defined as in the compound of the formula (I) to be prepared.

6. An herbicidal or plant growth-regulating composition, comprising one or more compounds of formula (I) or salt thereof as defined in claim 1 and one or more formulation auxiliaries customary in crop protection.

7. A method for controlling one or more harmful plants and/or for regulating the growth of one or more useful and/or ornamental plants, comprising applying an effective amount of one or more compounds of formula (I) or salt thereof as defined in claim 1 onto the plants, plant seeds, soil in which or on which the plants grow and/or an area under cultivation.

8. The method according to claim 7, wherein the compound of formula (I) or salt thereof is employed for selective control of one or more harmful plants and/or for regulating growth in one or more crops of useful plants and/or ornamental plants.

9. The compound or salt thereof according to claim 1, wherein $R^1$ represents H, or $R^1$ represents $(C_1-C_{18})$-alkyl, $(C_2-C_{18})$-alkenyl or $(C_2-C_{18})$-alkynyl that is optionally substituted with one or more halogen, $(C_1-C_4)$-alkoxy, $(C_1-C_4)$-alkylthio, cyclopropyl that is optionally substituted with one or more halogen or $(C_1-C_4)$-alkyl, cyclobutyl that is optionally substituted with one or more halogen or $(C_1-C_4)$-alkyl, phenyl that is optionally substituted with halogen, $(C_1-C_4)$-alkyl, $(C_1-C_4)$-alkoxy, or $(C_1-C_4)$-haloalkyl, phenylthio that is optionally substituted with halogen, $(C_1-C_4)$-alkyl, $(C_1-C_4)$-alkoxy, or $(C_1-C_4)$-haloalkyl, phenylsulphinyl that is optionally substituted with halogen, $(C_1-C_4)$-alkyl, $(C_1-C_4)$-alkoxy, or $(C_1-C_4)$-haloalkyl, or phenylsulphonyl that is optionally substituted with halogen, $(C_1-C_4)$-alkyl, $(C_1-C_4)$-alkoxy, or $(C_1-C_4)$-haloalkyl, or $R^1$ represents $(C_3-C_9)$-cycloalkyl, $(C_5-C_9)$-cycloalkenyl, $(C_5-C_9)$-cycloalkynyl or phenyl in which the cyclic moiety is optionally substituted with one or more halogen, cyano, nitro, $(C_1-C_6)$-alkyl, $(C_1-C_6)$-haloalkyl, $(C_1-C_4)$-alkoxy-$(C_1-C_4)$-alkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_3-C_6)$-cycloalkyl, $(C_3-C_6)$-cycloalkoxy, [$(C_1-C_4)$-alkoxy]carbonyl, or [$(C_1-C_4)$-haloalkoxy]carbonyl.

10. The compound or salt thereof according to claim 1, wherein $R^1$ represents H, or $R^1$ represents $(C_1-C_{18})$-alkyl, $(C_2-C_{18})$-alkenyl or $(C_2-C_{18})$-alkynyl that is optionally substituted with one or more halogen, $(C_1-C_4)$-alkoxy, $(C_1-C_4)$-alkylthio, cyclopropyl that is optionally substituted with one or more halogen or $(C_1-C_4)$-alkyl, cyclobutyl that is optionally substituted with one or more halogen or $(C_1-C_4)$-alkyl, phenyl that is optionally substituted with halogen, $(C_1-C_4)$-alkyl, $(C_1-C_4)$-alkoxy, or $(C_1-C_4)$-haloalkyl, phenylthio that is optionally substituted with halogen, $(C_1-C_4)$-alkyl, $(C_1-C_4)$-alkoxy, or $(C_1-C_4)$-haloalkyl, phenylsulphinyl that is optionally substituted with halogen, $(C_1-C_4)$-alkyl, $(C_1-C_4)$-alkoxy, or $(C_1-C_4)$-haloalkyl, or phenylsulphonyl that is optionally substituted with halogen, $(C_1-C_4)$-alkyl, $(C_1-C_4)$-alkoxy, or $(C_1-C_4)$-haloalkyl, or $R^1$ represents $(C_3-C_9)$-cycloalkyl, $(C_5-C_9)$-cycloalkenyl, $(C_5-C_9)$-cycloalkynyl or phenyl in which the cyclic moiety is optionally substituted with one or more halogen, cyano, nitro, $(C_1-C_6)$-alkyl, $(C_1-C_6)$-haloalkyl, $(C_1-C_4)$-alkoxy-$(C_1-C_4)$-alkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_3-C_6)$-cycloalkyl, $(C_3-C_6)$-cycloalkoxy, [$(C_1-C_4)$-alkoxy]carbonyl, or [$(C_1-C4)$-haloalkoxy]carbonyl, and $(R^2)_n$ represents n substituents $R^2$, where $R^2$, if n=1, or each of the substituents $R^2$, if n is greater than 1, independently of the others represents fluorine, chlorine, bromine, or iodine, and n represents 0, 1, or 2.

11. The compound or salt thereof according to claim 1, wherein $R^1$ represents H, methyl, ethyl, n-propyl, isopropyl, n-butyl, s-butyl, isobutyl, t-butyl, phenyl, benzyl, (4-chlorophenyl)methyl, (4-fluorophenyl)methyl, (4-methoxyphenyl)-methyl, 2-fluorobenzyl, 2-fluorobenzyl, 3-fluorobenzyl, 4-fluorobenzyl, 2,3-difluoro-benzyl, 2,4-difluorobenzyl, 2,5-difluorobenzyl, 2,6-difluorobenzyl, 3,4-difluorobenzyl, 3,5-difluorobenzyl, 2-phenoxyethyl, 2-ethylthioethyl, 2-ethylsulphinylethyl, 2-ethyl-sulphonylethyl, 2-phenylthioethyl, 2-phenylsulphinylethyl, 2-phenylsulphonylethyl, methoxymethyl, 2-methoxyethyl, tetrahydrofuran-2-ylmethyl, 2-(dimethylamino)ethyl, oxetan-3-yl, (3-methyloxetan-3-yl)methyl, thietan-3-yl, trifluoromethyl, difluoromethyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, tetrahydrofuran-2-ylmethyl, allyl, ethynyl, propargyl, prop-1-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1l-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1- (2E)-1-methylbut-2-en-1-yl, (E)-pent-3-en-2-yl or (Z)-pent-3-en-2-yl, cyclobutylmethyl, cyclopentylmethyl, cyclohexylmethyl, or (1-ethyl-5-methyl-1H-pyrazol-4-yl)methyl, and $(R^2)_n$ represents 3-chloro, 4-chloro, 2-fluoro, 3-fluoro, 4-fluoro, 3-bromo, 4-bromo, 2,3-difluoro, 2,4-difluoro, 2,5-difluoro, 2,6-difluoro, 3,4-difluoro, 3,5-difluoro, 3,4,5-trifluoro, 3,4-dichloro, 3,5-dichloro, (3-Cl-2-F), (3-Cl-4-F), (3-Cl-5-F), (3-Cl-6-F), (4-Cl-2-F), (4-Cl-3-F), (3-Br-4-F), or (4-Br-3-F).

12. A 4-cyano-3-(pyridyl)-4-phenylbutanoate of formula (I) or a salt thereof according to claim 1

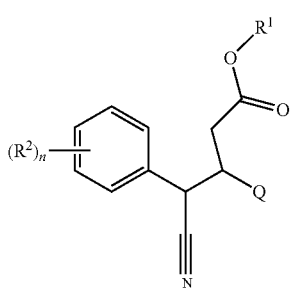

wherein
(a) $R^1$ is $CH_3$, $(R^2)_n$ is 3-Cl, and Q is 4-chloropyridin-2-yl,
(b) $R^1$ is $CH_3$, $(R^2)_n$ is 3-Cl, and Q is 5-chloropyridin-2-yl,
(c) $R^1$ is $CH_3$, $(R^2)_n$ is 3,4-$F_2$, and Q is 5-chloropyridin-2-yl,
(d) $R^1$ is $CH_3$, $(R^2)_n$ is 3-Cl-4-F, and Q is 5-chloropyridin-2-yl,
(e) $R^1$ is $CH_3$, $(R^2)_n$ is 3-Cl-4-F, and Q is 6-fluoropyridin-2-yl,
(f) $R^1$ is $CH_3$, $(R^2)_n$ is 3,4-$F_2$, and Q is 6-fluoropyridin-2-yl as the threo-2-isomer,
(g) $R^1$ is $CH_3$, $(R^2)_n$ is 3,4-$F_2$, and Q is 2,4-difluoropyridin-3-yl as the threo-2-isomer,
(h) $R^1$ is $CH_3$, $(R^2)_n$ is 3,4-$F_2$, and Q is 5-fluoropyridin-3-yl as the threo-2-isomer,
(i) $R^1$ is $CH_3$, $(R^2)_n$ is 3-Cl-4-F, and Q is 5-fluoropyridin-3-yl,
(j) $R^1$ is $CH_3CH_2$, $(R^2)_n$ is 3-Cl, and Q is 6-chloropyridin-3-yl as the threo-2-isomer,
(k) $R^1$ is $CH_3CH_2$, $(R^2)_n$ is 3,4-$F_2$, and Q is 6-chloropyridin-3-yl as the threo-2-isomer,
(l) $R^1$ is $CH_3$, $(R^2)_n$ is 3-Cl, and Q is 2-chloropyridin-4-yl,
(m) $R^1$ is $CH_3$, $(R^2)_n$ is 3,4-$F_2$, and Q is 2-chloropyridin-4-yl as the threo-2-isomer,
(n) $R^1$ is $CH_3$, $(R^2)_n$ is 3-Cl, 4-F, and Q is 2-chloropyridin-4-yl,
(o) $R^1$ is $CH_3$, $(R^2)_n$ is 3-Cl, 4-F, and Q is 3,5-difluoropyridin-4-yl.

13. A 4-cyano-3-(pyridyl)-4-phenylbutanoate of formula (I)or a salt thereof according to claim 1

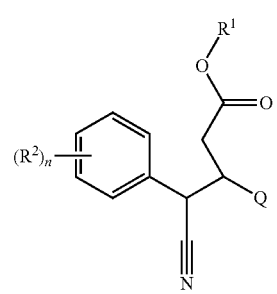

wherein
(a) $R^1$ is $CH_3$, $(R^2)_n$ is 3-Cl-4-F, and Q is 6-fluoropyridin-2-yl as the threo-2-isomer,
(b) $R^1$ is $CH_3$, $(R^2)_n$ is 3-Cl-4-F, and Q is 5-fluoropyridin-3-yl as the threo-2-isomer, and
(C) $R^1$ is $CH_3$, $(R^2)_n$ is 3-Cl, 4-F, and Q is 2-chloropyridin-4-yl as the threo-2-isomer.

* * * * *